(12) United States Patent
Cheng et al.

(10) Patent No.: US 11,780,895 B2
(45) Date of Patent: Oct. 10, 2023

(54) TARGETED DNA DEMETHYLATION AND METHYLATION

(71) Applicant: The Jackson Laboratory, Bar Harbor, ME (US)

(72) Inventors: Albert Cheng, Bar Harbor, ME (US); Aziz Taghbalout, Bar Harbor, ME (US); Nathaniel Jillette, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 1096 days.

(21) Appl. No.: 16/333,134

(22) PCT Filed: Sep. 13, 2017

(86) PCT No.: PCT/US2017/051409
§ 371 (c)(1),
(2) Date: Mar. 13, 2019

(87) PCT Pub. No.: WO2018/053035
PCT Pub. Date: Mar. 22, 2018

(65) Prior Publication Data
US 2020/0071369 A1    Mar. 5, 2020

Related U.S. Application Data

(60) Provisional application No. 62/535,113, filed on Jul. 20, 2017, provisional application No. 62/485,210, filed on Apr. 13, 2017, provisional application No. 62/393,944, filed on Sep. 13, 2016.

(51) Int. Cl.
| | | |
|---|---|---|
| *C12N 9/22* | (2006.01) | |
| *C07K 14/47* | (2006.01) | |
| *C12N 9/06* | (2006.01) | |
| *C12N 9/02* | (2006.01) | |
| *C12N 9/24* | (2006.01) | |
| *C12N 15/09* | (2006.01) | |
| *C07K 14/315* | (2006.01) | |
| *C12N 15/113* | (2010.01) | |
| *C12N 15/85* | (2006.01) | |
| *C12N 15/90* | (2006.01) | |

(52) U.S. Cl.
CPC ........ *C07K 14/4702* (2013.01); *C07K 14/315* (2013.01); *C12N 9/0032* (2013.01); *C12N 9/0069* (2013.01); *C12N 9/0071* (2013.01); *C12N 9/22* (2013.01); *C12N 9/2497* (2013.01); *C12N 15/09* (2013.01); *C12N 15/113* (2013.01); *C12N 15/85* (2013.01); *C12N 15/902* (2013.01); *C12Y 114/11* (2013.01); *C07K 2319/09* (2013.01); *C07K 2319/85* (2013.01); *C07K 2319/90* (2013.01); *C12Y 113/1102* (2013.01); *C12Y 301/21001* (2013.01)

(58) Field of Classification Search
CPC .......................... C07K 14/4702; C12N 15/11
See application file for complete search history.

(56) References Cited

U.S. PATENT DOCUMENTS

| | | |
|---|---|---|
| 6,613,318 B1 | 9/2003 | Wang et al. |
| 2006/0088888 A1 | 4/2006 | Wang et al. |
| 2009/0028861 A1 | 1/2009 | Takagi et al. |
| 2011/0059502 A1 | 3/2011 | Chalasani et al. |
| 2012/0088812 A1 | 4/2012 | Song et al. |
| 2013/0323200 A1 | 12/2013 | Schneider |
| 2013/0323220 A1 | 12/2013 | Joung et al. |
| 2014/0315985 A1 | 10/2014 | May et al. |
| 2016/0238593 A1 | 8/2016 | Boyden et al. |
| 2019/0218261 A1 | 7/2019 | Cheng et al. |

FOREIGN PATENT DOCUMENTS

| | | |
|---|---|---|
| WO | WO 2011/160052 A2 | 12/2011 |
| WO | WO 2013/176772 A1 | 11/2013 |
| WO | WO 2016/022363 A2 | 2/2016 |
| WO | WO 2016/148994 A1 | 9/2016 |
| WO | WO 2018/035495 A1 | 2/2018 |

OTHER PUBLICATIONS

Williams et al. 2012; DNA methylation: TET proteins-guardians of CpG islands? EMBO Reports. 13(1): 28-25.*
Cheng et al., Casilio: a versatile CRISPR-Cas9-Pumilio hybrid for gene regulation and genomic labeling. Cell Res. Feb. 2016;26(2):254-7. doi: 10.1038/cr.2016.3. Epub Jan. 15, 2016.
Choudhury et al., Engineering RNA endonucleases with customized sequence specificities. NatCommun. 2012;3:1147. doi: 10.1038/ncomms2154. Author manuscript.
Deng et al., Methylation of CpG in a small region of the hMLH1 promoter invariably correlates with the absence of gene expression. Cancer Res. May 1, 1999;59(9):2029-33.
He et al., Tet-mediated formation of 5-carboxylcytosine and its excision by TDG in mammalian DNA. Science. Sep. 2, 2011;333(6047):1303-7. doi: 10.1126/science.1210944. Epub Aug. 4, 2011. Author manuscript.
Ito et al., Role of Tet proteins in 5mC to 5hmC conversion, ES-cell self-renewal and inner cell mass specification. Nature. Aug. 26, 2010;466(7310):1129-33. doi: 10.1038/nature09303. Author manuscript.

(Continued)

*Primary Examiner* — Karen Cochrane Carlson
(74) *Attorney, Agent, or Firm* — Wolf, Greenfield & Sacks, P.C.

(57) ABSTRACT

Provided herein are, inter alia, compositions and methods for demethylating and methylating a target DNA sequences in a mammalian cell. The compositions and methods are, useful for activity modulation of a targeted gene, or to create a gene regulatory network.

22 Claims, 14 Drawing Sheets
Specification includes a Sequence Listing.

(56) References Cited

OTHER PUBLICATIONS

Kriaucionis et al., The nuclear DNA base 5-hydroxymethylcytosine is present in Purkinje neurons and the brain. Science. May 15, 2009;324(5929):929-30. doi: 10.1126/science.1169786. Epub Apr. 16, 2009. Author manuscript.
Liu et al., Targeting cellular mRNAs translation by CRISPR-Cas9. Sci Rep. Jul. 13, 2016;6:29652. doi: 10.1038/srep29652.
Maiti et al., Thymine DNA glycosylase can rapidly excise 5-formylcytosine and 5-carboxylcytosine: potential implications for active demethylation of CpG sites. J Biol Chem. Oct. 14, 2011;286(41):35334-8. doi: 10.1074/jbc.C111.284620. Epub Aug. 23, 2011.
Morita et al., Targeted DNA demethylation in vivo using dCas9-peptide repeat and scFv-TET1 catalytic domain fusions. Nat Biotechnol. Oct. 2016;34(10):1060-1065. doi: 10.1038/nbt.3658. Epub Aug. 29, 2016.
Robertson, DNA methylation and human disease. Nat Rev Genet. Aug. 2005;6(8):597-610.
Spassov et al., Cloning and comparative sequence analysis of PUM1 and PUM2 genes, human members of the Pumilio family of RNA-binding proteins. Gene. Oct. 16, 2002;299(1-2):195-204.
Xu et al., A CRISPR-based approach for targeted DNA demethylation. Cell Discov. May 3, 2016;2:16009. doi: 10.1038/celldisc.2016.9. eCollection 2016.
Zhang et al., Chromatin methylation activity of Dnmt3a and Dnmt3a/3L is guided by interaction of the ADD domain with the histone H3 tail. Nucleic Acids Res. Jul. 2010;38(13):4246-53. doi: 10.1093/nar/gkq147. Epub Mar. 11, 2010.
U.S. Appl. No. 16/333,137, filed Mar. 13, 2019, Pending.
PCT/US2017/051409, dated Dec. 12, 2017, International Search Report and Written Opinion.
PCT/US2017/051409, dated Mar. 28, 2019, International Preliminary Report on Patentability.
U.S. Appl. No. 16/333,137, filed Mar. 13, 2019, Published, Patent or Publication No. 2019-0218261.
EP17851475.8, dated Apr. 7, 2020, Extended European Search Report.
PCT/US2017/051411, dated Dec. 4, 2017, International Search Report and Written Opinion.
PCT/US2017/051411, dated Mar. 28, 2019, International Preliminary Report on Patentability.
Extended European Search Report, dated Apr. 7, 2020 for European Application No. 17851475.8.
International Search Report and Written Opinion, dated Dec. 4, 2017 for International Application No. PCT/US2017/051411.
International Preliminary Report on Patentability, dated Mar. 28, 2019 for International Application No. PCT/US2017/051411.
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Taghbalout et al., Enhanced CRISPR-based DNA demethylation by Casilio-ME-mediated RNA-guided coupling of methylcytosine oxidation and DNA repair pathways. Nat Commun. Sep. 20, 2019;10(1):4296. doi: 10.1038/s41467-019-12339-7.
Kienhöfer et al., GADD45a physically and functionally interacts with TET1. Differentiation. Jul.-Oct. 2015;90(1-3):59-68. doi: 10.1016/j.diff.2015.10.003. Epub Nov. 3, 2015.
Müller et al., TET-mediated oxidation of methylcytosine causes TDG or NEIL glycosylase dependent gene reactivation. Nucleic Acids Res. Jul. 2014;42(13):8592-604. doi: 10.1093/nar/gku552. Epub Jun. 19, 2014.

\* cited by examiner dCas9 + PUF fusion(s) + sgX-4x(PBS32-PBS6272)

Direct dCas9 fusions i. Dnmt3a-dCas9 ii. Dnmt3L-dCas9 iii. Dnmt3a3L-dCas9 iv. dCas9-Dnmt3a v. dCas9-Dnmt3L vi. dCas9-Dnmt3a3L

Casilio Dnmt effectors i. dCas9/Dnmt3a-PUF ii. dCas9/Dnmt3L-PUF iii. dCas9/Dnmt3a3L-PUF iv. dCas9/PUF-Dnmt3a v. dCas9/PUF-Dnmt3L vi. dCas9/PUF-Dnmt3a3L Casilio Dnmt complex

TARGETED DNA DEMETHYLATION AND METHYLATION

CROSS-REFERENCES TO RELATED APPLICATIONS

This application is a national stage filing under 35 U.S.C. § 371 of international application number PCT/US2017/051409, filed Sep. 13, 2017, which was published under PCT Article 21(2) in English and claims the benefit of U.S. Provisional Application No. 62/393,944, filed on Sep. 13, 2016, U.S. Provisional Application No. 62/485,210, filed on Apr. 13, 2017, and U.S. Provisional Application No. 62/535,113, filed on Jul. 20, 2017, each of which is incorporated herein by reference in its entirety.

REFERENCE TO A "SEQUENCE LISTING," A TABLE, OR A COMPUTER PROGRAM LISTING APPENDIX SUBMITTED AS AN ASCII FILE

The Sequence Listing named J022770055US03-SEQ-HJD having a size of 1 KB is hereby incorporated by reference.

BACKGROUND

In the CRISPR/Cas system, Cas9 protein and sgRNA (single guide RNA) constitute a sufficient two-component DNA endonuclease whose specificity is provided by target-matching sequence on the sgRNA while endonuclease activity resides on the Cas9 protein.

Nuclease-defective or nuclease-deficient Cas9 protein (e.g., dCas9) with mutations on its nuclease domains retains DNA binding activity when complexed with sgRNA. dCas9 protein can tether and localize effector domains or protein tags by means of protein fusions to sites matched by sgRNA, thus constituting an RNA-guided DNA binding enzyme. dCas9 can be fused to transcriptional activation domain (e.g., VP64) or repressor domain (e.g., KRAB), and be guided by sgRNA to activate or repress target genes, respectively. dCas9 can also be fused with fluorescent proteins and achieve live-cell fluorescent labeling of chromosomal regions. However, in such systems, only one Cas9-effector fusion is possible because sgRNA:Cas9 pairing is exclusive. Also, in cases where multiple copies of protein tags or effector fusions are necessary to achieve some biological threshold or signal detection threshold, multimerization of effector or protein tags by direct fusion with dCas9 protein is technically limited, by constraints such as difficulty in delivering the large DNA encoding such fusions, or difficulty in translating or translocating such large proteins into the nucleus due to protein size.

Methylcytosine is an epigenetic mark generated via a process that covalently adds a methyl group at position 5 of the cytosine ring of a CpG DNA sequence. In mammalian cells, formation of 5-methylcytosine (5mC) is catalyzed and maintained by DNA methyltransferases. Demethylation pathways, which remove the methyl group to restore unmethylated DNA, involve the ten-eleven translocation (TET) family of proteins. These are TET methylcytosine dioxygenases that catalyze the initial and critical step leading to replacing 5mC with unmethylated cytosine.

CpG methylation is part of the multifaceted epigenetic modifications of chromatin that shape cellular differentiation, gene expression, and maintenance of cellular homeostasis. DNA methylation is a major mechanism in imprinting, tuning allelic expression of genes. Aberrant DNA methylation is implicated in various diseases including but not limited to cancer, imprinting disorders and neurological diseases (Robertson, K. D., *DNA methylation and human disease.* Nat Rev Genet, 2005. 6(8): p. 597-610).

Attempts have been made to modulate the methylation status in target cells by introducing DNA demethylase and/or DNA methyltransferase. However, such attempts result in non-specific global changes in methylation status of the target cells.

Meanwhile, the causal effects of CpG methylation events at a specific genomic locus have remained challenging to define essentially due to the lack of simple methods for targeted conversion of 5mC to unmethylated cytosine in living cells. Thus, there is a need in the art for tools that permit editing the methylation state at specific loci to understand the biology of cytosine methylation and to develop therapies for diseases associated with altered cytosine methylation/demethylation pathways.

Disclosed herein are, inter alia, solutions to these and other problems in the art.

BRIEF SUMMARY OF THE INVENTION

In one aspect, a demethylation complex is provided. The demethylation complex includes:
(a) a ribonucleoprotein complex including:
  (i) a nuclease-deficient RNA-guided DNA endonuclease enzyme; and
  (ii) a polynucleotide including:
    (1) a DNA-targeting sequence that is complementary to a target polynucleotide sequence;
    (2) a binding sequence for the nuclease-deficient RNA-guided DNA endonuclease enzyme; and
    (3) one or more PUF binding site (PBS) sequences,
  wherein the nuclease-deficient RNA-guided DNA endonuclease enzyme is bound to the polynucleotide via the binding sequence; and
(b) a demethylation protein conjugate including:
  (i) a PUF domain; and
  (ii) a demethylation domain, the demethylation domain operably linked to the C-terminus of the PUF domain to form a protein conjugate,
  wherein the demethylation protein conjugate binds to the ribonucleoprotein complex via the PUF domain binding to the one or more PBS sequences to form a demethylation complex.

In another aspect, a methylation complex is provided. The methylation complex includes:
(a) a ribonucleoprotein complex including:
  (i) a nuclease-deficient RNA-guided DNA endonuclease enzyme; and
  (ii) a polynucleotide including:
    (1) a DNA-targeting sequence that is complementary to a target polynucleotide sequence;
    (2) a binding sequence for the nuclease-deficient RNA-guided DNA endonuclease enzyme; and
    (3) one or more PUF binding site (PBS) sequences,
  wherein the nuclease-deficient RNA-guided DNA endonuclease enzyme is bound to the polynucleotide via the binding sequence; and
(b) a methylation protein conjugate including:
  (i) a PUF domain; and
  (ii) a methylation domain, the methylation domain operably linked to the N-terminus of the PUF domain to form a protein conjugate, wherein the methylation protein conjugate binds to the ribonucleoprotein complex via the PUF domain binding to the one or more PBS sequences to form a methylation complex.

In another aspect, a cell is provided including a complex as provided herein including embodiments thereof is provided.

In another aspect, a method of demethylating a target nucleic acid sequence in a mammalian cell is provided. The method includes:
(a) providing a mammalian cell containing a target nucleic acid requiring demethylation;
(b) delivering to the mammalian cell a first polynucleotide encoding a nuclease-deficient RNA-guided DNA endonuclease enzyme;
(c) delivering to the mammalian cell a second polynucleotide including:
  (i) a DNA-targeting sequence that is complementary to a target polynucleotide sequence;
  (ii) a binding sequence for the nuclease-deficient RNA-guide DNA endonuclease enzyme; and
  (iii) one or more PUF binding site (PBS) sequences,
  wherein the nuclease-deficient RNA-guided DNA endonuclease enzyme is bound to the second polynucleotide via the binding sequence; and
(d) delivering to the mammalian cell a third polynucleotide encoding a demethylation protein conjugate including:
  (i) a PUF domain; and
  (ii) a demethylation domain, the demethylation domain operably linked to the C-terminus of the PUF domain,
  whereby the delivered demethylation protein conjugate demethylates the target nucleic acid sequence in the cell.

In another aspect, a method of methylating a target nucleic acid sequence in a mammalian cell is provided. The method includes:
(a) providing a mammalian cell containing a target nucleic acid requiring methylation;
(b) delivering to the mammalian cell a first polynucleotide encoding a nuclease-deficient RNA-guided DNA endonuclease enzyme;
(c) delivering to the mammalian cell a second polynucleotide including:
  (i) a DNA-targeting sequence that is complementary to a target polynucleotide sequence;
  (ii) a binding sequence for the nuclease-deficient RNA-guide DNA endonuclease enzyme; and
  (iii) one or more PUF binding site (PBS) sequences,
  wherein the nuclease-deficient RNA-guided DNA endonuclease enzyme is bound to the second polynucleotide via the binding sequence; and
(d) delivering to the mammalian cell a third polynucleotide encoding a methylation protein conjugate including:
  (i) a PUF domain; and
  (ii) a methylation domain, the methylation domain operably linked to the N-terminus of the PUF domain,
  whereby the delivered methylation protein conjugate methylates the target nucleic acid sequence in the cell.

In another aspect, a kit is provided. The kit includes:
(i) a ribonucleoprotein complex as provided herein including embodiments thereof or a nucleic acid encoding the same; and
(ii) a methylation modifying protein conjugate as provided herein including embodiments thereof or a nucleic acid encoding the same.

One aspect of the invention provides a method of modulating transcription and/or methylation state of a target gene having a target polynucleotide sequence in a cell, the method comprises:
(a) introducing into the cell a coding sequence for a PUF domain fusion protein, wherein said PUF domain fusion protein comprises a PUF domain, and a DNA methyltransferase activity domain or a DNA demethylase activity domain;
(b) introducing into the cell a coding sequence for a dCas9 protein; and,
(c) introducing into the cell a polynucleotide or a coding sequence for said polynucleotide, wherein said polynucleotide comprising:
  (i) a DNA-targeting sequence that is complementary to the target polynucleotide sequence;
  (ii) one or more copies of PUF binding sites (PBS), wherein each of said one or more copies of PBS bind to the same or a different PUF domain fusion protein; and,
  (iii) a Cas9-binding sequence capable of binding to the dCas9 protein;
  wherein said PUF domain fusion protein, said dCas9 protein, and said polynucleotide form a complex at the target polynucleotide sequence within the target gene of said cell, thereby modulating the transcription and/or methylation state of the target gene.

Another aspect of the invention provides a method of modulating transcription and/or methylation state of a target gene in a cancer cell according to any method of the invention, wherein the cancer cell is associated with or characterized by abonormal DNA methylation.

Another aspect of the invention provides a complex comprising the polynucleotide, the dCas9 protein, and the PUF-domain fusion protein of the invention.

Yet another aspect of the invention provide a kit comprising: (1) any of the polynucleotide of the invention; (2) a coding sequence encoding a dCas9 protein; and (3) a coding sequence encoding a PUF domain fused to an effector domain selected from a DNA methyltransferase activity domain or a DNA demethylase activity domain.

It should be understood that any embodiments described herein, including those only described in the Example section or only under one aspect of the invention, can be combined with any one or more other embodiments, unless specifically disclaimed or otherwise improper.

BRIEF DESCRIPTION OF THE DRAWINGS

FIG. 1A is a schematic drawing showing the subject 3-component CRISPR/Cas complex/system (upper right), which improves the conventional two-hybrid dCas9 fusion design (upper left) by splitting it into a three-hybrid system, in which sgRNA-PBS bridges the DNA binding activity of dCas9/sgRNA with the effector function provided by a PUF fusion. The middle panels represent the structure of a representative PUF (i.e., Pumilio/FBF) domain, showing the 8 repeats in the C to N direction and the corresponding interaction with the 8-mer target RNA in the 5' to 3' direction. PUF RNA recognition code table shows exemplary di-residues and the corresponding RNA base recognized. In the lower panel, a table of notation adopted for simplicity to describe the 4 PUF isotypes and the corresponding PUF binding sites (PBS) and their sequences. FIG. 1B, upper panel, is a schematic for the experiment to test the ability of dCas9-VP64 to bind and activate a tdTomato transgene after inserting varying number of PBS at the 3' end of the sgRNA, e.g., experimental set up for testing the effect of sgRNA-PBS (with 0, 5, 15, 25, or 47 PBS) on the ability of the dCas9::VP64 construct to activate a TetO::tdTomato transgene. The lower panel is column plot showing the mean fold changes (±S.E.M.) in tdTomato fluorescence (relative to the dCas9-VP64/sgCtl-0×PBSa control), as measured by fluorescence activated cell sorting (FACS), of cells transfected with the different constructs indicated in the legend below the plot. The legend describes the sgRNA used in three parameters: sgRNA match refers to the DNA target recognized by the sgRNA; #PBS and PBS Type indicate the number and the types of PBS, respectively, appended to the end of the sgRNA. FIG. 1C, upper panel, is a schematic describing the experiment to test activation of a TetO::tdTomato transgene by the subject activator with different numbers of appended PBS. The lower panel is a column plot showing the fold changes (±S.E.M.) of tdTomato fluorescence (relative to control dCas9/PUFb-VP64/sgCtl-0×PBSb) of cells transfected with the different constructs indicated in the legend blow the plot. The legend describes the PUF isotype (PUF-VP64) used and the sgRNA-PBS used in terms of the number and type of PBS as well as the DNA target recognized by sgRNA indicated by shaded boxes.

FIG. 1D, upper panel, is a schematic illustrating the experiment to test the independency of the subject activator isotypes in activating a TetO::tdTomato transgene. The lower panel is a column plot showing the mean fold changes (±S.E.M.) of tdTomato fluorescence (relative to the respective controls dCas9/PUFx-VP64/sgCt1-5×PBSx for PUF/PBS isotype x) of cells transfected with the different constructs indicated in the legend below the plot. The legends indicate the PUF isotype used (PUF-VP64), the PBS isotype (5×PBS; "–" indicates sgRNA without PBS) and DNA target indicated by shaded boxes (sgRNA Match). All plots show results of three replicate measurements.

FIG. 2A and FIG. 2B relate to the assembly of the subject 3-component CRISPR/Cas complex/system comprising VP64 and P65-HSF1. FIG. 2A is a schematic of the experiment testing the assembly of PUF(3-2)::VP64 and PUF(6-2/7-2)::P65-HSF1 via recruitment by sgRNA containing both PBS32 and PBS6272. The activity was measured by the tdTomato fluorescent reporter activity. FIG. 2B is a column chart showing the relative mean tdTomato fluorescence resulting from transfecting the activator protein(s) with non-targeting (sgControl) and Tet-targeting (sgTetO) sgRNAs with 4×[PBS32-PBS6272] heterodimer sites. FIG. 2C shows comparison of the subject 3-component system activator using VP64 (PUFa::VP64) versus p65HSF1 (PUFa::p65HSF1) as the activation domain in conjunction with Control sgRNA with 5×PBSa or TetO-targeting sgRNA with 0, 1, 5, 15, or 25 copies of PBSa. Columns show mean fold change (with S.E.M.; n=3) of tdTomato fluorescence relative to experiments using control sgRNA (sgCt1). The legend indicates the number of PBSa (#PBSa) on the sgRNA-PBS as well as the DNA match indicated by the shaded boxes.

FIG. 3A is a schematic representation of the hMLH1 promoter with regions of CpG hypermethylation shown by lollipops. Numbering of nucleotide is according to previous study reporting a strong association of hypermethylation in region C with hMLH1 silencing (Deng, G., et al., *Methylation of CpG in a small region of the hMLH1 promoter invariably correlates with the absence of gene expression*. Cancer Res, 1999. 59(9): p. 2029-33). sgRNAs designed around the hypermethylated region C are shown by numbers over short lines, and sgRNA-1 and 2 target sense and anti-sense strands respectively. FIG. 3B shows relative change in hMLH1 mRNA levels in cells transfected with Casilio components PUFa-TET1(CD), TET1(CD)-PUFa or PUFa-p65HSF1 and the combination of sgRNAs indicated by shaded boxes under the graph. Drawings depict the Casilio system showing the effector modules used in each set of experiments and data were plotted that reflect the respective effector in application. FIG. 3C shows relative change in hMLH1 mRNA levels in cells transfected with dCas9-tethered effectors dCas9-TET1(CD)C-terminal fusion, TET1(CD)-dCas9 N-terminal fusion or dCas9-p65HSF1 and the combination of sgRNAs indicated by shaded boxes under the graph. Drawings depict the dCas9 fusion used for each set of experiments and data were plotted to reflect the respective effector used. The letters "N" (i.e., N-terminus) and "C" (i.e., C-terminus) of the PUMa (aka/PUFa), the TET1(CD) and the p65HSF1 domain in FIGS. 3B and 3C refer to the N-terminus and the C-terminus of the corresponding protein domain.

FIG. 4A is a time course of relative change in hMLH1 mRNA levels in cells transfected with Casilio components PUFa-TET1(CD) and the combination of sgRNAs indicated by shaded boxes under the graph. Drawing over the plot depicts the Casilio-ME system showing the carboxyterminal-TET1(CD) fusion module used and relative changes in hMLH1 mRNA levels were plotted against post-transfection time in which cells were harvested for analyses. Error bars indicate s.e.m derived from triplicate experiments. FIG. 4B is Western blot analysis of protein extracted from indicated cell samples using anti-hMLH1 or anti-β Actin monoclonal antibodies as shown. Proteins extracted form untransfected cells HEK293T (untreated) or treated with 2.5 μM 5'-Azacytidine (AzaC), HEK293 cells (293), and transfected HEK293T cells in the presence of a non-targeting control guide RNA (NTC) were analyzed in parallel with extracts from time course samples that were transfected with Casilio-Me components targeting the hMLH1 promoter region. FIG. 4C shows frequency of cytosine to thymine bisulfite-mediated conversion of individual CpGs of the hMLH1 promoter region. Arrows indicate CpG that overlaps with the binding site of the targeting sgRNA. Coordinates indicate the position of the CpG relative to hMLH1 transcription start site (Deng, G., et al., *Methylation of CpG in a small region of the hMLH1 promoter invariably correlates with the absence of gene expression*. Cancer Res, 1999. 59(9): p. 2029-33). The distal part of hMLH1 promoter of HEK293 cells (293) was not included in this analysis. The letter "N" of the PUMa (aka PUFa) and the TET1(CD) domain in FIG. 4A refers to the N-terminus of the corresponding protein domain.

FIG. 5A shows a direct fusions of C-terminal regions of (i) Dnmt3a, (ii) Dnmt3L, and (iii) Dnmt3a-3L (hybrid) to N-terminus of dCas9; (iv) Dnmt3a, (v) Dnmt3L, and (vi) Dnmt3a-3L hybrid to C-terminus of dCas9. FIG. 5B shows PUF effector fusion of C-terminal regions of (i) Dnmt3a, (ii) Dnmt3L, and (iii) Dnmt3a-3L to N-terminus of PUF domain; (iv) Dnmt3a, (v) Dnmt3L and (vi) Dnmt3a-3L to C-terminus of PUF domain. FIG. 5C shows Casilio can potentially recruit different Dnmt effectors fused to different PUF domains via a guide containing the corresponding PBS.

FIG. 6A shows relative SOX2 expression level in cells transfected with different dCas9-Dnmt enzymes and control guides or guides targeting SOX2 promoter. FIG. 6B shows relative SOX2 expression level in cells transfected with different dCas9-Dnmt enzymes and control guides or guides targeting SOX2 promoter.

DETAILED DESCRIPTION

Demethylation and Methylation Complexes

Figure 1A:
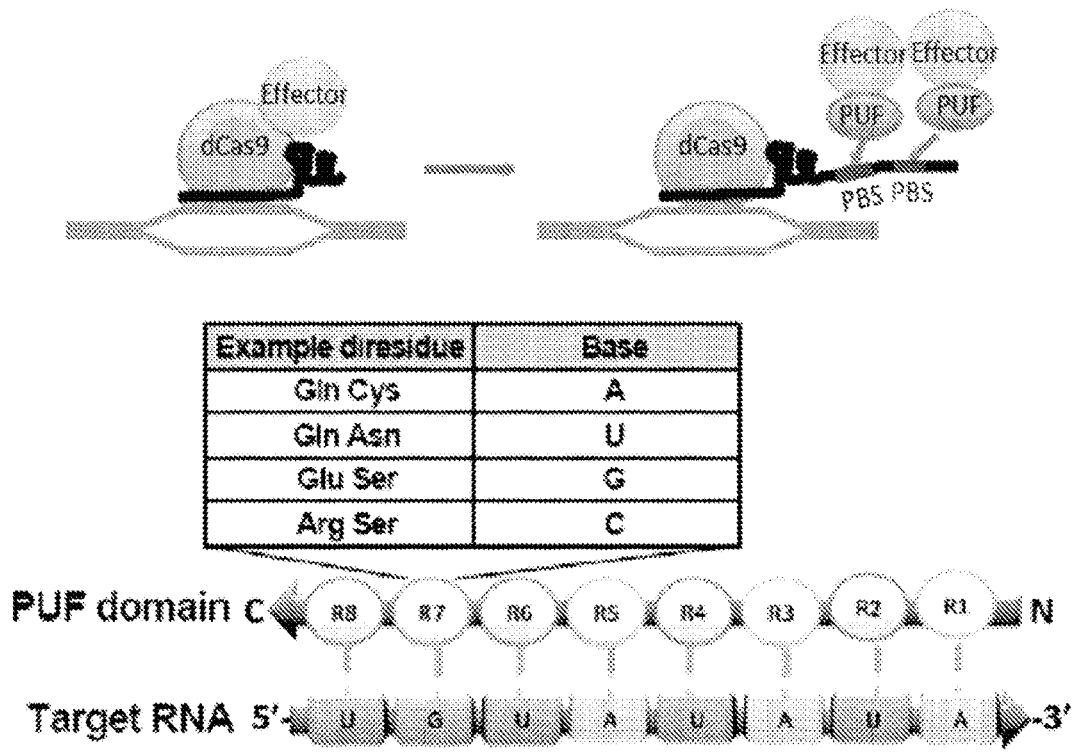
FIGS. 1A-1D. The figures show that insertion of PUF binding site (PBS) sequences to sgRNA 3'-end did not substantially impact dCas9/sgRNA function, and that independent recruitment and multimerization of activators can be achieved using the subject 3-component CRISPR/Cas complex/system.

The compositions and methods provided herein including embodiments thereof provide a methylation-editing (ME) platform allowing for targeted delivery of methylation and demethylation activity by delivering for example, DNMT or TET or functional fragments thereof (e.g., DNMT catalytic domain, TET catalytic domain), to specific genomic loci, such as CpG islands, and thereby inducing DNA demethylation or methylation, respectively. The methylation and demethylation domains provided herein are delivered to a specific site in the genome of a mammalian cell by using a complex (ME platform) which includes a polynucleotide (e.g., guide RNA) bound to a nuclease-deficient DNA endonuclease (e.g., dCas9) and a protein conjugate which includes a PUF domain conjugated to the methylation domain (e.g., DNMT catalytic domain) or demethylation domain (e.g., TET catalytic domain).

The methylation and demethylation complexes provided herein including embodiments thereof are based on a three-component hybrid system that includes CRISPR/Cas9 and Pumilio proteins. For purpose of this invention, the three-component hybrid system that includes CRISPR/Cas9 and Pumilio proteins may also be referred to interchangeably as the Casilio system, and the methylation-editing (ME) platform based on the Casilio system is sometimes referred to as Casilio-ME. In essence, the methylation or demethylation domain (e.g., DNA methyltransferase or demethylase) is fused to Pumilio proteins or functional fragments thereof (PUF domains) that bind PBS in the Casilio system, thus bringing such domains to the vicinity of any target locus of interest that is specifically recognized by the Casilio system. Any aspects or embodiments of the three-component CRISPR/Cas complex system disclosed in international application PCT/US2016/021491 and published as WO2016148994 A8, which is hereby incorporated by reference and for all purposes, may be used for the invention provided herein.

The compositions and methods provided herein including embodiments thereof are advantageous over the past attempts to modulate methylation status of a target gene by introducing a DNA methyltransferase or a DNA demethylase into a target cell, in that the present invention permits the methylation status at specific locations or genes in the genome of the target cell (such as the hMLH1 gene) to be modulated, while previous attempts affect the global methylation pattern of the target cell genome non-specifically.

Applicants were the first to show that the efficiency of methylation or demethylation of the complexes provided herein is surprisingly dependent on the orientation in which the methylation or demethylation catalytic domain is linked to the PUF domain. Applicants found that complexes where the demethylation catalytic domain (e.g., TET1 domain) is linked to the C-terminus of the PUF domain are significantly more effective relative to complexes including the demethylation domain (e.g., TET1 domain) linked to the N-terminus of the PUF domain. Surprisingly, the opposite is observed with methylation complexes. In particular, Applicants show that complexes where the methylation catalytic domain (e.g., DNMT domain) is linked to the N-terminus of the PUF domain are significantly more effective relative to complexes including the methylation domain (e.g., DNMT domain) linked to the C-terminus of the PUF domain.

A demethylation domain as referred to herein is a protein domain capable of demethylating a target nucleic acid. Likewise, a methylation domain as provided herein is a protein domain capable of methylating a target nucleic acid. In certain embodiments, the demethylation domain includes the catalytic domain of a demethylation enzyme (e.g., the catalytic domain of TET1). In certain embodiments, the demethylation domain is the catalytic domain of a demethylation enzyme. Therefore, the demethylation domain is referred to herein as demethylation catalytic domain.

In certain embodiments, the methylation domain includes the catalytic domain of a methylation enzyme (e.g., the catalytic domain of DNMT). In certain embodiments, the methylation domain is the catalytic domain of a methylation enzyme. Therefore, the methylation domain is referred to herein as methylation catalytic domain.

Thus, in one aspect, a demethylation complex is provided. The demethylation complex includes:
(a) a ribonucleoprotein complex including:
  (i) a nuclease-deficient RNA-guided DNA endonuclease enzyme; and
  (ii) a polynucleotide including:
    (1) a DNA-targeting sequence that is complementary to a target polynucleotide sequence;
    (2) a binding sequence for the nuclease-deficient RNA-guided DNA endonuclease enzyme; and
    (3) one or more PUF binding site (PBS) sequences,
  wherein the nuclease-deficient RNA-guided DNA endonuclease enzyme is bound to the polynucleotide via the binding sequence; and
(b) a demethylation protein conjugate including:
  (i) a PUF domain; and
  (ii) a demethylation domain, the demethylation domain operably linked to the C-terminus of the PUF domain to form a protein conjugate,
  wherein the demethylation protein conjugate binds to the ribonucleoprotein complex via the PUF domain binding to the one or more PBS sequences to form a demethylation complex.

In another aspect, a methylation complex is provided. The methylation complex includes:
(a) a ribonucleoprotein complex including:
  (i) a nuclease-deficient RNA-guided DNA endonuclease enzyme; and
  (ii) a polynucleotide including:
    (1) a DNA-targeting sequence that is complementary to a target polynucleotide sequence;
    (2) a binding sequence for the nuclease-deficient RNA-guided DNA endonuclease enzyme; and
    (3) one or more PUF binding site (PBS) sequences,
  wherein the nuclease-deficient RNA-guided DNA endonuclease enzyme is bound to the polynucleotide via the binding sequence; and (b) a methylation protein conjugate including:
  (i) a PUF domain; and
  (ii) a methylation domain, the methylation domain operably linked to the N-terminus of the PUF domain to form a protein conjugate,
  wherein the methylation protein conjugate binds to the ribonucleoprotein complex via the PUF domain binding to the one or more PBS sequences to form a methylation complex.

In certain embodiments, the methylation domain includes a DNA methyltransferase (DNMT) domain. In certain embodiments, the DNA methyltransferase domain is a Dnmt3a domain or a Dnmt3a-3L domain.

Ribonucleoprotein Complex

A "ribonucleoprotein complex" as provided herein refers to a complex including a nucleoprotein and a ribonucleic acid. A "nucleoprotein" as provided herein refers to a protein capable of binding a nucleic acid (e.g., RNA, DNA). Where the nucleoprotein binds a ribonucleic acid it is referred to as "ribonucleoprotein." The interaction between the ribonucleoprotein and the ribonucleic acid may be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In certain embodiments, the ribonucleoprotein includes an RNA-binding motif non-covalently bound to the ribonucleic acid. For example, positively charged aromatic amino acid residues (e.g., lysine residues) in the RNA-binding motif may form electrostatic interactions with the negative nucleic acid phosphate backbones of the RNA, thereby forming a ribonucleoprotein complex. Non-limiting examples of ribonucleoproteins include ribosomes, telomerase, RNAseP, hnRNP, CRISPR associated protein 9 (Cas9) and small nuclear RNPs (snRNPs). The ribonucleoprotein may be an enzyme. In certain embodiments, the ribonucleoprotein is an endonuclease. In certain embodiments, the ribonucleoprotein is a nuclease-deficient RNA-guided DNA endonuclease enzyme. Thus, in certain embodiments, the ribonucleoprotein complex includes an nuclease-deficient RNA-guided DNA endonuclease enzyme and a ribonucleic acid. In certain embodiments, the nuclease-deficient RNA-guided DNA endonuclease enzyme includes a nuclear localization signal (NLS). The nuclear localization signal (NLS) provided herein provides for nuclear transport of the protein domain or protein, for example the nuclease-deficient RNA-guided DNA endonuclease enzyme, the NLS is linked to.

In certain embodiments, the nuclease-deficient RNA-guided DNA endonuclease enzyme is nuclease-deficient CRISPR associated protein 9 (dCas9). In certain embodiments, the nuclease-deficient RNA-guided DNA endonuclease enzyme is nuclease-deficient Clustered Regularly Interspaced Short Palindromic Repeats from *Prevotella* and *Francisella* 1 (Cpf1).

Polynucleotide

The polynucleotide provided herein includes (1) a DNA-targeting sequence that is complementary to a target polynucleotide sequence, (2) a binding sequence for the nuclease-deficient RNA-guided DNA endonuclease enzyme (e.g., dCas9), and (3) one or more PUF binding site (PBS) sequences. In certain embodiments, the complex includes dCas9 bound to the polynucleotide thereby forming a ribonucleoprotein complex. In certain embodiments, the polynucleotide is a ribonucleic acid. In certain embodiments, the polynucleotide is a guide RNA. A "guide RNA" or "gRNA" as provided herein refers to a ribonucleotide sequence capable of binding a nucleoprotein, thereby forming ribonucleoprotein complex.

In certain embodiments, the polynucleotide (e.g., gRNA) is a single-stranded ribonucleic acid. In certain embodiments, the polynucleotide (e.g., gRNA) is 10, 20, 30, 40, 50, 60, 70, 80, 90, 100 or more nucleic acid residues in length. In certain embodiments, the polynucleotide (e.g., gRNA) is from 10 to 30 nucleic acid residues in length. In certain embodiments, the polynucleotide (e.g., gRNA) is 20 nucleic acid residues in length. In certain embodiments, the length of the polynucleotide (e.g., gRNA) can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In certain embodiments, the polynucleotide (e.g., gRNA) is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In certain embodiments, the polynucleotide (e.g., gRNA) is from 10 to 15, 10 to 20, 10 to 30, 10 to 40, or 10 to 50 residues in length.

In certain embodiments, transcription of the polynucleotide is under the control of a constitutive promoter, such as a CMV promoter or a Ubc promoter, or an inducible promoter, such as a tetracycline-responsive promoter or a steroid-responsive promoter. In certain embodiments, the polynucleotide is a vector.

In certain embodiments, the vector encoding the polynucleotide (for use in the methods of the invention) is active in a cell from a mammal (a human; a non-human primate; a non-human mammal; a rodent such as a mouse, a rat, a hamster, a guinea pig; a livestock mammal such as a pig, a sheep, a goat, a horse, a camel, cattle; or a pet mammal such as a cat or a dog); a bird, a fish, an insect, a worm, a yeast, or a bacterium.

In certain embodiments, the vector is a plasmid, a viral vector (such as adenoviral, retroviral, or lentiviral vector, or AAV vector), or a transposon (such as piggyBac transposon). The vector can be transiently transfected into a host cell, or be integrated into a host genome by infection or transposition.

DNA-Targeting Sequence

The polynucleotide includes a nucleotide sequence complementary to a target site (e.g., target polynucleotide sequence), which is referred to herein as "DNA-targeting sequence." The DNA-targeting sequence may mediate binding of the ribonucleoprotein complex to a complementary target polynucleotide sequence thereby providing the sequence specificity of the ribonucleoprotein complex. Thus, in certain embodiments, the polynucleotide (e.g., gRNA) or parts thereof are complementary to a target polynucleotide sequence. In certain embodiments, the polynucleotide (e.g., gRNA) binds a target polynucleotide sequence. In certain embodiments, the complement of the polynucleotide has a sequence identity of 50%, 55%, 60%, 65%, 70%, 75%, 80%, 85%, 90%, 95%, 96%, 97%, 98% or 99% to the target polynucleotide sequence. In certain embodiments, the complement of the DNA-targeting sequence has a sequence identity of 50%, 55%, 60%, 65%, 70%, 75%, 80%, 85%, 90%, 95%, 96%, 97%, 98% or 99% to the target polynucleotide sequence.

It should be noted that the DNA-targeting sequence may or may not be 100% complementary to the target polynucleotide sequence. In certain embodiments, the DNA-targeting sequence is complementary to the target polynucleotide sequence over 8-25 nucleotides (nts), 12-22 nucleotides, 14-20 nts, 16-20 nts, 18-20 nts, or 8, 9, 10, 11, 12, 13, 14, 15, 16, 17, 18, 19, 20, 21, 22, 23, 24, or 25 nts. In certain embodiments, the complementary region comprises a continuous stretch of 12-22 nts, preferably at the 3' end of the DNA-targeting sequence. In certain embodiments, the 5' end of the DNA-targeting sequence has up to 8 nucleotide mismatches with the target polynucleotide sequence. In certain embodiments, the DNA-binding sequence is 50, 55, 60, 65, 70, 75, 80, 85, 90, 95, or 100% complementary to the target polynucleotide sequence.

In a related embodiment, there is no more than 15-nucleotide match at the 3' end of the DNA-targeting sequence compared to the complementary target polynucleotide sequence, and the nuclease-deficient RNA-guided DNA endonuclease in the complex is a nuclease-deficient wild-type Cas9 protein (nuclease-deficient wt Cas9 protein) which, under the circumstance, binds but does not cut a target DNA (e.g., dCas9 protein). In certain embodiments, the nuclease-deficient RNA-guided DNA endonuclease is a nuclease-deficient Clustered Regularly Interspaced Short Palindromic Repeats from *Prevotella* and *Francisella* 1 (Cpf1).

The DNA-targeting sequence is functionally similar or equivalent to the crRNA or guide RNA or gRNA of the CRISPR/Cas complex/system. However, in the context of the instant invention, the DNA-targeting sequence may not originate from any particular crRNA or gRNA, but can be arbitrarily designed based on the sequence of the target polynucleotide sequence.

The DNA-targeting sequence includes a nucleotide sequence that is complementary to a specific sequence within a target DNA (or the complementary strand of the target DNA). In other words, the DNA-targeting sequence interacts with a target polynucleotide sequence of the target DNA in a sequence-specific manner via hybridization (i.e., base pairing). As such, the nucleotide sequence of the DNA-targeting sequence may vary, and it determines the location within the target DNA that the subject polynucleotide and the target DNA will interact. The DNA-targeting sequence can be modified or designed (e.g., by genetic engineering) to hybridize to any desired sequence within the target DNA. In certain embodiments, the target polynucleotide sequence is immediately 3' to a PAM (protospacer adjacent motif) sequence of the complementary strand, which can be 5'-CCN-3', wherein N is any DNA nucleotide. That is, in this embodiment, the complementary strand of the target polynucleotide sequence is immediately 5' to a PAM sequence that is 5'-NGG-3', wherein N is any DNA nucleotide. In related embodiments, the PAM sequence of the complementary strand matches the nuclease-deficient wt Cas9 protein or dCas9.

The DNA-targeting sequence can have a length of from 12 nucleotides to 100 nucleotides. For example, the DNA-targeting sequence can have a length of from 12 nucleotides (nt) to 80 nt, from 12 nt to 50 nt, from 12 nt to 40 nt, from 12 nt to 30 nt, from 12 nt to 25 nt, from 12 nt to 20 nt, or from 12 nt to 19 nt. For example, the DNA-targeting sequence can have a length of from 19 nt to 20 nt, from 19 nt to 25 nt, from 19 nt to 30 nt, from 19 nt to 35 nt, from 19 nt to 40 nt, from 19 nt to 45 nt, from 19 nt to 50 nt, from 19 nt to 60 nt, from 19 nt to 70 nt, from 19 nt to 80 nt, from 19 nt to 90 nt, from 19 nt to 100 nt, from 20 nt to 25 nt, from 20 nt to 30 nt, from 20 nt to 35 nt, from 20 nt to 40 nt, from 20 nt to 45 nt, from 20 nt to 50 nt, from 20 nt to 60 nt, from 20 nt to 70 nt, from 20 nt to 80 nt, from 20 nt to 90 nt, or from 20 nt to 100 nt.

The nucleotide sequence of the DNA-targeting sequence that is complementary to a target polynucleotide sequence of the target DNA can have a length of at least 12 nt. For example, the DNA-targeting sequence that is complementary to a target polynucleotide sequence of the target DNA can have a length at least 12 nt, at least 15 nt, at least 18 nt, at least 19 nt, at least 20 nt, at least 25 nt, at least 30 nt, at least 35 nt or at least 40 nt. For example, the DNA-targeting sequence that is complementary to a target polynucleotide sequence of a target DNA can have a length of from 12 nucleotides (nt) to 80 nt, from 12 nt to 50 nt, from 12 nt to 45 nt, from 12 nt to 40 nt, from 12 nt to 35 nt, from 12 nt to 30 nt, from 12 nt to 25 nt, from 12 nt to 20 nt, from 12 nt to 19 nt, from 19 nt to 20 nt, from 19 nt to 25 nt, from 19 nt to 30 nt, from 19 nt to 35 nt, from 19 nt to 40 nt, from 19 nt to 45 nt, from 19 nt to 50 nt, from 19 nt to 60 nt, from 20 nt to 25 nt, from 20 nt to 30 nt, from 20 nt to 35 nt, from 20 nt to 40 nt, from 20 nt to 45 nt, from 20 nt to 50 nt, or from 20 nt to 60 nt. The nucleotide sequence of the DNA-targeting sequence that is complementary to the target polynucleotide sequence of the target DNA can have a length of at least 12 nt.

In some cases, the DNA-targeting sequence that is complementary to a target polynucleotide sequence of the target DNA is 20 nucleotides in length. In some cases, the DNA-targeting sequence that is complementary to a target polynucleotide sequence of the target DNA is 19 nucleotides in length.

The percent complementarity between the DNA-targeting sequence and the target polynucleotide sequence of the target DNA can be at 50% (e.g., at least 55%, at least 60%, at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the target polynucleotide sequence is 100% over the seven or eight contiguous 5'-most nucleotides of the target polynucleotide sequence. In some cases, the percent complementarity between the DNA-targeting sequence and the target polynucleotide sequence is at least 60% over 20 contiguous nucleotides. In some cases, the percent complementarity between the DNA-targeting sequence and the target polynucleotide sequence is 100% over the 7, 8, 9, 10, 11, 12, 13, or 14 contiguous 5'-most nucleotides of the target polynucleotide sequence (i.e., the 7, 8, 9, 10, 11, 12, 13, or 14 contiguous 3'-most nucleotides of the DNA-targeting sequence), and as low as 0% over the remainder. In such a case, the DNA-targeting sequence can be considered to be 7, 8, 9, 10, 11, 12, 13, or 14 nucleotides in length, respectively.

Target Polynucleotide Sequence

A "target polynucleotide sequence" as provided herein is a nucleic acid sequence expressed by a cell. In certain embodiments, the target polynucleotide sequence is an exogenous nucleic acid sequence. In certain embodiments, the target polynucleotide sequence is an endogenous nucleic acid sequence. In certain embodiments, the target polynucleotide sequence forms part of a cellular gene. In certain embodiments, the target polynucleotide sequence is part of a gene. In certain embodiments, the target polynucleotide sequence is part of a Sox gene. In certain embodiments, the target polynucleotide sequence is part of a transcriptional regulatory sequence. In certain embodiments, the target polynucleotide sequence is part of a promoter, enhancer or silencer. In certain embodiments, the target polynucleotide sequence is a hypermethylated nucleic acid sequence. In certain embodiments, the target polynucleotide sequence is a hypermethylated CpG sequence. In certain embodiments, the target polynucleotide sequence is part of an hMLH1 promoter.

In certain embodiments, the target sequence is an RNA. In certain embodiments, the target sequence is a DNA. In the description herein, the first segment is generally referred to as the "DNA-targeting sequence" when the target sequence is a DNA (such as a genomic DNA). In related embodiments in which the target sequence is an RNA, the description herein below applies generally as well except that the reference to "DNA-targeting sequence" is replaced with "RNA-targeting sequence," in order to avoid redundancy. That is, the polynucleotide includes a nucleotide sequence complementary to the target polynucleotide sequence (DNA or RNA).

In certain embodiments, the three segments (1)-(3) are arranged, in that order, from 5' to 3'.

In certain embodiments, the polynucleotide of the invention can be a single RNA molecule (single RNA polynucleotide), which may include a "single-guide RNA," or "sgRNA." In another embodiment, the polynucleotide of the invention includes two RNA molecules (e.g., joined together via hybridization at the binding sequence (e.g., nuclease-deficient wt Cas9 protein- or dCas9-binding sequence)). Thus the subject polynucleotide is inclusive, referring both to two-molecule polynucleotides and to single-molecule polynucleotides (e.g., sgRNAs).

In certain embodiments, the target polynucleotide sequence is at, near, or within a promoter sequence. In certain embodiments, the target polynucleotide sequence is within a CpG island. In certain embodiments, the target polynucleotide sequence is known to be associated with a disease or condition characterized by DNA hypo- or hyper-methylation. In certain embodiments, the target polynucleotide sequence is within a tumor suppressor gene or an oncogene, such as within a transcriptional regulatory sequence/element of the tumor suppressor gene or oncogene.

In certain embodiments, the target polynucleotide sequence is immediately 3' to a PAM (protospacer adjacent motif) sequence of the target polynucleotide sequence. For example, in certain embodiments, the PAM sequence of the target polynucleotide sequence is 5'-CCN-3', wherein N is any DNA nucleotide. In other embodiments, the PAM sequence of the target polynucleotide sequence matches the specific nuclease-deficient wt Cas9 protein or dCas9 protein or homologs or orthologs to be used.

As is known in the art, for nuclease-deficient wt Cas9 protein or dCas9 protein to successfully bind to DNA, the target polynucleotide sequence in the genomic DNA must be complementary to the guide RNA sequence and must be immediately followed by the correct protospacer adjacent motif or PAM sequence. The PAM sequence is present in the target polynucleotide sequence but not in the guide RNA sequence. Any DNA sequence with the correct target polynucleotide sequence followed by the PAM sequence will be bound by nuclease-deficient wt Cas9 protein or dCas9 protein. In certain embodiments, the PAM sequence is any of the PAM sequences disclosed in international application PCT/US2016/021491 and published as WO2016148994 A8, which is hereby incorporated by reference and for all purposes.

In embodiments, the polynucleotide (e.g., gRNA) is 50%, 55%, 60%, 65%, 70%, 75%, 80%, 85%, 90%, 95%, 96%, 97%, 98% or 99% to the target polynucleotide sequence. In certain embodiments, the polynucleotide (e.g., gRNA) is 50%, 55%, 60%, 65%, 70%, 75%, 80%, 85%, 90%, 95%, 96%, 97%, 98% or 99% complementary to the sequence of a cellular gene. In certain embodiments, the polynucleotide (e.g., gRNA) binds a cellular gene sequence.

Binding Sequence

In certain embodiments, the complex includes dCas9 bound to the polynucleotide through binding a binding sequence of the polynucleotide and thereby forming a ribonucleoprotein complex. In certain embodiments, the binding sequence forms a hairpin structure. In certain embodiments, the binding sequence is 30-100 nt, 35-50 nt, 37-47 nt, or 42 nt in length. An exemplary binding sequence is the sequence of SEQ ID NO:6 GTTTTAGAGCTAGAAATAGCAAGT-TAAAATAAGGCTA. Another exemplary binding sequence is the sequence of SEQ ID NO:7 GTTTAAGAGC-TATGCTGGAAACAGCATAGCAAGTT-TAAATAAGGCTA.

In certain embodiments, the binding sequence includes the sequence of SEQ ID NO: 6. In certain embodiments, the binding sequence includes the sequence of SEQ ID NO: 7. In certain embodiments, the binding sequence is the sequence of SEQ ID NO: 6. In certain embodiments, the binding sequence is the sequence of SEQ ID NO: 7.

The binding sequence (protein-binding segment or protein-binding sequence) of the subject polynucleotide binds to a modified dCas9 protein (e.g., nuclease-deficient nickase or dCas9) which has reduced endonuclease activity, or lacks endonuclease activity. For simplicity, the binding sequence (protein-binding segment or protein-binding sequence), which may bind to modified Cas9 proteins (e.g., dCas9 protein) may simply be referred to as "Cas9-binding sequence" or "binding sequence" herein. However, it should be understood that when the binding sequence (Cas9-binding sequence) of the invention binds to a dCas9, it is not prevented from binding to a wt Cas9 or a Cas9 nickase. In certain embodiments, the binding sequence (Cas9-binding sequence) of the invention binds to dCas9 as well as wt Cas9 and/or Cas9 nickase.

The binding sequence (Cas9-binding sequence) interacts with or binds to a Cas9 protein (e.g., nuclease-deficient wt Cas9 protein, or dCas9 protein), and together they bind to the target polynucleotide sequence recognized by the DNA-targeting sequence. The binding sequence (Cas9-binding sequence) includes two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the binding sequence (Cas9-binding sequence), thus resulting in a stem-loop structure. Alternatively, in some embodiment, the two complementary stretches of nucleotides may not be covalently linked, but instead are held together by hybridization between complementary sequences (e.g., in the case of a two-molecule polynucleotide of the invention).

The binding sequence (Cas9-binding sequence) can have a length of from 10 nucleotides to 100 nucleotides, e.g., from 10 nucleotides (nt) to 20 nt, from 20 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. For example, the Cas9-binding sequence can have a length of from 15 nucleotides (nt) to 80 nt, from 15 nt to 50 nt, from 15 nt to 40 nt, from 15 nt to 30 nt, from 37 nt to 47 nt (e.g., 42 nt), or from 15 nt to 25 nt.

The dsRNA duplex of the binding sequence (Cas9-binding sequence) can have a length from 6 base pairs (bp) to 50 bp. For example, the dsRNA duplex of the binding sequence (Cas9-binding sequence) can have a length from 6 bp to 40 bp, from 6 bp to 30 bp, from 6 bp to 25 bp, from 6 bp to 20 bp, from 6 bp to 15 bp, from 8 bp to 40 bp, from 8 bp to 30 bp, from 8 bp to 25 bp, from 8 bp to 20 bp or from 8 bp to 15 bp. For example, the dsRNA duplex of the binding sequence (Cas9-binding sequence) can have a length from 8 bp to 10 bp, from 10 bp to 15 bp, from 15 bp to 18 bp, from 18 bp to 20 bp, from 20 bp to 25 bp, from 25 bp to 30 bp, from 30 bp to 35 bp, from 35 bp to 40 bp, or from 40 bp to 50 bp. In some embodiments, the dsRNA duplex of the binding sequence (Cas9-binding sequence) has a length of 36 base pairs. The percent complementarity between the nucleotide sequences that hybridize to form the dsRNA duplex of the binding sequence (Cas9-binding sequence) can be at least 60%. For example, the percent complementarity between the nucleotide sequences that hybridize to form the dsRNA duplex of the binding sequence (Cas9-binding sequence) can be at least 65%, at least 70%, at least 75%, at least 80%, at least 85%, at least 90%, at least 95%, at least 98%, or at least 99%. In some cases, the percent complementarity between the nucleotide sequences that hybridize to form the dsRNA duplex of the binding sequence (Cas9-binding sequence) is 100%.

In certain embodiments, the polynucleotide further includes a linker sequence linking the DNA-targeting sequence to the binding sequence (Cas9-binding sequence). The linker can have a length of from 3 nucleotides to 100 nucleotides. For example, the linker can have a length of 3 nucleotides (nt) to 90 nt, from 3 nucleotides (nt) to 80 nt, from 3 nucleotides (nt) to 70 nt, from 3 nucleotides (nt) to 60 nt, from 3 nucleotides (nt) to 50 nt, from 3 nucleotides (nt) to 40 nt, from 3 nucleotides (nt) to 30 nt, from 3 nucleotides (nt) to 20 nt or from 3 nucleotides (nt) to 10 nt. For example, the linker can have a length of from 3 nt to 5 nt, from 5 nt to 10 nt, from 10 nt to 15 nt, from 15 nt to 20 nt, from 20 nt to 25 nt, from 25 nt to 30 nt, from 30 nt to 35 nt, from 35 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some embodiments, the linker is 4 nt.

Non-limiting examples of nucleotide sequences that can be included in a suitable binding sequence (Cas9-binding sequence, i.e., Cas9 handle) are set forth in SEQ ID NOs: 563-682 of WO 2013/176772 (see, for examples, FIGS. 8 and 9 of WO 2013/176772), which is hereby incorporated by reference in its entirety and for all purposes.

In some cases, a suitable binding sequence (Cas9-binding sequence) includes a nucleotide sequence that differs by 1, 2, 3, 4, or 5 nucleotides from any one of the above-listed sequences.

PBS Sequences

The term "PBS" or "PUF binding site" as provided herein refers to a site that is bound by a Pumilio/fem-3 mRNA binding factor (PUF). A PUF binding site (PBS) may form part of a guide RNA and provide for the binding of a PUF protein or PUF domain as provided herein (e.g., PUFa, PUFb, PUFc or functional fragments thereof) to said guide RNA. The PUF binding site includes a nucleic acid sequence (i.e., a PBS sequence or PUF binding site sequence) which is characteristic of the PBS and may be bound directly by the PUF protein. The polynucleotide (e.g., gRNA) provided herein further includes one or more PUF binding site (PBS) sequences. In certain embodiments, the one or more PBS sequences contain 8 nucleotides in length. In certain embodiments, the one or more PBS sequences are identical. In certain embodiments, the polynucleotide includes 1 to 50 PBS sequences. In certain embodiments, one or more PBS sequences comprise the nucleotide sequence of SEQ ID NO:1. Any one of the PBS sequences disclosed in international application PCT/US2016/021491 and published as WO2016148994 A8, which is hereby incorporated by reference in its entirety and for all purposes, are contemplated for the compositions and methods provided herein.

In certain embodiments, each of the one or more PBS sequences has 8 nucleotides. One exemplary PBS sequence may have a sequence of SEQ ID NO:8 (5'-UGUAUGUA-3'), which can be bound by the PUF domain PUF(3-2). Another exemplary PBS may have a sequence of SEQ ID NO:9 (5'-UUGAUAUA-3'), which can be bound by the PUF domain PUF(6-2/7-2). Additional PBS sequences and the corresponding PUF domains are described in international application PCT/US2016/021491 and published as WO2016148994 A8, which is hereby incorporated by reference in its entirety and for all purposes.

The polynucleotide of the invention may have more than one copy of the PBS sequences. In certain embodiments, the polynucleotide comprises 1, 2, 3, 4, 5, 10, 15, 20, 25, 30, 35, 40, 45, 46, 47, 48, 49, or 50 copies of PBS sequences, such as 5, 6, 7, 8, 9, 10, 11, 12, 13, 14, or 15 copies of PBS sequences. In certain embodiments, the range of the PBS sequence copy number is L to H, wherein L is any one of 1, 2, 3, 4, 5, 6, 7, 8, 9, 10, 11, 12, 13, 14, 15, 20, 25, 30, 35, or 40, and wherein H is any one of 2, 3, 4, 5, 6, 7, 8, 9, 10, 11, 12, 13, 14, 15, 20, 25, 30, 35, 40, 45, 50, 55, 60, 65, 70, 80, 90, or 100, so long as H is greater than L. Each PBS sequence may be the same or different.

In certain embodiments, the polynucleotide includes 1, 2, 3, 4, 5, 10, 15, 20, 25, 30, 35, 40, 45, 46, 47, 48, 49, or 50 copies, or 1-50, 2-45, 3-40, 5-35, 5-10, 10-20 copies of identical or different PBS sequences.

In certain embodiments, the polynucleotide includes 5-15 copies of PBS sequences, or 5-14 copies, 5-13 copies, 5-12 copies, 5-11 copies, 5-10 copies, or 5-9 copies of PBS sequences.

In certain embodiments, the amount of the gRNA-PBS sequences and/or the amount of the protein conjugate (methylation or demethylation protein conjugate) transfected or expressed is adjusted to maximize PBS/PUF domain binding. For example, this can be achieved by increasing the expression of the PUF domain by a stronger promoter or using an inducible promoter, such as a Dox-inducible promoter.

In certain embodiments, the spacing between PBS sequences and/or spacer sequences are optimized to improve system efficiency. For example, spacing optimization can be subject to particular protein conjugates (methylation or demethylation protein conjugates), and can be different between protein conjugates (methylation or demethylation protein conjugate) that work as individual proteins and those protein conjugates (methylation or demethylation protein conjugate) that may need to be positioned close enough to function (e.g., protein complexes).

In certain embodiments, one or more spacer region(s) separate two adjacent PBS sequences. The spacer regions may have a length of from 3 nucleotides to 100 nucleotides.

For example, the spacer can have a length of from 3 nucleotides (nt) to 90 nt, from 3 nucleotides (nt) to 80 nt, from 3 nucleotides (nt) to 70 nt, from 3 nucleotides (nt) to 60 nt, from 3 nucleotides (nt) to 50 nt, from 3 nucleotides (nt) to 40 nt, from 3 nucleotides (nt) to 30 nt, from 3 nucleotides (nt) to 20 nt or from 3 nucleotides (nt) to 10 nt. For example, the spacer can have a length of from 3 nt to 5 nt, from 5 nt to 10 nt, from 10 nt to 15 nt, from 15 nt to 20 nt, from 20 nt to 25 nt, from 25 nt to 30 nt, from 30 nt to 35 nt, from 35 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some embodiments, the spacer is 4 nt.

In embodiments, the PBS sequence includes the sequence of SEQ ID NO:1, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:27. In certain embodiments, the PBS sequence is the sequence of SEQ ID NO:1, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:27.

Protein Conjugates

PUF Domains

PUF proteins (named after *Drosophila* Pumilio and *C. elegans* fern-3 binding factor) are known to be involved in mediating mRNA stability and translation. These proteins contain a unique RNA-binding domain known as the PUF domain. The RNA-binding PUF domain, such as that of the human Pumilio 1 protein (referred here also as PUM), contains 8 repeats (each repeat called a PUF motif or a PUF repeat) that bind consecutive bases in an anti-parallel fashion, with each repeat recognizing a single base—i.e., PUF repeats R1 to R8 recognize nucleotides N8 to N1, respectively. For example, PUM is composed of eight tandem repeats, each repeat consisting of 34 amino acids that folds into tightly packed domains composed of alpha helices.

The protein conjugates provided herein including embodiments thereof may be demethylation or methylation protein conjugates including a PUF domain operably linked to a demethylation domain or a methylation domain, respectively. Where the protein conjugate is a demethylation conjugate the demethylation domain is operably linked to the C-terminus of the PUF domain to form a protein conjugate. Where the protein conjugate is a methylation conjugate the methylation domain is operably linked to the N-terminus of the PUF domain to form a protein conjugate.

As used herein, the term "PUF domain" refers to a wildtype or naturally existing PUF domain, as well as a PUF homologue domain that is based on/derived from a natural or existing PUF domain, such as the prototype human Pumilio 1 PUF domain. The PUF domain of the invention specifically binds to an RNA sequence (e.g., an 8-mer RNA sequence), wherein the overall binding specificity between the PUF domain and the RNA sequence is defined by sequence specific binding between each PUF motif/PUF repeat within the PUF domain and the corresponding single RNA nucleotide.

Also included in the scope of the invention are functional variants of the subject PUF domains or fusions thereof. The term "functional variant" as used herein refers to a PUF domain having substantial or significant sequence identity or similarity to a parent PUF domain, which functional variant retains the biological activity of the PUF domain of which it is a variant—e.g., one that retains the ability to recognize target RNA to a similar extent, the same extent, or to a higher extent in terms of binding affinity, and/or with substantially the same or identical binding specificity, as the parent PUF domain. The functional variant PUF domain can, for instance, be at least 30%, 50%, 75%, 80%, 90%, 98% or more identical in amino acid sequence to the parent PUF domain. The functional variant can, for example, comprise the amino acid sequence of the parent PUF domain with at least one conservative amino acid substitution, for example, conservative amino acid substitutions in the scaffold of the PUF domain (i.e., amino acids that do not interact with the RNA). Alternatively or additionally, the functional variants can comprise the amino acid sequence of the parent PUF domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent PUF domain, or may alter the stability of the PUF domain to a desired level (e.g., due to substitution of amino acids in the scaffold). The PUF domain can consist essentially of the specified amino acid sequence or sequences described herein, such that other components, e.g., other amino acids, do not materially change the biological activity of the functional variant. In certain embodiments, the PUF domain is a Pumilio homology domain (PU-HUD). In a particular embodiment, the PU-HUD is a human Pumilio 1 domain. In certain embodiments, the PUF domain has the sequence of any one of the PUF domains disclosed in international application PCT/US2016/021491, published as WO2016148994 A8, in international application PCT/US2011/040933, published as WO 2011/160052A2, and Spassov & Jurecic ("Cloning and comparative sequence analysis of PUM1 and PUM2 genes, human members of the Pumilio family of RNA-binding proteins," *Gene*, 299:195-204, October 2002), which are hereby incorporated by reference in their entirety and for all purposes.

In embodiments, the PUF domain includes a PUFa domain, a PUFb domain, a PUFc domain, or a PUFw domain. In certain embodiments, the PUFa domain has the amino acid sequence of SEQ ID NO:2. In certain embodiments, the PUFb domain has the amino acid sequence of SEQ ID NO:3. In certain embodiments, the PUFc domain has the amino acid sequence of SEQ ID NO:4. In certain embodiments, the PUFw domain has the amino acid sequence of SEQ ID NO:5.

The subject polynucleotide includes one or more tandem sequences, each of which can be specifically recognized and bound by a specific PUF domain (infra). Since a PUF domain can be engineered to bind virtually any PBS sequence based on the nucleotide-specific interaction between the individual PUF motifs of PUF domain and the single RNA nucleotide they recognize, the PBS sequences can be any designed sequence that bind their corresponding PUF domain.

In certain embodiments, a PBS of the invention has 8-mer. In other embodiments, a PBS of the invention has 5, 6, 7, 8, 9, 10, 11, 12, 13, 14, 15, 16 or more RNA nucleotides. In certain embodiments, the PBS of the invention has the sequence of SEQ ID NO:10 (5'-UGUAUAUA-3'), and binds the wt human Pumilio 1 PUF domain.

In certain embodiments, the PBS sequence of the invention has the sequence of SEQ ID NO:8 (5'-UGUAUGUA-3'), and binds the PUF domain PUF(3-2).

In certain embodiments, the PBS sequence of the invention has the sequence of SEQ ID NO:9 (5'-UUGAUAUA-3'), and binds the PUF domain PUF(6-2/7-2).

In certain embodiments, the PBS sequence of the invention has the sequence of SEQ ID NO:11 (5'-UGGAUAUA-3'), and binds the PUF domain PUF(6-2).

In certain embodiments, the PBS sequence of the invention has the sequence of SEQ ID NO:12 (5'-UUUAUAUA-3'), and binds the PUF domain PUF(7-2).

In certain embodiments, the PBS sequence of the invention has the sequence of SEQ ID NO:13 (5'-UGUGUGUG-3'), and binds the PUF domain PUF$^{531}$.

In certain embodiments, the PBS sequence of the invention has the sequence of SEQ ID NO:14 (5'-UGUAUAUG-3'), and binds the PUF domain PUF(1-1).

In certain embodiments, the PBS sequence of the invention has the sequence of SEQ ID NO:12 (5'-UUUAUAUA-3') or sequence of SEQ ID NO:15 (5'-UAUAUAUA-3'), and binds the PUF domain PUF(7-1).

In certain embodiments, the PBS sequence of the invention has the sequence of SEQ ID NO:16 (5'-UGUAUUUA-3'), and binds the PUF domain PUF(3-1).

In certain embodiments, the PBS sequence of the invention has the sequence of SEQ ID NO:17 (5'-UUUAUUUA-3'), and binds the PUF domain PUF(7-2/3-1).

In embodiments, the PUF domain PUF(3-2) has the sequence of SEQ ID NO:18. In certain embodiments, the PUF domain PUF(6-2/7-2) has the sequence of SEQ ID NO:19. In certain embodiments, the PUF domain PUF$^{531}$ has the sequence of SEQ ID NO:22. In certain embodiments, the PUF domain includes the sequence of SEQ ID NO:18, SEQ ID NO:19, SEQ ID NO:22, SEQ ID NO:28, SEQ ID NO:29, SEQ ID NO:30 or SEQ ID NO:31. In certain embodiments, the PUF domain is the sequence of SEQ ID NO:18, SEQ ID NO:19, SEQ ID NO:22, SEQ ID NO:28, SEQ ID NO:29, SEQ ID NO:30 or SEQ ID NO:31.

Applicant has created 65,536 8-mer PBS sequence and their corresponding PUF domain sequences (see below) that can bind the specific PBS sequence. Applicant has also created a python script to retrieve any of the 65,536 individual PUF domain sequences that binds a given 8-mer PBS sequence. For example, for the 8-mer UUGAUGUA (SEQ ID NO:27), one possible PUF domain sequence can be SEQ ID NO:28:

GRSRLLEDFRNNRYPNLQLREIAGHIMEFSQDQHGCRFIQLKLERATPAE

RQLVFNEILQAAYQLMVDVFGNYVIQKFFEFGSLEQK

PUF (6-2/7-2)
SEQ ID NO: 19

Gly Arg Ser Arg Leu Leu Glu Asp

Phe Arg Asn Asn Arg Tyr Pro Asn

Leu Gln Leu Arg Glu Ile Ala Gly

His Ile Met Glu Phe Ser Gln Asp

Gln His Gly Ser Arg Phe Ile Gln

Leu Lys Leu Glu Arg Ala Thr Pro

Ala Glu Arg Gln Leu Val Phe Asn

Glu Ile Leu Gln Ala Ala Tyr Gln

Leu Met Val Asp Val Phe Gly Asn

Tyr Val Ile Gln Lys Phe Phe Glu

Phe Gly Ser Leu Glu Gln Lys Leu

Ala Leu Ala Glu Arg Ile Arg Gly

His Val Leu Ser Leu Ala Leu Gln

Met Tyr Gly Cys Arg Val Ile Gln

Lys Ala Leu Glu Phe Ile Pro Ser

Asp Gln Gln Asn Glu Met Val Arg

Glu Leu Asp Gly His Val Leu Lys

Cys Val Lys Asp Gln Asn Gly Asn

His Val Val Gln Lys Cys Ile Glu

Cys Val Gln Pro Gln Ser Leu Gln

Phe Ile Ile Asp Ala Phe Lys Gly

Gln Val Phe Ala Leu Ser Thr His

Pro Tyr Gly Cys Arg Val Ile Gln

Arg Ile Leu Glu His Cys Leu Pro

Asp Gln Thr Leu Pro Ile Leu Glu

Glu Leu His Gln His Thr Glu Gln

Leu Val Gln Asp Gln Tyr Gly Ser

Tyr Val Ile Glu His Val Leu Glu

His Gly Arg Pro Glu Asp Lys Ser

Lys Ile Val Ala Glu Ile Arg Gly

Asn Val Leu Val Leu Ser Gln His

Lys Phe Ala Asn Asn Val Val Gln

Lys Cys Val Thr His Ala Ser Arg

Thr Glu Arg Ala Val Leu Ile Asp

Glu Val Cys Thr Met Asn Asp Gly

Pro His Ser Ala Leu Tyr Thr Met

Met Lys Asp Gln Tyr Ala Asn Tyr

Val Val Gln Lys Met Ile Asp Val

Ala Glu Pro Gly Gln Arg Lys Ile

Val Met His Lys Ile Arg Pro His

Ile Ala Thr Leu Arg Lys Tyr Thr

Tyr Gly Lys His Ile Leu Ala Lys

Leu Glu Lys Tyr Tyr Met Lys Asn

Gly Val Asp Leu Gly

PUF (6-2/7-2) (SEQ ID NO:19) has double point mutations (N1043S/Q1047E and S1079N/E1083Q) in repeats 6 and 7, respectively, and recognizes a cognate RNA sequence with two mutations at positions 2 and 3 of the NRE (GU/UG; SEQ ID NO:9 (5'-UUGAUAUA-3')).

A related PUF (6-2) has point mutations (N1043S/Q1047E) in repeats 6, and recognizes a cognate RNA sequence with a mutation at position 3 of the NRE (SEQ ID NO:11 (5'-UGGAUAUA-3')).

Another related PUF (7-2) has point mutations (S1079N/E1083Q) in repeats 7, and recognizes a cognate RNA sequence with a mutation at position 2 of the NRE (SEQ ID NO:12 (5'-UUUAUAUA-3')).

PUF531
SEQ ID NO: 22

Gly Arg Ser Arg Leu Leu Glu Asp

Phe Arg Asn Asn Arg Tyr Pro Asn

Leu Gln Leu Arg Glu Ile Ala Gly

His Ile Met Glu Phe Ser Gln Asp

Gln His Gly Ser Arg Phe Ile Glu

Leu Lys Leu Glu Arg Ala Thr Pro

Ala Glu Arg Gln Leu Val Phe Asn

Glu Ile Leu Gln Ala Ala Tyr Gln

Leu Met Val Asp Val Phe Gly Asn

Tyr Val Ile Gln Lys Phe Phe Glu

Phe Gly Ser Leu Glu Gln Lys Leu

Ala Leu Ala Glu Arg Ile Arg Gly

His Val Leu Ser Leu Ala Leu Gln Met

Tyr Gly Ser Arg Val Ile Glu

Lys Ala Leu Glu Phe Ile Pro Ser Asp

Gln Gln Asn Glu Met Val Arg

Glu Leu Asp Gly His Val Leu Lys Cys

Val Lys Asp Gln Asn Gly Asn

His Val Val Gln Lys Cys Ile Glu Cys

Val Gln Pro Gln Ser Leu Gln

Phe Ile Ile Asp Ala Phe Lys Gly Gln

Val Phe Ala Leu Ser Thr His

Pro Tyr Gly Ser Arg Val Ile Glu Arg

Ile Leu Glu His Cys Leu Pro

Asp Gln Thr Leu Pro Ile Leu Glu Glu

Leu His Gln His Thr Glu Gln

```
Leu Val Gln Asp Gln Tyr Gly Asn Tyr

Val Ile Gln His Val Leu Glu

His Gly Arg Pro Glu Asp Lys Ser Lys

Ile Val Ala Glu Ile Arg Gly

Asn Val Leu Val Leu Ser Gln His Lys

Phe Ala Ser Asn Val Val Glu

Lys Cys Val Thr His Ala Ser Arg Thr

Glu Arg Ala Val Leu Ile Asp

Glu Val Cys Thr Met Asn Asp Gly Pro

His Ser Ala Leu Tyr Thr Met

Met Lys Asp Gln Tyr Ala Asn Tyr Val

Val Gln Lys Met Ile Asp Val

Ala Glu Pro Gly Gln Arg Lys Ile Val

Met His Lys Ile Arg Pro His

Ile Ala Thr Leu Arg Lys Tyr Thr Tyr

Gly Lys His Ile Leu Ala Lys

Leu Glu Lys Tyr Tyr Met Lys Asn Gly

Val Asp Leu Gly
```

The PUF domain PUF$^{531}$ (SEQ ID NO:22) has mutations (Q867E/Q939E/C935S/Q1011E/C1007S) in wild type PUF repeats 1, 3 and 5, and recognizes the sequence of SEQ ID NO:13 (5'-UGUGUGUG-3'). The PUF$^{531}$ can recognize its new target sequence with very high affinity, compared to the wild type PUF RNA.

Another modified PUF domain PUF(1-1) has one point mutation (Q867E) in the PUF repeat 1, and recognizes a cognate RNA with a mutation at position 8 of the NRE (A8G; SEQ ID NO:14 (5'-UGUAUAUG-3')).

Yet another modified PUF domain PUF(7-1) has one point mutation (E1083Q) in the PUF repeat 7, and recognizes a cognate RNA with a mutation at position 2 of the NRE (G2U; SEQ ID NO:12 (5'-UUUAUAUA-3'); or G2A; SEQ ID NO:15 (5'-UAUAUAUA-3')).

Still another modified PUF domain PUF(3-1) has one point mutation (C935N) in the PUF repeat 3, and recognizes a cognate RNA with a mutation at position 6 of the NRE (A6U; SEQ ID NO:16 (5'-UGUAUUUA-3')).

A further modified PUF (7-2/3-1) has point mutations (C935N/S1079N/E1083Q) in repeats 7 and 3, and recognizes a cognate RNA sequence with mutations at positions 2 and 6 of the NRE (SEQ ID NO:17 (5'-UUUAUUUA-3')).

In embodiments, the PUF domain has a sequence of SEQ ID NO:29.

```
Gly Arg Ser Arg Leu Leu Glu Asp

Phe Arg Asn Asn Arg Tyr Pro Asn

Leu Gln Leu Arg Glu Ile Ala Gly

His Ile Met Glu Phe Ser Gln Asp

Gln His Gly Ser Arg Phe Ile Glu

Leu Lys Leu Glu Arg Ala Thr Pro

Ala Glu Arg Gln Leu Val Phe Asn

Glu Ile Leu Gln Ala Ala Tyr Gln

Leu Met Val Asp Val Phe Gly Cys

Arg Val Ile Gln Lys Phe Phe Glu

Phe Gly Ser Leu Glu Gln Lys Leu

Ala Leu Ala Glu Arg Ile Arg Gly

His Val Leu Ser Leu Ala Leu Gln

Met Tyr Gly Cys Arg Val Ile Gln

Lys Ala Leu Glu Phe Ile Pro Ser

Asp Gln Gln Asn Glu Met Val Arg

Glu Leu Asp Gly His Val Leu Lys

Cys Val Lys Asp Gln Asn Gly Asn

His Val Val Gln Lys Cys Ile Glu

Cys Val Gln Pro Gln Ser Leu Gln

Phe Ile Ile Asp Ala Phe Lys Gly

Gln Val Phe Ala Leu Ser Thr His

Pro Tyr Gly Cys Arg Val Ile Gln

Arg Ile Leu Glu His Cys Leu Pro

Asp Gln Thr Leu Pro Ile Leu Glu

Glu Leu His Gln His Thr Glu Gln

Leu Val Gln Asp Gln Tyr Gly Ser

Tyr Val Ile Glu His Val Leu Glu

His Gly Arg Pro Glu Asp Lys Ser

Lys Ile Val Ala Glu Ile Arg Gly

Asn Val Leu Val Leu Ser Gln His

Lys Phe Ala Asn Asn Val Val Gln

Lys Cys Val Thr His Ala Ser Arg

Thr Glu Arg Ala Val Leu Ile Asp

Glu Val Cys Thr Met Asn Asp Gly

Pro His Ser Ala Leu Tyr Thr Met

Met Lys Asp Gln Tyr Ala Ser Tyr

Val Val Glu Lys Met Ile Asp Val

Ala Glu Pro Gly Gln Arg Lys Ile

Val Met His Lys Ile Arg Pro His

Ile Ala Thr Leu Arg Lys Tyr Thr

Tyr Gly Lys His Ile Leu Ala Lys

Leu Glu Lys Tyr Tyr
```

SEQ ID NO: 30
```
Gly Arg Ser Arg Leu Leu Glu Asp

Phe Arg Asn Asn Arg Tyr Pro Asn
```

-continued

Leu Gln Leu Arg Glu Ile Ala Gly
His Ile Met Glu Phe Ser Gln Asp
Gln His Gly Asn Arg Phe Ile Gln
Leu Lys Leu Glu Arg Ala Thr Pro
Ala Glu Arg Gln Leu Val Phe Asn
Glu Ile Leu Gln Ala Ala Tyr Gln
Leu Met Val Asp Val Phe Gly Ser
Tyr Val Ile Glu Lys Phe Phe Glu
Phe Gly Ser Leu Glu Gln Lys Leu
Ala Leu Ala Glu Arg Ile Arg Gly
His Val Leu Ser Leu Ala Leu Gln
Met Tyr Gly Ser Arg Val Ile Glu
Lys Ala Leu Glu Phe Ile Pro Ser
Asp Gln Gln Asn Glu Met Val Arg
Glu Leu Asp Gly His Val Leu Lys
Cys Val Lys Asp Gln Asn Gly Asn
His Val Val Gln Lys Cys Ile Glu
Cys Val Gln Pro Gln Ser Leu Gln
Phe Ile Ile Asp Ala Phe Lys Gly
Gln Val Phe Ala Leu Ser Thr His
Pro Tyr Gly Ser Arg Val Ile Glu
Arg Ile Leu Glu His Cys Leu Pro
Asp Gln Thr Leu Pro Ile Leu Glu
Glu Leu His Gln His Thr Glu Gln
Leu Val Gln Asp Gln Tyr Gly Ser
Tyr Val Ile Glu His Val Leu Glu
His Gly Arg Pro Glu Asp Lys Ser
Lys Ile Val Ala Glu Ile Arg Gly
Asn Val Leu Val Leu Ser Gln His
Lys Phe Ala Cys Asn Val Val Gln
Lys Cys Val Thr His Ala Ser Arg
Thr Glu Arg Ala Val Leu Ile Asp
Glu Cys Val Thr Met Asn Asp Gly
Pro His Ser Ala Leu Tyr Thr Met
Met Lys Asp Gln Tyr Ala Ser Tyr
Val Val Glu Lys Met Ile Asp Val
Ala Glu Pro Gly Gln Arg Lys Ile
Val Met His Lys Ile Arg Pro His
Ile Ala Thr Leu Arg Lys Tyr Thr
Tyr Gly Lys His Ile Leu Ala Lys
Leu Glu Lys Tyr Tyr

SEQ ID NO: 31

Gly Arg Ser Arg Leu Leu Glu Asp
Phe Arg Asn Asn Arg Tyr Pro Asn
Leu Gln Leu Arg Glu Ile Ala Gly
His Ile Met Glu Phe Ser Gln Asp
Gln His Gly Cys Arg Phe Ile Gln
Leu Lys Leu Glu Arg Ala Thr Pro
Ala Glu Arg Gln Leu Val Phe Asn
Glu Ile Leu Gln Ala Ala Tyr Gln
Leu Met Val Asp Val Phe Gly Ser
Tyr Val Ile Glu Lys Phe Phe Glu
Phe Gly Ser Leu Glu Gln Lys Leu
Ala Leu Ala Glu Arg Ile Arg Gly
His Val Leu Ser Leu Ala Leu Gln
Met Tyr Gly Asn Arg Val Ile Gln
Lys Ala Leu Glu Phe Ile Pro Ser
Asp Gln Gln Asn Glu Met Val Arg
Glu Leu Asp Gly His Val Leu Lys
Cys Val Lys Asp Gln Asn Gly Asn
His Val Val Gln Lys Cys Ile Glu
Cys Val Gln Pro Gln Ser Leu Gln
Phe Ile Ile Asp Ala Phe Lys Gly
Gln Val Phe Ala Leu Ser Thr His
Pro Tyr Gly Cys Arg Val Ile Gln
Arg Ile Leu Glu His Cys Leu Pro
Asp Gln Thr Leu Pro Ile Leu Glu
Glu Leu His Gln His Thr Glu Gln
Leu Val Gln Asp Gln Tyr Gly Ser
Tyr Val Ile Glu His Val Leu Glu
His Gly Arg Pro Glu Asp Lys Ser
Lys Ile Val Ala Glu Ile Arg Gly
Asn Val Leu Val Leu Ser Gln His
Lys Phe Ala Cys Asn Val Val Gln
Lys Cys Val Thr His Ala Ser Arg
Thr Glu Arg Ala Val Leu Ile Asp
Glu Cys Val Thr Met Asn Asp Gly
Pro His Ser Ala Leu Tyr Thr Met
Met Lys Asp Gln Tyr Ala Cys Tyr
Val Val Gln Lys Met Ile Asp Val
Ala Glu Pro Gly Gln Arg Lys Ile
Val Met His Lys Ile Arg Pro His

-continued

```
Ile Ala Thr Leu Arg Lys Tyr Thr

Tyr Gly Lys His Ile Leu Ala Lys

Leu Glu Lys Tyr Tyr
```

The demethylation domain (e.g., TET1 domain) or methylation domain (e.g., Dnmt3a domain) provided herein may be linked to a PUF domain as provided herein including embodiments thereof. Alternatively, the demethylation domain (e.g., TET1 domain) or methylation domain (e.g., Dnmt3a domain) provided herein may be linked to the nuclease-deficient RNA-guided DNA endonuclease (e.g., dCas9). Where the demethylation domain or methylation domain provided herein is directly linked (fused) to the nuclease-deficient RNA-guided DNA endonuclease (e.g., dCas9) a chemical linker may link the demethylation domain or methylation domain to the nuclease-deficient RNA-guided DNA endonuclease. In certain embodiments, the chemical linker is a peptide linker. In certain embodiments, the chemical linker is a poly-glycine linker. In certain embodiments, the demethylation domain or methylation domain is linked to the C-terminus of the nuclease-deficient RNA-guided DNA endonuclease (e.g., dCas9). In certain embodiments, the demethylation domain or methylation domain is linked to the N-terminus of the nuclease-deficient RNA-guided DNA endonuclease (e.g., dCas9).

Where the demethylation domain or methylation domain provided herein is directly linked (fused) to the nuclease-deficient RNA-guided DNA endonuclease (e.g., dCas9), the demethylation domain or methylation domain and the nuclease-deficient RNA-guided DNA endonuclease (e.g., dCas9) form a dCas9-demethylation domain conjugate or a dCas9-methylation domain conjugate. In certain embodiments, the dCas9-demethylation domain (e.g., TET1 domain) conjugate has the sequence of SEQ ID NO:52. In certain embodiments, the dCas9-demethylation domain conjugate has the sequence of SEQ ID NO:53. In certain embodiments, the dCas9-methylation (e.g., Dnmt3a) domain conjugate has the sequence of SEQ ID NO:59. In certain embodiments, the dCas9-methylation domain conjugate has the sequence of SEQ ID NO:60. In certain embodiments, the dCas9-methylation domain conjugate has the sequence of SEQ ID NO:61. In certain embodiments, the dCas9-methylation domain conjugate has the sequence of SEQ ID NO:62. In certain embodiments, the dCas9-methylation domain conjugate has the sequence of SEQ ID NO:63. In certain embodiments, the dCas9-methylation domain conjugate has the sequence of SEQ ID NO:64.

Thus, the complexes provided herein may include an additional bioactive domain operably linked to the PUF domain or the nuclease-deficient RNA-guided DNA endonuclease (e. g., dCas9 protein). Thus, according to the invention, a heterologous polypeptide (also referred to as a "fusion partner") can be fused to the PUF domain of the demethylation or methylation protein conjugate provided herein including embodiments thereof, that binds to at least one of the PBS on the subject polynucleotide. In addition, if desired, the same or different fusion partner can also optionally be fused to the nuclease-deficient RNA-guided DNA endonuclease (e.g., nuclease-deficient wt Cas9 protein or dCas9 protein). Thus as described herein, unless specifically disclaimed, any of the fusion partners are intended to be fused to the PUF domain of the demethylation or methylation protein conjugate provided herein including embodiments thereof, and optionally also fused to the nuclease-deficient RNA-guided DNA endonuclease (e.g., nuclease-deficient wt Cas9 protein or dCas9 protein). The fusion partner fused to the PUF domain can be the same or different from the optional fusion partner fused to the nuclease-deficient RNA-guided DNA endonuclease (e.g., nuclease-deficient wt Cas9 protein or dCas9 protein) (infra). In certain embodiments the fusion partner is a bioactive moiety. In certain embodiments the fusion partner is a detectable moiety or a therapeutic moiety.

The fusion partner may exhibit an activity (e.g., enzymatic activity). Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying the DNA directly (e.g., methylation of DNA) or at modifying a DNA-associated polypeptide (e.g., a histone or DNA binding protein). Additional fusion partners may include the various fluorescent protein, polypeptides, variants, or functional domains thereof, such as GFP, Superfolder GFP, EGFP, BFP, EBFP, EBFP2, Azurite, mKalamal, CFP, ECFP, Cerulean, CyPet, mTurquoise2, YFP, Citrine, Venus, Ypet, BFPms1, roGFP, and bilirubin-inducible fluorescent proteins such as UnaG, dsRed, eqFP611, Dronpa, TagRFPs, KFP, EosFP, Dendra, IrisFP, etc.

Any of the fusion partners described in international application PCT/US2016/021491 and published as WO2016148994 A8, which is hereby incorporated by reference and for all purposes, is contemplated for the invention.

In embodiments, the fusion partner is a demethylation domain. In certain embodiments, the fusion partner is a methylation domain.

Any of the subject PUF domain can be made using, for example, a Golden Gate Assembly kit (see Abil et al., Journal of Biological Engineering 8:7, 2014), which is available at Addgene (Kit #1000000051).

Demethylation and Methylation Domains

In certain embodiments, the demethylation domain is a DNA demethylation domain. In certain embodiments, the DNA demethylation domain includes a Ten-Eleven translocation (TET) domain. In certain embodiments, the DNA demethylation domain includes a Ten-Eleven translocation 1 (TET1) domain. In certain embodiments, the DNA demethylation domain includes a Ten-Eleven translocation 2 (TET2) domain. In certain embodiments, the DNA demethylation domain includes a Ten-Eleven translocation 3 (TET3) domain. In certain embodiments, the TET demethylation domain is a TET1 domain (i.e., TET1 catalytic domain), a TET2 domain (i.e., TET2 catalytic domain) or a TET3 domain (i.e., TET3 catalytic domain). In certain embodiments, the TET demethylation domain is a TET1 domain. In certain embodiments, the TET demethylation domain is a TET2 domain. In certain embodiments, the TET demethylation domain is a TET3 domain. In certain embodiments, the TET demethylation domain is a TET1 catalytic domain. In certain embodiments, the TET demethylation domain is a TET2 catalytic domain. In certain embodiments, the TET demethylation domain is a TET3 catalytic domain. In certain embodiments, the TET1 domain includes the sequence of SEQ ID NO:51. In certain embodiments, the TET1 domain is the sequence of SEQ ID NO:51.

In certain embodiments, the protein conjugate (PUF domain fusion protein) includes a DNA demethylation domain (DNA demethylase activity domain), such as a cytosine demethylase, e.g., hTET1, hTET2, and hTET3, and other enzymes of the cytosine demethylation pathway, and transcription of the target gene is enhanced/stimulated; or the protein conjugate (PUF domain fusion protein) includes a DNA methylation domain (DNA methyltransferase activity domain), and transcription of the target gene is inhibited.

In certain embodiments, the DNA demethylation domain (DNA demethylase activity domain) includes a TET (Ten-Eleven Translocation) protein, and the DNA methylation domain (DNA methyltransferase activity domain) includes a DNMT (DNA Methyltransferase).

In certain embodiments, the TET protein is a TET methylcytosine dioxygenase. TET methylcytosine dioxygenase catalyzes the initial and critical step leading to replacing 5mC with unmethylated cytosine.

DNA methylation is catalyzed and maintained by methyltranferases. In human, Dnmt1 is the maintenance MTase, while Dnmt3a and Dnmt3b are de novo methyltranferases. Dnmt3L is catalyltically inactive but can interact with Dnmt3a and Dnmt3b and stimulate their activities. Different pathways for DNA demethylation have been proposed. One such pathway involves conversion of 5mC to 5hmC by Tet enzymes, then subsequently through other enzymes to form unmethylated cytosine. In certain embodiments, the DNMT is Dnmt3a or Dnmt3a-3L.

It was discovered that, when the hTET1 demethylase catalytic domain (CD) was fused to the C-terminus of the PUF domain, the observed demethylase activity was surprisingly higher as compared to when the hTET1 demethylase catalytic domain (CD) was fused to the N-terminus of the PUF domain. Thus, in certain embodiments, the demethylation protein conjugate (PUF domain fusion protein) includes a hTET1 functional domain fused to the C-terminus of the PUF domain. In certain embodiments, the PUF domain is PUFa. In certain embodiments, transcription of the target gene is increased by more than 10-fold, 15-fold, 20-fold, 25-fold, 30-fold, 50-fold, 75-fold, 100-fold, 125-fold, 135-fold, 150-fold, 200-fold or more. In certain embodiments, the target gene is SOX.

In certain embodiments, the PUF domain fusion protein comprises a Dnmt functional domain fused to the N-terminus of the PUF domain. In certain embodiments, the PUF domain is PUFa.

In certain embodiments, the PUF domain fusion protein comprises a Dnmt functional domain fused to the N-terminus of the PUF domain. In certain embodiments, the PUF domain is PUFa. In certain embodiments, the Dnmt functional domain is Dnmt3a, Dnmt3b, a hybrid Dnmt3b-3L, a hybrid Dnmt3a-3L, or a combination thereof.

In certain embodiments, the target gene comprises two or more target polynucleotide sequences. In certain embodiments, at least two of said same or different PUF domains are fused to different DNA methyltransferase or demethylase domains.

In embodiments, the demethylation protein conjugate includes the sequence of SEQ ID NO:54 or SEQ ID NO:55. In certain embodiments, the demethylation protein conjugate is the sequence of SEQ ID NO:54 or SEQ ID NO:55.

In embodiments, the methylation protein conjugate includes the sequence of SEQ ID NO:56, SEQ ID NO:57 or SEQ ID NO:58.

In embodiments, the methylation protein conjugate includes the sequence of SEQ ID NO:65, SEQ ID NO:66, SEQ ID NO:67, SEQ ID NO:68 or SEQ ID NO:69. In certain embodiments, the methylation protein conjugate is the sequence of SEQ ID NO:65, SEQ ID NO:66, SEQ ID NO:67, SEQ ID NO:68 or SEQ ID NO:69.

Additional Complexes

Another aspect of the invention provides a complex comprising any one of the polynucleotide of the invention, and the modified Cas9 protein, e.g., nuclease-deficient wt Cas9 protein or dCas9 protein. In certain embodiments, the complex comprises a nuclease-deficient wt Cas9 protein.

In certain embodiments, the complex may further comprise one or more PUF domain or fusion thereof bound to the one or more PBS(s). In certain embodiments, each of the PUF domain is fused to an effector domain. In certain embodiments, at least two of the PUF domains are fused to different effector domains.

In certain embodiments, the nuclease-deficient wt Cas9 protein (e.g., nuclease-deficient wt Cas9 protein or dCas9 protein), the PUF domain, and/or the effector domain further comprises a nuclear localization signal (NLS).

In certain embodiments, the complex is bound to the target polynucleotide sequence through the DNA-targeting sequence of the polynucleotide.

In certain embodiments, the effector domain is a TET (Ten-Eleven Translocation) protein, or a fragment thereof that retains demethylase catalytic activity; or a DNMT (DNA Methyltransferase), or a fragment thereof that retains methyltransferase catalytic activity. For example, the TET protein may be a TET methylcytosine dioxygenase; and the DNMT may be Dnmt3a or Dnmt3a-3L.

In certain embodiments, the PUF domain fusion protein comprises a TET1 functional domain fused to the C-terminus of the PUF domain (e.g., PUFa).

In certain embodiments, the PUF domain fusion protein comprises a Dnmt functional domain fused to the N-terminus of the PUF domain (e.g., PUFa).

In certain embodiments, the Dnmt functional domain is Dnmt3a, a hybrid Dnmt3a-3L, or a combination thereof.

Cells

In another aspect, a cell is provided including a complex as provided herein including embodiments thereof is provided. In certain embodiments, the cell is a mammalian cell. In certain embodiments, the cell is a cancer cell. In certain embodiments, the cell is a cancer cell, and/or the target gene is hMLH1 with a hypermethylated promoter region. For example, the target polynucleotide sequence may be within the hypermethylated promoter region of hMLH1, and methylation of the target polynucleotide sequence is associated with down-regulation of hMLH1 in cancer cells.

In certain embodiments, the cancer cell is from a stomach cancer, esophageal cancer, head and neck squamous cell carcinoma (HNSCC), non-small cell lung cancer (NSCLC), and colorectal cancer (such as HNPCC). The stomach cancer may include foveolar type tumors, and stomach cancer in high-incidence Kashmir Valley.

Another aspect of the invention provides a host cell including any one of the subject vector, polynucleotide, and complex.

In certain embodiments, the host cell further includes a second vector encoding the nuclease-deficient wt Cas9 protein (e.g., nuclease-deficient wt Cas9 protein or dCas9 protein). In certain embodiments, the second vector further encodes a methylation or demethylation (effector) domain fused to the nuclease-deficient wt Cas9 protein (e.g., nuclease-deficient wt Cas9 protein or dCas9 protein). The expression of the Cas9 protein (e.g., wt, nickase, or dCas9 protein) can be under the control of a constitutive promoter or an inducible promoter.

In certain embodiments, the host cell may further include a third vector encoding the one or more PUF domains, each fused to a methylation or demethylation (effector) domain. The expression of the one or more PUF domains can be independently under the control of a constitutive promoter or an inducible promoter.

In certain embodiments, the second vector may further encode a nuclear localization signal (NLS) fused to the nuclease-deficient wt Cas9 protein (e.g., nuclease-deficient wt Cas9 protein or dCas9 protein) or the methylation or demethylation (effector) domain, and/or the third vector may further encode a nuclear localization signal (NLS) fused to the PUF domain or the methylation or demethylation (effector) domain.

In certain embodiments, sequences that can be encoded by different vectors may be on the same vector. For example, in certain embodiments, the second vector may be the same as the vector, and/or the third vector may be the same as the vector or the second vector.

The host cell may be in a live animal, or may be a cultured cell.

Methods

The methods and complexes provided herein provide, inter alia, for a versatile delivery platform of methylation and demethylation activities. Using the methods and complexes provided herein methylation and/or demethylation domains (e.g., demethylation or methylation enzymes or functional fragments thereof) or combinations thereof, may be delivered to a cell sequentially or concomitantly. Delivery of a combination of methylation or demethylation domains to a cell, allows for fine tuning the methylation status of a targeted gene locus. The invention further provides for the delivery of a plurality of methylation or demethylation domains, wherein the domains may be the same or different. Where a plurality of methylation or demethylation domains is delivered to a cell, the domains may form part of a plurality of methylation or demethylation protein conjugates, each linked to a PUF domain, and/or they may be directly fused to the nuclease-deficient RNA-guided DNA endonuclease enzyme (e.g., dCas9). Further, and by virtue of the target-gene specificity of the guide RNA, the present invention allows for the delivery of methylation and demethylation domains to different target sites in a cell at the same time. Applicants were the first to show that due to the different steric requirement for the methylation domain and the demethylation domain, methylation and demethylation using the complexes provided herein is more efficient compared to, for example, directly linking methylation or demethylation activities to the nuclease-deficient RNA-guided DNA endonuclease enzyme (e.g., dCas9). Without being bound to any particular theory, it is thought that N-terminal fusion of the methylation domain to a PUF domain provides.

For the methods of demethylating or methylating provided herein including embodiments thereof, any of the element of the complexes described above may be used. Thus, in certain embodiments, the method includes delivering a first polynucleotide encoding a nuclease-deficient RNA-guided DNA endonuclease enzyme as provided herein including embodiments thereof (e.g., dCas9). Thus, the method may include delivering a second polynucleotide, which is the polynucleotide described herein including embodiments thereof and which encodes a DNA-targeting sequence, a binding sequence and one or more PUF binding site (PBS) sequences provided herein.

In another aspect, a method of demethylating a target nucleic acid sequence in a mammalian cell is provided. The method includes:
(a) providing a mammalian cell containing a target nucleic acid requiring demethylation;
(b) delivering to the mammalian cell a first polynucleotide encoding a nuclease-deficient RNA-guided DNA endonuclease enzyme;
(c) delivering to the mammalian cell a second polynucleotide including:
   (i) a DNA-targeting sequence that is complementary to a target polynucleotide sequence;
   (ii) a binding sequence for the nuclease-deficient RNA-guide DNA endonuclease enzyme; and
   (iii) one or more PUF binding site (PBS) sequences,
   wherein the nuclease-deficient RNA-guided DNA endonuclease enzyme is bound to the second polynucleotide via the binding sequence; and
(d) delivering to the mammalian cell a third polynucleotide encoding a demethylation protein conjugate including:
   (i) a PUF domain; and
   (ii) a demethylation domain, the demethylation domain operably linked to the C-terminus of the PUF domain, whereby the delivered demethylation protein conjugate demethylates the target nucleic acid sequence in the cell.

In embodiments, the demethylation protein conjugate is bound to the second polynucleotide via binding of the PUF domain to the one or more PBS sequences. In certain embodiments, the first polynucleotide is contained within a first vector. In certain embodiments, the second polynucleotide is contained within a second vector. In certain embodiments, the third polynucleotide is contained within a third vector. In certain embodiments, either the first, the second or the third vector is the same. In certain embodiments, the delivering is performed by transfection.

In another aspect, a method of methylating a target nucleic acid sequence in a mammalian cell is provided. The method includes:
(a) providing a mammalian cell containing a target nucleic acid requiring methylation;
(b) delivering to the mammalian cell a first polynucleotide encoding a nuclease-deficient RNA-guided DNA endonuclease enzyme;
(c) delivering to the mammalian cell a second polynucleotide including:
   (i) a DNA-targeting sequence that is complementary to a target polynucleotide sequence;
   (ii) a binding sequence for the nuclease-deficient RNA-guide DNA endonuclease enzyme; and
   (iii) one or more PUF binding site (PBS) sequences,
   wherein the nuclease-deficient RNA-guided DNA endonuclease enzyme is bound to the second polynucleotide via the binding sequence; and
(d) delivering to the mammalian cell a third polynucleotide encoding a methylation protein conjugate including:
   (i) a PUF domain; and
   (ii) a methylation domain, the methylation domain operably linked to the N-terminus of the PUF domain, whereby the delivered methylation protein conjugate methylates the target nucleic acid sequence in the cell.

In certain embodiments, the methylation protein conjugate is bound to the second polynucleotide via binding of the PUF domain to the one or more PBS sequences. In certain embodiments, the first polynucleotide is contained within a first vector. In certain embodiments, the second polynucleotide is contained within a second vector. In certain embodiments, the third polynucleotide is contained within a third vector. In certain embodiments, the first, the second or the third vector is the same. In certain embodiments, the delivering is performed by transfection.

In certain embodiments, the method of the invention utilizes a plurality or a library of the vectors, each encoding a polynucleotide of the invention, wherein two of the vectors differ in the encoded polynucleotides in their respective DNA-targeting sequences, Cas9-binding sequences, and/or the copy number, identity (sequence, binding specificity, etc.), or relative order of the PBS. In a related embodiment, instead of using vectors, non-vector coding sequences are used.

In certain embodiments, the method further comprises introducing into the cell a plurality of any one of the subject vectors, wherein two of the vectors differ in the encoded polynucleotides in their respective DNA-targeting sequences, Cas9-binding sequences, and/or the copy number, identity, or relative order of the PBS. In a related embodiment, instead of using vectors, non-vector coding sequences are used.

Methods of Treatment

The methods of methylating or demethylating a target nucleic acid in a cell may be used, inter alia, for the treatment of diseases related to or caused by abnormal DNA methylation (e.g., cancer). A role for both epigenetic (DNA methylation) and genetic (mutations) actions of cytidine deaminases in cancer has been proposed, and a possible role in demethylation which is widespread. The present invention has practical application in ameliorating/treating the cancer disease process by altering the demethylation or methylation status within the cancer cell. Using the methods and compositions provided herein methylated genes can be targeted for demethylation in vivo, which may lead to their expression (methylation being a repressive modification most of the time).

Most if not all cancers undergo epigenetic changes, including significantly the methylation and silencing of tumor suppressor genes. Demethylation of tumor suppressor genes can ameliorate cancer phenotype. Hence, a method of targeting demethylation in vivo to tumor suppressor genes is a very promising avenue to cancer therapy.

Targeting of cytidine deaminase activity to genes of interest in cancer can include, for example, fusion of the cytidine deaminase to a tumor suppressor DNA binding domain (such as the zinc finger DNA core binding region of the p53 protein). It is believed that in many cancers, mutation of the DNA binding domain of p53 can contribute to transformation. In addition, the promoter regions of many tumor suppressor genes, including p53 targets, are methylated in cancer cells.

The molecules and pharmaceutical compositions of the present invention can be assessed for their anti-cancer/anti-tumorigenic effects by utilizing in vitro and ex vivo assays. In one suitable assay, a nucleic acid vector that expresses a molecule of the invention is transfected into a cancer cell. Appropriate controls are established comprising the cancer cell line transfected with vector backbone only, or vector plus a molecule of the invention in which the cytidine deaminase domain is rendered non-functional described in more detail below. Induced apoptosis in the cancer cell line transfected with the molecules of the invention but not in the control cells would be indicative of an anti-cancer effect for the molecule of the invention.

In another aspect, a method of treating cancer in a subject in need thereof is provided. The method includes, administering to a subject a therapeutically effective amount of a demethylation complex or methylation complex as provided herein including embodiments thereof, thereby treating cancer in the subject. In a preferred embodiment, the method includes administering to a subject a therapeutically effective amount of a demethylation complex as provided herein.

In another aspect, pharmaceutical composition is provided. The pharmaceutical composition includes therapeutically effective amount of a demethylation complex as provided herein including embodiments thereof and a pharmaceutically acceptable excipient.

In another aspect, a method of treating cancer in a subject in need thereof is provided. The method includes, administering to a subject a therapeutically effective amount of a methylation complex as provided herein including embodiments thereof, thereby treating cancer in the subject.

In another aspect, pharmaceutical composition is provided. The pharmaceutical composition includes therapeutically effective amount of a methylation complex as provided herein including embodiments thereof and a pharmaceutically acceptable excipient.

Additional applications for the methods and compositions provided herein include modulating gene expression during development. For example, the presence of a site specific DNA binding domain allows for targeted demethylation of specific subsets of genes activated at particular times in development or during the cell cycle. For instance, the DNA binding domains of the (e.g., Oct4 or SOX-2) proteins when fused to a PUF domain could provide for a demethylation activity that is directed towards genes that are involved in cell fate decisions relating to promotion of a pluripotent or stem cell-like phenotype. Alternatively, the demethylation domain may be linked via a linker to PUF binding domain. DNA binding domains that could optionally be utilized include those from T-box transcription factors or steroid hormone receptor DNA binding domains such as the RAR and RXR DNA binding domains. Nevertheless, the present demethylation protein conjugate may be sufficient to demethylate the promoters of a pluripotent gene and alter the methylation status of a cell during differentiation.

Additional Methods

Another aspect of the invention provides a method of modulating transcription and/or methylation state of a target gene in a cancer cell according to any method of the invention, wherein the cancer cell is associated with or characterized by abonormal DNA methylation.

A related aspect of the invention provides a method of modulating transcription and/or methylation state of a target gene in a cancer cell in a patient according to any method of the invention, wherein the cancer cell is associated with or characterized by abonormal DNA methylation.

Another related aspect of the invention provides a method for treating a patient in need of treatment a disease or condition associated with abnormal DNA methylation, such as CpG methylation, of a target gene, the method comprising allowing the formation of the complex of the invention near or at the target gene to modulate transcription and/or methylation state of the target gene in the patient.

Another related aspect of the invention provides a method for treating a patient in need of treatment a disease or condition associated with abnormal DNA methylation (such as CpG methylation) of a target gene, the method comprising modulating transcription and/or methylation state of the target gene in the patient according to any of the subject methods.

Another related aspect of the invention provides a method for treating a patient in need of treatment a disease or condition associated with abnormal DNA methylation (such as CpG methylation) of a target gene, the method comprising allowing the formation of the complex of the invention near or at the target gene to modulate transcription and/or methylation state of the target gene in the patient.

In a related aspect, the invention provides a method of treating cancer in a patient in need of treatment, wherein said cancer is associated with or characterized by abnormal DNA methylation of hMLH1, the method comprising modulating transcription and/or methylation state of hMLH1 in the patient according to any one of the methods of the invention. For example, in certain embodiment, the PUF domain fusion protein may comprise a hTET1 functional domain fused to the C-terminus of the PUF domain such as PUFa. In certain embodiments, the methylation level of the hypermethylated promoter region of hMLH1 is decreased. In certain embodiments, transcription/translation of hMLH1 is increased.

In certain embodiments, the target gene is hMLH1.

In certain embodiments, the disease is a cancer. In certain embodiments, the disease is an imprinting disorder. In certain embodiments, the disease is a neurological disease.

In certain embodiments, the cancer is associated with or characterized by hyper- or hypomethylation of a tumor suppressor gene or an oncogene, respectively.

In certain embodiments, the cancer is a stomach cancer (including foveolar type tumors, and stomach cancer in high-incidence Kashmir Valley), esophageal cancer, head and neck squamous cell carcinoma (HNSCC), non-small cell lung cancer (NSCLC), and colorectal cancer (such as HNPCC).

Yet another aspect of the invention provides a method of assembling the complex of the invention at the target polynucleotide sequence, the method comprising contacting or bringing to the vicinity of the target polynucleotide sequence: (1) any one of the subject polynucleotide, or any one of the subject vector, or the plurality of vectors; (2) the nuclease-deficient wt Cas9 protein (e.g., nuclease-deficient wt Cas9 protein or dCas9 protein), or any one of the subject second vector encoding the nuclease-deficient wt Cas9 protein (e.g., nuclease-deficient wt Cas9 protein or dCas9 protein); and, (3) one or more of the PUF domains, each fused to an effector domain, or any one of the third vector encoding the PUF domain fusions. In certain embodiments, the fusion is with a DNA methyltransferase or a demethylase.

In certain embodiments, the complex is assembled inside a cell, the target polynucleotide sequence is a part of the genomic DNA of the cell, and wherein the subject vector, second vector, and third vector are introduced into the cell.

A related aspect of the invention provides a method of modulating transcription of a plurality of target genes in a cell, the method comprising: introducing into the cell the subject plurality of the vectors, a coding sequence for a dCas9 protein, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the dCas9 protein, and a PUF domain fusion; and (2) transcription modulation of the target gene comprising the target polynucleotide sequence.

In a related aspect, the invention also provides a method of epigenetic modulation (e.g., modulating the epigenetic states of chromatin not directly related to transcriptional activity), at a plurality of target genes in a cell, the method comprising: introducing into the cell the subject plurality of the vectors, a coding sequence for a nuclease-deficient wt Cas9 protein, and a coding sequence for one or more PUF domain fusions, wherein each of the target genes comprises a target polynucleotide sequence that permits (1) the assembly, at the target polynucleotide sequence, of a tripartite complex of a polynucleotide encoded by one of the plurality of the vector, the wt Cas9 protein or the Cas9 nickase, and a PUF domain fusion; and (2) epigenetic modulation of the target gene comprising the target polynucleotide sequence. The method can be useful, for example, to change epigenetic state (e.g., opening up the chromatin) at the same time to gain access/stability of nuclease-deficient wt Cas9 protein (e.g., dCas9) binding to closed chromatin sites (e.g., to increase cut and genome editing at those sites).

In certain embodiments, the transcription of at least one target gene is enhanced/stimulated, while the transcription of at least another target gene is inhibited.

In one aspect of the invention provides a method of modulating transcription and/or methylation state of a target gene having a target polynucleotide sequence in a cell, the method comprises:
(a) introducing into the cell a coding sequence for a PUF domain fusion protein, wherein said PUF domain fusion protein comprises a PUF domain, and a DNA methyltransferase activity domain or a DNA demethylase activity domain;
(b) introducing into the cell a coding sequence for a dCas9 protein; and,
(c) introducing into the cell a polynucleotide or a coding sequence for said polynucleotide, wherein said polynucleotide comprising:
  (i) a DNA-targeting sequence that is complementary to the target polynucleotide sequence;
  (ii) one or more copies of PUF binding site (PBS) sequence, wherein each of said one or more copies of PBS bind to the same or a different PUF domain fusion protein; and,
  (iii) a Cas9-binding sequence capable of binding to the dCas9 protein;
wherein said PUF domain fusion protein, said dCas9 protein, and said polynucleotide form a complex at the target polynucleotide sequence within the target gene of said cell, thereby modulating the transcription and/or methylation state of the target gene.

It should be noted that the coding sequence for a PUF domain fusion protein, the coding sequence for the nuclease-deficient RNA-guided DNA endonuclease (dCas9 protein), and the polynucleotide (or a vector encoding the polynucleotide) can be introduced into the cell together (e.g., by including all coding sequences on the same vector, by co-transfecting different vectors encoding different coding sequences, etc.), or separately, in any order or sequence as desired. In certain preferred embodiments, the coding sequence for a PUF domain fusion protein, the coding sequence for a nuclease-deficient RNA-guided DNA endonuclease (dCas9 protein), and the polynucleotide (or a vector encoding the polynucleotide) are co-introduced into the cell.

In addition, it is not intended that the (a), (b), and (c) steps of the invention necessarily have to be performed in any specific order, if they are to be performed separately.

The target polynucleotide sequence can be any DNA sequence. In certain embodiments, the target polynucleotide sequence comprises, or is adjacent to, one or more transcription regulatory element(s). In certain embodiments, the transcription regulatory element(s) comprises one or more of: a core promoter, a proximal promoter element, an enhancer, a silencer, an insulator, and a locus control region.

Kits

In another aspect, a kit is provided. The kit includes:
(i) a ribonucleoprotein complex as provided herein including embodiments thereof or a nucleic acid encoding the same; and
(ii) a methylation modifying protein conjugate as provided herein including embodiments thereof or a nucleic acid encoding the same. In certain embodiments, the kit further includes a transfection agent. In certain embodiments, the kit further includes a sample collection device for collecting a sample from a cancer patient.

In embodiments, a subject kit may include: a) a polynucleotide of the present invention, or a nucleic acid (e.g., vector) including a nucleotide sequence encoding the same; optionally, b) a subject nuclease-deficient wt Cas9 protein (e.g., nuclease-deficient wt Cas9 protein or dCas9 protein), or a vector encoding the same (including an expressible mRNA encoding the same); and optionally, c) one or more subject demethylation or methylation protein conjugate (PUF domain fusion) each including a PUF domain fused to a demethylation or methylation domain (effector domain) that may be the same or different among the different demethylation or methylation protein conjugates (PUF domain fusions), or a vector encoding the same (including an expressible mRNA encoding the same).

In certain embodiments, one or more of a)-c) may be encoded by the same vector.

In certain embodiments, the kit also comprises one or more buffers or reagents that facilitate the introduction of any one of a)-c) into a host cell, such as reagents for transformation, transfection, or infection.

For example, a subject kit can further include one or more additional reagents, where such additional reagents can be selected from: a buffer; a wash buffer; a control reagent; a control expression vector or RNA polynucleotide; a reagent for in vitro production of the nuclease-deficient wt Cas9 protein or dCas9 or PUF domain fusion from DNA; and the like.

Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

With the invention generally described above, various features of the invention will be further elaborated below. It should be understood that features of the invention, even when described in the context of separate embodiments, or even separate embodiments under different aspects of the invention, may be provided in combination in a single embodiment. Conversely, various features of the invention described in the context of a single embodiment, may also be provided separately or in any suitable subcombination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA and mRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In certain embodiments, the internucleotide linkages in DNA are phosphodiester, phosphodiester derivatives, or a combination of both.

As used herein, the range of values provided includes the specified value. As recognized by a person of ordinary skill in the art such specified value would reasonably include a standard deviation using measurements generally acceptable in the art. In certain embodiments, the standard deviation includes a range extending to +/−10% of the specified value.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, 50 to 200, or 100 to 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than 0.2, more preferably less than 0.01, and most preferably less than 0.001.

An indication that two nucleic acid sequences or polypeptides are substantially identical is that the polypeptide encoded by the first nucleic acid is immunologically crossreactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "bioactive moiety" as provided herein refers to a moiety that upon administration to a cell, tissue or organism has a detectable effect on the biological function of said cell, tissue or organism. In certain embodiments, the detectable effect is a biological effect. In certain embodiments, the detectable effect is a therapeutic effect. In certain embodiments, the detectable effect is a diagnostic effect.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

For specific proteins described herein (e.g., dCas9), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

Thus, a "methylcytosine dioxygenase TET1" or "TET1" protein as referred to herein includes any of the recombinant or naturally-occurring forms of the TET1 dioxygenase or variants or homologs thereof that maintain TET1 dioxygenase enzyme activity (e.g. within at least 50%, 80%, 90%, 95%, 96%, 97%, 98%, 99% or 100% activity compared to TET1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TET1 protein. In certain embodiments, the TET1 protein is substantially identical to the protein identified by the UniProt reference number Q8NFU7 or a variant or homolog having substantial identity thereto.

Thus, a "methylcytosine dioxygenase TET2" or "TET2" protein as referred to herein includes any of the recombinant or naturally-occurring forms of the TET2 dioxygenase or variants or homologs thereof that maintain TET2 dioxygenase enzyme activity (e.g. within at least 50%, 80%, 90%, 95%, 96%, 97%, 98%, 99% or 100% activity compared to TET2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TET2 protein. In certain embodiments, the TET2 protein is substantially identical to the protein identified by the UniProt reference number Q6N021 or a variant or homolog having substantial identity thereto.

Thus, a "methylcytosine dioxygenase TET3" or "TET3" protein as referred to herein includes any of the recombinant or naturally-occurring forms of the TET3 dioxygenase or variants or homologs thereof that maintain TET3 dioxygenase enzyme activity (e.g. within at least 50%, 80%, 90%, 95%, 96%, 97%, 98%, 99% or 100% activity compared to TET3). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TET3 protein. In certain embodiments, the TET3 protein is substantially identical to the protein identified by the UniProt reference number O43151 or a variant or homolog having substantial identity thereto.

The TET family of enzymes (e.g., TET1, TET2, TET3) catalyze the conversion of 5mC to 5hmC as well as its further oxidation into 5-formylcytosine (5fC) and 5 carboxylcytosine (5caC) (Ito et al., 2010). TET dioxygenases oxidize the methyl group at C5 to yield 5-hydroxymethyl-(hmC) (Kriaucionis and Heintz, 2009), 5-formyl-(fC) (Maiti and Drohat, 2011) and 5-carboxylcytosine (caC) (He et al., 2011).

A "DNMT3a", "DNA (cytosine-5)-methyltransferase 3A" or "DNA methyltransferase 3a" protein as referred to herein includes any of the recombinant or naturally-occurring forms of the DNMT3a enzyme or variants or homologs thereof that maintain DNMT3a enzyme activity (e.g. within at least 50%, 80%, 90%, 95%, 96%, 97%, 98%, 99% or 100% activity compared to DNMT3a). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DNMT3a protein. In certain embodiments, the DNMT3a protein is substantially identical to the protein identified by the UniProt reference number Q9Y6K1 or a variant or homolog having substantial identity thereto.

A "DNMT3L", "DNA (cytosine-5)-methyltransferase 3L" or "DNA methyltransferase 3L" protein as referred to herein includes any of the recombinant or naturally-occurring forms of the DNMT3L enzyme or variants or homologs thereof that maintain DNMT3L enzyme activity (e.g. within at least 50%, 80%, 90%, 95%, 96%, 97%, 98%, 99% or 100% activity compared to DNMT3L). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DNMT3L protein. In certain embodiments, the DNMT3L protein is substantially identical to the protein identified by the UniProt reference number Q9UJW3 or a variant or homolog having substantial identity thereto.

MLH1 (MutL homolog 1) is a human homolog of the *E. coli* DNA mismatch repair gene, mutL, which mediates protein-protein interactions during mismatch recognition, strand discrimination, and strand removal. The human gene, hMLH1, is located on Chromosome 3. Defects in hMLH1 are commonly associated with the microsatellite instability (MSI) observed in hereditary nonpolyposis colorectal cancer (HNPCC). In addition, deficient expression of the hMLH1 has been observed in many cancers, including stomach cancer (including foveolar type tumors, and stomach cancer in high-incidence Kashmir Valley), esophageal cancer, head and neck squamous cell carcinoma (HNSCC), non-small cell lung cancer (NSCLC), and colorectal cancer (such as HNPCC). In these cancers, the majority of deficiencies of hMLH1 were due to methylation of the promoter region of the hMLH1 gene.

Cas9 Proteins

As used herein, the term "Cas9 protein" as referred to herein includes a nuclease-deficient wt Cas9 protein in which one of the two catalytic sites for endonuclease activity (RuvC and HNH) is defective or lacks activity, and a dCas9 protein in which both catalytic sites for endonuclease activity are defective or lack activity. In certain embodiments, the Cas9 protein is a nuclease-deficient wt Cas9 protein. In certain embodiments, the Cas9 protein lacks nuclease activity or is nuclease-deficient. In certain embodiments, the Cas9 protein is a nickase (e.g., for example, the nickase can be a Cas9 Nickase with a mutation at a position corresponding to D10A of S. pyogenes Cas9; or the nickase can be a Cas9 Nickase with a mutation at a position corresponding to H840A of S. pyogenes Cas9). In certain embodiments, the Cas9 protein is a dCas9 (e.g., a dCas9 with mutations at positions corresponding to D10A and H840A of S. pyogenes Cas9.

In certain embodiments, a "modified Cas9 protein" refers to a Cas9 that is not a wt Cas9 protein. In certain embodiments, the modified Cas9 protein is a dCas9. In certain embodiments, the modified Cas9 protein is a nickase.

The modified Cas9 protein (nickase or dCas9) may have reduced nuclease activity, or lacks nuclease activity at one or both endonuclease catalytic sites. In certain embodiments, the dCas9 protein lacks endonuclease activity due to point mutations at both endonuclease catalytic sites (RuvC and HNH) of wild type Cas9. For example, the point mutations may be D10A and H840A, respectively, in the S. pyogenes Cas9, or in the corresponding residues in species other than S. pyogenes. In certain embodiments, the modified Cas9 protein lacks endonuclease catalytic activity at one but not both sites of wt Cas9, and is able to create a nick on a dsDNA target (Cas9 nickase).

In certain embodiments, the Cas9 nickase protein lacks endonuclease activity due to point mutations at one endonuclease catalytic sites (RuvC and HNH) of wild type Cas9. The point mutations can be D10A or H840A.

In certain embodiments, the dCas9 protein is nuclease-deficient but retains DNA-binding ability when complexed with the polynucleotide.

In certain embodiments, the dCas9 protein lacks endonuclease activity due to point mutations at both endonuclease catalytic sites (RuvC and HNH) of wild type Cas9. The point mutations can be D10A and H840A.

Figure 3A:
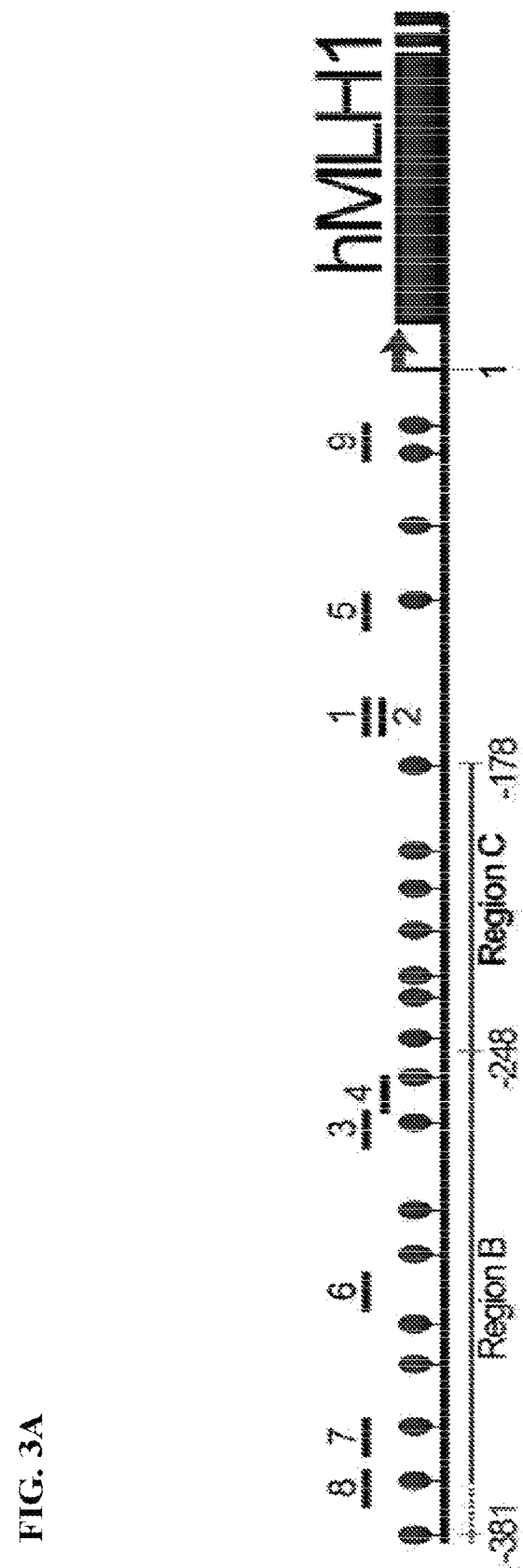
FIGS. 3A-3C. The figures show Casilio-ME outperforms dCas9-direct tethering system in delivering TET1(CD) to genomic loci and mediating gene activation.

In certain embodiments, the modified Cas9 protein has reduced or lacks endonuclease (e.g., endodeoxyribonuclease) activity. For example, a modified Cas9 suitable for use in a method of the present invention may be a Cas9 nickase, or exhibits less than 20%, less than 15%, less than 10%, less than 5%, less than 1%, or less than 0.1%, of the endonuclease (e.g., endodeoxyribonuclease) activity of a wild-type Cas9 polypeptide, e.g., a wild-type Cas9 polypeptide comprising an amino acid sequence as depicted in FIG. 3 and SEQ ID NO: 8 of WO 2013/176772 (incorporated herein by reference in its entirety and for all purposes). In some embodiments, the dCas9 has substantially no detectable endonuclease (e.g., endodeoxyribonuclease) activity. In some embodiments when a dCas9 has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the polypeptide can still bind to target DNA in a site-specific manner, because it is still guided to a target polynucleotide sequence by a DNA-targeting sequence of the subject polynucleotide, as long as it retains the ability to interact with the Cas9-binding sequence of the subject polynucleotide.

Any one of the Cas9 proteins, homologs or fragments thereof, having at least 75%, at least 80%, at least 85%, at least 90%, at least 95%, at least 99% or 100% amino acid sequence identity to the Cas9 proteins disclosed in International Application No.: PCT/US2013/032589, published as WO 2013/176772, which is hereby incorporated by reference in its entirety and for all purposes, are contemplated for the complexes and methods provided herein.

In some cases, the nuclease-deficient wt Cas9 protein (e.g., nuclease-deficient wt Cas9 protein or dCas9 protein) is optionally a fusion polypeptide including: i) a Cas9 protein (e.g., nuclease-deficient wt Cas9 protein or dCas9 protein) a covalently linked heterologous polypeptide (also referred to as a "fusion partner"), which can be the same or different from the fusion partner fused to the PUF domains (infra).

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In certain embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma (Mantel cell lymphoma), head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (e.g., Mantel cell lymphoma, follicular lymphoma, diffuse large B-cell lymphoma, marginal zona lymphoma, Burkitt's lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia (e.g., lymphoblastic leukemia, chronic lymphocytic leukemia, hairy cell leukemia), acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "associated" or "associated with" in the context of a substance or substance activity or function associated with a disease (e.g., cancer (e.g. leukemia, lymphoma, B cell lymphoma, or multiple myeloma)) means that the disease (e.g. cancer, (e.g. leukemia, lymphoma, B cell lymphoma, or multiple myeloma)) is caused by (in whole or in part), or a symptom of the disease is caused by (in whole or in part) the substance or substance activity or function.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Formulations suitable for oral administration can consist of (a) liquid solutions, such as an effective amount of the complexes provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administration contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like, that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In certain embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Other Suitable Sequences

For the complexes and methods provided herein including embodiments thereof the polynucleotides (e.g., first or second polynucleotide) may include a stability control sequence (e.g., transcriptional terminator segment) which influences the stability of the respective polynucleotide it forms part of (e.g., an RNA (e.g., a subject polynucleotide). One example of a suitable stability control sequence is a transcriptional terminator segment (i.e., a transcription termination sequence). A transcriptional terminator segment of a subject polynucleotide can have a total length of from 10 nucleotides to 100 nucleotides, e.g., from 10 nucleotides (nt) to 20 nt, from 20 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. For example, the transcriptional terminator segment can have a length of from 15 nucleotides (nt) to 80 nt, from 15 nt to 50 nt, from 15 nt to 40 nt, from 15 nt to 30 nt or from 15 nt to 25 nt.

In some cases, the transcription termination sequence is one that is functional in a eukaryotic cell. In some cases, the transcription termination sequence is one that is functional in a prokaryotic cell. Non-limiting examples of nucleotide sequences that can be included in a stability control sequence (e.g., transcriptional termination segment, or in any segment of the DNA-targeting RNA to provide for increased stability) include sequences set forth in SEQ ID NO: 683-696 of WO 2013/176772 (incorporated herein by reference in its entirety and for all purposes), see, for example, SEQ ID NO: 795 of WO 2013/176772, a Rho-independent transcription termination site.

Modulation of Transcription

The demethylation of methylation protein conjugates provided herein are targeted by the DNA-targeting sequence of the subject polynucleotide to a specific location (i.e., target polynucleotide sequence) in the target DNA, and exert locus-specific modification of the target DNA (e.g., modifying the local chromatin status). In some cases, the changes are transient (e.g., transcription repression or activation). In some cases, the changes are inheritable (e.g., when epigenetic modifications are made to the target DNA or to proteins associated with the target DNA, e.g., nucleosomal histones).

The biological effects of a method using the complexes provided herein including embodiments thereof can be detected by any convenient method (e.g., gene expression assays; chromatin-based assays, e.g., Chromatin immuno-Precipitation (ChiP), Chromatin in vivo Assay (CiA), etc.; and the like).

Thus, in certain embodiments, a transcription modulation method of the present invention provides for selective modulation (e.g., reduction or increase) of a target nucleic acid in a host cell. For example, "selective" reduction of transcription of a target nucleic acid reduces transcription of the target nucleic acid by at least 10%, at least 20%, at least 30%, at least 40%, at least 50%, at least 60%, at least 70%, at least 80%, at least 90%, or greater than 90%, compared to the level of transcription of the target nucleic acid in the absence of a DNA-targeting sequence/modified Cas9 polypeptide/PUF domain-fusion complex. Selective reduction of transcription of a target nucleic acid reduces transcription of the target nucleic acid, but does not substantially reduce transcription of a non-target nucleic acid, e.g., transcription of a non-target nucleic acid is reduced, if at all, by less than 10% compared to the level of transcription of the non-target nucleic acid in the absence of the DNA-targeting sequence/modified Cas9 polypeptide/PUF domain-fusion complex.

On the other hand, "selective" increased transcription of a target DNA can increase transcription of the target DNA by at least 1.1 fold (e.g., at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20-fold) compared to the level of transcription of the target DNA in the absence of the complexes provided herein including embodiments thereof (e.g., DNA-targeting sequence/modified Cas9 polypeptide/PUF domain-fusion complex). Selective increase of transcription of a target DNA increases transcription of the target DNA, but does not substantially increase transcription of a non-target DNA, e.g., transcription of a non-target DNA is increased, if at all, by less than 5-fold (e.g., less than 4-fold, less than 3-fold, less than 2-fold, less than 1.8-fold, less than 1.6-fold, less than 1.4-fold, less than 1.2-fold, or less than 1.1-fold) compared to the level of transcription of the non-targeted DNA in the absence of the complexes provided herein including embodiments thereof (e.g., DNA-targeting sequence/modified Cas9 polypeptide/PUF domain-fusion complex).

In some embodiments, multiple subject polynucleotides are used simultaneously in the same cell to simultaneously modulate transcription at different locations on the same target DNA or on different target DNAs. In some embodiments, two or more subject polynucleotides target the same gene or transcript or locus. In some embodiments, two or more subject polynucleotides target different unrelated loci. In some embodiments, two or more subject polynucleotides target different, but related loci.

Because the subject polynucleotides are small and robust, they can be simultaneously present on the same expression vector and can even be under the same transcriptional control if so desired. In some embodiments, two or more (e.g., 3 or more, 4 or more, 5 or more, 10 or more, 15 or more, 20 or more, 25 or more, 30 or more, 35 or more, 40 or more, 45 or more, or 50 or more) subject polynucleotides are simultaneously expressed in a target cell, from the same or different vectors. The expressed subject polynucleotides can be differently recognized by orthogonal nuclease-deficient RNA-guided DNA endonucleases (dCas9 proteins) from different bacteria, such as *S. pyogenes, S. thermophilus, L. innocua*, and *N. meningitidis*.

To express multiple subject polynucleotides, the artificial RNA processing system mediated by the Csy4 endoribonuclease described in international application PCT/US2016/021491 and published as WO2016148994 A8, which is hereby incorporated by reference and for all purposes, may be used for the invention provided herein.

Host Cells

A method of the present invention to modulate transcription may be employed to induce transcriptional modulation in mitotic or post-mitotic cells in vivo and/or ex vivo and/or in vitro. Because the subject polynucleotide provides specificity by hybridizing to target polynucleotide sequence of a target DNA, a mitotic and/or post-mitotic cell can be any of a variety of host cells, where suitable host cells include, but are not limited to, a bacterial cell; an archaeal cell; a single-celled eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell; an animal cell; a cell from an invertebrate animal (e.g., an insect, a cnidarian, an echinoderm, a nematode, etc.); a eukaryotic parasite (e.g., a malarial parasite, e.g., *Plasmodium falciparum*; a helminth; etc.); a cell from a vertebrate animal (e.g., fish, amphibian, reptile, bird, mammal); a mammalian cell, e.g., a rodent cell, a human cell, a non-human primate cell, etc. Suitable host cells include naturally-occurring cells; genetically modified cells (e.g., cells genetically modified in a laboratory, e.g., by the "hand of man"); and cells manipulated in vitro in any way. In some cases, a host cell is isolated or cultured.

Any type of cell may be of interest (e.g., a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells," "primary cell lines," and "primary cultures" are used interchangeably herein to refer to cells and cells cultures that have been derived from a subject and allowed to grow in vitro for a limited number of passages, i.e. splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are in many embodiments unicellular organisms, or are grown in culture.

If the cells are primary cells, such cells may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g., from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or other solutions commonly used in the art to preserve cells at such freezing temperatures, and thawed in a manner as commonly known in the art for thawing frozen cultured cells.

Introducing Nucleic Acid into a Host Cell

A subject polynucleotide, a nucleic acid comprising a nucleotide sequence encoding same, or a nucleic acid comprising a nucleotide sequence encoding the subject nuclease-deficient RNA-guided DNA endonuclease (dCas9 protein) or demethylation or methylation protein conjugate (PUF domain fusion), can be introduced into a host cell by any of a variety of well-known methods.

Methods of introducing a nucleic acid into a host cell are known in the art, and any known method can be used to introduce a nucleic acid (e.g., vector or expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., *Adv. Drug Deliv. Rev.*, pii: 50169-409X(12) 00283-9.doi:10.1016/j.addr.2012.09.023), and the like.

Thus the present invention also provides an isolated nucleic acid comprising a nucleotide sequence encoding a subject polynucleotide. In some cases, a subject nucleic acid also comprises a nucleotide sequence encoding a nuclease-deficient RNA-guided DNA endonuclease (dCas9 protein) and/or a demethylation or methylation protein conjugate (PUF domain fusion).

In some embodiments, a subject method involves introducing into a host cell (or a population of host cells) one or more nucleic acids (e.g., vectors) comprising nucleotide sequences encoding a subject polynucleotide and/or a nuclease-deficient RNA-guided DNA endonuclease (dCas9 protein) and/or a demethylation or methylation protein conjugate (PUF domain fusion). In some embodiments a host cell comprising a target DNA is in vitro. In some embodiments a host cell comprising a target DNA is in vivo. Suitable nucleic acids comprising nucleotide sequences encoding a subject polynucleotide and/or a nuclease-deficient RNA-guided DNA endonuclease (dCas9 protein) and/or a subject demethylation or methylation protein conjugate (PUF domain fusion) include expression vectors, where the expression vectors may be recombinant expression vector.

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., *Invest Opthalmol. Vis. Sci.*, 35:2543-2549, 1994; Borras et al., *Gene Ther.*, 6:515-524, 1999; Li and Davidson, *Proc. Natl. Acad. Sci. USA*, 92:7700-7704, 1995; Sakamoto et al., *Hum. Gene Ther.*, 5:1088-1097, 1999; WO 94/12649, WO 93/03769; WO 93/19191; WO 94/28938; WO 95/11984 and WO 95/00655); adeno-associated virus (see, e.g., Ali et al., *Hum. Gene Ther.*, 9:81-86, 1998, Flannery et al., *Proc. Natl. Acad. Sci. USA*, 94:6916-6921, 1997; Bennett et al., *Invest Opthalmol Vis Sci* 38:2857-2863, 1997; Jomary et al., *Gene Ther.*, 4:683-690, 1997, Rolling et al., *Hum. Gene Ther.*, 10:641-648, 1999; Ali et al., *Hum. Mol. Genet.*, 5:591-594, 1996; Srivastava in WO 93/09239, Samulski et al., *J. Vir.*, 63:3822-3828, 1989; Mendelson et al., *Virol.*, 166: 154-165, 1988; and Flotte et al., *Proc. Natl. Acad. Sci. USA*, 90: 10613-10617, 1993); SV40; herpes simplex virus; human immunodeficiency virus (see, e.g., Miyoshi et al., *Proc. Natl. Acad. Sci. USA*, 94: 10319-23, 1997; Takahashi et al., *J. Virol.*, 73:7812-7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, HIV virus, myeloproliferative sarcoma virus, and mammary tumor virus); and the like.

Numerous suitable expression vectors are known to those skilled in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell. Any one of the vectors described in international application PCT/US2016/021491 and published as WO2016148994 A8, which is hereby incorporated by reference and for all purposes, is contemplated for the complexes and methods provided herein including embodiments thereof.

Exemplary Utilities

A method for modulating transcription according to the present invention finds use in a variety of applications, including research applications; diagnostic applications; industrial applications; and treatment applications.

Research applications may include, e.g., determining the effect of reducing or increasing transcription of a target nucleic acid on, e.g., development, metabolism, expression of a downstream gene, and the like.

High through-put genomic analysis can be carried out using a subject transcription modulation method, in which only the DNA-targeting sequence of the subject polynucleotide needs to be varied, while the binding sequence (Cas9-binding sequence) and the PBS sequence can (in some cases) be held constant. A library (e.g., a subject library) comprising a plurality of nucleic acids used in the genomic analysis would include: a promoter operably linked to a subject polynucleotide-encoding nucleotide sequence, where each nucleic acid would include a different DNA-targeting sequence, a common binding sequence (Cas9-binding sequence), and a common PBS sequence. A chip could contain over $5 \times 10^4$ unique polynucleotide of the invention.

Applications would include large-scale phenotyping, gene-to-function mapping, and meta-genomic analysis as described in international application PCT/US2016/021491 and published as WO2016148994 A8, which is hereby incorporated by reference and for all purposes.

The subject methods disclosed herein can also find use in the field of metabolic engineering as described in international application PCT/US2016/021491 and published as WO2016148994 A8, which is hereby incorporated by reference and for all purposes.

The methods disclosed herein can also be used to design integrated networks (i.e., a cascade or cascades) of control as described in international application PCT/US2016/021491 and published as WO2016148994 A8, which is hereby incorporated by reference and for all purposes.

A subject transcription modulation method can also be used for drug discovery and target validation as described in international application PCT/US2016/021491 and published as WO2016148994 A8, which is hereby incorporated by reference and for all purposes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Examples

Example 1: sgRNA Scaffold Remains Functional with Insertion of 47 Copies of Engineered Pumilio Binding Sites This example demonstrates that the subject 3-component CRISPR/Cas complex/system can have at least 47 copies of the engineered 8-mer Pumilio homologue domain-binding sequences (PBSs) at the 3' end of sgRNA, without substantially affecting the function of the dCas9/sgRNA complex.

In particular, to test whether appending PBS to the 3' end of sgRNA affects sgRNA function, a series of modified Tet-targeting (sgTetO) or non-targeting control (sgControl) sgRNA were generated, with 0 copy, 5 copies, 15 copies, 25 copies, and 47 copies of the 8-mer Pumilio homologue domain-binding sequence (PBS) for PUF (3-2) (also simply referred to as PUFa) [PBS32 or PBSa: SEQ ID NO:8 (5'-UGUAUgUGA-3')], PUF(6-2/7-2) (also simply referred to as PUFb) [PBS6272 or PBSb: SEQ ID NO:9 (5'-UugAUAUA-3')]. See FIG. 1A. The ability of these constructs to direct the dCas9-VP64 transcriptional activator to activate tdTomato expression in a HEK293T/TetO::tdTomato cell line was tested.

Figure 1B:
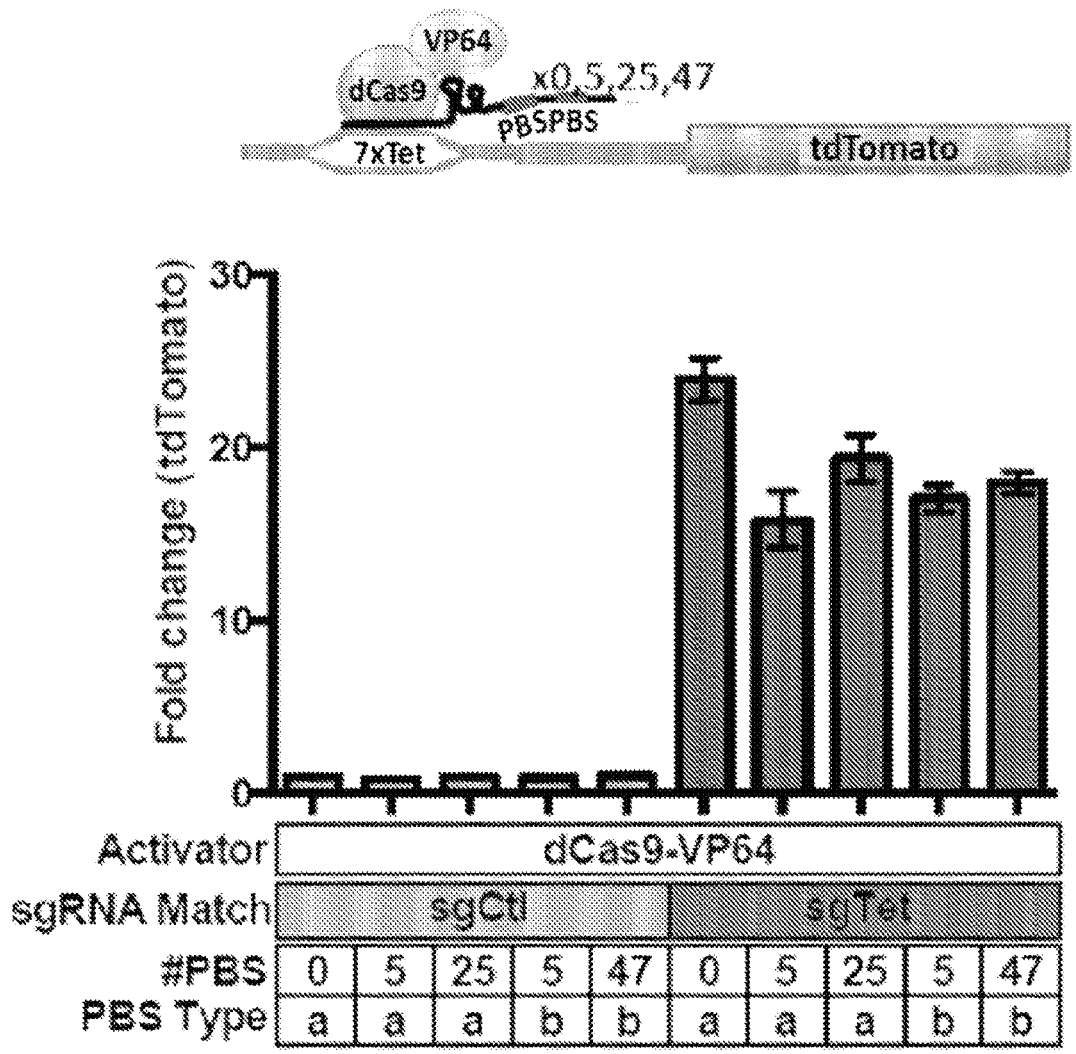
Figure 1C:
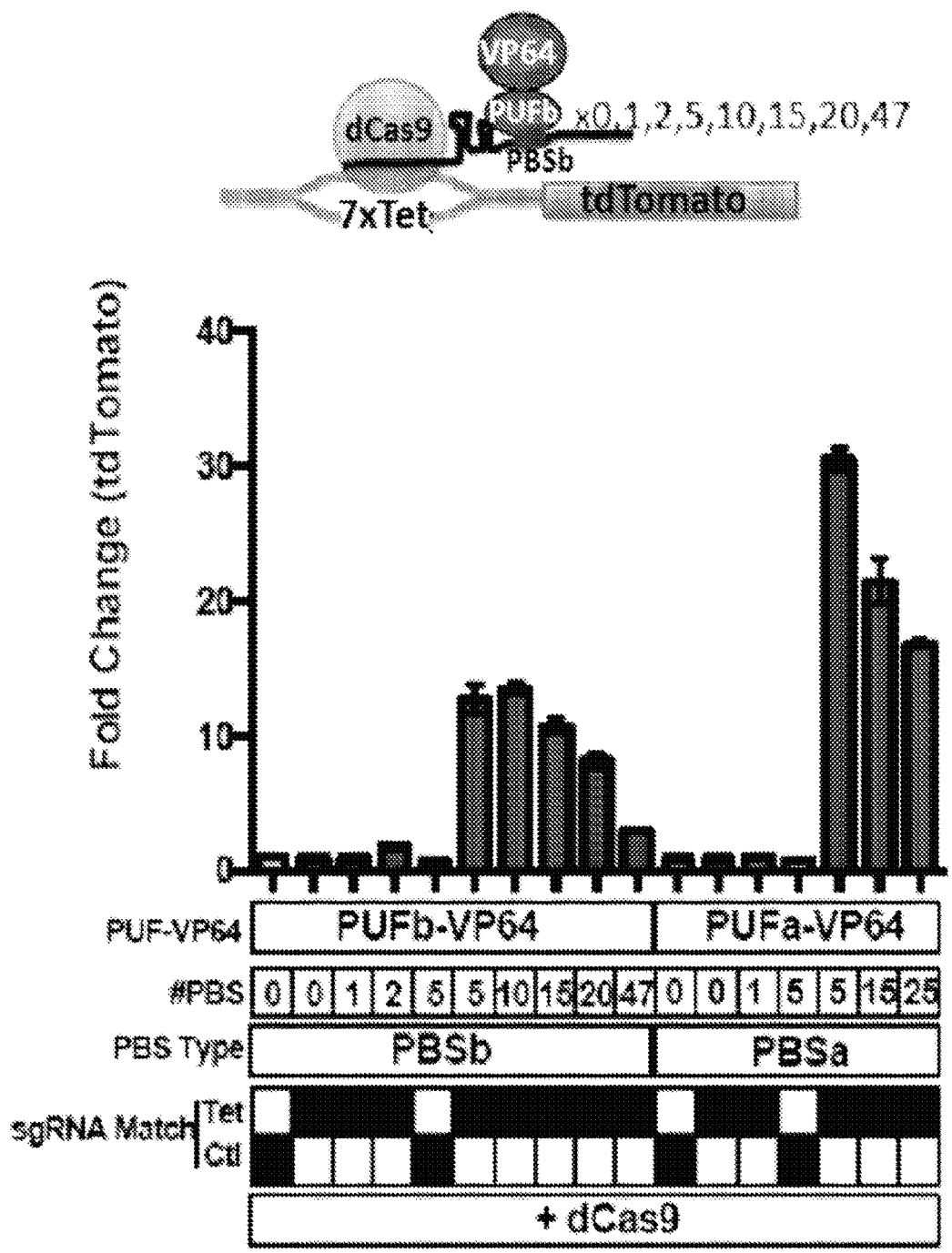

Cells were transfected with dCas9-VP64 with the different sgRNA scaffolds, and were analyzed by fluorescent-activated cell sorting (FACS) two days after transfection (FIG. 1B). All the control non-targeting sgRNAs did not activate tdTomato expression. Meanwhile, all the Tet-targeting sgRNAs with different number of PBS could direct dCas9-VP64 to activate tdTomato expression, showing that insertion of at least 47 copies of 8-mer sites do not substantially impact the activity of sgRNA in directing dCas9-VP64 to its targets (FIG. 1C).

Under the test condition, and for both PUFa-VP64/PBSa and PUFb-VP64/PBSb, 5-10 copies of PBS appended to the sgRNA were best able to activate the target transgene. Meanwhile, 15, 20, and 47 copies of PBS led to slightly lower, albeit still substantial transgene activation (FIG. 1C).

Example 2: The Subject 3-Component CRISPR/Cas Complexes/Systems are Orthogonal to Each Other Due to the Specificity of the Engineered Pumilio with the Cognate 8-mer Binding Sites This example demonstrates that specificity between the differently programmed PUF domains and their corresponding sgRNA with their cognate 8-mer motifs provide independence or orthogonality between each of the subject 3-component CRISPR/Cas complex/system.

Fusions of PUF(3-2)::VP64 and PUF(6-2/7-2)::VP64, which interacts with sgRNA (sgRNA-PBS32) with 5'-UGUAUgUA-3' binding sites and sgRNA-PBS6272 with 5'-UugAUAUA-3' binding sites, respectively, were created, and their activity to turn on tdTomato expression in conjunction with dCas9 was tested. In addition, two additional pairs, PUFw-VP64 recognizing PBSw (5'-UGUAUAUA-3') and PUFc-VP64 recognizing PBSc (5'-UugAUgUA-3'), were also constructed to test their ability to activate the same TetO::tdTomato expression in conjunction with dCas9 (FIG. 1D).

Figure 1D:
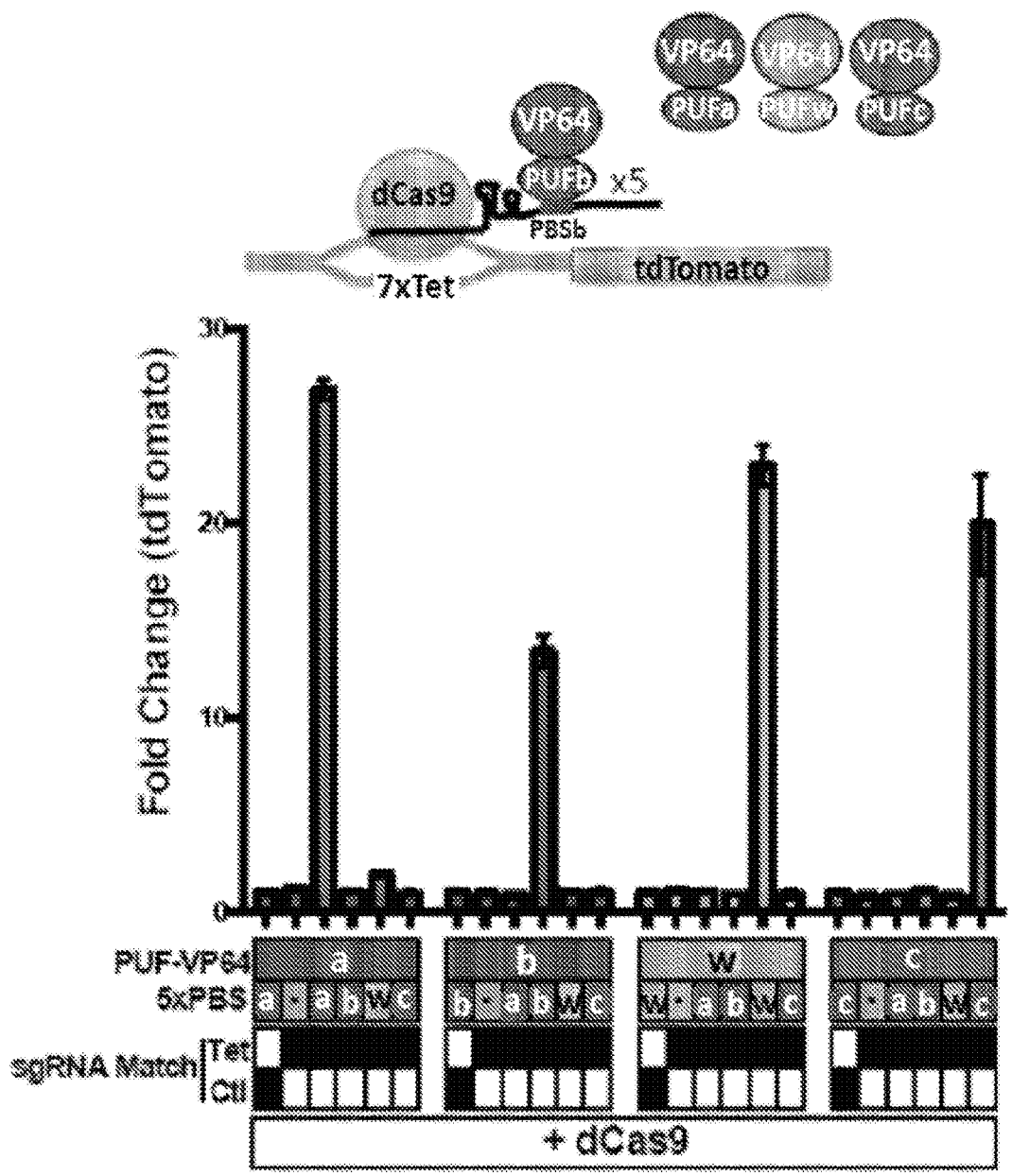

As shown in FIG. 1D, PUF::VP64 can activate tdTomato expression only when the sgRNA with the cognate binding sites were provided. This demonstrates that the subject 3-component CRISPR/Cas complex/system provides independence or orthogonality of effector function based on the pairing of PUF domains and their 8-mer binding sites on the sgRNA-PBS. Impressively, although PBSa and PBSw binding sites only differ by one nucleotide, their gene activation remains target-specific, demonstrating the high specificity of the subject 3-component CRISPR/Cas complex/system.

Example 3: The Subject 3-Component CRISPR/Cas Complex/System Allows Assembly of Protein Complex at Target Loci This example demonstrates that protein complexes with two or more different protein components can be assembled on sgRNA and operate at defined loci using the subject system.

Figure 2A:
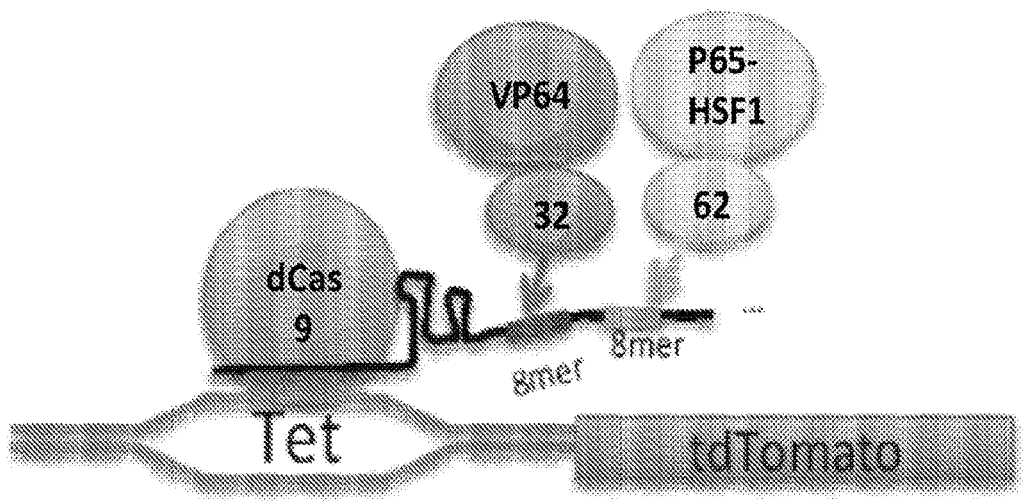
FIGS. 2A-2C.
Figure 2B:
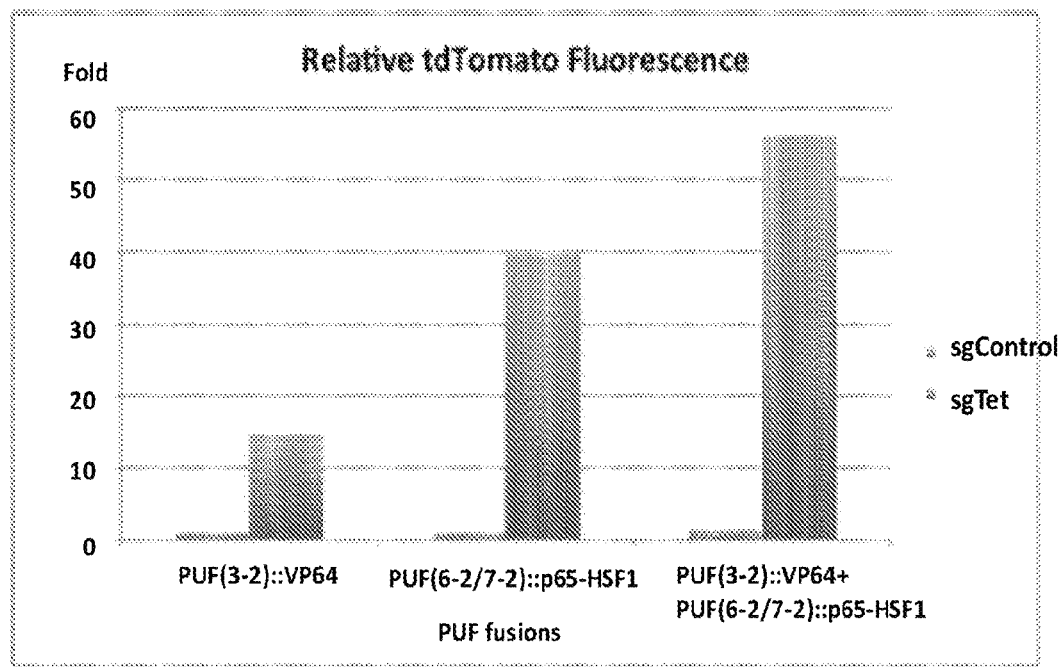

Specifically, p65-HSF1 has recently been shown to be a potent activator domain. An sgRNA with both PBS32 and PBS6272 positioned next to each other, and PUF(3-2)::VP64 and PUF(6-2/7-2)::p65-HSF1 fusions that would occupy the two different sites, were generated (FIG. 2A). Co-transfection of both PUF(3-2)::VP64 and PUF(6-2/7-2)::p65-HSF1 induced a tdTomato fluorescence, with an intensity about the sum of the fluorescent intensity resulting from transfecting the single activators alone. This indicates that sgRNA with binding sites for both PUF(3-2) and PUF(6-2/7-2) allows both fusion proteins of both types to assemble on the targeted genomic locus.

Figure 2C:
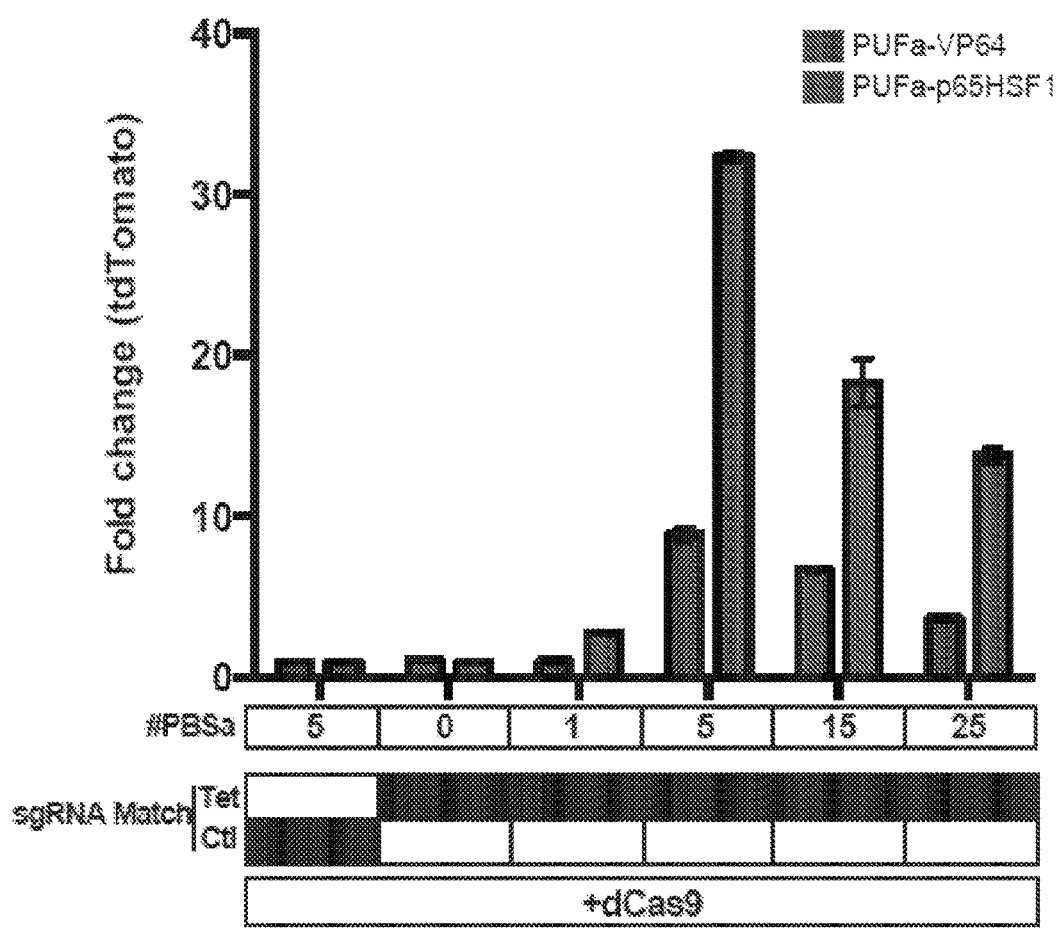

A recent paper has tested both VP64 and p65HSF1 as transcriptional activation domains, and found p65HSF1 to be a more potent activator. To directly compare these two transcriptional activation domains, p65HSF1 PUF fusion (PUFa-p65HSF1) and VP64 PUF fusion (PUFa-VP64) were used to activate the TetO::tdTomato transgene using sgRNA with different number of PBSa (FIG. 2C). PUFa-p65HSF1 provided up to 3 times more activation as did PUFa-VP64. Activation was observed even with only one PBSa (previously not observed with PUFa-VP64 module). Thus p65HSF1 is confirmed to be a more potent transcriptional activation domain than VP64.

Cloning. A list of vectors, links to their Addgene entries are provided in Table Si below. Detailed description of cloning strategies and sequences are given below.

PUFa [PUF(3-2)] and PUFb [PUF(6-2/7-2)] with N-terminal NLS were amplified from constructs containing these coding sequences with primers containing SgrAI and PacI sites and were used to replace SgrAI-dCas9-FseI from pAC164:pmax-dCas9Master_VP64 to create pAC1355: pmax-NLSPUFa_VP64 and pAC1356:pmax-NLSPUFb_VP64. A fusion PCR with 5' fragment up to repeat 4 of NLSPUFb and 3' fragment from repeat 5 to the end of NLSPUFa was used to create pAC1357:pmax-NLSPUFw_VP64. A fusion PCR of 5' fragment of NLSPUFa with 3' fragment of NLSPUb was used to create pAC1358: pmax-NLSPUFc_VP64.

p65HSF1 activator ORF was amplified from MS2-P65-HSF1_GFP (Addgene: 61423) with FseI PacI sites to replace VP64 fragment in pAC164 to create pAC1410:pmax-dCas9_p65HSF1, and replace VP64 in pAC1355 and pAC1358 to create pAC1393: pmax-NLSPUFa_p65HSF1 and pAC1411:pmax-NLSPUFc_p65HSF1, respectively.

The FseI-p65HSF1-PacI fragment was released from pAC1393 and ligated with SgrAI-NLSPUMb fragment released from pAC1356 and pAC1360 digested with SgrAI-PacI as vector to create pAC1413: PB3-neo(-)-pmax-NLSPUFb_p65HSF1. The BFPKRAB fragment was amplified from pHR-SFFV-dCas9-BFP-KRAB (Addgene #46911) and was used to replace Clover fragment from pAC1360 to create pAC1414: PB3-neo(-)-pmax-BFPKRAB_NLSPUFa. Then, an NheI-CAGGS-NLSPUFb_p65HSF1-NheI fragment was amplified from pAC1413 and inserted into pAC1414 digested with NheI to create a dual expression vector for BFPKRAB-NLSPUFa and NLSPUFb-p65HSF1 (pAC1414: PB3-NLSPUFb_p65HSF1(-)neo(-)-BFPKRAB2_NLSPUFa).

Four gateway donor vectors with improved linker sequences and three extra NLS on the N-terminal and one additional NLS on the C-terminal of PUF as well as cloning sites for N-terminal (SgrAI, ClaI) and C-terminal (FseI-PacI) insertions were created (pAC1404-1408). HAT sequence was amplified from mouse Crebbp gene using mouse cDNA with primers containing FseI-PacI site and inserted into pAC164 to create pAC1364: pmax-dCas9Master_CBPHAT and into pAC1405 to create pAC1415: pCR8-4×NLSPUFa_2×NLS_CBPHAT. HAT sequence was amplified with another pair of primers containing SgrAI-AclI site and cloned into SgrAI-ClaI site of pAC1405 to create pAC1416: pCR8-CBPHAT_4×NLSPUFa_2×NLS. pAC1415 and pAC1416 were recombined into pAC90:pmax-DEST (Addgene #48222) to create expression vectors pAC1417: pmax-4×NLSPUFa_2×NLS_CBPHAT and pAC1418: pmax-CBPHAT_4×NLSPUFa_2×NLS, respectively. FseI-mCherry-PacI fragment was amplified from a plasmid containing mCherry sequence and ligated with SgrAI-dCas9-FseI to PB3-neo(-)-pmax to generate pAC1419: PB3-neo(-)-pmax-dCas9Master_mCherry.

Expression vectors for sgRNA-PBS were constructed as follows: First, a sgRNA scaffold based on sgF+E with BbsI for oligo cloning of guide sequence and with 3' BsaI (right upstream of the terminator) for insertion of PBS were ordered as a gBlock (IDT), and were cloned into pX330 (Addgene #42230) replacing the AflIII-NotI region to create vector pAC1394: pX-sgFE-BsaI(AGAT). Then, oligos encoding 5×PBSa sites each separated by ggc-spacer flanked by 5'-AGAT-3' overhangs on one side and 5'-ATCT-3' on the other side were treated with T4PNK and annealed and ligated into pAC1394 digested with BsaI (to create compatible overhangs). Clones were then screened for 1 copy (5×PBS), 2 copies (10×PBS), etc of the oligo insertions for the different number of PBS. For 1×PBS and 2×PBS vectors, they were constructed using oligo containing one PBS site. Guide sequence for each target were then cloned onto the sgRNA-PBS expression vectors via BbsI site as previously described. For sgRNA expression vectors with GFP expression markers, they were constructed by transferring the sgRNA-PBS expression cassette from the pX vectors onto a PB-GFP vector via AscI site. The different sgRNA expression constructs are listed in Table S1.

Cell Culture for Experiments. HEK293T cells were cultivated in Dulbecco's modified Eagle's medium (DMEM) (Sigma) with 10% fetal bovine serum (FBS)(Lonza), 4% Glutamax (Gibco), 1% Sodium Pyruvate (Gibco) and penicillin-streptomycin (Gibco). Incubator conditions were 37° C. and 5% $CO_2$. For activation experiments, cells were seeded into 12-well plates at 100,000 cells per well the day before being transfected with 200 ng of dCas9 construct, 100 ng of modified sgRNA and 100 ng of PUF-fusion with Attractene transfection reagent (Qiagen). After transfection, cells were grown for 48 hrs and harvested for either RNA extraction or fluorescent-activated cell sorting (FACS). For dual activation-repression experiments, transfection remained the same, however cells were seeded into 12-well plates at 150,000 cells per well and were grown for 72 hrs before being harvested for FACS. For experiments with OCT4 and SOX2 dual activation-repression, cells were triple-sorted by BFP (for the activator-repressor module PUFb-p65HSF1/BFPKRAB-PUFa), mCherry (for dCas9mCherry) and GFP (for the sgRNA-PBS on vectors co-expressing EGFP) before RNA extraction. For imaging experiments, cells were seeded into 6-well plates with 22×22×1 microscope cover glass at 300,000 cells per well the day before being transfected with 50 ng of dCas9 construct, 500 ng of modified sgRNA, and 50 ng of a PUF-fluorescent fusion with Attractene transfection reagent. After transfection, cells were grown for 48 hrs then immunostained.

Quantitative RT-PCR Analysis. Cells were harvested with trypsin, washed with Dulbecco's phosphate-buffered saline (dPBS), centrifuged at 125 g for 5 mins and then RNA was extracted using RNeasy Plus Mini Kit (Qiagen). A cDNA library was made using Applied Biosystems High Capacity RNA-to-cDNA kit with 1 μg of RNA. TaqMan Gene expression assays (Applied Biosystems) were designed using GAPDH (Hs03929097, VIC) as endogenous control and OCT4 (Hs00999632, FAM) and SOX2 (Hs01053049, FAM) as targets. TaqMan Universal Master Mix II, with UNG (Applied Biosystems) was used for Quantitative PCR (qPCR), with 2 μl of 1:10 diluted cDNA used for each reaction. Activation was analyzed with the Applied Biosystems ViiA7 instrument. Gene expression levels were calculated by "delta delta Ct" algorithm and normalized to control samples.

Fluorescent-Activated Cell Sorting. Cells were trypsinized and fixed for 10 min with 2% paraformaldehyde. Afterwards, the cells were centrifuged at 125 g for 5 min and resuspended in dPBS. Samples were analyzed on a FACScalibur flow cytometer using CellQuest Pro software (BD Bioscience). thousands events were collected in each run.

Sequences of some of the constructs used in the examples above and the related sequences are listed herein below.

>NLSPUFa_VP64 Key: NLS PUFa VP64

SEQ ID NO: 32

MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID

In the above sequence, the NLS sequence is residues 6-12, PUFa (SEQ ID NO:2) is residues 15-363, and VP64 is residues 371-421.

>NLSPUFb_VP64 Key: NLS PUFb VP64

SEQ ID NO: 33

MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGCRVIQKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGSYVIEHVLEHGRPEDKSKIVA

EIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID

In the above sequence, the NLS sequence is residues 6-12, PUFb (SEQ ID NO:3)is residues 15-363, and VP64 is residues 371-421.

>NLSPUFw_VP64 Key: NLS PUFw VP64

SEQ ID NO: 34

MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGCRVIQKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGNYVIQHVLEHGRPEDKSKIVA

EIRGNVLVLSQHKFASNVVEKCVTHASRTERAVLIDEVCTMNDGPHSALY

TMMKDQYANYVVQKMIDVAEPGQRKIVMHKIRPHIATLRKYTYGKHILAK

-continued

LEKYYMKNGVDLGGPAGSGRADALDDFDLDMLGSDALDDFDLDMLGSDAL

DDFDLDMLGSDALDDFDLDMLYID

In the above sequence, the NLS sequence is residues 6-12, PUFw (SEQ ID NO:5) is residues 15-363, and VP64 is residues 371-421.

>NLSPUFc_VP64 Key: NLS PUFc VP64

SEQ ID NO: 35

MGILPPKKKRKVSRGRSRLLEDFRNNRYPNLQLREIAGHIMEFSQDQHGS

RFIQLKLERATPAERQLVFNEILQAAYQLMVDVFGNYVIQKFFEFGSLEQ

KLALAERIRGHVLSLALQMYGSRVIEKALEFIPSDQQNEMVRELDGHVLK

CVKDQNGNHVVQKCIECVQPQSLQFIIDAFKGQVFALSTHPYGCRVIQRI

LEHCLPDQTLPILEELHQHTEQLVQDQYGSYVIEHVLEHGRPEDKSKIVA

EIRGNVLVLSQHKFANNVVQKCVTHASRTERAVLIDEVCTMNDGPHSALY

TMMKDQYANYVVQKMIDVAEPGQRKIVMHKIRPHIATLRKYTYGKHILAK

LEKYYMKNGVDLGGPAGSGRADALDDFDLDMLGSDALDDFDLDMLGSDAL

DDFDLDMLGSDALDDFDLDMLYID

In the above sequence, the NLS sequence is residues 6-12, PUFc (SEQ ID NO:4) is residues 15-363, and VP64 is residues 371-421.

Example 4: Targeted DNA Demethylation and Methylation Using the Subject 3-Component CRISPR/Cas Complex/System (Casilio) and dCas9-Tethered Enzymes For the sake of simplicity, the subject 3-component CRISPR/Cas Complex/System may also be referred to as "Casilio" herein.

Using Casilio-ME with a Tet1 effector, the Example demonstrated a robust activation of hMLH1 transcription, a gene that is epigenetically silenced in HEK293T cells and other cancer cells due to hypermethylation in the promoter regions. Reactivation of hMLH1 transcription leads to (restoration of) expression of MLH1 protein. The Example showed that Casilio-ME-mediated delivery of TET1 activity to hMLH1 promoter region induced a robust cytosine demethylation within the targeted CpG island, providing a proof-of-principal that Casilio-ME is a robust platform to editing methylcytosine mark of the epigenome.

On the other hand, it was also shown that targeting Casilio-ME with a Dnmt effector to the SOX2 promoter leads to gene repression, demonstrating the potential of directed Dnmt-mediated DNA methylation to modify gene expression or epigenetic states at desired loci.

Results

Effect of Casilio-mediated delivery of demethylation enzymes to specific genomic locus on gene expression. To develop simple yet effective tools that enable delivery of demethylation enzymes to specific genomic locus to permit targeted alteration of its epigenetic methylation state, the Casilio-ME system was engineered. This is built on the three-component Casilio platform (see PCT/US2016/021491; 62/132,644; and 62/221,249; also see Cheng, A. W., et al., *Casilio: a versatile CRISPR-Cas9-Pumilio hybrid for gene regulation and genomic labeling*. Cell Res, 2016. 26(2): p. 254-7, incorporated by reference) that uses nuclease-deficient dCas9, modified sgRNAs containing sites for Pumilio (PUF) RNA binding domain (sgRNA-PBS) and an effector module made of Pumilio RNA binding domain fused to an effector protein. dCas9 binds DNA when complexed with sgRNA without producing double-stranded breaks, serving as a RNA-programmable DNA binding protein whose specificity is determined by a sequence in the sgRNA component of the system. PUF domains can be programmed to bind to any 8-mer RNA sequences (PBS) appended in multiple copies to the 3' end of the sgRNA without interfering with the sgRNA-mediated DNA binding of dCas9 (Cheng, A. W., et al., *Casilio: a versatile CRISPR-Cas9-Pumilio hybrid for gene regulation and genomic labeling*. Cell Res, 2016. 26(2): p. 254-7). The presence of PBS in multiple copies on sgRNA allows tethering of multiple copies of PUF-effector module(s) to genomic sites, and therefore potentiates achieving strong amplification of the response to any effector module in application.

To enable a Casilio-mediated cytosine demethylation and subsequent gene activation at specific genomic locus, TET1-effector modules were constructed as N-terminal or C-terminal fusions of PUFa to hTET1 catalytic domain that includes residues 1418 to 2136 (TET1(CD)). The promoter region of hMLH1, whose hypermethylation is known to induce silencing of hMLH1 expression (Deng, G., et al., *Methylation of CpG in a small region of the hMLH1 promoter invariably correlates with the absence of gene expression*. Cancer Res, 1999. 59(9): p. 2029-33), was chosen as the target for this study.

MLH1 protein is a component of the methyl directed mismatch repair system of the cell. hMLH1 is in fact silenced in HEK293T cells as is in other cancer cells, and therefore represents a good cellular model to test TET1-effectors in their ability to induce demethylation-mediated gene activation. Nine sgRNAs were designed around the promoter region whose methylation is associated with down-regulation of hMLH1 in cancer cells (FIG. 3A) (Deng, G., et al., *Methylation of CpG in a small region of the hMLH1 promoter invariably correlates with the absence of gene expression*. Cancer Res, 1999. 59(9): p. 2029-33).

Figure 3B:
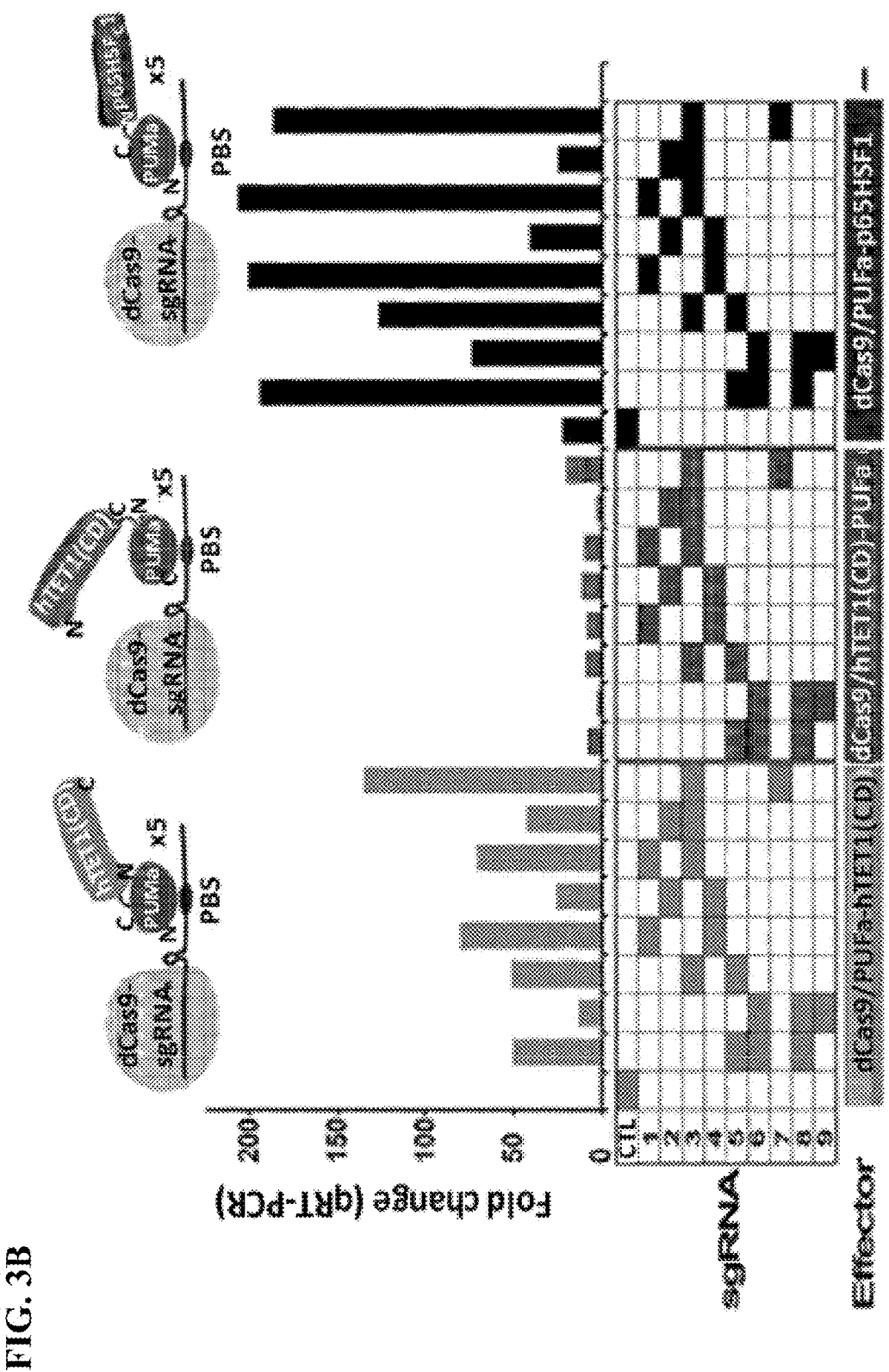

To test the system, HEK293T cells were transfected with Casilio-ME components including Ct or Nt-fusion TET1-effector and a combination of 3 or 2 sgRNAs. Relative levels of hMLH1 mRNA were determined in TaqMan assays by using RNA extracted from cells 60 hours post-transfection and GAPDH as endogenous control for normalization of qRT-PCR measurements. This showed that PUFa-TET1 (CD)C-terminal fusion effector restored a robust hMLH1 expression that reached 135 fold over background in the presence sgRNAs 3+7 (FIG. 3B). However, TET1(CD)-PUFa N-terminal effector fusion showed a much weaker activation (20 fold at best) in the presence of the same sgRNA combo, presumably due to steric hindrance as TET1 (CD) is natively located at the C-terminus of TET1 full length protein. Thus indicating that Casilio-mediated delivery of demethylation enzymes to specific genomic locus enables robust alteration of gene expression.

To compare the obtained TET1-mediated activation of hMLH1 expression with an activation induced by recruiting transcription factor and transcription machinery to hMLH1 promoter, TET1-effector was replaced by p65HSF1-effector. Using the same sgRNAs combo, this showed higher activation that reached 200-fold over the background (FIG. 3B). This therefore shows that Casilio-ME-mediated activation of hMLH1 expression can achieve about 70% of the activation obtained by a strong transcription activator module such as p65HSF1, indicating that Casilio-ME is an efficient tool enabling efficient targeting and delivery of demethylation enzymes to alter methylation state of the genome and the associated silencing activities.

Effect of delivery of dCas9-tethered demethylation enzymes to specific locus on gene expression. Direct fusions to dCas9 protein had extensively been used to target effectors to specific genomic locus and had also recently been used to deliver TET1(CD) to induce demethylation and associated gene activation (Morita, S., et al., Targeted DNA demethylation in vivo using dCas9-peptide repeat and scFv-TET1 catalytic domain fusions. Nat Biotechnol, 2016; Xu, X., et al., A CRISPR-based approach for targeted DNA demethylation. Cell Discov, 2016. 2: p. 16009).

Figure 3C:
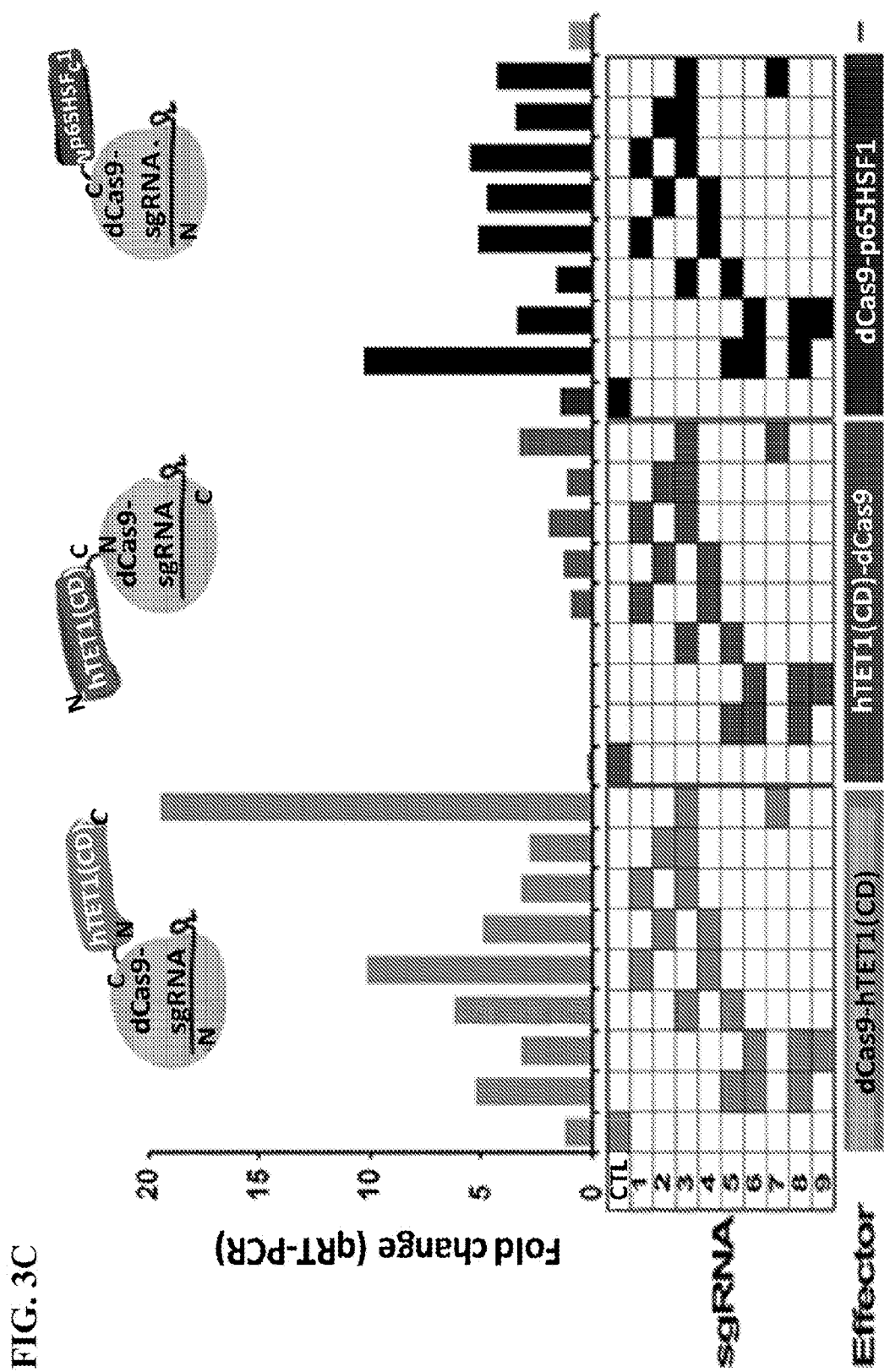

To assess the efficiency of dCas9-TET1(CD) direct fusion to activate hMLH1 expression in HEK293T cells in comparison to Casilio-ME, N-terminal and C-terminal fusions of dCas9 to TET1(CD) were constructed. Using the same combination of sgRNAs as in the Casilio-ME experiments, the dCas9-TET1(CD)C-terminal fusion showed a relatively weak activation of hMLH1, as indicated by the relative change in mRNA levels (FIG. 3C). dCas9-TET1(CD)-induced activation represents at best about 14% of the obtained activation using the Casilio-ME with the same sgRNAs combination in parallel experiment (19- vs 135-fold change in mRNA levels). In contrast, TET1(CD)-dCas9 fusion showed a much weaker activation than its respective C-terminal fusion, indicating a possible steric hindrance affecting TET1 activity when N-terminally fused to either dCas9 or PUFa proteins (FIGS. 3B & 3C).

To compare hMLH1 activation obtained with dCas9-TET1 to that of a transcriptional activator, HEK293T cells were transfected with dCas9-p65HSF1 along with the same sgRNA combination. Analysis of mRNA levels showed that dCas9-TET1 activation of hMLH1 was at best twice the activity obtained with transcription activator dCas9 fusion (FIG. 3C), therefore indicating that TET1 targeting to specific locus can activate gene, presumably via alteration of epigenetic DNA methylation at the target site. However hMLH1 activation obtained with Casilio-ME is significantly more efficient than that obtained with dCas9-TET1(CD) direct fusion, indicating the great potential of Casilio-ME platform as an effective and adaptable tool to deciphering the implication of cytosine hypermethylation in numerous biological and pathological systems.

Casilio-mediated delivery of demethylation enzymes alters methylation state of targeted genomic locus. Evidence that the shown Casilio-ME-induced activation of hMLH1 transcription is a result of TET1-mediated cytosine demethylation within the targeted promoter region came from DNA sequencing of hMLH1 promoter after bisulfite conversion. Bisulfite treatment of genomic DNA deaminates unmethylated cytosines to produce uracils that are subsequently replicated as thymine. However, methylated cytosines are protected from conversion to uracils, thus allowing one to determine cytosine methylation states at single-nucleotide resolution by direct sequencing.

Figure 4A:
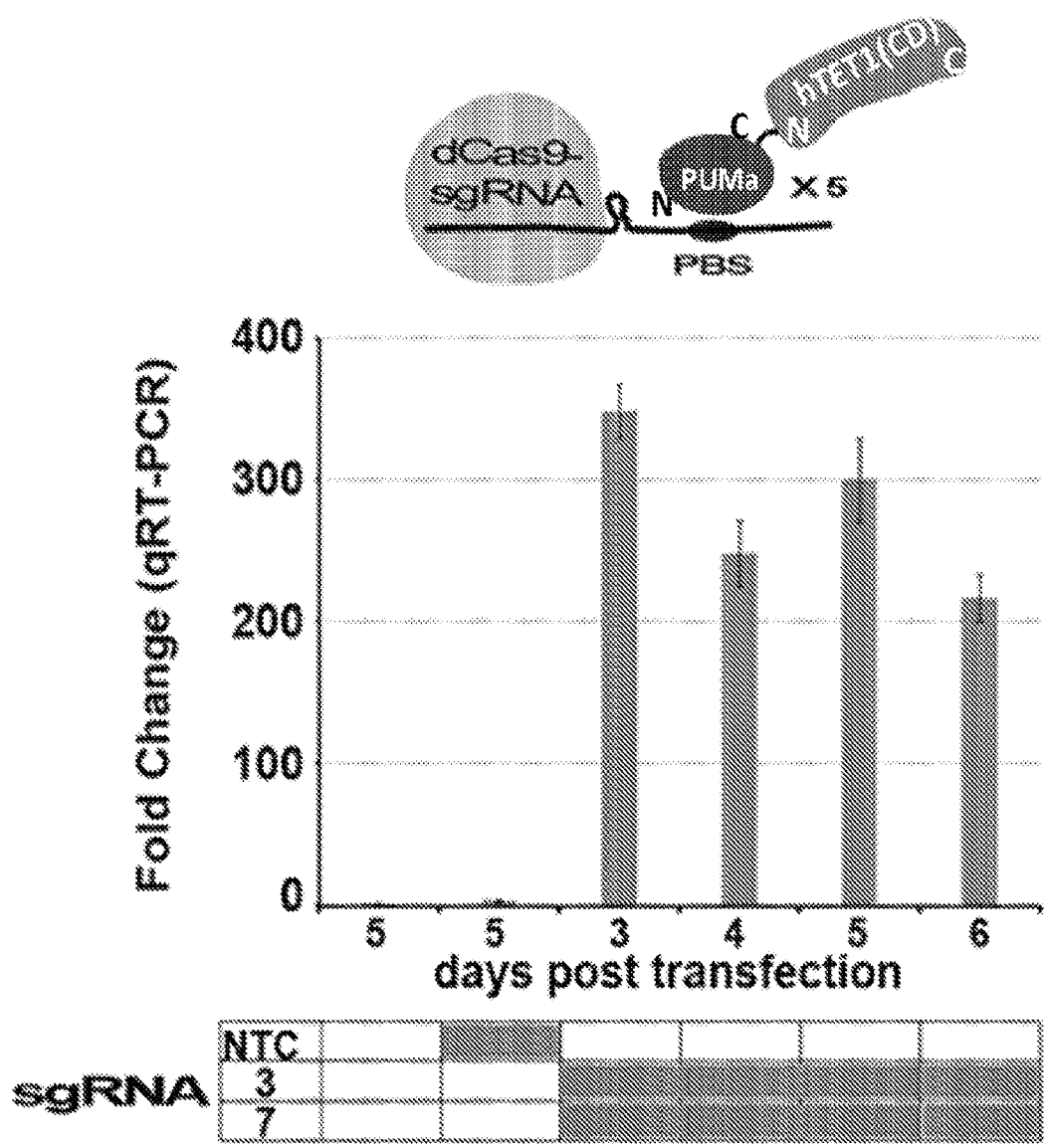
FIGS. 4A-4C. The figures show that Casilio-ME mediates robust demethylation of methylcytosine via targeting TET1 activity to hMLH1 promoter region.

To assess changes in methylation states of CpG island within hMLH1 promoter region after Casilio-ME-mediated transcription activation, time course experiment were carried out where cells were collected 3, 4, 5, and 6 days post transfection, for analysis of cytosine methylation as well as transcription activation, and protein expression. HEK293T were transfected with Casilio-ME components that includes Ct-fusion PUFa-TET1 effector and a combination of 2 sgRNAs (RNA guides 3 and 7). TaqMan assays showed that the activation of hMLH1 transcription was maintained during the course of these transient transfections (FIG. 4A), thus showing a sustained change of hMLH1 mRNA levels during the 6 days of the experiment.

Figure 4B:
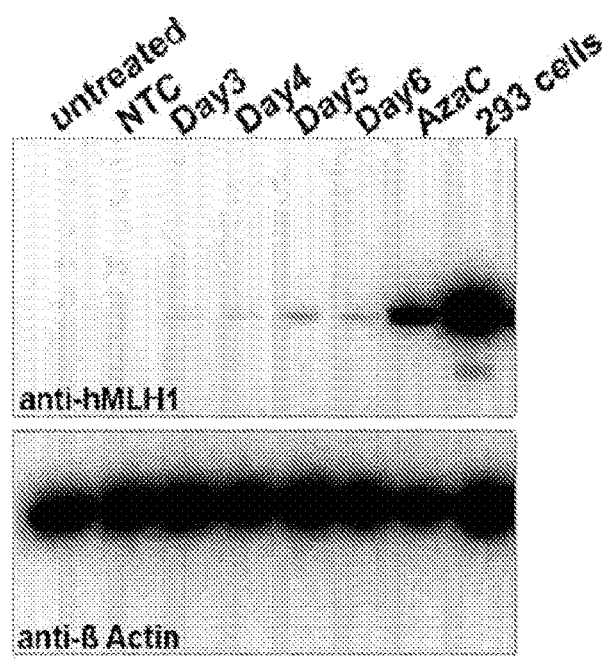
Figure 4C:
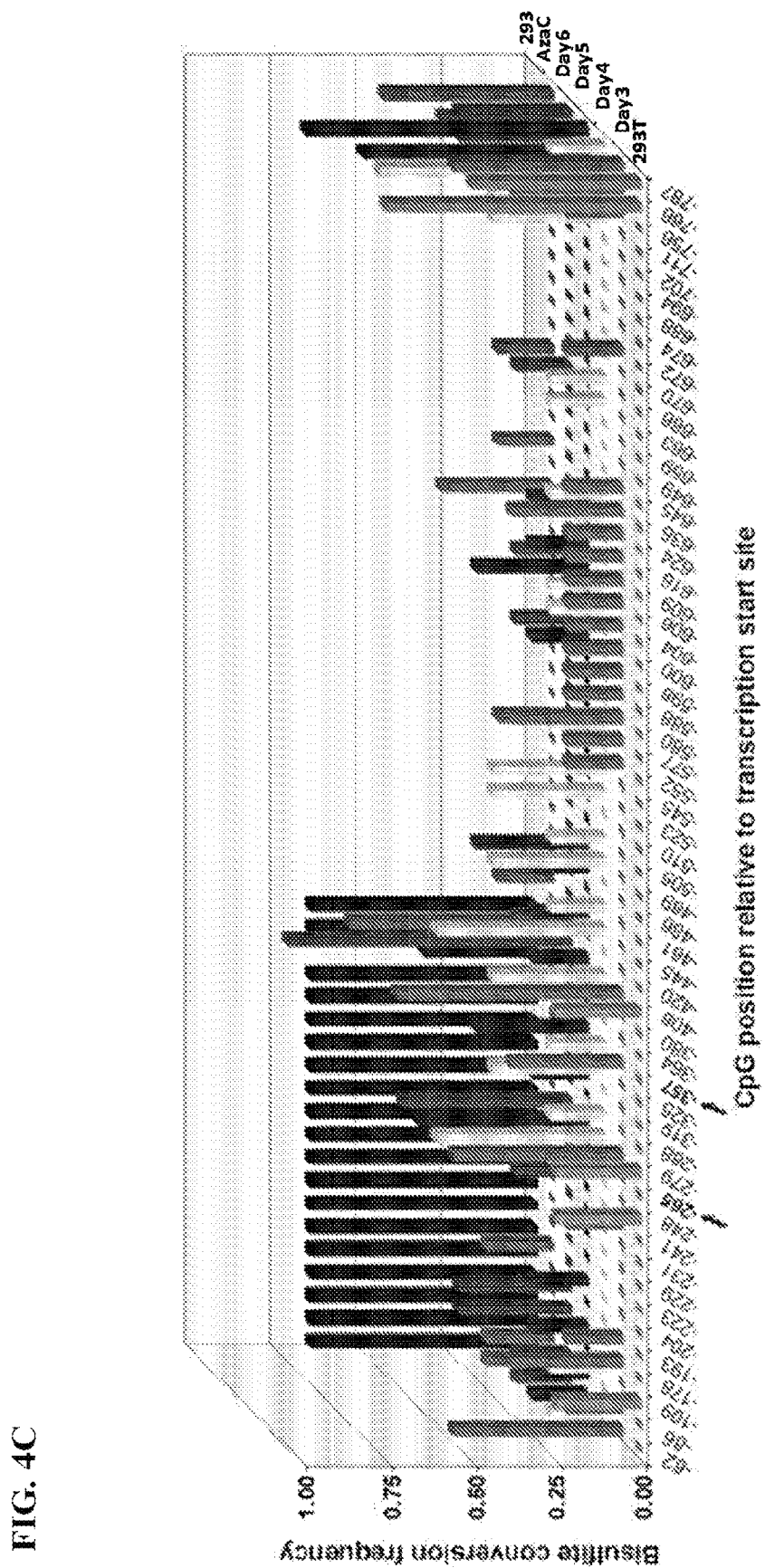

Sequencing of hMLH1 promoter DNA fragments that were cloned after bisulfite treatment of extracted genomic DNA and subsequent PCR-amplification showed a dramatic changes of the methylation landscape of the CpGs within hMLH1 promoter as indicated by the increased frequency of bisulfite conversion induced by Casilio-ME targeting (FIG. 4C). While no significant cytosine to uracil conversion was obtained with untransfected HEK293T cells, as expected for a hypermethylated DNA, transfected HEK293T cells showed significant demethylation frequency with highest activities observed close to binding-sites of the targeting RNAs (FIG. 4C (arrows)). The Casilio-ME-mediated demethylation activity was sustained during the course of the experiment and seems to spread away from the binding-sites of the guide RNAs for about 300 pb, albeit with a relatively weaker activities.

In control experiments, untransfected HEK293 cells, whose hMLH1 promoter is hypomethylated and transcriptionally active, were also analyzed. As shown in FIG. 4C (black columns), the sequenced region showed high frequency of cytosine conversion as expected. Untransfected HEK293T cells treated for 6 days with 5'azacytidine (AzaC) drug, an inhibitor or cytosine methyltransferases, were also analyzed. This also showed an increased bisulfite conversion frequency on multiple CpG sites within the promoter region (FIG. 4C, purple columns).

To determine the effect of Casilio-ME targeting on MLH1 protein synthesis, Western blot analyses were performed on total protein extracted from HEK293T transfected cells as well as untransfected HEK293 and AzaC-treated HEK293T cells using anti-hMLH1 monoclonal antibody. The results showed that transfected cells produced detectable amounts of MLH1 protein that reached higher levels by day 5 and 6 post transfection (FIG. 4B). However, the amounts of MLH1 produced by transfected cells are significantly lower that the protein levels produced by HEK293 cells that constitutively express hMLH1. Casilio-ME-mediated induction of MLH1 synthesis is still remarkable and could be improved by, for example, tilling multiple guide RNAs to augment the range and efficiency of CpG demethylation to achieving better activation of hMLH1 expression.

Taken the fact that Casilio-ME delivery of TET1 activity to hMLH1 promoter region activated transcription, together with the dramatic induced change of the methylation sate of the associated CpG island, the findings provide a proof-of-principal that the Casilio-ME is a robust platform to editing methylcytosine mark of the epigenome. This technology paves the way to new area of research investigations to address with high resolution the causal-effect relationships of methylcytosine epigenomic marks in numerous biological and pathological systems.

Figure 5A:
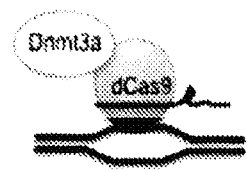
FIGS. 5A-5C. The figures show that different configurations of Casilio-ME Dnmt effectors were tested.
Figure 5A:
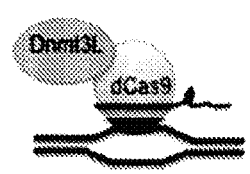
Figure 5A:
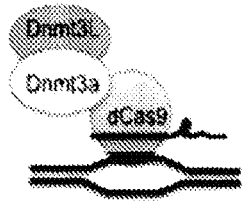
Figure 5A:
Figure 5A:
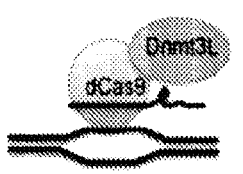
Figure 5A:
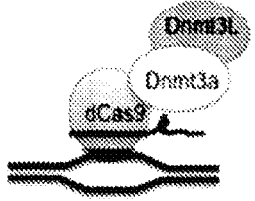
Figure 5B:
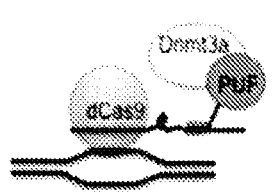
Figure 5B:
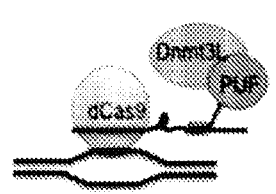
Figure 5B:
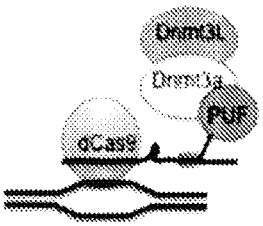
Figure 5B:
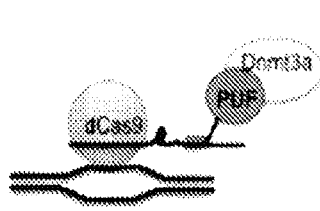
Figure 5B:
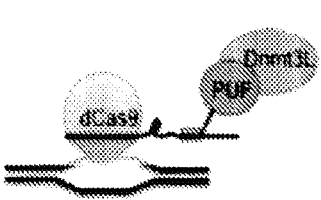
Figure 5B:
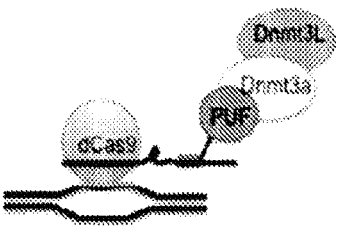
Figure 5C:
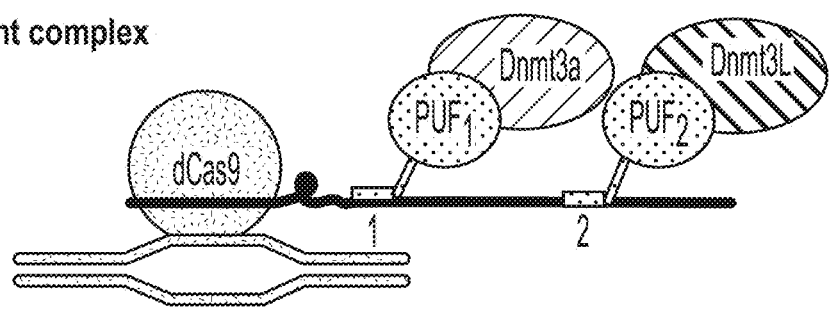
Figure 6A:
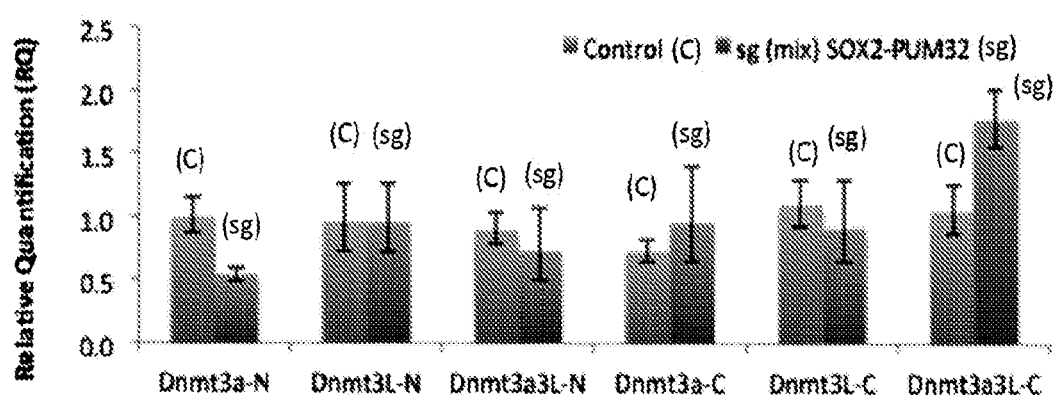
FIGS. 6A-6B. The figures show SOX2 gene expression changes induced by targeting of Casilio-ME Dnmt modules to SOX2 promoter.
Figure 6B:
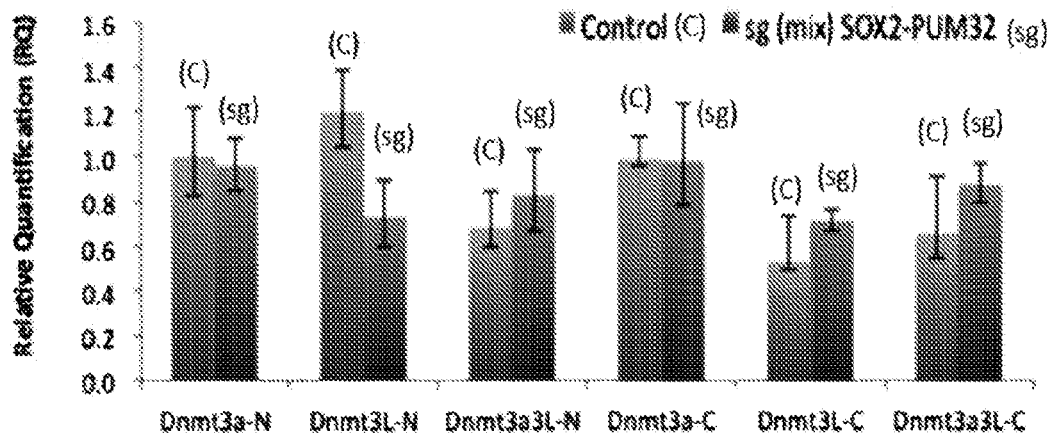

Casilio-mediated delivery of methyltranferases silent gene expression. Programmable methyltranferases were constructed by either direct fusions of catalytic domains of Dnmt3a, Dnmt3L, or a hybrid Dnmt3a-3L to N-terminus or C-terminus of dCas9 (FIG. 5A). N- or C-terminal fusions of these effectors to PUFa were also constructed, for use with dCas9 and sgRNA-PBS (Casilio-ME with Dnmt effectors; FIG. 5B). Casilio-ME with a Dnmt3a-PUF achieved more robust repression of SOX2 gene expression compared to direct fusions, demonstrating superior activity using Casilio-ME for directed DNA methylation (FIGS. 6A and 6B).

Materials and Methods

DNA Demethylation by Tet1 Effectors

Cell culture and transfection. HEK293T cells were cultivated in Dulbecco's modified Eagle's medium (DMEM) (Sigma) with 10% fetal bovine serum (FBS)(Lonza), 4% Glutamax (Gibco), 1% Sodium Pyruvate (Gibco) and penicillin-streptomycin (Gibco) in an incubator set to 37° C. and 5% $CO_2$. When indicated cells were treated with 2.5 μM or 5 μM 5-Azacytidine (sigma) as indicated with a daily change of medium containing freshly diluted drug. Cells were seeded into 12-well plates at 150,000 cells per well the day before being transfected with 100 ng of dCas9 construct, 100 ng of modified sgRNA construct and 200 ng of PUF-fusion with Attractene transfection reagent according to manufacturer's instructions (Qiagen). In dCas9-direct fusion experiments, cells were transfected with 200 ng dCas9-fusion constructs and 200 ng of modified sgRNA constructs. Transfected cells were harvested 60 hours after transfection, or otherwise indicated, and cell pellets were used for extractions of RNA, genomic DNA and protein.

Quantitative RT-PCR analysis. Cells were harvested, washed with Dulbecco's phosphate-buffered saline (dPBS), centrifuged at 125×g for 5 min and then the flash-frozen pellets were stored at −80° C. RNA was extracted using RNeasy Plus Mini Kit according to the manufacturer's instructions (Qiagen). cDNA libraries were made using Applied Biosystems High Capacity RNA-to-cDNA kit with 200 ng to 1 μg of RNA. TaqMan gene expression assays (Applied Biosystems) were designed using GAPDH (Hs03929097, VIC) as endogenous control and hMLH1 (Hs00179866, FAM) as target. TaqMan Universal Master Mix II, with UNG (Applied Biosystems) was used for Quantitative PCR (qPCR), with 2 μl of diluted cDNA used for each reaction. Activation was analyzed with the Applied Biosystems ViiA7 instrument. Gene expression levels were calculated by "delta delta Ct" algorithm and normalized to control samples.

Bisulfite conversion and sequencing. Genomic DNAs were extracted using all AllPrep DNA/RNA/Protein Mini Kit according the manufacturer's instructions (Qiagen). The kit allows extraction of genomic DNA as well as RNA and total protein from the same cellular pellet for parallel downstream analyses. Bisulfite conversion experiments were performed by using EpiTect Fast DNA Bisulfite Kit and extracted genomic DNAs according to manufacturer's instructions (Qiagen). Bisulfite treated DNAs served then as templates to PCR amplify two DNA fragments of 350-400 bp long that cover the whole hMLH1 promoter region using ZymoTaq PreMix according to manufacturer's instructions (Zymo Research). The PCR fragments were then cloned by SLIC into EcoRI-linearized PUC19 plasmid using T4 DNA polymerize (Jeong, J. Y., et al., *One-step sequence-and ligation-independent cloning as a rapid and versatile cloning method for functional genomics studies*. Appl Environ Microbiol, 2012. 78(15): p. 5440-3). Six independent positive clones for each sample were then subjected to Singer sequencing for determination of the frequency of cytosine to thymine conversion at individual CpG of the hMLH1 promoter region.

Western blot analysis. Protein from cell extracts (30 μg) were separated by electrophoresis on 10% SDS-polyacrylamide gels and then transferred to nitrocellulose membranes at 100 V for 1 hour using Bjerrum Schafer-Nielsen Buffer with SDS. Blocked membrane in 5% Blotting-Grade Blocker (BioRad) in TBS-T were then incubated overnight at 4° C. with the indicated antibodies, and the protein bands were detected using Horseradish peroxidase-conjugated secondary antibodies and Clarity Western ECL Substrate according to manufacturer's instructions (BioRad). Gels were imaged using a G:Box (Syngene).

DNA Methylation by Dnmt Effectors

Establishment of a dCas9-expressing cell line. The day prior to transfection, Lenti-X 293T cells were seeded into 6-well plates at 1.2 million cells per well. The cells were transfected with the supercoiled packaging plasmids (pLP1 (gag/pol), pLP2 (rev), and VSV-G (envelope)) and a dCas9 lentiviral expression plasmid through Lipofectamine 3000 reagent (Invitrogen). At 6 h posttransfection, medium was exchanged for fresh. At 24 h posttransfection, 2 ml of medium containing the lentivirus were collected and centrifuged for 10 minutes at 2,000 rpm to remove cellular debris. The supernatant was filtered utilizing a 45 μm pore filter (Millipore), and the lentivirus was frozen at −80° C. until needed. HEK293T cells, seeded into a 12-well plate at 150,000 cells per well, were transduced with 500 μl of the dCas9 lentivirus in culture medium supplemented with 5 μg/ml polybrene for 12 hours, and subsequently selected with Blasticidin antibiotics on the third day post transduction.

Transfection. HEK293T, and HEK293T/dCas9 cell lines were seeded into 12-well plates at 150,000 cells per well. Cells were transfected with 200 ng of the Dnmt effector constructs and 200 ng of the sgRNA-PBS with Attractene transfection reagent (Qiagen). At 3 day post-transfection, the cells were sorted for GFP (sgRNA expression constructs are marked by GFP) with fluorescence-activated cell sorting (FACS) and re-plated into 12 or 24-well plates.

Quantitative reverse-transcription PCR. Cells were harvested 7-10 day post-transfection with 100 μl of trypsin, 500 μl of DMEM, and 500 μl of Dulbecco's phosphate-buffered saline (dPBS), and centrifuged at 700 g for 5 minutes. RNA was extracted from the pelleted cells utilizing the RNeasy Plus Mini Kit (Qiagen). cDNA synthesis was performed using the Applied Biosystems High Capacity RNA-to-cDNA kit with 2 μg of RNA. TaqMan Gene expression assays (Applied Biosystems) were completed with GAPDH as the endogenous control and SOX2 as target.

Sequences

List of sgRNA spacer sequences targeting the MLH1 and SOX2 genes.

| | |
|---|---|
| MLH1 sgRNA spacer sequences | SEQ ID NO: 36 ACAGAGTTGAGAAATTTGAC |
| | SEQ ID NO: 37 GTCAAATTTCTCAACTCTGT |
| | SEQ ID NO: 38 GCTCCTAAAAACGAACCAAT |
| | SEQ ID NO: 39 AAACGAACCAATAGGAAGAG |
| | SEQ ID NO: 40 CTTCAGCGGCAGCTATTGAT |
| | SEQ ID NO: 41 GCATCTCTGCTCCTATTGGC |
| | SEQ ID NO: 42 GCGCCAGATCACCTCAGCAG |
| | SEQ ID NO: 43 GCAGAGCGGAGGAGGTGCT |
| | SEQ ID NO: 44 GAAGGAAGAACGTGAGCACG |
| | SEQ ID NO: 45 GGCAGTAGCCGCTTCAGGGA |
| | SEQ ID NO: 46 GCGCAAGCGCATATCCTTCT |
| SOX2 sgRNA spacer sequences | SEQ ID NO: 47 GCATGTGACGGGGCTGTCA |
| | SEQ ID NO: 48 GCTGCCGGGTTTTGCATGAA |
| | SEQ ID NO: 49 GCCGGCCGCGCGGGGGAGGC |
| | SEQ ID NO: 50 GGCAGGCGAGGAGGGGGAGG |

List of protein sequences

| Name | Protein Sequence |
|---|---|
| TET1(CD) SEQ ID NO: 51 | ELPTCSCLDRVIQKDKGPYYTHLGAGPSVAAVREIMENRYGQKGNAIRIEIVVYTG KEGKSSHGCPIAKWVLRRSSDEEKVLCLVRQRTGHHCPTAVMVVLIMVWDGIPLPM ADRLYTELTENLKSYNGHPTDRRCTLNENRTCTCQGIDPETCGASFSFGCSWSMYF NGCKFGRSPSPRRFRIDPSSPLHEKNLEDNLQSLATRLAPIYKQYAPVAYQNQVEY ENVARECRLGSKEGRPFSGVTACLDFCAHPHRDIHNMNNGSTVVCTLTREDNRSLG VIPQDEQLHVLPLYKLSDTDEFGSKEGMEAKIKSGAIEVLAPRRKKRTCFTQPVPR SGKKRAAMMTEVLAHKIRAVEKKPIPRIKRKNNSTTTNNSKPSSLPTLGSNTETVQ PEVKSETEPHFILKSSDNTKTYSLMPSAPHPVKEASPGFSWSPKTASATPAPLKND ATASCGFSERSSTPHCTMPSGRLSGANAAAADGPGISQLGEVAPLPTLSAPVMEPL INSEPSTGVTEPLTPHQPNHQPSFLTSPQDLASSPMEEDEQHSEADEPPSDEPLSD DPLSPAEEKLPHIDEYWSDSEHIFLDANIGGVAIAPAHGSVLIECARRELHATTPV EHPNRNHPTRLSLVFYQHKNLNKPQHGFELNKIKFEAKEAKNKKMKASEQKDQAAN EGPEQSSEVNELNQIPSHKALTLTHDNVVTVSPYALTHVAGPYNHWV |
| TET1(CD)- dCas9 SEQ ID NO: 52 | MGPAELPTCSCLDRVIQKDKGPYYTHLGAGPSVAAVREIMENRYGQKGNAIRIEIV VYTGKEGKSSHGCPIAKWVLRRSSDEEKVLCLVRQRTGHHCPTAVMVVLIMVWDGI PLPMADRLYTELTENLKSYNGHPTDRRCTLNENRTCTCQGIDPETCGASFSFGCSW SMYFNGCKFGRSPSPRRFRIDPSSPLHEKNLEDNLQSLATRLAPIYKQYAPVAYQN QVEYENVARECRLGSKEGRPFSGVTACLDFCAHPHRDIHNMNNGSTVVCTLTREDN RSLGVIPQDEQLHVLPLYKLSDTDEFGSKEGMEAKIKSGAIEVLAPRRKKRTCFTQ PVPRSGKKRAAMMTEVLAHKIRAVEKKPIPRIKRKNNSTTTNNSKPSSLPTLGSNT ETVQPEVKSETEPHFILKSSDNTKTYSLMPSAPHPVKEASPGFSWSPKTASATPAP LKNDATASCGFSERSSTPHCTMPSGRLSGANAAAADGPGISQLGEVAPLPTLSAPV MEPLINSEPSTGVTEPLTPHQPNHQPSFLTSPQDLASSPMEEDEQHSEADEPPSDE PLSDDPLSPAEEKLPHIDEYWSDSEHIFLDANIGGVAIAPAHGSVLIECARRELHA TTPVEHPNRNHPTRLSLVFYQHKNLNKPQHGFELNKIKFEAKEAKNKKMKASEQKD QAANEGPEQSSEVNELNQIPSHKALTLTHDNVVTVSPYALTHVAGPYNHWVIDGGG GSGGGGSGGGGSMYPYDVPDYASPKKKRKVEASDKKYSIGLAIGTNSVGWAVITDE YKVPSKKFKVLGNTDRHSIKKNLIGALLFDSGETAEATRLKRTARRRYTRRKNRIC YLQEIFSNEMAKVDDSFFHRLEESFLVEEDKKHERHPIFGNIVDEVAYHEKYPTIY HLRKKLVDSTDKADLRLIYLALAHMIKFRGHFLIEGDLNPDNSDVDKLFIQLVQTY NQLFEENPINASGVDAKAILSARLSKSRRLENLIAQLPGEKKNGLFGNLIALSLGL TPNFKSNFDLAEDAKLQLSKDTYDDDLDNLLAQIGDQYADLFLAAKNLSDAILLSD ILRVNTEITKAPLSASMIKRYDEHHQDLTLLKALVRQQLPEKYKEIFFDQSKNGYA GYIDGGASQEEFYKFIKPILEKMDGTEELLVKLNREDLLRKQRTFDNGSIPHQIHL GELHAILRRQEDFYPFLKDNREKIEKILTFRIPYYVGPLARGNSRFAWMTRKSEET ITPWNFEEVVDKGASAQSFIERMTNFDKNLPNEKVLPKHSLLYEYFTVYNELTKVK YVTEGMRKPAFLSGEQKKAIVDLLFKTNRKVTVKQLKEDYFKKIECFDSVEISGVE DRFNASLGTYHDLLKIIKDKDFLDNEENEDILEDIVLTLTLFEDREMIEERLKTYA HLFDDKVMKQLKRRRYTGWGRLSRKLINGIRDKQSGKTILDFLKSDGFANRNFMQL IHDDSLTFKEDIQKAQVSGQGDSLHEHIANLAGSPAIKKGILQTVKVVDELVKVMG RHKPENIVIEMARENQTTQKGQKNSRERMKRIEEGIKELGSQILKEHPVENTQLQN EKLYLYYLQNGRDMYVDQELDINRLSDYDVDAIVPQSFLKDDSIDNKVLTRSDKNR GKSDNVPSEEVVKKMKNYWRQLLNAKLITQRKFDNLTKAERGGLSELDKAGFIKRQ LVETRQITKHVAQILDSRMNTKYDENDKLIREVKVITLKSKLVSDFRKDFQFYKVR EINNYHHAHDAYLNAVVGTALIKKYPKLESEFVYGDYKVYDVRKMIAKSEQEIGKA TAKYFFYSNIMNFFKTEITLANGEIRKRPLIETNGETGEIVWDKGRDFATVRKVLS MPQVNIVKKTEVQTGGFSKESILPKRNSDKLIARKKDWDPKKYGGFDSPTVAYSVL VVAKVEKGKSKKLKSVKELLGITIMERSSFEKNPIDFLEAKGYKEVKKDLIIKLPK YSLFELENGRKRMLASAGELQKGNELALPSKYVNFLYLASHYEKLKGSPEDNEQKQ LFVEQHKHYLDEIIEQISEFSKRVILADANLDKVLSAYNKHRDKPIREQAENIIHL FTLTNLGAPAAFKYFDTTIDRKRYTSTKEVLDATLIHQSITGLYETRIDLSQLGGD SPKKKRKVEASGGGGSGGGGSGGGGSGPA |
| dCas9- TET1(CD) SEQ ID NO: 53 | MIDGGGGSGGGGSGGGGSMYPYDVPDYASPKKKRKVEASDKKYSIGLAIGTNSVGW AVITDEYKVPSKKFKVLGNTDRHSIKKNLIGALLFDSGETAEATRLKRTARRRYTR RKNRICYLQEIFSNEMAKVDDSFFHRLEESFLVEEDKKHERHPIFGNIVDEVAYHE KYPTIYHLRKKLVDSTDKADLRLIYLALAHMIKFRGHFLIEGDLNPDNSDVDKLFI QLVQTYNQLFEENPINASGVDAKAILSARLSKSRRLENLIAQLPGEKKNGLFGNLI ALSLGLTPNFKSNFDLAEDAKLQLSKDTYDDDLDNLLAQIGDQYADLFLAAKNLSD AILLSDILRVNTEITKAPLSASMIKRYDEHHQDLTLLKALVRQQLPEKYKEIFFDQ SKNGYAGYIDGGASQEEFYKFIKPILEKMDGTEELLVKLNREDLLRKQRTFDNGSI PHQIHLGELHAILRRQEDFYPFLKDNREKIEKILTFRIPYYVGPLARGNSRFAWMT RKSEETITPWNFEEVVDKGASAQSFIERMTNFDKNLPNEKVLPKHSLLYEYFTVYN ELTKVKYVTEGMRKPAFLSGEQKKAIVDLLFKTNRKVTVKQLKEDYFKKIECFDSV EISGVEDRFNASLGTYHDLLKIIKDKDFLDNEENEDILEDIVLTLTLFEDREMIEE RLKTYAHLFDDKVMKQLKRRRYTGWGRLSRKLINGIRDKQSGKTILDFLKSDGFAN RNFMQLIHDDSLTFKEDIQKAQVSGQGDSLHEHIANLAGSPAIKKGILQTVKVVDE LVKVMGRHKPENIVIEMARENQTTQKGQKNSRERMKRIEEGIKELGSQILKEHPVE NTQLQNEKLYLYYLQNGRDMYVDQELDINRLSDYDVDAIVPQSFLKDDSIDNKVLT RSDKNRGKSDNVPSEEVVKKMKNYWRQLLNAKLITQRKFDNLTKAERGGLSELDKA GFIKRQLVETRQITKHVAQILDSRMNTKYDENDKLIREVKVITLKSKLVSDFRKDF QFYKVREINNYHHAHDAYLNAVVGTALIKKYPKLESEFVYGDYKVYDVRKMIAKSE QEIGKATAKYFFYSNIMNFFKTEITLANGEIRKRPLIETNGETGEIVWDKGRDFAT VRKVLSMPQVNIVKKTEVQTGGFSKESILPKRNSDKLIARKKDWDPKKYGGFDSPT VAYSVLVVAKVEKGKSKKLKSVKELLGITIMERSSFEKNPIDFLEAKGYKEVKKDL IIKLPKYSLFELENGRKRMLASAGELQKGNELALPSKYVNFLYLASHYEKLKGSPE |

| Name | Protein Sequence |
|---|---|
| | DNEQKQLFVEQHKHYLDEIIEQISEFSKRVILADANLDKVLSAYNKHRDKPIREQA<br>ENIIHLFTLTNLGAPAAFKYFDTTIDRKRYTSTKEVLDATLIHQSITGLYETRIDL<br>SQLGGDSPKKKRKVEASGGGGSGGGGSGGGGSGPAELPTCSCLDRVIQKDKGPYYT<br>HLGAGPSVAAVREIMENRYGQKGNAIRIEIVVYTGKEGKSSHGCPIAKWVLRRSSD<br>EEKVLCLVRQRTGHHCPTAVMVVLIMVWDGIPLPMADRLYTELTENLKSYNGHPTD<br>RRCTLNENRTCTCQGIDPETCGASFSFGCSWSMYFNGCKFGRSPSPRRFRIDPSSP<br>LHEKNLEDNLQSLATRLAPIYKQYAPVAYQNQVEYENVARECRLGSKEGRPFSGVT<br>ACLDFCAHPRDIHNMNNGSTVVCTLTREDNRSLGVIPQDEQLHVLPLYKLSDTDE<br>FGSKEGMEAKIKSGAIEVLAPRRKKRTCFTQPVPRSGKKRAAMMTEVLAHKIRAVE<br>KKPIPRIKRKNNSTTTNNSKPSSLPTLGSNTETVQPEVKSETEPHFILKSSDNTKT<br>YSLMPSAPHPVKEASPGFSWSPKTASATPAPLKNDATASCGFSERSSTPHCTMPSG<br>RLSGANAAAADGPGISQLGEVAPLPTLSAPVMEPLINSEPSTGVTEPLTPHQPNHQ<br>PSFLTSPQDLASSPMEEDEQHSEADEPPSDEPLSDDPLSPAEEKLPHIDEYWSDSE<br>HIFLDANIGGVAIAPAHGSVLIECARRELHATTPVEHPNRNHPTRLSLVFYQHKNL<br>NKPQHGFELNKIKFEAKEAKNKKMKASEQKDQAANEGPEQSSEVNELNQIPSHKAL<br>TLTHDNVVTVSPYALTHVAGPYNHWVID |
| TET1-PUFa<br>SEQ ID NO: 54 | MGPAELPTCSCLDRVIQKDKGPYYTHLGAGPSVAAVREIMENRYGQKGNAIRIEIV<br>VYTGKEGKSSHGCPIAKWVLRRSSDEEKVLCLVRQRTGHHCPTAVMVVLIMVWDGI<br>PLPMADRLYTELTENLKSYNGHPTDRRCTLNENRTCTCQGIDPETCGASFSFGCSW<br>SMYFNGCKFGRSPSPRRFRIDPSSPLHEKNLEDNLQSLATRLAPIYKQYAPVAYQN<br>QVEYENVARECRLGSKEGRPFSGVTACLDFCAHPRDIHNMNNGSTVVCTLTREDN<br>RSLGVIPQDEQLHVLPLYKLSDTDEFGSKEGMEAKIKSGAIEVLAPRRKKRTCFTQ<br>PVPRSGKKRAAMMTEVLAHKIRAVEKKPIPRIKRKNNSTTTNNSKPSSLPTLGSNT<br>ETVQPEVKSETEPHFILKSSDNTKTYSLMPSAPHPVKEASPGFSWSPKTASATPAP<br>LKNDATASCGFSERSSTPHCTMPSGRLSGANAAAADGPGISQLGEVAPLPTLSAPV<br>MEPLINSEPSTGVTEPLTPHQPNHQPSFLTSPQDLASSPMEEDEQHSEADEPPSDE<br>PLSDDPLSPAEEKLPHIDEYWSDSEHIFLDANIGGVAIAPAHGSVLIECARRELHA<br>TTPVEHPNRNHPTRLSLVFYQHKNLNKPQHGFELNKIKFEAKEAKNKKMKASEQKD<br>QAANEGPEQSSEVNELNQIPSHKALTLTHDNVVTVSPYALTHVAGPYNHWVIDGGG<br>GSDPKKKRKVDPKKKRKVDPKKKRKVGSTGSRNDGGGGSGGGGSGGGGSGRAGILP<br>PKKKRKVSRGRSRLLEDFRNNRYPNLQLREIAGHIMEFSQDQHGSRFIQLKLERAT<br>PAERQLVFNEILQAAYQLMVDVFGNYVIQKFFEFGSLEQKLALAERIRGHVLSLAL<br>QMYGSRVIEKALEFIPSDQQNEMVRELDGHVLKCVKDQNGNHVVQKCIECVQPQSL<br>QFIIDAFKGQVFALSTHPYGCRVIQRILEHCLPDQTLPILEELHQHTEQLVQDQYG<br>NYVIQHVLEHGRPEDKSKIVAEIRGNVLVLSQHKFASNVVEKCVTHASRTERAVLI<br>DEVCTMNDGPHSALYTMMKDQYANYVVQKMIDVAEPGQRKIVMHKIRPHIATLRKY<br>TYGKHILAKLEKYYMKNGVDLGDPKKKRKVDPKKKRKVGGRGGGGSGGGGSGGGGS<br>GPA |
| PUFa-TET1<br>SEQ ID NO: 55 | MIDGGGGSDPKKKRKVDPKKKRKVDPKKKRKVGSTGSRNDGGGGSGGGGSGGGGSG<br>RAGILPPKKKRKVSRGRSRLLEDFRNNRYPNLQLREIAGHIMEFSQDQHGSRFIQL<br>KLERATPAERQLVFNEILQAAYQLMVDVFGNYVIQKFFEFGSLEQKLALAERIRGH<br>VLSLALQMYGSRVIEKALEFIPSDQQNEMVRELDGHVLKCVKDQNGNHVVQKCIEC<br>VQPQSLQFIIDAFKGQVFALSTHPYGCRVIQRILEHCLPDQTLPILEELHQHTEQL<br>VQDQYGNYVIQHVLEHGRPEDKSKIVAEIRGNVLVLSQHKFASNVVEKCVTHASRT<br>ERAVLIDEVCTMNDGPHSALYTMMKDQYANYVVQKMIDVAEPGQRKIVMHKIRPHI<br>ATLRKYTYGKHILAKLEKYYMKNGVDLGDPKKKRKVDPKKKRKVGGRGGGGSGGGG<br>SGGGGSGPAELPTCSCLDRVIQKDKGPYYTHLGAGPSVAAVREIMENRYGQKGNAI<br>RIEIVVYTGKEGKSSHGCPIAKWVLRRSSDEEKVLCLVRQRTGHHCPTAVMVVLIM<br>VWDGIPLPMADRLYTELTENLKSYNGHPTDRRCTLNENRTCTCQGIDPETCGASFS<br>FGCSWSMYFNGCKFGRSPSPRRFRIDPSSPLHEKNLEDNLQSLATRLAPIYKQYAP<br>VAYQNQVEYENVARECRLGSKEGRPFSGVTACLDFCAHPRDIHNMNNGSTVVCTL<br>TREDNRSLGVIPQDEQLHVLPLYKLSDTDEFGSKEGMEAKIKSGAIEVLAPRRKKR<br>TCFTQPVPRSGKKRAAMMTEVLAHKIRAVEKKPIPRIKRKNNSTTTNNSKPSSLPT<br>LGSNTETVQPEVKSETEPHFILKSSDNTKTYSLMPSAPHPVKEASPGFSWSPKTAS<br>ATPAPLKNDATASCGFSERSSTPHCTMPSGRLSGANAAAADGPGISQLGEVAPLPT<br>LSAPVMEPLINSEPSTGVTEPLTPHQPNHQPSFLTSPQDLASSPMEEDEQHSEADE<br>PPSDEPLSDDPLSPAEEKLPHIDEYWSDSEHIFLDANIGGVAIAPAHGSVLIECAR<br>RELHATTPVEHPNRNHPTRLSLVFYQHKNLNKPQHGFELNKIKFEAKEAKNKKMKA<br>SEQKDQAANEGPEQSSEVNELNQIPSHKALTLTHDNVVTVSPYALTHVAGPYNHWV<br>ID |
| hDNMT3a<br>(609-909)<br>SEQ ID NO: 56 | NHDQEFDPPKVYPPVPAEKRKPIRVLSLFDGIATGLLVLKDLGIQVDRYIASEVCE<br>DSITVGMVRHQGKIMYVGDVRSVTQKHIQEWGPFDLVIGGSPCNDLSIVNPARKGL<br>YEGTGRLFFEFYRLLHDARPKEGDDRPFFWLFENVVAMGVSDKRDISRFLESNPVM<br>IDAKEVSAAHRARYFWGNLPGMNRPLASTVNDKLELQECLEHGRIAKFSKVRTITT<br>RSNSIKQGKDQHFPVFMNEKEDILWCTEMERVFGFPVHYTDVSNMSRLARQRLLGR<br>SWSVPVIRHLFAPLKEYFACV |
| mDnmt3L<br>(208-421)<br>SEQ ID NO: 57 | GPMEIYKTVSAWKRQPVRVLSLFRNIDKVLKSLGFLESGSGSGGGTLKYVEDVTNV<br>VRRDVEKWGPFDLVYGSTQPLGSSCDRCPGWYMFQFHRILQYALPRQESQRPFFWI<br>FMDNLLLTEDDQETTTRFLQTEAVTLQDVRGRDYQNAMRVWSNIPGLKSKHAPLTP<br>KEEEYLQAQVRSRSKLDAPKVDLLVKNCLLPLREYFKYFSQNSLPL |
| Dnmt3a3L<br>SEQ ID NO: 58 | NHDQEFDPPKVYPPVPAEKRKPIRVLSLFDGIATGLLVLKDLGIQVDRYIASEVCE<br>DSITVGMVRHQGKIMYVGDVRSVTQKHIQEWGPFDLVIGGSPCNDLSIVNPARKGL |

| Name | Protein Sequence |
|---|---|
| | YEGTGRLFFEFYRLLHDARPKEGDDRPFFWLFENVVAMGVSDKRDISRFLESNPVM<br>IDAKEVSAAHRARYFWGNLPGMNRPLASTVNDKLELQECLEHGRIAKFSKVRTITT<br>RSNSIKQGKDQHFPVFMNEKEDILWCTEMERVFGFPVHYTDVSNMSRLARQRLLGR<br>SWSVPVIRHLFAPLKEYFACVSSGNSNANSRGPSFSSGLVPLSLRGSHMGPMEIYK<br>TVSAWKRQPVRVLSLFRNIDKVLKSLGFLESGSGSGGGTLKYVEDVTNVVRRDVEK<br>WGPFDLVYGSTQPLGSSCDRCPGWYMFQFHRILQYALPRQESQRPFFWIFMDNLLL<br>TEDDQETTTRFLQTEAVTLQDVRGRDYQNAMRVWSNIPGLKSKHAPLTPKEEEYLQ<br>AQVRSRSKLDAPKVDLLVKNCLLPLREYFKYFSQNSLPL |
| Dnmt3a-dCas9<br>SEQ ID NO: 59 | MGPANHDQEFDPPKVYPPVPAEKRKPIRVLSLFDGIATGLLVLKDLGIQVDRYIAS<br>EVCEDSITVGMVRHQGKIMYVGDVRSVTQKHIQEWGPFDLVIGGSPCNDLSIVNPA<br>RKGLYEGTGRLFFEFYRLLHDARPKEGDDRPFFWLFENVVAMGVSDKRDISRFLES<br>NPVMIDAKEVSAAHRARYFWGNLPGMNRPLASTVNDKLELQECLEHGRIAKFSKVR<br>TITTRSNSIKQGKDQHFPVFMNEKEDILWCTEMERVFGFPVHYTDVSNMSRLARQR<br>LLGRSWSVPVIRHLFAPLKEYFACVIDGGGGSGGGGSGGGGSMYPYDVPDYASPKK<br>KRKVEASDKKYSIGLAIGTNSVGWAVITDEYKVPSKKFKVLGNTDRHSIKKNLIGA<br>LLFDSGETAEATRLKRTARRRYTRRKNRICYLQEIFSNEMAKVDDSFFHRLEESFL<br>VEEDKKHERHPIFGNIVDEVAYHEKYPTIYHLRKKLVDSTDKADLRLIYLALAHMI<br>KFRGHFLIEGDLNPDNSDVDKLFIQLVQTYNQLFEENPINASGVDAKAILSARLSK<br>SRRLENLIAQLPGEKKNGLFGNLIALSLGLTPNFKSNFDLAEDAKLQLSKDTYDDD<br>LDNLLAQIGDQYADLFLAAKNLSDAILLSDILRVNTEITKAPLSASMIKRYDEHHQ<br>DLTLLKALVRQQLPEKYKEIFFDQSKNGYAGYIDGGASQEEFYKFIKPILEKMDGT<br>EELLVKLNREDLLRKQRTFDNGSIPHQIHLGELHAILRRQEDFYPFLKDNREKIEK<br>ILTFRIPYYVGPLARGNSRFAWMTRKSEETITPWNFEEVVDKGASAQSFIERMTNF<br>DKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNE<br>ENEDILEDIVLTLTLFEDREMIEERLKTYAHLFDDKVMKQLKRRRYTGWGRLSRKL<br>INGIRDKQSGKTILDFLKSDGFANRNFMQLIHDDSLTFKEDIQKAQVSGQGDSLHE<br>HIANLAGSPAIKKGILQTVKVVDELVKVMGRHKPENIVIEMARENQTTQKGQKNSR<br>ERMKRIEEGIKELGSQILKEHPVENTQLQNEKLYLYYLQNGRDMYVDQELDINRLS<br>DYDVDAIVPQSFLKDDSIDNKVLTRSDKNRGKSDNVPSEEVVKKMKNYWRQLLNAK<br>LITQRKFDNLTKAERGGLSELDKAGFIKRQLVETRQITKHVAQILDSRMNTKYDEN<br>DKLIREVKVITLKSKLVSDFRKDFQFYKVREINNYHHAHDAYLNAVVGTALIKKYP<br>KLESEFVYGDYKVYDVRKMIAKSEQEIGKATAKYFFYSNIMNFFKTEITLANGEIR<br>KRPLIETNGETGEIVWDKGRDFATVRKVLSMPQVNIVKKTEVQTGGFSKESILPKR<br>NSDKLIARKKDWDPKKYGGFDSPTVAYSVLVVAKVEKGKSKKLKSVKELLGITIME<br>RSSFEKNPIDFLEAKGYKEVKKDLIIKLPKYSLFELENGRKRMLASAGELQKGNEL<br>ALPSKYVNFLYLASHYEKLKGSPEDNEQKQLFVEQHKHYLDEIIEQISEFSKRVIL<br>ADANLDKVLSAYNKHRDKPIREQAENIIHLFTLTNLGAPAAFKYFDTTIDRKRYTS<br>TKEVLDATLIHQSITGLYETRIDLSQLGGDSPKKKRKVEASGGGGSGGGGSGGGGS<br>GPA |
| Dnmt3L-dCas9<br>SEQ ID NO: 60 | MGPAGPMEIYKTVSAWKRQPVRVLSLFRNIDKVLKSLGFLESGSGSGGGTLKYVED<br>VTNVVRRDVEKWGPFDLVYGSTQPLGSSCDRCPGWYMFQFHRILQYALPRQESQRP<br>FFWIFMDNLLLTEDDQETTTRFLQTEAVTLQDVRGRDYQNAMRVWSNIPGLKSKHA<br>PLTPKEEEYLQAQVRSRSKLDAPKVDLLVKNCLLPLREYFKYFSQNSLPLIDGGGG<br>SGGGGSGGGGSMYPYDVPDYASPKKKRKVEASDKKYSIGLAIGTNSVGWAVITDEY<br>KVPSKKFKVLGNTDRHSIKKNLIGALLFDSGETAEATRLKRTARRRYTRRKNRICY<br>LQEIFSNEMAKVDDSFFHRLEESFLVEEDKKHERHPIFGNIVDEVAYHEKYPTIYH<br>LRKKLVDSTDKADLRLIYLALAHMIKFRGHFLIEGDLNPDNSDVDKLFIQLVQTYN<br>QLFEENPINASGVDAKAILSARLSKSRRLENLIAQLPGEKKNGLFGNLIALSLGLT<br>PNFKSNFDLAEDAKLQLSKDTYDDDLDNLLAQIGDQYADLFLAAKNLSDAILLSDI<br>LRVNTEITKAPLSASMIKRYDEHHQDLTLLKALVRQQLPEKYKEIFFDQSKNGYAG<br>YIDGGASQEEFYKFIKPILEKMDGTEELLVKLNREDLLRKQRTFDNGSIPHQIHLG<br>ELHAILRRQEDFYPFLKDNREKIEKILTFRIPYYVGPLARGNSRFAWMTRKSEETI<br>TPWNFEEVVDKGASAQSFIERMTNFDKNLPNEKVLPKHSLLYEYFTVYNELTKVKY<br>VTEGMRKPAFLSGEQKKAIVDLLFKTNRKVTVKQLKEDYFKKIECFDSVEISGVED<br>RFNASLGTYHDLLKIIKDKDFLDNEENEDILEDIVLTLTLFEDREMIEERLKTYAH<br>LFDDKVMKQLKRRRYTGWGRLSRKLINGIRDKQSGKTILDFLKSDGFANRNFMQLI<br>HDDSLTFKEDIQKAQVSGQGDSLHEHIANLAGSPAIKKGILQTVKVVDELVKVMGR<br>HKPENIVIEMARENQTTQKGQKNSRERMKRIEEGIKELGSQILKEHPVENTQLQNE<br>KLYLYYLQNGRDMYVDQELDINRLSDYDVDAIVPQSFLKDDSIDNKVLTRSDKNRG<br>KSDNVPSEEVVKKMKNYWRQLLNAKLITQRKFDNLTKAERGGLSELDKAGFIKRQL<br>VETRQITKHVAQILDSRMNTKYDENDKLIREVKVITLKSKLVSDFRKDFQFYKVRE<br>INNYHHAHDAYLNAVVGTALIKKYPKLESEFVYGDYKVYDVRKMIAKSEQEIGKAT<br>AKYFFYSNIMNFFKTEITLANGEIRKRPLIETNGETGEIVWDKGRDFATVRKVLSM<br>PQVNIVKKTEVQTGGFSKESILPKRNSDKLIARKKDWDPKKYGGFDSPIVAYSVLV<br>VAKVEKGKSKKLKSVKELLGITIMERSSFEKNPIDFLEAKGYKEVKKDLIIKLPKY<br>SLFELENGRKRMLASAGELQKGNELALPSKYVNFLYLASHYEKLKGSPEDNEQKQL<br>FVEQHKHYLDEIIEQISEFSKRVILADANLDKVLSAYNKHRDKPIREQAENIIHLF<br>TLINLGAPAAFKYFDTTIDRKRYISTKEVLDATLIHQSITGLYETRIDLSQLGGDS<br>PKKKRKVEASGGGGSGGGGSGGGGSGPA |
| Dnmt3a3L-<br>dCas9<br>SEQ ID NO: 61 | MGPANHDQEFDPPKVYPPVPAEKRKPIRVLSLFDGIATGLLVLKDLGIQVDRYIAS<br>EVCEDSITVGMVRHQGKIMYVGDVRSVIQKHIQEWGPFDLVIGGSPCNDLSIVNPA<br>RKGLYEGTGRLFFEFYRLLHDARPKEGDDRPFFWLFENVVAMGVSDKRDISRFLES<br>NPVMIDAKEVSAAHRARYFWGNLPGMNRPLASTVNDKLELQECLEHGRIAKFSKVR |

| Name | Protein Sequence |
|---|---|
| | TITTTRSNSIKQGKDQHFPVFMNEKEDILWCTEMERVFGFPVHYTDVSNMSRLARQR<br>LLGRSWSVPVIRHLFAPLKEYFACVSSGNSNANSRGPSFSSGLVPLSLRGSHMGPM<br>EIYKTVSAWKRQPVRVLSLFRNIDKVLSKLGFLESGSGSGGGILKYVEDVINVVRR<br>DVEKWGPFDLVYGSTQPLGSSCDRCPGWYMFQFHRILQYALPRQESQRPFFWIFMD<br>NLLLTEDDQETTIRFLQTEAVTLQDVRGRDYQNAMRVWSNIPGLKSKHAPLIPKEE<br>EYLQAVRSRSKLDAPKVDLLVKNCLLPLREYFKYFSQNSLPLIDGGGGSGGGGSG<br>GGGSMYPYDVPDYASPKKKRKVEASDKKYSIGLAIGINSVGWAVITDEYKVPSKKF<br>KVLGNIDRHSIKKNLIGALLFDSGETAEATRLKRTARRRYTRRKNRICYLQEIFSN<br>EMAKVDDSFFHRLEESFLVEEDKKHERHPIFGNIVDEVAYHEKYPTIYHLRKKLVD<br>STDKADLRLIYLALAHMIKFRGHFLIEGDLNPDNSDVDKLFIQLVQTYNQLFEENP<br>INASGVDAKAILSARLSKSRRLENLIAQLPGEKKNGLFGNLIALSLGLITNFKSNF<br>DLAEDAKLQLSKDTYDDDLDNLLAQIGDQYADLFLAAKNLSDAILLSDILRVNTEI<br>TKAPLSASMIKRYDEHHQDLILLKALVRQQLPEKYKEIFFDQSKNGYAGYIDGGAS<br>QEEFYKFIKPILEKMDGTEELLVKLNREDLLRKQRTFDNGSIPHQIHLGELHAILR<br>RQEDFYPFLKDNREKIEKILTFRIPYYVGPLARGNSRFAWMTRKSEETITPWNFEE<br>VVDKGASAQSFIERMINFDKNLPNEKVLPKHSLLYEYFTVYNELTKVKYVTEGMRK<br>PAFLSGEQKKAIVDLLFKINRKVIVKQLKEDYFKKIECFDSVEISGVEDRFNASLG<br>TYHDLLKIIKDKDFLDNEENEDILEDIVLILTLFEDREMIEERLKTYAHLFDDKVM<br>KQLKRRRYTGWGRLSRKLINGIRDKQSGKTILDFLKSDGFANRNFMQLIHDDSLIF<br>KEDIQKAQVSGQGDSLHEHIANLAGSPAIKKGILQTVKVVDELVKVMGRHKPENIV<br>IEMARENQTTQKGQKNSRERMKRIEEGIKELGSQILKEHPVENTQLQNEKLYLYYL<br>QNGRDMYVDQELDINRLSDYDVDAIVPQSFLKDDSIDNKVLIRSDKNRGKSDNVPS<br>EEVVKKMKNYWRQLLNAKLITQRKFDNLIKAERGGLSELDKAGFIKRQLVETRQIT<br>KHVAQILDSRMNIKYDENDKLIREVKVITLKSKLVSDFRKDFQFYKVREINNYHHA<br>HDAYLNAVVGIALIKKYPKLESEFVYGDYKVYDVRKMIAKSEQEIGKATAKYFFYS<br>NIMNFFKTEITLANGEIRKRPLIETNGETGEIVWDKGRDFATVRKVLSMPQVNIVK<br>KTEVQTGGFSKESILPKRNSDKLIARKKDWDPKKYGGFDSPTVAYSVLVVAKVEKG<br>KSKKLKSVKELLGITIMERSSFEKNPIDFLEAKGYKEVKKDLIIKLPKYSLFELEN<br>GRKRMLASAGELQKGNELALPSKYVNFLYLASHYEKLKGSPEDNEQKQLFVEQHKH<br>YLDEIIEQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGDSPKKKRKV<br>EASGGGGSGGGGSGGGGSGPA |
| dCas9-Dnmt3a | MIDGGGGSGGGGSGGGGSMYPYDVPDYASPKKKRKVEASDKKYSIGLAIGTNSVGW<br>RKNRICYLQEIFSNEMAKVDDSFFHRLEESFLVEEDKKHERHPIFGNIVDEVAYHE<br>KYPTIYHLRKKLVDSTDKADLRLIYLALAHMIKFRGHFLIEGDLNPDNSDVDKLFI<br>QLVQTYNQLFEENPINASGVDAKAILSARLSKSRRLENLIAQLPGEKKNGLFGNLI<br>ALSLGLTPNFKSNFDLAEDAKLQLSKDTYDDDLDNLLAQIGDQYADLFLAAKNLSD<br>AILLSDILRVNTEITKAPLSASMIKRYDEHHQDLTLLKALVRQQLPEKYKEIFFDQ<br>SKNGYAGYIDGGASQEEFYKFIKPILEKMDGTEELLVKLNREDLLRKQRTFDNGSI<br>PHQIHLGELHAILRRQEDFYPFLKDNREKIEKILTFRIPYYVGPLARGNSRFAWMT<br>RKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSV<br>EISGVEDRFNASLGTYHDLLKIIKDKDFLDNEENEDILEDIVLTLTLFEDREMIEE<br>RLKTYAHLFDDKVMKQLKRRRYTGWGRLSRKLINGIRDKQSGKTILDFLKSDGFAN<br>RNFMQLIHDDSLTFKEDIQKAQVSGQGDSLHEHIANLAGSPAIKKGILQTVKVVDE<br>LVKVMGRHKPENIVIEMARENQTTQKGQKNSRERMKRIEEGIKELGSQILKEHPVE<br>NTQLQNEKLYLYYLQNGRDMYVDQELDINRLSDYDVDAIVPQSFLKDDSIDNKVLT<br>RSDKNRGKSDNVPSEEVVKKMKNYWRQLLNAKLITQRKFDNLTKAERGGLSELDKA<br>GFIKRQLVETRQITKHVAQILDSRMNTKYDENDKLIREVKVITLKSKLVSDFRKDF<br>QFYKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPT<br>VAYSVLVVAKVEKGKSKKLKSVKELLGITIMERSSFEKNPIDFLEAKGYKEVKKDL<br>IIKLPKYSLFELENGRKRMLASAGELQKGNELALPSKYVNFLYLASHYEKLKGSPE<br>DNEQKQLFVEQHKHYLDEIIEQISEFSKRVILADANLDKVLSAYNKHRDKPIREQA<br>ENIIHLFTLTNLGAPAAFKYFDTTIDRKRYTSTKEVLDATLIHQSITGLYETRIDL<br>SQLGGDSPKKKRKVEASGGGGSGGGGSGGGGSGPANHDQEFDPPKVYPPVPAEKRK<br>PIRVLSLFDGIATGLLVLKDLGIQVDRYIASEVCEDSITVGMVRHQGKIMYVGDVR<br>SVTQKHIQEWGPFDLVIGGSPCNDLSIVNPARKGLYEGTGRLFFEFYRLLHDARPK<br>EGDDRPFFWLFENVVAMGVSDKRDISRFLESNPVMIDAKEVSAAHRARYFWGNLPG<br>MNRPLASTVNDKLELQECLEHGRIAKFSKVRTITTRSNSIKQGKDQHFPVFMNEKE<br>DILWCTEMERVFGFPVHYTDVSNMSRLARQRLLGRSWSVPVIRHLFAPLKEYFACV<br>ID |
| dCas9-Dnmt3L<br>SEQ ID NO: 63 | MIDGGGGSGGGGSGGGGSMYPYDVPDYASPKKKRKVEASDKKYSIGLAIGTNSVGW<br>AVITDEYKVPSKKFKVLGNTDRHSIKKNLIGALLFDSGETAEATRLKRTARRRYTR<br>RKNRICYLQEIFSNEMAKVDDSFFHRLEESFLVEEDKKHERHPIFGNIVDEVAYHE<br>KYPTIYHLRKKLVDSTDKADLRLIYLALAHMIKFRGHFLIEGDLNPDNSDVDKLFI<br>QLVQTYNQLFEENPINASGVDAKAILSARLSKSRRLENLIAQLPGEKKNGLFGNLI<br>ALSLGLTPNFKSNFDLAEDAKLQLSKDTYDDDLDNLLAQIGDQYADLFLAAKNLSD<br>AILLSDILRVNTEITKAPLSASMIKRYDEHHQDLTLLKALVRQQLPEKYKEIFFDQ<br>SKNGYAGYIDGGASQEEFYKFIKPILEKMDGTEELLVKLNREDLLRKQRTFDNGSI<br>PHQIHLGELHAILRRQEDFYPFLKDNREKIEKILTFRIPYYVGPLARGNSRFAWMT<br>RKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSV<br>EISGVEDRFNASLGTYHDLLKIIKDKDFLDNEENEDILEDIVLTLTLFEDREMIEE |

| Name | Protein Sequence |
|---|---|
| | RLKTYAHLFDDKVMKQLKRRRYTGWGRLSRKLINGIRDKQSGKTILDFLKSDGFAN<br>RNFMQLIHDDSLTFKEDIQKAQVSGQGDSLHEHIANLAGSPAIKKGILQTVKVVDE<br>LVKVMGRHKPENIVIEMARENQTTQKGQKNSRERMKRIEEGIKELGSQILKEHPVE<br>NTQLQNEKLYLYYLQNGRDMYVDQELDINRLSDYDVDAIVPQSFLKDDSIDNKVLT<br>RSDKNRGKSDNVPSEEVVKKMKNYWRQLLNAKLITQRKFDNLTKAERGGLSELDKA<br>GFIKRQLVETRQITKHVAQILDSRMNTKYDENDKLIREVKVITLKSKLVSDFRKDF<br>QFYKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPT<br>VAYSVLVVAKVEKGKSKKLKSVKELLGITIMERSSFEKNPIDFLEAKGYKEVKKDL<br>IIKLPKYSLFELENGRKRMLASAGELQKGNELALPSKYVNFLYLASHYEKLKGSPE<br>DNEQKQLFVEQHKHYLDEIIEQISEFSKRVILADANLDKVLSAYNKHRDKPIREQA<br>ENIIHLFTLTNLGAPAAFKYFDTTIDRKRYTSTKEVLDATLIHQSITGLYETRIDL<br>SQLGGDSPKKKRKVEASGGGGSGGGGSGGGGSGPAGPMEIYKTVSAWKRQPVRVLS<br>LFRNIDKVLKSLGFLESGSGSGGGTLKYVEDVTNVVRRDVEKWGPFDLVYGSTQPL<br>GSSCDRCPGWYMFQFHRILQYALPRQESQRPFFWIFMDNLLLTEDDQETTTRFLQT<br>EAVTLQDVRGRDYQNAMRVWSNIPGLKSKHAPLTPKEEEYLQAQVRSRSKLDAPKV<br>DLLVKNCLLPLREYFKYFSQNSLPLID |
| dCas9-<br>Dnmt3a3L<br>SEQ ID NO: 64 | MIDGGGGSGGGGSGGGGSMYPYDVPDYASPKKKRKVEASDKKYSIGLAIGTNSVGW<br>AVITDEYKVPSKKFKVLGNTDRHSIKKNLIGALLFDSGETAEATRLKRTARRRYTR<br>RKNRICYLQEIFSNEMAKVDDSFFHRLEESFLVEEDKKHERHPIFGNIVDEVAYHE<br>KYPTIYHLRKKLVDSTDKADLRLIYLALAHMIKFRGHFLIEGDLNPDNSDVDKLFI<br>QLVQTYNQLFEENPINASGVDAKAILSARLSKSRRLENLIAQLPGEKKNGLFGNLI<br>ALSLGLTPNFKSNFDLAEDAKLQLSKDTYDDDLDNLLAQIGDQYADLFLAAKNLSD<br>AILLSDILRVNTEITKAPLSASMIKRYDEHHQDLTLLKALVRQQLPEKYKEIFFDQ<br>SKNGYAGYIDGGASQEEFYKFIKPILEKMDGTEELLVKLNREDLLRKQRTFDNGSI<br>PHQIHLGELHAILRRRQEDFYPFLKDNREKIEKILTFRIPYYVGPLARGNSRFAWMT<br>RKSEETITPWNFEEVVDKGASAQSFIERMTNFDKNLPNEKVLPKHSLLYEYFTVYN<br>ELTKVKYVTEGMRKPAFLSGEQKKAIVDLLFKTNRKVTVKQLKEDYFKKIECFDSV<br>EISGVEDRFNASLGTYHDLLKIIKDKDFLDNEENEDILEDIVLTLTLFEDREMIEE<br>RLKTYAHLFDDKVMKQLKRRRYTGWGRLSRKLINGIRDKQSGKTILDFLKSDGFAN<br>RNFMQLIHDDSLTFKEDIQKAQVSGQGDSLHEHIANLAGSPAIKKGILQTVKVVDE<br>LVKVMGRHKPENIVIEMARENQTTQKGQKNSRERMKRIEEGIKELGSQILKEHPVE<br>NTQLQNEKLYLYYLQNGRDMYVDQELDINRLSDYDVDAIVPQSFLKDDSIDNKVLT<br>RSDKNRGKSDNVPSEEVVKKMKNYWRQLLNAKLITQRKFDNLTKAERGGLSELDKA<br>GFIKRQLVETRQITKHVAQILDSRMNTKYDENDKLIREVKVITLKSKLVSDFRKDF<br>QFYKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDFAT<br>VRKVLSMPQVNIVKKTEVQTGGFSKESILPKRNSDKLIARKKDWDPKKYGGFDSPT<br>VAYSVLVVAKVEKGKSKKLKSVKELLGITIMERSSFEKNPIDFLEAKGYKEVKKDL<br>IIKLPKYSLFELENGRKRMLASAGELQKGNELALPSKYVNFLYLASHYEKLKGSPE<br>DNEQKQLFVEQHKHYLDEIIEQISEFSKRVILADANLDKVLSAYNKHRDKPIREQA<br>ENIIHLFTLTNLGAPAAFKYFDTTIDRKRYTSTKEVLDATLIHQSITGLYETRIDL<br>SQLGGDSPKKKRKVEASGGGGSGGGGSGGGGSGPANHDQEFDPPKVYPPVPAEKRK<br>PIRVLSLFDGIATGLLVLKDLGIQVDRYIASEVCEDSITVGMVRHQGKIMYVGDVR<br>SVTQKHIQEWGPFDLVIGGSPCNDLSIVNPARKGLYEGTGRLFFEFYRLLHDARPK<br>EGDDRPFFWLFENVVAMGVSDKRDISRFLESNPVMIDAKEVSAAHRARYFWGNLPG<br>MNRPLASTVNDKLELQECLEHGRIAKFSKVRTITTRSNSIKQGKDQHFPVFMNEKE<br>DILWCTEMERVFGFPVHYTDVSNMSRLARQRLLGRSWSVPVIRHLFAPLKEYFACV<br>SSGNSNANSRGPSFSSGLVPLSLRGSHMGPMEIYKTVSAWKRQPVRVLSLFRNIDK<br>VLKSLGFLESGSGSGGGTLKYVEDVTNVVRRDVEKWGPFDLVYGSTQPLGSSCDRC<br>PGWYMFQFHRILQYALPRQESQRPFFWIFMDNLLLTEDDQETTTRFLQTEAVTLQD<br>VRGRDYQNAMRVWSNIPGLKSKHAPLTPKEEEYLQAQVRSRSKLDAPKVDLLVKNC<br>LLPLREYFKYFSQNSLPLID |
| Dnmt3a-PUFa<br>SEQ ID NO: 65 | MGPANHDQEFDPPKVYPPVPAEKRKPIRVLSLFDGIATGLLVLKDLGIQVDRYIAS<br>EVCEDSITVGMVRHQGKIMYVGDVRSVTQKHIQEWGPFDLVIGGSPCNDLSIVNPA<br>RKGLYEGTGRLFFEFYRLLHDARPKEGDDRPFFWLFENVVAMGVSDKRDISRFLES<br>NPVMIDAKEVSAAHRARYFWGNLPGMNRPLASTVNDKLELQECLEHGRIAKFSKVR<br>TITTRSNSIKQGKDQHFPVFMNEKEDILWCTEMERVFGFPVHYTDVSNMSRLARQR<br>LLGRSWSVPVIRHLFAPLKEYFACVIDGGGGSDPKKKRKVDPKKKRKVDPKKKRKV<br>GSTGSRNDGGGSGGGGSGGGGSGRAGILPPKKKRKVSRGRSRLLEDFRNNRYPNL<br>QLREIAGHIMEFSQDQHGSRFIQLKLERATPAERQLVFNEILQAAYQLMVDVFGNY<br>VIQKFFEFGSLEQKLALAERIRGHVLSLALQMYGSRVIEKALEFIPSDQQNEMVRE<br>LDGHVLKCVKDQNGNHVVQKCIECVQPQSLQFIIDAFKGQVFALSTHPYGCRVIQR<br>ILEHCLPDQTLPILEELHQHTEQLVQDQYGNYVIQHVLEHGRPEDKSKIVAEIRGN<br>VLVLSQHKFASNVVEKCVTHASRTERAVLIDEVCTMNDGPHSALYTMMKDQYANYV<br>VQKMIDVAEPGQRKIVMHKIRPHIATLRKYTYGKHILAKLEKYYMKNGVDLGDPKK<br>KRKVDPKKKRKVGGRGGGSGGGGSGGGGSGPA |
| Dnmt3L-PUFa<br>SEQ ID NO: 66 | MGPAGPMEIYKTVSAWKRQPVRVLSLFRNIDKVLKSLGFLESGSGSGGGTLKYVED<br>VTNVVRRDVEKWGPFDLVYGSTQPLGSSCDRCPGWYMFQFHRILQYALPRQESQRP<br>FFWIFMDNLLLTEDDQETTTRFLQTEAVTLQDVRGRDYQNAMRVWSNIPGLKSKHA<br>PLTPKEEEYLQAQVRSRSKLDAPKVDLLVKNCLLPLREYFKYFSQNSLPLIDGGGG<br>SDPKKKRKVDPKKKRKVDPKKKRKVGSTGSRNDGGGSGGGGSGGGGSGRAGILPP<br>KKKRKVSRGRSRLLEDFRNNRYPNLQLREIAGHIMEFSQDQHGSRFIQLKLERATP |

| Name | Protein Sequence |
|---|---|
| | AERQLVFNEILQAAYQLMVDVFGNYVIQKFFEFGSLEQKLALAERIRGHVLSLALQ<br>MYGSRVIEKALEFIPSDQQNEMVRELDGHVLKCVKDQNGNHVVQKCIECVQPQSLQ<br>FIIDAFKGQVFALSTHPYGCRVIQRILEHCLPDQTLPILEELHQHTEQLVQDQYGN<br>YVIQHVLEHGRPEDKSKIVAEIRGNVLVLSQHKFASNVVEKCVTHASRTERAVLID<br>EVCTMNDGPHSALYTMMKDQYANYVVQKMIDVAEPGQRKIVMHKIRPHIATLRKYT<br>YGKHILAKLEKYYMKNGVDLGDPKKKRKVDPKKKRKVGGRGGGGSGGGGSGGGGSG<br>PA |
| PUFa-Dnmt3a<br>SEQ ID NO: 67 | MIDGGGGSDPKKKRKVDPKKKRKVDPKKKRKVGSTGSRNDGGGGSGGGGSGGGGSG<br>RAGILPPKKKRKVSRGRSRLLEDFRNNRYPNLQLREIAGHIMEFSQDQHGSRFIQL<br>KLERATPAERQLVFNEILQAAYQLMVDVFGNYVIQKFFEFGSLEQKLALAERIRGH<br>VLSLALQMYGSRVIEKALEFIPSDQQNEMVRELDGHVLKCVKDQNGNHVVQKCIEC<br>VQPQSLQFIIDAFKGQVFALSTHPYGCRVIQRILEHCLPDQTLPILEELHQHTEQL<br>VQDQYGNYVIQHVLEHGRPEDKSKIVAEIRGNVLVLSQHKFASNVVEKCVTHASRT<br>ERAVLIDEVCTMNDGPHSALYTMMKDQYANYVVQKMIDVAEPGQRKIVMHKIRPHI<br>ATLRKYTYGKHILAKLEKYYMKNGVDLGDPKKKRKVDPKKKRKVGGRGGGGSGGGG<br>SGGGGSGPANHDQEFDPPKVYPPVPAEKRKPIRVLSLFDGIATGLLVLKDLGIQVD<br>RYIASEVCEDSITVGMVRHQGKIMYVGDVRSVTQKHIQEWGPFDLVIGGSPCNDLS<br>IVNPARKGLYEGTGRLFFEFYRLLHDARPKEGDDRPFFWLFENVVAMGVSDKRDIS<br>RFLESNPVMIDAKEVSAAHRARYFWGNLPGMNRPLASTVNDKLELQECLEHGRIAK<br>FSKVRTITTRSNSIKQGKDQHFPVFMNEKEDILWCTEMERVFGFPVHYTDVSNMSR<br>LARQRLLGRSWSVPVIRHLFAPLKEYFACVID |
| PUFa-Dnmt3L<br>SEQ ID NO: 68 | MIDGGGGSDPKKKRKVDPKKKRKVDPKKKRKVGSTGSRNDGGGGSGGGGSGGGGSG<br>RAGILPPKKKRKVSRGRSRLLEDFRNNRYPNLQLREIAGHIMEFSQDQHGSRFIQL<br>KLERATPAERQLVFNEILQAAYQLMVDVFGNYVIQKFFEFGSLEQKLALAERIRGH<br>VLSLALQMYGSRVIEKALEFIPSDQQNEMVRELDGHVLKCVKDQNGNHVVQKCIEC<br>VQPQSLQFIIDAFKGQVFALSTHPYGCRVIQRILEHCLPDQTLPILEELHQHTEQL<br>VQDQYGNYVIQHVLEHGRPEDKSKIVAEIRGNVLVLSQHKFASNVVEKCVTHASRT<br>ERAVLIDEVCTMNDGPHSALYTMMKDQYANYVVQKMIDVAEPGQRKIVMHKIRPHI<br>ATLRKYTYGKHILAKLEKYYMKNGVDLGDPKKKRKVDPKKKRKVGGRGGGGSGGGG<br>SGGGGSGPAGPMEIYKTVSAWKRQPVRVLSLFRNIDKVLKSLGFLESGSGSGGGTL<br>KYVEDVTNVVRRDVEKWGPFDLVYGSTQPLGSSCDRCPGWYMFQFHRILQYALPRQ<br>ESQRPFFWIFMDNLLLTEDDQETTTRFLQTEAVTLQDVRGRDYQNAMRVWSNIPGL<br>KSKHAPLTPKEEEYLQAQVRSRSKLDAPKVDLLVKNCLLPREYFKYFSQNSLPLI<br>D |
| PUFa-Dnmt3a3L<br>SEQ ID NO: 69 | MIDGGGGSDPKKKRKVDPKKKRKVDPKKKRKVGSTGSRNDGGGGSGGGGSGGGGSG<br>RAGILPPKKKRKVSRGRSRLLEDFRNNRYPNLQLREIAGHIMEFSQDQHGSRFIQL<br>KLERATPAERQLVFNEILQAAYQLMVDVFGNYVIQKFFEFGSLEQKLALAERIRGH<br>VLSLALQMYGSRVIEKALEFIPSDQQNEMVRELDGHVLKCVKDQNGNHVVQKCIEC<br>VQPQSLQFIIDAFKGQVFALSTHPYGCRVIQRILEHCLPDQTLPILEELHQHTEQL<br>VQDQYGNYVIQHVLEHGRPEDKSKIVAEIRGNVLVLSQHKFASNVVEKCVTHASRT<br>ERAVLIDEVCTMNDGPHSALYTMMKDQYANYVVQKMIDVAEPGQRKIVMHKIRPHI<br>ATLRKYTYGKHILAKLEKYYMKNGVDLGDPKKKRKVDPKKKRKVGGRGGGGSGGGG<br>SGGGGSGPANHDQEFDPPKVYPPVPAEKRKPIRVLSLFDGIATGLLVLKDLGIQVD<br>RYIASEVCEDSITVGMVRHQGKIMYVGDVRSVTQKHIQEWGPFDLVIGGSPCNDLS<br>IVNPARKGLYEGTGRLFFEFYRLLHDARPKEGDDRPFFWLFENVVAMGVSDKRDIS<br>RFLESNPVMIDAKEVSAAHRARYFWGNLPGMNRPLASTVNDKLELQECLEHGRIAK<br>FSKVRTITTRSNSIKQGKDQHFPVFMNEKEDILWCTEMERVFGFPVHYTDVSNMSR<br>LARQRLLGRSWSVPVIRHLFAPLKEYFACVSSGNSNANSRGPSFSSGLVPLSLRGS<br>HMGPMEIYKTVSAWKRQPVRVLSLFRNIDKVLKSLGFLESGSGSGGGTLKYVEDVT<br>NVVRRDVEKWGPFDLVYGSTQPLGSSCDRCPGWYMFQFHRILQYALPRQESQRPFF<br>WIFMDNLLLTEDDQETTTRFLQTEAVTLQDVRGRDYQNAMRVWSNIPGLKSKHAPL<br>TPKEEEYLQAQVRSRSKLDAPKVDLLVKNCLLPREYFKYFSQNSLPLID |

List of protein sequences

| Name | sgRNA-PBS sequence |
|---|---|
| sgSOX2-1-5xPBSa<br>SEQ ID NO: 70 | GCATGTGACGGGGGCTGTCAgtttAagagctaTGCTGGAAACAGCAta<br>gcaagttTaaataaggctagtccgttatcaacttgaaaaagtggcacc<br>gagtcggtgcAATTGggtctccagatTGTATGTAGCCTGTATGTAGC<br>CTGTATGTAGCCTGTATGTAGCCTGTATGTAagatCTTTTTTT |
| sgSOX2-2-5xPBSa<br>SEQ ID NO: 71 | GCTGCCGGGTTTTGCATGAAgtttAagagctaTGCTGGAAACAGCAta<br>gcaagttTaaataaggctagtccgttatcaacttgaaaaagtggcacc<br>gagtcggtgcAATTGggtctccagatTGTATGTAGCCTGTATGTAGC<br>CTGTATGTAGCCTGTATGTAGCCTGTATGTAagatCTTTTTTT |
| sgSOX2-3-5xPBSa<br>SEQ ID NO: 72 | GCCGGCCGCGCGGGGGAGGCgtttAagagctaTGCTGGAAACAGCAta<br>gcaagttTaaataaggctagtccgttatcaacttgaaaaagtggcacc<br>gagtcggtgcAATTGggtctccagatTGTATGTAGCCTGTATGTAGC<br>CTGTATGTAGCCTGTATGTAGCCTGTATGTAagatCTTTTTTT |

| Name | sgRNA-PBS sequence |
|---|---|
| sgSOX2-4-5xPBSa SEQ ID NO: 73 | GGCAGGCGAGGAGGGGGAGGgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAGCCTGTATGTAagatCTTTTTTT |
| sgMLH1-PBSa sequences | SEQ ID NO: 74<br>ACAGAGTTGAGAAATTTGACgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 75<br>GTCAAATTTCTCAACTCTGTgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 76<br>GCTCCTAAAAACGAACCAATgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 77<br>AAACGAACCAATAGGAAGAGgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 78<br>CTTCAGCGGCAGCTATTGATgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 79<br>GCATCTCTGCTCCTATTGGCgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 80<br>GCGCCAGATCACCTCAGCAGgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 81<br>GCAGAGCGGAGGAGGTGCTgtttAagagctaTGCTGGAAACAGCAtag caagttTaaataaggctagtccgttatcaacttgaaaaagtggcaccg agtcggtgcCAATTGggtctccagatTGTATGTAGCCTGTATGTAGCC TGTATGTAGCCTGTATGTAGCCTGTATGTAagatCTTTTTTT<br>SEQ ID NO: 82<br>GAAGGAAGAACGTGAGCACGgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 83<br>GGCAGTAGCCGCTTCAGGGAgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT<br>SEQ ID NO: 84<br>GCGCAAGCGCATATCCTTCTgtttAagagctaTGCTGGAAACAGCAta gcaagttTaaataaggctagtccgttatcaacttgaaaaagtggcacc gagtcggtgcCAATTGggtctccagatTGTATGTAGCCTGTATGTAGC CTGTATGTAGCCTGTATGTAagatCTTTTTTT |

REFERENCES

Barreto G., Schäfer A., Marhold J., Stach D., Swaminathan S. K., Handa V., Doderlein G., Maltry N., Wu W., Lyko F., Niehrs C. Gadd45a promotes epigenetic gene activation by repair-mediated DNA demethylation. Nature. 2007; 445:671-675.

Le May N., Mota-Fernandes D., Velez-Cruz R., Iltis I., Biard D., Egly J. M. NER factors are recruited to active promoters and facilitate chromatin modification for transcription in the absence of exogenous genotoxic attack. Mol. Cell. 2010; 38:54-66

Schmitz K. M., Schmitt N., Hoffmann-Rohrer U., Schäfer A., Grummt I., Mayer C. TAF12 recruits Gadd45a and the nucleotide excision repair complex to the promoter of rRNA genes leading to active DNA demethylation. Mol. Cell. 2009; 33:344-353

Kriaucionis S., Heintz N. The nuclear DNA base 5-hydroxymethylcytosine is present in Purkinje neurons and the brain. Science. 2009; 324:929-930

Maiti A., Drohat A. C. Thymine DNA glycosylase can rapidly excise 5-formylcytosine and 5-carboxylcytosine: potential implications for active demethylation of CpG sites. J. Biol. Chem. 2011; 286:35334-35338.

He Y. F., Li B. Z., Li Z., Liu P., Wang Y., Tang Q., Ding J., Jia Y., Chen Z., Li L., Sun Y., Li X., Dai Q., Song C. X., Zhang K., He C., Xu G. L. Tet-mediated formation of 5-carboxylcytosine and its excision by TDG in mammalian DNA. Science. 2011; 333:1303-1307.

Ito, S., et al., Role of Tet proteins in 5mC to 5hmC conversion, ES-cell self-renewal and inner cell mass specification. Nature, 2010.466(7310): p. 1129-33.

Kienhofer, S., et al., GADD45a physically and functionally interacts with TET1. Differentiation, 2015. 90(1-3): p. 59-68.

Muller, U., et al., TET-mediated oxidation of methylcytosine causes TDG or NEIL glycosylase dependent gene reactivation. Nucleic Acids Res, 2014. 42(13): p. 8592-604.

What is claimed is:

1. A composition comprising:
    a guide RNA (gRNA) comprising a PUF binding site (PBS) sequence;
    a nuclease-deficient DNA endonuclease that binds to the gRNA; and
    a PUF domain linked to a demethylation domain or a methylation domain, wherein the PUF domain binds to the PBS of the gRNA.

2. The composition of claim 1, wherein the gRNA targets a sequence selected from gene sequences, transcriptional regulatory sequences, promoter sequences, enhancer sequences, and silencer sequences.

3. The composition of claim 1, wherein the gRNA comprises 1-50 PBS sequences.

4. The composition of claim 1, wherein the PBS sequence comprises the sequence of SEQ ID NO: 1.

5. The composition of claim 1, wherein the nuclease-deficient DNA endonuclease enzyme is a nuclease-deficient Cas9 protein (dCas9).

6. The composition of claim 1, wherein the nuclease-deficient DNA endonuclease enzyme further comprises a nuclear localization signal (NLS).

7. The composition of claim 1, wherein the PUF domain comprises a PUFa domain, a PUFb domain, a PUFc domain, or a PUFw domain.

8. The composition of claim 7, wherein the PUFa domain comprises the sequence of SEQ ID NO:2, the PUFb domain comprises the sequence of SEQ ID NO:3, the PUFc domain comprises the sequence of SEQ ID NO:4, and/or the PUFw domain comprises the sequence of SEQ ID NO:5.

9. The composition of claim 1, wherein the PUF domain is linked to a demethylation domain.

10. The composition of claim 9, wherein the demethylation domain comprises a ten eleven translocation (TET) domain.

11. The composition of claim 10, wherein the TET domain is a TET1 domain.

12. The composition of claim 9, wherein the gRNA targets a hypermethylated nucleic acid sequence.

13. The composition of claim 12, wherein the hypermethylated nucleic acid sequence is a hypermethylated CpG sequence.

14. The composition of claim 9, wherein the gRNA targets a human mutL homolog 1 (hMLH1) gene.

15. The composition of claim 1, wherein the PUF domain is linked to a methylation domain.

16. The composition of claim 15, wherein the methylation domain comprises a DNA methyltransferase (DNMT) domain.

17. The composition of claim 16, wherein the DNMT domain is a DNMT3A domain or a DNMT3A-3L domain.

18. A mammalian cell comprising the composition of claim 1.

19. A kit comprising: a guide RNA (gRNA) comprising a PUF binding site (PBS) sequence; a nuclease-deficient DNA endonuclease that binds to the gRNA; and a PUF domain linked to a demethylation domain or a methylation domain, wherein the PUF domain binds to the PBS of the gRNA.

20. A complex comprising: a guide RNA (gRNA) comprising a PUF binding site (PBS) sequence; and a protein comprising a PUF domain linked to a demethylation domain or a methylation domain, wherein the PUF domain is bound to the PBS of the gRNA.

21. The complex of claim 20 further comprising a nuclease-deficient DNA endonuclease that binds to the gRNA.

22. A method of modulating methylation state of a nucleic acid of a mammalian cell, the method comprising delivering to the mammalian cell the composition of claim 1, wherein the gRNA targets the nucleic acid, and methylation state of the nucleic acid is modulated.

* * * * *

SEQUENCE LISTING

```
<160> NUMBER OF SEQ ID NOS: 84

<210> SEQ ID NO 1
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 1 uguaugua                                                            8

<210> SEQ ID NO 2
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 2

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160
```

```
Phe Ile Ile Asp Ala Phe Lys Gly Gln Val Phe Ala Leu Ser Thr His
             165                 170                 175
Pro Tyr Gly Cys Arg Val Ile Gln Arg Ile Leu Glu His Cys Leu Pro
             180                 185                 190
Asp Gln Thr Leu Pro Ile Leu Glu Glu Leu His Gln His Thr Glu Gln
             195                 200                 205
Leu Val Gln Asp Gln Tyr Gly Asn Tyr Val Ile Gln His Val Leu Glu
             210                 215                 220
His Gly Arg Pro Glu Asp Lys Ser Lys Ile Val Ala Glu Ile Arg Gly
225                 230                 235                 240
Asn Val Leu Val Leu Ser Gln His Lys Phe Ala Ser Asn Val Val Glu
             245                 250                 255
Lys Cys Val Thr His Ala Ser Arg Thr Glu Arg Ala Val Leu Ile Asp
             260                 265                 270
Glu Val Cys Thr Met Asn Asp Gly Pro His Ser Ala Leu Tyr Thr Met
             275                 280                 285
Met Lys Asp Gln Tyr Ala Asn Tyr Val Val Gln Lys Met Ile Asp Val
             290                 295                 300
Ala Glu Pro Gly Gln Arg Lys Ile Val Met His Lys Ile Arg Pro His
305                 310                 315                 320
Ile Ala Thr Leu Arg Lys Tyr Thr Tyr Gly Lys His Ile Leu Ala Lys
             325                 330                 335
Leu Glu Lys Tyr Tyr Met Lys Asn Gly Val Asp Leu Gly Gly Arg Ser
             340                 345                 350
Arg Leu Leu Glu Asp Phe Arg Asn Asn Arg Tyr Pro Asn Leu Gln Leu
             355                 360                 365
Arg Glu Ile Ala Gly His Ile Met Glu Phe Ser Gln Asp Gln His Gly
             370                 375                 380
Ser Arg Phe Ile Gln Leu Lys Leu Glu Arg Ala Thr Pro Ala Glu Arg
385                 390                 395                 400
Gln Leu Val Phe Asn Glu Ile Leu Gln Ala Ala Tyr Gln Leu Met Val
             405                 410                 415
Asp Val Phe Gly Asn Tyr Val Ile Gln Lys Phe Phe Glu Phe Gly Ser
             420                 425                 430
Leu Glu Gln Lys Leu Ala Leu Ala Glu Arg Ile Arg Gly His Val Leu
             435                 440                 445
Ser Leu Ala Leu Gln Met Tyr Gly Ser Arg Val Ile Glu Lys Ala Leu
             450                 455                 460
Glu Phe Ile Pro Ser Asp Gln Gln Asn Glu Met Val Arg Glu Leu Asp
465                 470                 475                 480
Gly His Val Leu Lys Cys Val Lys Asp Gln Asn Gly Asn His Val Val
             485                 490                 495
Gln Lys Cys Ile Glu Cys Val Gln Pro Gln Ser Leu Gln Phe Ile Ile
             500                 505                 510
Asp Ala Phe Lys Gly Gln Val Phe Ala Leu Ser Thr His Pro Tyr Gly
             515                 520                 525
Cys Arg Val Ile Gln Arg Ile Leu Glu His Cys Leu Pro Asp Gln Thr
             530                 535                 540
Leu Pro Ile Leu Glu Glu Leu His Gln His Thr Glu Gln Leu Val Gln
545                 550                 555                 560
Asp Gln Tyr Gly Asn Tyr Val Ile Gln His Val Leu Glu His Gly Arg
             565                 570                 575
Pro Glu Asp Lys Ser Lys Ile Val Ala Glu Ile Arg Gly Asn Val Leu
```

```
                   580                 585                 590
Val Leu Ser Gln His Lys Phe Ala Ser Asn Val Val Glu Lys Cys Val
            595                 600                 605

Thr His Ala Ser Arg Thr Glu Arg Ala Val Leu Ile Asp Glu Val Cys
    610                 615                 620

Thr Met Asn Asp Gly Pro His Ser Ala Leu Tyr Thr Met Met Lys Asp
625                 630                 635                 640

Gln Tyr Ala Asn Tyr Val Val Gln Lys Met Ile Asp Val Ala Glu Pro
                645                 650                 655

Gly Gln Arg Lys Ile Val Met His Lys Ile Arg Pro His Ile Ala Thr
            660                 665                 670

Leu Arg Lys Tyr Thr Tyr Gly Lys His Ile Leu Ala Lys Leu Glu Lys
        675                 680                 685

Tyr Tyr Met Lys Asn Gly Val Asp Leu Gly
    690                 695

<210> SEQ ID NO 3
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 3

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Ser Tyr Val Ile Glu His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
```

```
                        245                 250                 255
Lys Cys Val Thr His Ala Ser Arg Thr Glu Arg Ala Val Leu Ile Asp
            260                 265                 270
Glu Val Cys Thr Met Asn Asp Gly Pro His Ser Ala Leu Tyr Thr Met
        275                 280                 285
Met Lys Asp Gln Tyr Ala Asn Tyr Val Val Gln Lys Met Ile Asp Val
    290                 295                 300
Ala Glu Pro Gly Gln Arg Lys Ile Val Met His Lys Ile Arg Pro His
305                 310                 315                 320
Ile Ala Thr Leu Arg Lys Tyr Thr Tyr Gly Lys His Ile Leu Ala Lys
                325                 330                 335
Leu Glu Lys Tyr Tyr Met Lys Asn Gly Val Asp Leu Gly
            340                 345

<210> SEQ ID NO 4
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 4

Gly Arg Ser Arg Leu Leu Glu Asp Phe Arg Asn Asn Arg Tyr Pro Asn
1               5                   10                  15
Leu Gln Leu Arg Glu Ile Ala Gly His Ile Met Glu Phe Ser Gln Asp
                20                  25                  30
Gln His Gly Ser Arg Phe Ile Gln Leu Lys Leu Glu Arg Ala Thr Pro
            35                  40                  45
Ala Glu Arg Gln Leu Val Phe Asn Glu Ile Leu Gln Ala Ala Tyr Gln
        50                  55                  60
Leu Met Val Asp Val Phe Gly Asn Tyr Val Ile Gln Lys Phe Phe Glu
65                  70                  75                  80
Phe Gly Ser Leu Glu Gln Lys Leu Ala Leu Ala Glu Arg Ile Arg Gly
                85                  90                  95
His Val Leu Ser Leu Ala Leu Gln Met Tyr Gly Ser Arg Val Ile Glu
                100                 105                 110
Lys Ala Leu Glu Phe Ile Pro Ser Asp Gln Gln Asn Glu Met Val Arg
            115                 120                 125
Glu Leu Asp Gly His Val Leu Lys Cys Val Lys Asp Gln Asn Gly Asn
        130                 135                 140
His Val Val Gln Lys Cys Ile Glu Cys Val Gln Pro Gln Ser Leu Gln
145                 150                 155                 160
Phe Ile Ile Asp Ala Phe Lys Gly Gln Val Phe Ala Leu Ser Thr His
                165                 170                 175
Pro Tyr Gly Cys Arg Val Ile Gln Arg Ile Leu Glu His Cys Leu Pro
            180                 185                 190
Asp Gln Thr Leu Pro Ile Leu Glu Glu Leu His Gln His Thr Glu Gln
        195                 200                 205
Leu Val Gln Asp Gln Tyr Gly Ser Tyr Val Ile Glu His Val Leu Glu
    210                 215                 220
His Gly Arg Pro Glu Asp Lys Ser Lys Ile Val Ala Glu Ile Arg Gly
225                 230                 235                 240
Asn Val Leu Val Leu Ser Gln His Lys Phe Ala Asn Asn Val Val Gln
                245                 250                 255
Lys Cys Val Thr His Ala Ser Arg Thr Glu Arg Ala Val Leu Ile Asp
```

```
                        260                 265                 270
Glu Val Cys Thr Met Asn Asp Gly Pro His Ser Ala Leu Tyr Thr Met
                275                 280                 285

Met Lys Asp Gln Tyr Ala Asn Tyr Val Val Gln Lys Met Ile Asp Val
            290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
                340                 345
```

<210> SEQ ID NO 5
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 5

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
```

```
            275                 280                 285
Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
            340                 345

<210> SEQ ID NO 6
<211> LENGTH: 37
<212> TYPE: DNA
<213> ORGANISM: Artificial Sequence
<220> FEATURE:
<223> OTHER INFORMATION: Synthetic Nucleotide

<400> SEQUENCE: 6
gttttagagc tagaaatagc aagttaaaat aaggcta                            37

<210> SEQ ID NO 7
<211> LENGTH: 47
<212> TYPE: DNA
<213> ORGANISM: Artificial Sequence
<220> FEATURE:
<223> OTHER INFORMATION: Synthetic Nucleotide

<400> SEQUENCE: 7
gtttaagagc tatgctggaa acagcatagc aagtttaaat aaggcta                 47

<210> SEQ ID NO 8
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 8 uguaugua                                                            8

<210> SEQ ID NO 9
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 9 uugauaua                                                            8

<210> SEQ ID NO 10
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 10 uguauaua                                                            8

<210> SEQ ID NO 11
<211> LENGTH: 8
<212> TYPE: RNA
<213> ORGANISM: Artificial Sequence
```

```
<220> FEATURE:
<223> OTHER INFORMATION: Synthetic Nucleotide

<400> SEQUENCE: 11 uggauaua                                                                 8

<210> SEQ ID NO 12
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 12 uuuauaua                                                                 8

<210> SEQ ID NO 13
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 13 ugugugug                                                                 8

<210> SEQ ID NO 14
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 14 uguauaug                                                                 8

<210> SEQ ID NO 15
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 15 uauauaua                                                                 8

<210> SEQ ID NO 16
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 16 uguauuua                                                                 8

<210> SEQ ID NO 17
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 17 uuuauuua                                                                 8
```

<210> SEQ ID NO 18
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 18

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr Met Lys Asn Gly Val Asp Leu Gly
            340                 345
```

<210> SEQ ID NO 19
<211> LENGTH: 349

```
<212> TYPE: PRT
<213> ORGANISM: Artificial Sequence
<220> FEATURE:
<223> OTHER INFORMATION: Synthetic Polypeptide

<400> SEQUENCE: 19
```

| | | | | | | | | | | | | | | |
|---|---|---|---|---|---|---|---|---|---|---|---|---|---|---|
| Gly | Arg | Ser | Arg | Leu | Leu | Glu | Asp | Phe | Arg | Asn | Asn | Arg | Tyr | Pro | Asn |
| 1 | | | | 5 | | | | | 10 | | | | | 15 | |
| Leu | Gln | Leu | Arg | Glu | Ile | Ala | Gly | His | Ile | Met | Glu | Phe | Ser | Gln | Asp |
| | | | 20 | | | | | 25 | | | | | 30 | | |
| Gln | His | Gly | Ser | Arg | Phe | Ile | Gln | Leu | Lys | Leu | Glu | Arg | Ala | Thr | Pro |
| | | | 35 | | | | | 40 | | | | | 45 | | |
| Ala | Glu | Arg | Gln | Leu | Val | Phe | Asn | Glu | Ile | Leu | Gln | Ala | Ala | Tyr | Gln |
| | 50 | | | | | 55 | | | | | 60 | | | | |
| Leu | Met | Val | Asp | Val | Phe | Gly | Asn | Tyr | Val | Ile | Gln | Lys | Phe | Phe | Glu |
| 65 | | | | | 70 | | | | | 75 | | | | | 80 |
| Phe | Gly | Ser | Leu | Glu | Gln | Lys | Leu | Ala | Leu | Ala | Glu | Arg | Ile | Arg | Gly |
| | | | | 85 | | | | | 90 | | | | | 95 | |
| His | Val | Leu | Ser | Leu | Ala | Leu | Gln | Met | Tyr | Gly | Cys | Arg | Val | Ile | Gln |
| | | | | 100 | | | | | 105 | | | | | 110 | |
| Lys | Ala | Leu | Glu | Phe | Ile | Pro | Ser | Asp | Gln | Gln | Asn | Glu | Met | Val | Arg |
| | | | 115 | | | | | 120 | | | | | 125 | | |
| Glu | Leu | Asp | Gly | His | Val | Leu | Lys | Cys | Val | Lys | Asp | Gln | Asn | Gly | Asn |
| | 130 | | | | | 135 | | | | | 140 | | | | |
| His | Val | Val | Gln | Lys | Cys | Ile | Glu | Cys | Val | Gln | Pro | Gln | Ser | Leu | Gln |
| 145 | | | | | 150 | | | | | 155 | | | | | 160 |
| Phe | Ile | Ile | Asp | Ala | Phe | Lys | Gly | Gln | Val | Phe | Ala | Leu | Ser | Thr | His |
| | | | | 165 | | | | | 170 | | | | | 175 | |
| Pro | Tyr | Gly | Cys | Arg | Val | Ile | Gln | Arg | Ile | Leu | Glu | His | Cys | Leu | Pro |
| | | | | 180 | | | | | 185 | | | | | 190 | |
| Asp | Gln | Thr | Leu | Pro | Ile | Leu | Glu | Glu | Leu | His | Gln | His | Thr | Glu | Gln |
| | | | 195 | | | | | 200 | | | | | 205 | | |
| Leu | Val | Gln | Asp | Gln | Tyr | Gly | Ser | Tyr | Val | Ile | Glu | His | Val | Leu | Glu |
| | 210 | | | | | 215 | | | | | 220 | | | | |
| His | Gly | Arg | Pro | Glu | Asp | Lys | Ser | Lys | Ile | Val | Ala | Glu | Ile | Arg | Gly |
| 225 | | | | | 230 | | | | | 235 | | | | | 240 |
| Asn | Val | Leu | Val | Leu | Ser | Gln | His | Lys | Phe | Ala | Asn | Asn | Val | Val | Gln |
| | | | | 245 | | | | | 250 | | | | | 255 | |
| Lys | Cys | Val | Thr | His | Ala | Ser | Arg | Thr | Glu | Arg | Ala | Val | Leu | Ile | Asp |
| | | | 260 | | | | | 265 | | | | | 270 | | |
| Glu | Val | Cys | Thr | Met | Asn | Asp | Gly | Pro | His | Ser | Ala | Leu | Tyr | Thr | Met |
| | | 275 | | | | | 280 | | | | | 285 | | | |
| Met | Lys | Asp | Gln | Tyr | Ala | Asn | Tyr | Val | Val | Gln | Lys | Met | Ile | Asp | Val |
| | 290 | | | | | 295 | | | | | 300 | | | | |
| Ala | Glu | Pro | Gly | Gln | Arg | Lys | Ile | Val | Met | His | Lys | Ile | Arg | Pro | His |
| 305 | | | | | 310 | | | | | 315 | | | | | 320 |
| Ile | Ala | Thr | Leu | Arg | Lys | Tyr | Thr | Tyr | Gly | Lys | His | Ile | Leu | Ala | Lys |
| | | | | 325 | | | | | 330 | | | | | 335 | |
| Leu | Glu | Lys | Tyr | Tyr | Met | Lys | Asn | Gly | Val | Asp | Leu | Gly | | | |
| | | | 340 | | | | | 345 | | | | | | | |

```
<210> SEQ ID NO 20

<400> SEQUENCE: 20

000
```

<210> SEQ ID NO 21

<400> SEQUENCE: 21

000

<210> SEQ ID NO 22
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 22

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Glu Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Ser Arg Val Ile Glu Arg Ile Leu Glu His Cys Leu Pro
            180                 185                 190

Asp Gln Thr Leu Pro Ile Leu Glu Glu Leu His Gln His Thr Glu Gln
        195                 200                 205

Leu Val Gln Asp Gln Tyr Gly Asn Tyr Val Ile Gln His Val Leu Glu
    210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Ser Asn Val Val Glu
                245                 250                 255

Lys Cys Val Thr His Ala Ser Arg Thr Glu Arg Ala Val Leu Ile Asp
            260                 265                 270

Glu Val Cys Thr Met Asn Asp Gly Pro His Ser Ala Leu Tyr Thr Met
        275                 280                 285

Met Lys Asp Gln Tyr Ala Asn Tyr Val Val Gln Lys Met Ile Asp Val
    290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
```

```
              325                 330                 335
Leu Glu Lys Tyr Tyr Met Lys Asn Gly Val Asp Leu Gly
            340                 345

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27
<211> LENGTH: 8
<212> TYPE: RNA
<213> ORGANISM: Artificial Sequence
<220> FEATURE:
<223> OTHER INFORMATION: Synthetic Nucleotide

<400> SEQUENCE: 27 uugaugua                                                                 8

<210> SEQ ID NO 28
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 28

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Cys Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
            100                 105                 110

Lys Ala Leu Glu Phe Ile Pro Ser Asp Gln Gln Asn Glu Met Val Arg
        115                 120                 125
```

```
Glu Leu Asp Gly His Val Leu Lys Cys Val Lys Asp Gln Asn Gly Asn
        130                 135                 140

His Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                    165                 170                 175

Pro Tyr Gly Cys Arg Val Ile Gln Arg Ile Leu Glu His Cys Leu Pro
                180                 185                 190

Asp Gln Thr Leu Pro Ile Leu Glu Glu Leu His Gln His Thr Glu Gln
                195                 200                 205

Leu Val Gln Asp Gln Tyr Gly Ser Tyr Val Ile Glu His Val Leu Glu
            210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                    245                 250                 255

Lys Cys Val Thr His Ala Ser Arg Thr Glu Arg Ala Val Leu Ile Asp
                260                 265                 270

Glu Val Cys Thr Met Asn Asp Gly Pro His Ser Ala Leu Tyr Thr Met
            275                 280                 285

Met Lys Asp Gln Tyr Ala Asn Tyr Val Val Gln Lys Met Ile Asp Val
290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                    325                 330                 335

Leu Glu Lys Tyr Tyr Met Lys Asn Gly Val Asp Leu Gly
                340                 345

<210> SEQ ID NO 29
<211> LENGTH: 341
<212> TYPE: PRT
<213> ORGANISM: Artificial Sequence
<220> FEATURE:
<223> OTHER INFORMATION: Synthetic Polypeptide

<400> SEQUENCE: 29

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Glu Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Cys Arg Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
                100                 105                 110

Lys Ala Leu Glu Phe Ile Pro Ser Asp Gln Gln Asn Glu Met Val Arg
            115                 120                 125

Glu Leu Asp Gly His Val Leu Lys Cys Val Lys Asp Gln Asn Gly Asn
        130                 135                 140
```

His Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175

Pro Tyr Gly Cys Arg Val Ile Gln Arg Ile Leu Glu His Cys Leu Pro
                180                 185                 190

Asp Gln Thr Leu Pro Ile Leu Glu Glu Leu His Gln His Thr Glu Gln
                195                 200                 205

Leu Val Gln Asp Gln Tyr Gly Ser Tyr Val Ile Glu His Val Leu Glu
                210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Asn Asn Val Val Gln
                245                 250                 255

Lys Cys Val Thr His Ala Ser Arg Thr Glu Arg Ala Val Leu Ile Asp
                260                 265                 270

Glu Val Cys Thr Met Asn Asp Gly Pro His Ser Ala Leu Tyr Thr Met
                275                 280                 285

Met Lys Asp Gln Tyr Ala Ser Tyr Val Val Glu Lys Met Ile Asp Val
290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr
                340

<210> SEQ ID NO 30
<211> LENGTH: 341
<212> TYPE: PRT
<213> ORGANISM: Artificial Sequence
<220> FEATURE:
<223> OTHER INFORMATION: Synthetic Polypeptide

<400> SEQUENCE: 30

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Asn Arg Phe Ile Gln Leu Lys Leu Glu Arg Ala Thr Pro
                35                  40                  45

Ala Glu Arg Gln Leu Val Phe Asn Glu Ile Leu Gln Ala Ala Tyr Gln
            50                  55                  60

Leu Met Val Asp Val Phe Gly Ser Tyr Val Ile Glu Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Ser Arg Val Ile Glu
                100                 105                 110

Lys Ala Leu Glu Phe Ile Pro Ser Asp Gln Gln Asn Glu Met Val Arg
                115                 120                 125

Glu Leu Asp Gly His Val Leu Lys Cys Val Lys Asp Gln Asn Gly Asn
            130                 135                 140

His Val Val Gln Lys Cys Ile Glu Cys Val Gln Pro Gln Ser Leu Gln
145                 150                 155                 160

```
Phe Ile Ile Asp Ala Phe Lys Gly Gln Val Phe Ala Leu Ser Thr His
                165                 170                 175

Pro Tyr Gly Ser Arg Val Ile Glu Arg Ile Leu Glu His Cys Leu Pro
            180                 185                 190

Asp Gln Thr Leu Pro Ile Leu Glu Glu Leu His Gln His Thr Glu Gln
            195                 200                 205

Leu Val Gln Asp Gln Tyr Gly Ser Tyr Val Ile Glu His Val Leu Glu
        210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Cys Asn Val Val Gln
                245                 250                 255

Lys Cys Val Thr His Ala Ser Arg Thr Glu Arg Ala Val Leu Ile Asp
            260                 265                 270

Glu Cys Val Thr Met Asn Asp Gly Pro His Ser Ala Leu Tyr Thr Met
            275                 280                 285

Met Lys Asp Gln Tyr Ala Ser Tyr Val Val Glu Lys Met Ile Asp Val
        290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
                325                 330                 335

Leu Glu Lys Tyr Tyr
            340
```

```
<210> SEQ ID NO 31
<211> LENGTH: 341
<212> TYPE: PRT
<213> ORGANISM: Artificial Sequence
<220> FEATURE:
<223> OTHER INFORMATION: Synthetic Polypeptide

<400> SEQUENCE: 31

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Cys Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Ser Tyr Val Ile Glu Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Asn Arg Val Ile Gln
            100                 105                 110

Lys Ala Leu Glu Phe Ile Pro Ser Asp Gln Gln Asn Glu Met Val Arg
        115                 120                 125

Glu Leu Asp Gly His Val Leu Lys Cys Val Lys Asp Gln Asn Gly Asn
    130                 135                 140

His Val Val Gln Lys Cys Ile Glu Cys Val Gln Pro Gln Ser Leu Gln
145                 150                 155                 160

Phe Ile Ile Asp Ala Phe Lys Gly Gln Val Phe Ala Leu Ser Thr His
                165                 170                 175
```

```
Pro Tyr Gly Cys Arg Val Ile Gln Arg Ile Leu Glu His Cys Leu Pro
            180                 185                 190

Asp Gln Thr Leu Pro Ile Leu Glu Glu Leu His Gln His Thr Glu Gln
            195                 200                 205

Leu Val Gln Asp Gln Tyr Gly Ser Tyr Val Ile Glu His Val Leu Glu
            210                 215                 220

His Gly Arg Pro Glu Asp Lys Ser Lys Ile Val Ala Glu Ile Arg Gly
225                 230                 235                 240

Asn Val Leu Val Leu Ser Gln His Lys Phe Ala Cys Asn Val Val Gln
            245                 250                 255

Lys Cys Val Thr His Ala Ser Arg Thr Glu Arg Ala Val Leu Ile Asp
            260                 265                 270

Glu Cys Val Thr Met Asn Asp Gly Pro His Ser Ala Leu Tyr Thr Met
            275                 280                 285

Met Lys Asp Gln Tyr Ala Cys Tyr Val Val Gln Lys Met Ile Asp Val
            290                 295                 300

Ala Glu Pro Gly Gln Arg Lys Ile Val Met His Lys Ile Arg Pro His
305                 310                 315                 320

Ile Ala Thr Leu Arg Lys Tyr Thr Tyr Gly Lys His Ile Leu Ala Lys
            325                 330                 335

Leu Glu Lys Tyr Tyr
            340

<210> SEQ ID NO 32
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 32

Met Gly Ile Leu Pro Pro Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
            35                  40                  45

Gly Ser Arg Phe Ile Gln Leu Lys Leu Glu Arg Ala Thr Pro Ala Glu
50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
            85                  90                  95

Ser Leu Glu Gln Lys Leu Ala Leu Ala Glu Arg Ile Arg Gly His Val
            100                 105                 110

Leu Ser Leu Ala Leu Gln Met Tyr Gly Ser Arg Val Ile Glu Lys Ala
            115                 120                 125

Leu Glu Phe Ile Pro Ser Asp Gln Gln Asn Glu Met Val Arg Glu Leu
            130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
            165                 170                 175

Ile Asp Ala Phe Lys Gly Gln Val Phe Ala Leu Ser Thr His Pro Tyr
            180                 185                 190
```

```
Gly Cys Arg Val Ile Gln Arg Ile Leu Glu His Cys Leu Pro Asp Gln
            195                 200                 205

Thr Leu Pro Ile Leu Glu Glu Leu His Gln His Thr Glu Gln Leu Val
    210                 215                 220

Gln Asp Gln Tyr Gly Asn Tyr Val Ile Gln His Val Leu Glu His Gly
225                 230                 235                 240

Arg Pro Glu Asp Lys Ser Lys Ile Val Ala Glu Ile Arg Gly Asn Val
            245                 250                 255

Leu Val Leu Ser Gln His Lys Phe Ala Ser Asn Val Val Glu Lys Cys
        260                 265                 270

Val Thr His Ala Ser Arg Thr Glu Arg Ala Val Leu Ile Asp Glu Val
    275                 280                 285

Cys Thr Met Asn Asp Gly Pro His Ser Ala Leu Tyr Thr Met Met Lys
290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
            325                 330                 335

Thr Leu Arg Lys Tyr Thr Tyr Gly Lys His Ile Leu Ala Lys Leu Glu
        340                 345                 350

Lys Tyr Tyr Met Lys Asn Gly Val Asp Leu Gly Gly Pro Ala Gly Ser
    355                 360                 365

Gly Arg Ala Asp Ala Leu Asp Asp Phe Asp Leu Asp Met Leu Gly Ser
    370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
            405                 410                 415

Asp Leu Asp Met Leu Tyr Ile Asp
            420
```

```
<210> SEQ ID NO 33
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 33
```

```
Met Gly Ile Leu Pro Pro Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
        35                  40                  45

Gly Ser Arg Phe Ile Gln Leu Lys Leu Glu Arg Ala Thr Pro Ala Glu
    50                  55                  60

Arg Gln Leu Val Phe Asn Glu Ile Leu Gln Ala Ala Tyr Gln Leu Met
65                  70                  75                  80

Val Asp Val Phe Gly Asn Tyr Val Ile Gln Lys Phe Phe Glu Phe Gly
            85                  90                  95

Ser Leu Glu Gln Lys Leu Ala Leu Ala Glu Arg Ile Arg Gly His Val
        100                 105                 110

Leu Ser Leu Ala Leu Gln Met Tyr Gly Cys Arg Val Ile Gln Lys Ala
    115                 120                 125
```

Leu Glu Phe Ile Pro Ser Asp Gln Gln Asn Glu Met Val Arg Glu Leu
130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
            165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
            195                 200                 205

Thr Leu Pro Ile Leu Glu Glu Leu His Gln His Thr Glu Gln Leu Val
210                 215                 220

Gln Asp Gln Tyr Gly Ser Tyr Val Ile Glu His Val Leu Glu His Gly
225                 230                 235                 240

Arg Pro Glu Asp Lys Ser Lys Ile Val Ala Glu Ile Arg Gly Asn Val
            245                 250                 255

Leu Val Leu Ser Gln His Lys Phe Ala Asn Asn Val Val Gln Lys Cys
            260                 265                 270

Val Thr His Ala Ser Arg Thr Glu Arg Ala Val Leu Ile Asp Glu Val
            275                 280                 285

Cys Thr Met Asn Asp Gly Pro His Ser Ala Leu Tyr Thr Met Met Lys
290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
            325                 330                 335

Thr Leu Arg Lys Tyr Thr Tyr Gly Lys His Ile Leu Ala Lys Leu Glu
            340                 345                 350

Lys Tyr Tyr Met Lys Asn Gly Val Asp Leu Gly Gly Pro Ala Gly Ser
            355                 360                 365

Gly Arg Ala Asp Ala Leu Asp Asp Phe Asp Leu Asp Met Leu Gly Ser
            370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
            405                 410                 415

Asp Leu Asp Met Leu Tyr Ile Asp
            420

<210> SEQ ID NO 34
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 34

Met Gly Ile Leu Pro Pro Lys Lys Lys Arg Lys Val Ser Arg Gly Arg
1               5                   10                  15

Ser Arg Leu Leu Glu Asp Phe Arg Asn Asn Arg Tyr Pro Asn Leu Gln
            20                  25                  30

Leu Arg Glu Ile Ala Gly His Ile Met Glu Phe Ser Gln Asp Gln His
            35                  40                  45

Gly Ser Arg Phe Ile Gln Leu Lys Leu Glu Arg Ala Thr Pro Ala Glu
50                  55                  60

Arg Gln Leu Val Phe Asn Glu Ile Leu Gln Ala Ala Tyr Gln Leu Met
 65                  70                  75                  80

Val Asp Val Phe Gly Asn Tyr Val Ile Gln Lys Phe Glu Phe Gly
                 85                  90                  95

Ser Leu Glu Gln Lys Leu Ala Leu Ala Glu Arg Ile Arg Gly His Val
                100                 105                 110

Leu Ser Leu Ala Leu Gln Met Tyr Gly Cys Arg Val Ile Gln Lys Ala
                115                 120                 125

Leu Glu Phe Ile Pro Ser Asp Gln Gln Asn Glu Met Val Arg Glu Leu
                130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
                180                 185                 190

Gly Cys Arg Val Ile Gln Arg Ile Leu Glu His Cys Leu Pro Asp Gln
                195                 200                 205

Thr Leu Pro Ile Leu Glu Glu Leu His Gln His Thr Glu Gln Leu Val
210                 215                 220

Gln Asp Gln Tyr Gly Asn Tyr Val Ile Gln His Val Leu Glu His Gly
225                 230                 235                 240

Arg Pro Glu Asp Lys Ser Lys Ile Val Ala Glu Ile Arg Gly Asn Val
                245                 250                 255

Leu Val Leu Ser Gln His Lys Phe Ala Ser Asn Val Val Glu Lys Cys
                260                 265                 270

Val Thr His Ala Ser Arg Thr Glu Arg Ala Val Leu Ile Asp Glu Val
                275                 280                 285

Cys Thr Met Asn Asp Gly Pro His Ser Ala Leu Tyr Thr Met Met Lys
                290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                325                 330                 335

Thr Leu Arg Lys Tyr Thr Tyr Gly Lys His Ile Leu Ala Lys Leu Glu
                340                 345                 350

Lys Tyr Tyr Met Lys Asn Gly Val Asp Leu Gly Gly Pro Ala Gly Ser
                355                 360                 365

Gly Arg Ala Asp Ala Leu Asp Asp Phe Asp Leu Asp Met Leu Gly Ser
370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
                405                 410                 415

Asp Leu Asp Met Leu Tyr Ile Asp
            420

<210> SEQ ID NO 35
<211> LENGTH: 424
<212> TYPE: PRT
<213> ORGANISM: Artificial Sequence
<220> FEATURE:
<223> OTHER INFORMATION: Synthetic Polypeptide

<400> SEQUENCE: 35

```
Met Gly Ile Leu Pro Lys Lys Arg Lys Val Ser Arg Gly Arg
1               5                   10                  15

Ser Arg Leu Leu Glu Asp Phe Arg Asn Arg Tyr Pro Asn Leu Gln
            20                  25                  30

Leu Arg Glu Ile Ala Gly His Ile Met Glu Phe Ser Gln Asp Gln His
            35                  40                  45

Gly Ser Arg Phe Ile Gln Leu Lys Leu Glu Arg Ala Thr Pro Ala Glu
50                  55                  60

Arg Gln Leu Val Phe Asn Glu Ile Leu Gln Ala Ala Tyr Gln Leu Met
65                      70                  75                  80

Val Asp Val Phe Gly Asn Tyr Val Ile Gln Lys Phe Phe Glu Phe Gly
                85                  90                  95

Ser Leu Glu Gln Lys Leu Ala Leu Ala Glu Arg Ile Arg Gly His Val
                100                 105                 110

Leu Ser Leu Ala Leu Gln Met Tyr Gly Ser Arg Val Ile Glu Lys Ala
            115                 120                 125

Leu Glu Phe Ile Pro Ser Asp Gln Gln Asn Glu Met Val Arg Glu Leu
            130                 135                 140

Asp Gly His Val Leu Lys Cys Val Lys Asp Gln Asn Gly Asn His Val
145                 150                 155                 160

Val Gln Lys Cys Ile Glu Cys Val Gln Pro Gln Ser Leu Gln Phe Ile
                165                 170                 175

Ile Asp Ala Phe Lys Gly Gln Val Phe Ala Leu Ser Thr His Pro Tyr
            180                 185                 190

Gly Cys Arg Val Ile Gln Arg Ile Leu Glu His Cys Leu Pro Asp Gln
            195                 200                 205

Thr Leu Pro Ile Leu Glu Glu Leu His Gln His Thr Glu Gln Leu Val
210                 215                 220

Gln Asp Gln Tyr Gly Ser Tyr Val Ile Glu His Val Leu Glu His Gly
225                 230                 235                 240

Arg Pro Glu Asp Lys Ser Lys Ile Val Ala Glu Ile Arg Gly Asn Val
                245                 250                 255

Leu Val Leu Ser Gln His Lys Phe Ala Asn Asn Val Val Gln Lys Cys
            260                 265                 270

Val Thr His Ala Ser Arg Thr Glu Arg Ala Val Leu Ile Asp Glu Val
            275                 280                 285

Cys Thr Met Asn Asp Gly Pro His Ser Ala Leu Tyr Thr Met Met Lys
            290                 295                 300

Asp Gln Tyr Ala Asn Tyr Val Val Gln Lys Met Ile Asp Val Ala Glu
305                 310                 315                 320

Pro Gly Gln Arg Lys Ile Val Met His Lys Ile Arg Pro His Ile Ala
                325                 330                 335

Thr Leu Arg Lys Tyr Thr Tyr Gly Lys His Ile Leu Ala Lys Leu Glu
            340                 345                 350

Lys Tyr Tyr Met Lys Asn Gly Val Asp Leu Gly Gly Pro Ala Gly Ser
            355                 360                 365

Gly Arg Ala Asp Ala Leu Asp Asp Phe Asp Leu Asp Met Leu Gly Ser
370                 375                 380

Asp Ala Leu Asp Asp Phe Asp Leu Asp Met Leu Gly Ser Asp Ala Leu
385                 390                 395                 400

Asp Asp Phe Asp Leu Asp Met Leu Gly Ser Asp Ala Leu Asp Asp Phe
                405                 410                 415

Asp Leu Asp Met Leu Tyr Ile Asp
```

-continued

```
                420

<210> SEQ ID NO 36
<211> LENGTH: 15
<212> TYPE: RNA
<213> ORGANISM: Artificial Sequence
<220> FEATURE:
<223> OTHER INFORMATION: Synthetic Nucleotide

<400> SEQUENCE: 36
acagaggaga aagac                                                          15

<210> SEQ ID NO 37
<211> LENGTH: 12
<212> TYPE: RNA
<213> ORGANISM: Artificial Sequence
<220> FEATURE:
<223> OTHER INFORMATION: Synthetic Polypeptide

<400> SEQUENCE: 37
gcaaaccaac cg                                                             12

<210> SEQ ID NO 38
<211> LENGTH: 17
<212> TYPE: RNA
<213> ORGANISM: Artificial Sequence
<220> FEATURE:
<223> OTHER INFORMATION: Synthetic Polypeptide

<400> SEQUENCE: 38
gcccaaaaac gaaccaa                                                        17

<210> SEQ ID NO 39
<211> LENGTH: 19
<212> TYPE: RNA
<213> ORGANISM: Artificial Sequence
<220> FEATURE:
<223> OTHER INFORMATION: Synthetic Nucleotide

<400> SEQUENCE: 39
aaacgaacca aaggaagag                                                      19

<210> SEQ ID NO 40
<211> LENGTH: 14
<212> TYPE: RNA
<213> ORGANISM: Artificial Sequence
<220> FEATURE:
<223> OTHER INFORMATION: Synthetic Nucleotide

<400> SEQUENCE: 40
ccagcggcag caga                                                           14

<210> SEQ ID NO 41
<211> LENGTH: 13
<212> TYPE: RNA
<213> ORGANISM: Artificial Sequence
<220> FEATURE:
<223> OTHER INFORMATION: Synthetic Nucleotide

<400> SEQUENCE: 41
gcaccgccca ggc                                                            13

<210> SEQ ID NO 42
<211> LENGTH: 18
<212> TYPE: RNA
<213> ORGANISM: Artificial Sequence
```

```
<220> FEATURE:
<223> OTHER INFORMATION: Synthetic Nucleotide

<400> SEQUENCE: 42
gcgccagaca cccagcag                                                  18

<210> SEQ ID NO 43
<211> LENGTH: 17
<212> TYPE: RNA
<213> ORGANISM: Artificial Sequence
<220> FEATURE:
<223> OTHER INFORMATION: Synthetic Nucleotide

<400> SEQUENCE: 43
gcagagcgga ggagggc                                                   17

<210> SEQ ID NO 44
<211> LENGTH: 19
<212> TYPE: RNA
<213> ORGANISM: Artificial Sequence
<220> FEATURE:
<223> OTHER INFORMATION: Synthetic Nucleotide

<400> SEQUENCE: 44
gaaggaagaa cggagcacg                                                 19

<210> SEQ ID NO 45
<211> LENGTH: 17
<212> TYPE: RNA
<213> ORGANISM: Artificial Sequence
<220> FEATURE:
<223> OTHER INFORMATION: Synthetic Nucleotide

<400> SEQUENCE: 45
ggcagagccg ccaggga                                                   17

<210> SEQ ID NO 46
<211> LENGTH: 15
<212> TYPE: RNA
<213> ORGANISM: Artificial Sequence
<220> FEATURE:
<223> OTHER INFORMATION: Synthetic Nucleotide

<400> SEQUENCE: 46
gcgcaagcgc aaccc                                                     15

<210> SEQ ID NO 47
<211> LENGTH: 15
<212> TYPE: RNA
<213> ORGANISM: Artificial Sequence
<220> FEATURE:
<223> OTHER INFORMATION: Synthetic Nucleotide

<400> SEQUENCE: 47
gcaggacggg ggcgc                                                     15

<210> SEQ ID NO 48
<211> LENGTH: 14
<212> TYPE: RNA
<213> ORGANISM: Artificial Sequence
<220> FEATURE:
<223> OTHER INFORMATION: Synthetic Nucleotide

<400> SEQUENCE: 48
gcgccggggc agaa                                                      14
```

<210> SEQ ID NO 49
<211> LENGTH: 20
<212> TYPE: RNA
<213> ORGANISM: Artificial Sequence
<220> FEATURE:
<223> OTHER INFORMATION: Synthetic Nucleotide

<400> SEQUENCE: 49
gccggccgcg cggggaggc                                          20

<210> SEQ ID NO 50
<211> LENGTH: 20
<212> TYPE: RNA
<213> ORGANISM: Artificial Sequence
<220> FEATURE:
<223> OTHER INFORMATION: Synthetic Nucleotide

<400> SEQUENCE: 50
ggcaggcgag gaggggagg                                          20

<210> SEQ ID NO 51
<211> LENGTH: 719
<212> TYPE: PRT
<213> ORGANISM: Artificial Sequence
<220> FEATURE:
<223> OTHER INFORMATION: Synthetic Polypeptide

<400> SEQUENCE: 51

Glu Leu Pro Thr Cys Ser Cys Leu Asp Arg Val Ile Gln Lys Asp Lys
1               5                   10                  15

Gly Pro Tyr Tyr Thr His Leu Gly Ala Gly Pro Ser Val Ala Ala Val
            20                  25                  30

Arg Glu Ile Met Glu Asn Arg Tyr Gly Gln Lys Gly Asn Ala Ile Arg
        35                  40                  45

Ile Glu Ile Val Val Tyr Thr Gly Lys Glu Gly Lys Ser Ser His Gly
    50                  55                  60

Cys Pro Ile Ala Lys Trp Val Leu Arg Arg Ser Ser Asp Glu Glu Lys
65                  70                  75                  80

Val Leu Cys Leu Val Arg Gln Arg Thr Gly His His Cys Pro Thr Ala
                85                  90                  95

Val Met Val Val Leu Ile Met Val Trp Asp Gly Ile Pro Leu Pro Met
            100                 105                 110

Ala Asp Arg Leu Tyr Thr Glu Leu Thr Glu Asn Leu Lys Ser Tyr Asn
        115                 120                 125

Gly His Pro Thr Asp Arg Arg Cys Thr Leu Asn Glu Asn Arg Thr Cys
    130                 135                 140

Thr Cys Gln Gly Ile Asp Pro Glu Thr Cys Gly Ala Ser Phe Ser Phe
145                 150                 155                 160

Gly Cys Ser Trp Ser Met Tyr Phe Asn Gly Cys Lys Phe Gly Arg Ser
                165                 170                 175

Pro Ser Pro Arg Arg Phe Arg Ile Asp Pro Ser Ser Pro Leu His Glu
            180                 185                 190

Lys Asn Leu Glu Asp Asn Leu Gln Ser Leu Ala Thr Arg Leu Ala Pro
        195                 200                 205

Ile Tyr Lys Gln Tyr Ala Pro Val Ala Tyr Gln Asn Gln Val Glu Tyr
    210                 215                 220

Glu Asn Val Ala Arg Glu Cys Arg Leu Gly Ser Lys Glu Gly Arg Pro
225                 230                 235                 240

-continued

```
Phe Ser Gly Val Thr Ala Cys Leu Asp Phe Cys Ala His Pro His Arg
                245                 250                 255
Asp Ile His Asn Met Asn Asn Gly Ser Thr Val Val Cys Thr Leu Thr
            260                 265                 270
Arg Glu Asp Asn Arg Ser Leu Gly Val Ile Pro Gln Asp Glu Gln Leu
        275                 280                 285
His Val Leu Pro Leu Tyr Lys Leu Ser Asp Thr Asp Glu Phe Gly Ser
    290                 295                 300
Lys Glu Gly Met Glu Ala Lys Ile Lys Ser Gly Ala Ile Glu Val Leu
305                 310                 315                 320
Ala Pro Arg Arg Lys Arg Thr Cys Phe Thr Gln Pro Val Pro Arg
                325                 330                 335
Ser Gly Lys Lys Arg Ala Ala Met Met Thr Glu Val Leu Ala His Lys
            340                 345                 350
Ile Arg Ala Val Glu Lys Lys Pro Ile Pro Arg Ile Lys Arg Lys Asn
        355                 360                 365
Asn Ser Thr Thr Thr Asn Asn Ser Lys Pro Ser Ser Leu Pro Thr Leu
    370                 375                 380
Gly Ser Asn Thr Glu Thr Val Gln Pro Glu Val Lys Ser Glu Thr Glu
385                 390                 395                 400
Pro His Phe Ile Leu Lys Ser Ser Asp Asn Thr Lys Thr Tyr Ser Leu
                405                 410                 415
Met Pro Ser Ala Pro His Pro Val Lys Glu Ala Ser Pro Gly Phe Ser
            420                 425                 430
Trp Ser Pro Lys Thr Ala Ser Ala Thr Pro Ala Pro Leu Lys Asn Asp
        435                 440                 445
Ala Thr Ala Ser Cys Gly Phe Ser Glu Arg Ser Ser Thr Pro His Cys
    450                 455                 460
Thr Met Pro Ser Gly Arg Leu Ser Gly Ala Asn Ala Ala Ala Ala Asp
465                 470                 475                 480
Gly Pro Gly Ile Ser Gln Leu Gly Glu Val Ala Pro Leu Pro Thr Leu
                485                 490                 495
Ser Ala Pro Val Met Glu Pro Leu Ile Asn Ser Glu Pro Ser Thr Gly
            500                 505                 510
Val Thr Glu Pro Leu Thr Pro His Gln Pro Asn His Gln Pro Ser Phe
        515                 520                 525
Leu Thr Ser Pro Gln Asp Leu Ala Ser Ser Pro Met Glu Glu Asp Glu
    530                 535                 540
Gln His Ser Glu Ala Asp Glu Pro Pro Ser Asp Glu Pro Leu Ser Asp
545                 550                 555                 560
Asp Pro Leu Ser Pro Ala Glu Glu Lys Leu Pro His Ile Asp Glu Tyr
                565                 570                 575
Trp Ser Asp Ser Glu His Ile Phe Leu Asp Ala Asn Ile Gly Gly Val
            580                 585                 590
Ala Ile Ala Pro Ala His Gly Ser Val Leu Ile Glu Cys Ala Arg Arg
        595                 600                 605
Glu Leu His Ala Thr Thr Pro Val Glu His Pro Asn Arg Asn His Pro
    610                 615                 620
Thr Arg Leu Ser Leu Val Phe Tyr Gln His Lys Asn Leu Asn Lys Pro
625                 630                 635                 640
Gln His Gly Phe Glu Leu Asn Lys Ile Lys Phe Glu Ala Lys Glu Ala
                645                 650                 655
Lys Asn Lys Lys Met Lys Ala Ser Glu Gln Lys Asp Gln Ala Ala Asn
```

```
                        660                 665                 670
Glu Gly Pro Glu Gln Ser Ser Glu Val Asn Glu Leu Asn Gln Ile Pro
            675                 680                 685

Ser His Lys Ala Leu Thr Leu Thr His Asp Asn Val Thr Val Ser
            690                 695                 700

Pro Tyr Ala Leu Thr His Val Ala Gly Pro Tyr Asn His Trp Val
705                 710                 715

<210> SEQ ID NO 52
<211> LENGTH: 2157
<212> TYPE: PRT
<213> ORGANISM: Artificial Sequence
<220> FEATURE:
<223> OTHER INFORMATION: Synthetic Polypeptide

<400> SEQUENCE: 52

Met Gly Pro Ala Glu Leu Pro Thr Cys Ser Cys Leu Asp Arg Val Ile
1               5                   10                  15

Gln Lys Asp Lys Gly Pro Tyr Tyr Thr His Leu Gly Ala Gly Pro Ser
            20                  25                  30

Val Ala Ala Val Arg Glu Ile Met Glu Asn Arg Tyr Gly Gln Lys Gly
        35                  40                  45

Asn Ala Ile Arg Ile Glu Ile Val Tyr Thr Gly Lys Glu Gly Lys
    50                  55                  60

Ser Ser His Gly Cys Pro Ile Ala Lys Trp Val Leu Arg Arg Ser Ser
65                  70                  75                  80

Asp Glu Glu Lys Val Leu Cys Leu Val Arg Gln Arg Thr Gly His His
                85                  90                  95

Cys Pro Thr Ala Val Met Val Val Leu Ile Met Val Trp Asp Gly Ile
            100                 105                 110

Pro Leu Pro Met Ala Asp Arg Leu Tyr Thr Glu Leu Thr Glu Asn Leu
        115                 120                 125

Lys Ser Tyr Asn Gly His Pro Thr Asp Arg Arg Cys Thr Leu Asn Glu
    130                 135                 140

Asn Arg Thr Cys Thr Cys Gln Gly Ile Asp Pro Glu Thr Cys Gly Ala
145                 150                 155                 160

Ser Phe Ser Phe Gly Cys Ser Trp Ser Met Tyr Phe Asn Gly Cys Lys
                165                 170                 175

Phe Gly Arg Ser Pro Ser Pro Arg Arg Phe Arg Ile Asp Pro Ser Ser
            180                 185                 190

Pro Leu His Glu Lys Asn Leu Glu Asp Asn Leu Gln Ser Leu Ala Thr
        195                 200                 205

Arg Leu Ala Pro Ile Tyr Lys Gln Tyr Ala Pro Val Ala Tyr Gln Asn
    210                 215                 220

Gln Val Glu Tyr Glu Asn Val Ala Arg Glu Cys Arg Leu Gly Ser Lys
225                 230                 235                 240

Glu Gly Arg Pro Phe Ser Gly Val Thr Ala Cys Leu Asp Phe Cys Ala
                245                 250                 255

His Pro His Arg Asp Ile His Asn Met Asn Asn Gly Ser Thr Val Val
            260                 265                 270

Cys Thr Leu Thr Arg Glu Asp Asn Arg Ser Leu Gly Val Ile Pro Gln
        275                 280                 285

Asp Glu Gln Leu His Val Leu Pro Leu Tyr Lys Leu Ser Asp Thr Asp
    290                 295                 300

Glu Phe Gly Ser Lys Glu Gly Met Glu Ala Lys Ile Lys Ser Gly Ala
```

```
                305                 310                 315                 320
Ile Glu Val Leu Ala Pro Arg Lys Lys Arg Thr Cys Phe Thr Gln
                    325                 330                 335

Pro Val Pro Arg Ser Gly Lys Lys Arg Ala Met Met Thr Glu Val
                    340                 345                 350

Leu Ala His Lys Ile Arg Ala Val Glu Lys Lys Pro Ile Pro Arg Ile
                    355                 360                 365

Lys Arg Lys Asn Asn Ser Thr Thr Thr Asn Asn Ser Lys Pro Ser Ser
370                 375                 380

Leu Pro Thr Leu Gly Ser Asn Thr Glu Thr Val Gln Pro Glu Val Lys
385                 390                 395                 400

Ser Glu Thr Glu Pro His Phe Ile Leu Lys Ser Ser Asp Asn Thr Lys
                    405                 410                 415

Thr Tyr Ser Leu Met Pro Ser Ala Pro His Pro Val Lys Glu Ala Ser
                    420                 425                 430

Pro Gly Phe Ser Trp Ser Pro Lys Thr Ala Ser Ala Thr Pro Ala Pro
                    435                 440                 445

Leu Lys Asn Asp Ala Thr Ala Ser Cys Gly Phe Ser Glu Arg Ser Ser
            450                 455                 460

Thr Pro His Cys Thr Met Pro Ser Gly Arg Leu Ser Gly Ala Asn Ala
465                 470                 475                 480

Ala Ala Ala Asp Gly Pro Gly Ile Ser Gln Leu Gly Glu Val Ala Pro
                    485                 490                 495

Leu Pro Thr Leu Ser Ala Pro Val Met Glu Pro Leu Ile Asn Ser Glu
                    500                 505                 510

Pro Ser Thr Gly Val Thr Glu Pro Leu Thr Pro His Gln Pro Asn His
            515                 520                 525

Gln Pro Ser Phe Leu Thr Ser Pro Gln Asp Leu Ala Ser Ser Pro Met
            530                 535                 540

Glu Glu Asp Glu Gln His Ser Glu Ala Asp Glu Pro Pro Ser Asp Glu
545                 550                 555                 560

Pro Leu Ser Asp Asp Pro Leu Ser Pro Ala Glu Glu Lys Leu Pro His
                    565                 570                 575

Ile Asp Glu Tyr Trp Ser Asp Ser Glu His Ile Phe Leu Asp Ala Asn
                    580                 585                 590

Ile Gly Gly Val Ala Ile Ala Pro Ala His Gly Ser Val Leu Ile Glu
            595                 600                 605

Cys Ala Arg Arg Glu Leu His Ala Thr Thr Pro Val Glu His Pro Asn
            610                 615                 620

Arg Asn His Pro Thr Arg Leu Ser Leu Val Phe Tyr Gln His Lys Asn
625                 630                 635                 640

Leu Asn Lys Pro Gln His Gly Phe Glu Leu Asn Lys Ile Lys Phe Glu
                    645                 650                 655

Ala Lys Glu Ala Lys Asn Lys Lys Met Lys Ala Ser Glu Gln Lys Asp
                    660                 665                 670

Gln Ala Ala Asn Glu Gly Pro Glu Gln Ser Ser Glu Val Asn Glu Leu
            675                 680                 685

Asn Gln Ile Pro Ser His Lys Ala Leu Thr Leu Thr His Asp Asn Val
            690                 695                 700

Val Thr Val Ser Pro Tyr Ala Leu Thr His Val Ala Gly Pro Tyr Asn
705                 710                 715                 720

His Trp Val Ile Asp Gly Gly Gly Ser Gly Gly Gly Gly Ser Gly
                    725                 730                 735
```

```
Gly Gly Gly Ser Met Tyr Pro Tyr Asp Val Pro Asp Tyr Ala Ser Pro
            740                 745                 750

Lys Lys Lys Arg Lys Val Glu Ala Ser Asp Lys Lys Tyr Ser Ile Gly
            755                 760                 765

Leu Ala Ile Gly Thr Asn Ser Val Gly Trp Ala Val Ile Thr Asp Glu
            770                 775                 780

Tyr Lys Val Pro Ser Lys Lys Phe Lys Val Leu Gly Asn Thr Asp Arg
785                 790                 795                 800

His Ser Ile Lys Lys Asn Leu Ile Gly Ala Leu Leu Phe Asp Ser Gly
            805                 810                 815

Glu Thr Ala Glu Ala Thr Arg Leu Lys Arg Thr Ala Arg Arg Arg Tyr
            820                 825                 830

Thr Arg Arg Lys Asn Arg Ile Cys Tyr Leu Gln Glu Ile Phe Ser Asn
            835                 840                 845

Glu Met Ala Lys Val Asp Asp Ser Phe Phe His Arg Leu Glu Glu Ser
            850                 855                 860

Phe Leu Val Glu Glu Asp Lys Lys His Glu Arg His Pro Ile Phe Gly
865                 870                 875                 880

Asn Ile Val Asp Glu Val Ala Tyr His Glu Lys Tyr Pro Thr Ile Tyr
            885                 890                 895

His Leu Arg Lys Lys Leu Val Asp Ser Thr Asp Lys Ala Asp Leu Arg
            900                 905                 910

Leu Ile Tyr Leu Ala Leu Ala His Met Ile Lys Phe Arg Gly His Phe
            915                 920                 925

Leu Ile Glu Gly Asp Leu Asn Pro Asp Asn Ser Asp Val Asp Lys Leu
            930                 935                 940

Phe Ile Gln Leu Val Gln Thr Tyr Asn Gln Leu Phe Glu Glu Asn Pro
945                 950                 955                 960

Ile Asn Ala Ser Gly Val Asp Ala Lys Ala Ile Leu Ser Ala Arg Leu
            965                 970                 975

Ser Lys Ser Arg Arg Leu Glu Asn Leu Ile Ala Gln Leu Pro Gly Glu
            980                 985                 990

Lys Lys Asn Gly Leu Phe Gly Asn Leu Ile Ala Leu Ser Leu Gly Leu
            995                 1000                1005

Thr Pro Asn Phe Lys Ser Asn Phe Asp Leu Ala Glu Asp Ala Lys
            1010                1015                1020

Leu Gln Leu Ser Lys Asp Thr Tyr Asp Asp Asp Leu Asp Asn Leu
            1025                1030                1035

Leu Ala Gln Ile Gly Asp Gln Tyr Ala Asp Leu Phe Leu Ala Ala
            1040                1045                1050

Lys Asn Leu Ser Asp Ala Ile Leu Leu Ser Asp Ile Leu Arg Val
            1055                1060                1065

Asn Thr Glu Ile Thr Lys Ala Pro Leu Ser Ala Ser Met Ile Lys
            1070                1075                1080

Arg Tyr Asp Glu His His Gln Asp Leu Thr Leu Leu Lys Ala Leu
            1085                1090                1095

Val Arg Gln Gln Leu Pro Glu Lys Tyr Lys Glu Ile Phe Phe Asp
            1100                1105                1110

Gln Ser Lys Asn Gly Tyr Ala Gly Tyr Ile Asp Gly Gly Ala Ser
            1115                1120                1125

Gln Glu Glu Phe Tyr Lys Phe Ile Lys Pro Ile Leu Glu Lys Met
            1130                1135                1140
```

```
Asp Gly Thr Glu Glu Leu Leu Val Lys Leu Asn Arg Glu Asp Leu
    1145                1150                1155

Leu Arg Lys Gln Arg Thr Phe Asp Asn Gly Ser Ile Pro His Gln
    1160                1165                1170

Ile His Leu Gly Glu Leu His Ala Ile Leu Arg Arg Gln Glu Asp
    1175                1180                1185

Phe Tyr Pro Phe Leu Lys Asp Asn Arg Glu Lys Ile Glu Lys Ile
    1190                1195                1200

Leu Thr Phe Arg Ile Pro Tyr Tyr Val Gly Pro Leu Ala Arg Gly
    1205                1210                1215

Asn Ser Arg Phe Ala Trp Met Thr Arg Lys Ser Glu Glu Thr Ile
    1220                1225                1230

Thr Pro Trp Asn Phe Glu Glu Val Val Asp Lys Gly Ala Ser Ala
    1235                1240                1245

Gln Ser Phe Ile Glu Arg Met Thr Asn Phe Asp Lys Asn Leu Pro
    1250                1255                1260

Asn Glu Lys Val Leu Pro Lys His Ser Leu Leu Tyr Glu Tyr Phe
    1265                1270                1275

Thr Val Tyr Asn Glu Leu Thr Lys Val Lys Tyr Val Thr Glu Gly
    1280                1285                1290

Met Arg Lys Pro Ala Phe Leu Ser Gly Glu Gln Lys Lys Ala Ile
    1295                1300                1305

Val Asp Leu Leu Phe Lys Thr Asn Arg Lys Val Thr Val Lys Gln
    1310                1315                1320

Leu Lys Glu Asp Tyr Phe Lys Lys Ile Glu Cys Phe Asp Ser Val
    1325                1330                1335

Glu Ile Ser Gly Val Glu Asp Arg Phe Asn Ala Ser Leu Gly Thr
    1340                1345                1350

Tyr His Asp Leu Leu Lys Ile Ile Lys Asp Lys Asp Phe Leu Asp
    1355                1360                1365

Asn Glu Glu Asn Glu Asp Ile Leu Glu Asp Ile Val Leu Thr Leu
    1370                1375                1380

Thr Leu Phe Glu Asp Arg Glu Met Ile Glu Glu Arg Leu Lys Thr
    1385                1390                1395

Tyr Ala His Leu Phe Asp Asp Lys Val Met Lys Gln Leu Lys Arg
    1400                1405                1410

Arg Arg Tyr Thr Gly Trp Gly Arg Leu Ser Arg Lys Leu Ile Asn
    1415                1420                1425

Gly Ile Arg Asp Lys Gln Ser Gly Lys Thr Ile Leu Asp Phe Leu
    1430                1435                1440

Lys Ser Asp Gly Phe Ala Asn Arg Asn Phe Met Gln Leu Ile His
    1445                1450                1455

Asp Asp Ser Leu Thr Phe Lys Glu Asp Ile Gln Lys Ala Gln Val
    1460                1465                1470

Ser Gly Gln Gly Asp Ser Leu His Glu His Ile Ala Asn Leu Ala
    1475                1480                1485

Gly Ser Pro Ala Ile Lys Lys Gly Ile Leu Gln Thr Val Lys Val
    1490                1495                1500

Val Asp Glu Leu Val Lys Val Met Gly Arg His Lys Pro Glu Asn
    1505                1510                1515

Ile Val Ile Glu Met Ala Arg Glu Asn Gln Thr Thr Gln Lys Gly
    1520                1525                1530

Gln Lys Asn Ser Arg Glu Arg Met Lys Arg Ile Glu Glu Gly Ile
```

-continued

```
                1535                1540                1545

Lys Glu Leu Gly Ser Gln Ile Leu Lys Glu His Pro Val Glu Asn
    1550                1555                1560

Thr Gln Leu Gln Asn Glu Lys Leu Tyr Leu Tyr Tyr Leu Gln Asn
    1565                1570                1575

Gly Arg Asp Met Tyr Val Asp Gln Glu Leu Asp Ile Asn Arg Leu
    1580                1585                1590

Ser Asp Tyr Asp Val Asp Ala Ile Val Pro Gln Ser Phe Leu Lys
    1595                1600                1605

Asp Asp Ser Ile Asp Asn Lys Val Leu Thr Arg Ser Asp Lys Asn
    1610                1615                1620

Arg Gly Lys Ser Asp Asn Val Pro Ser Glu Glu Val Val Lys Lys
    1625                1630                1635

Met Lys Asn Tyr Trp Arg Gln Leu Leu Asn Ala Lys Leu Ile Thr
    1640                1645                1650

Gln Arg Lys Phe Asp Asn Leu Thr Lys Ala Glu Arg Gly Gly Leu
    1655                1660                1665

Ser Glu Leu Asp Lys Ala Gly Phe Ile Lys Arg Gln Leu Val Glu
    1670                1675                1680

Thr Arg Gln Ile Thr Lys His Val Ala Gln Ile Leu Asp Ser Arg
    1685                1690                1695

Met Asn Thr Lys Tyr Asp Glu Asn Asp Lys Leu Ile Arg Glu Val
    1700                1705                1710

Lys Val Ile Thr Leu Lys Ser Lys Leu Val Ser Asp Phe Arg Lys
    1715                1720                1725

Asp Phe Gln Phe Tyr Lys Val Arg Glu Ile Asn Asn Tyr His His
    1730                1735                1740

Ala His Asp Ala Tyr Leu Asn Ala Val Val Gly Thr Ala Leu Ile
    1745                1750                1755

Lys Lys Tyr Pro Lys Leu Glu Ser Glu Phe Val Tyr Gly Asp Tyr
    1760                1765                1770

Lys Val Tyr Asp Val Arg Lys Met Ile Ala Lys Ser Glu Gln Glu
    1775                1780                1785

Ile Gly Lys Ala Thr Ala Lys Tyr Phe Phe Tyr Ser Asn Ile Met
    1790                1795                1800

Asn Phe Phe Lys Thr Glu Ile Thr Leu Ala Asn Gly Glu Ile Arg
    1805                1810                1815

Lys Arg Pro Leu Ile Glu Thr Asn Gly Glu Thr Gly Glu Ile Val
    1820                1825                1830

Trp Asp Lys Gly Arg Asp Phe Ala Thr Val Arg Lys Val Leu Ser
    1835                1840                1845

Met Pro Gln Val Asn Ile Val Lys Lys Thr Glu Val Gln Thr Gly
    1850                1855                1860

Gly Phe Ser Lys Glu Ser Ile Leu Pro Lys Arg Asn Ser Asp Lys
    1865                1870                1875

Leu Ile Ala Arg Lys Lys Asp Trp Asp Pro Lys Lys Tyr Gly Gly
    1880                1885                1890

Phe Asp Ser Pro Thr Val Ala Tyr Ser Val Leu Val Val Ala Lys
    1895                1900                1905

Val Glu Lys Gly Lys Ser Lys Lys Leu Lys Ser Val Lys Glu Leu
    1910                1915                1920

Leu Gly Ile Thr Ile Met Glu Arg Ser Ser Phe Glu Lys Asn Pro
    1925                1930                1935
```

Ile Asp Phe Leu Glu Ala Lys Gly Tyr Lys Glu Val Lys Lys Asp
    1940                1945                1950

Leu Ile Ile Lys Leu Pro Lys Tyr Ser Leu Phe Glu Leu Glu Asn
    1955                1960                1965

Gly Arg Lys Arg Met Leu Ala Ser Ala Gly Glu Leu Gln Lys Gly
    1970                1975                1980

Asn Glu Leu Ala Leu Pro Ser Lys Tyr Val Asn Phe Leu Tyr Leu
    1985                1990                1995

Ala Ser His Tyr Glu Lys Leu Lys Gly Ser Pro Glu Asp Asn Glu
    2000                2005                2010

Gln Lys Gln Leu Phe Val Glu Gln His Lys His Tyr Leu Asp Glu
    2015                2020                2025

Ile Ile Glu Gln Ile Ser Glu Phe Ser Lys Arg Val Ile Leu Ala
    2030                2035                2040

Asp Ala Asn Leu Asp Lys Val Leu Ser Ala Tyr Asn Lys His Arg
    2045                2050                2055

Asp Lys Pro Ile Arg Glu Gln Ala Glu Asn Ile Ile His Leu Phe
    2060                2065                2070

Thr Leu Thr Asn Leu Gly Ala Pro Ala Ala Phe Lys Tyr Phe Asp
    2075                2080                2085

Thr Thr Ile Asp Arg Lys Arg Tyr Thr Ser Thr Lys Glu Val Leu
    2090                2095                2100

Asp Ala Thr Leu Ile His Gln Ser Ile Thr Gly Leu Tyr Glu Thr
    2105                2110                2115

Arg Ile Asp Leu Ser Gln Leu Gly Gly Asp Ser Pro Lys Lys Lys
    2120                2125                2130

Arg Lys Val Glu Ala Ser Gly Gly Gly Ser Gly Gly Gly Gly
    2135                2140                2145

Ser Gly Gly Gly Gly Ser Gly Pro Ala
    2150                2155

<210> SEQ ID NO 53
<211> LENGTH: 2156
<212> TYPE: PRT
<213> ORGANISM: Artificial Sequence
<220> FEATURE:
<223> OTHER INFORMATION: Synthetic Polypeptide

<400> SEQUENCE: 53

Met Ile Asp Gly Gly Gly Ser Gly Gly Gly Gly Ser Gly Gly Gly
1               5                   10                  15

Gly Ser Met Tyr Pro Tyr Asp Val Pro Asp Tyr Ala Ser Pro Lys Lys
            20                  25                  30

Lys Arg Lys Val Glu Ala Ser Asp Lys Lys Tyr Ser Ile Gly Leu Ala
            35                  40                  45

Ile Gly Thr Asn Ser Val Gly Trp Ala Val Ile Thr Asp Glu Tyr Lys
        50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Arg Tyr Thr Arg
            100                 105                 110

Arg Lys Asn Arg Ile Cys Tyr Leu Gln Glu Ile Phe Ser Asn Glu Met
            115                 120                 125

```
Ala Lys Val Asp Asp Ser Phe Phe His Arg Leu Glu Glu Ser Phe Leu
130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
                180                 185                 190

Tyr Leu Ala Leu Ala His Met Ile Lys Phe Arg Gly His Phe Leu Ile
            195                 200                 205

Glu Gly Asp Leu Asn Pro Asp Asn Ser Asp Val Asp Lys Leu Phe Ile
210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
            275                 280                 285

Asn Phe Lys Ser Asn Phe Asp Leu Ala Glu Asp Ala Lys Leu Gln Leu
290                 295                 300

Ser Lys Asp Thr Tyr Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
            355                 360                 365

Asp Leu Thr Leu Leu Lys Ala Leu Val Arg Gln Gln Leu Pro Glu Lys
        370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
            420                 425                 430

Arg Glu Asp Leu Leu Arg Lys Gln Arg Thr Phe Asp Asn Gly Ser Ile
        435                 440                 445

Pro His Gln Ile His Leu Gly Glu Leu His Ala Ile Leu Arg Arg Gln
450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
            500                 505                 510

Pro Trp Asn Phe Glu Glu Val Val Asp Lys Gly Ala Ser Ala Gln Ser
        515                 520                 525

Phe Ile Glu Arg Met Thr Asn Phe Asp Lys Asn Leu Pro Asn Glu Lys
530                 535                 540
```

```
Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
            580                 585                 590

Thr Asn Arg Lys Val Thr Val Lys Gln Leu Lys Glu Asp Tyr Phe Lys
        595                 600                 605

Lys Ile Glu Cys Phe Asp Ser Val Glu Ile Ser Gly Val Glu Asp Arg
    610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
            660                 665                 670

Arg Leu Lys Thr Tyr Ala His Leu Phe Asp Asp Lys Val Met Lys Gln
        675                 680                 685

Leu Lys Arg Arg Arg Tyr Thr Gly Trp Gly Arg Leu Ser Arg Lys Leu
    690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
        755                 760                 765

Pro Ala Ile Lys Lys Gly Ile Leu Gln Thr Val Lys Val Val Asp Glu
    770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
            820                 825                 830

Ile Leu Lys Glu His Pro Val Glu Asn Thr Gln Leu Gln Asn Glu Lys
        835                 840                 845

Leu Tyr Leu Tyr Tyr Leu Gln Asn Gly Arg Asp Met Tyr Val Asp Gln
    850                 855                 860

Glu Leu Asp Ile Asn Arg Leu Ser Asp Tyr Asp Val Asp Ala Ile Val
865                 870                 875                 880

Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
            900                 905                 910

Val Val Lys Lys Met Lys Asn Tyr Trp Arg Gln Leu Leu Asn Ala Lys
        915                 920                 925

Leu Ile Thr Gln Arg Lys Phe Asp Asn Leu Thr Lys Ala Glu Arg Gly
    930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
```

-continued

```
                965                 970                 975
Met Asn Thr Lys Tyr Asp Glu Asn Asp Lys Leu Ile Arg Glu Val Lys
            980                 985                 990
Val Ile Thr Leu Lys Ser Lys Leu Val Ser Asp Phe Arg Lys Asp Phe
            995                1000                1005
Gln Phe Tyr Lys Val Arg Glu Ile Asn Asn Tyr His His Ala His
   1010                1015                1020
Asp Ala Tyr Leu Asn Ala Val Val Gly Thr Ala Leu Ile Lys Lys
   1025                1030                1035
Tyr Pro Lys Leu Glu Ser Glu Phe Val Tyr Gly Asp Tyr Lys Val
   1040                1045                1050
Tyr Asp Val Arg Lys Met Ile Ala Lys Ser Glu Gln Glu Ile Gly
   1055                1060                1065
Lys Ala Thr Ala Lys Tyr Phe Phe Tyr Ser Asn Ile Met Asn Phe
   1070                1075                1080
Phe Lys Thr Glu Ile Thr Leu Ala Asn Gly Glu Ile Arg Lys Arg
   1085                1090                1095
Pro Leu Ile Glu Thr Asn Gly Glu Thr Gly Glu Ile Val Trp Asp
   1100                1105                1110
Lys Gly Arg Asp Phe Ala Thr Val Arg Lys Val Leu Ser Met Pro
   1115                1120                1125
Gln Val Asn Ile Val Lys Lys Thr Glu Val Gln Thr Gly Gly Phe
   1130                1135                1140
Ser Lys Glu Ser Ile Leu Pro Lys Arg Asn Ser Asp Lys Leu Ile
   1145                1150                1155
Ala Arg Lys Lys Asp Trp Asp Pro Lys Lys Tyr Gly Gly Phe Asp
   1160                1165                1170
Ser Pro Thr Val Ala Tyr Ser Val Leu Val Val Ala Lys Val Glu
   1175                1180                1185
Lys Gly Lys Ser Lys Lys Leu Lys Ser Val Lys Glu Leu Leu Gly
   1190                1195                1200
Ile Thr Ile Met Glu Arg Ser Ser Phe Glu Lys Asn Pro Ile Asp
   1205                1210                1215
Phe Leu Glu Ala Lys Gly Tyr Lys Glu Val Lys Lys Asp Leu Ile
   1220                1225                1230
Ile Lys Leu Pro Lys Tyr Ser Leu Phe Glu Leu Glu Asn Gly Arg
   1235                1240                1245
Lys Arg Met Leu Ala Ser Ala Gly Glu Leu Gln Lys Gly Asn Glu
   1250                1255                1260
Leu Ala Leu Pro Ser Lys Tyr Val Asn Phe Leu Tyr Leu Ala Ser
   1265                1270                1275
His Tyr Glu Lys Leu Lys Gly Ser Pro Glu Asp Asn Glu Gln Lys
   1280                1285                1290
Gln Leu Phe Val Glu Gln His Lys His Tyr Leu Asp Glu Ile Ile
   1295                1300                1305
Glu Gln Ile Ser Glu Phe Ser Lys Arg Val Ile Leu Ala Asp Ala
   1310                1315                1320
Asn Leu Asp Lys Val Leu Ser Ala Tyr Asn Lys His Arg Asp Lys
   1325                1330                1335
Pro Ile Arg Glu Gln Ala Glu Asn Ile Ile His Leu Phe Thr Leu
   1340                1345                1350
Thr Asn Leu Gly Ala Pro Ala Ala Phe Lys Tyr Phe Asp Thr Thr
   1355                1360                1365
```

-continued

```
Ile Asp Arg Lys Arg Tyr Thr Ser Thr Lys Glu Val Leu Asp Ala
1370                1375                1380

Thr Leu Ile His Gln Ser Ile Thr Gly Leu Tyr Glu Thr Arg Ile
1385                1390                1395

Asp Leu Ser Gln Leu Gly Gly Asp Ser Pro Lys Lys Arg Lys
1400                1405                1410

Val Glu Ala Ser Gly Gly Gly Ser Gly Gly Gly Ser Gly
1415                1420                1425

Gly Gly Gly Ser Gly Pro Ala Glu Leu Pro Thr Cys Ser Cys Leu
1430                1435                1440

Asp Arg Val Ile Gln Lys Asp Lys Gly Pro Tyr Tyr Thr His Leu
1445                1450                1455

Gly Ala Gly Pro Ser Val Ala Ala Val Arg Glu Ile Met Glu Asn
1460                1465                1470

Arg Tyr Gly Gln Lys Gly Asn Ala Ile Arg Ile Glu Ile Val Val
1475                1480                1485

Tyr Thr Gly Lys Glu Gly Lys Ser Ser His Gly Cys Pro Ile Ala
1490                1495                1500

Lys Trp Val Leu Arg Arg Ser Ser Asp Glu Glu Lys Val Leu Cys
1505                1510                1515

Leu Val Arg Gln Arg Thr Gly His His Cys Pro Thr Ala Val Met
1520                1525                1530

Val Val Leu Ile Met Val Trp Asp Gly Ile Pro Leu Pro Met Ala
1535                1540                1545

Asp Arg Leu Tyr Thr Glu Leu Thr Glu Asn Leu Lys Ser Tyr Asn
1550                1555                1560

Gly His Pro Thr Asp Arg Arg Cys Thr Leu Asn Glu Asn Arg Thr
1565                1570                1575

Cys Thr Cys Gln Gly Ile Asp Pro Glu Thr Cys Gly Ala Ser Phe
1580                1585                1590

Ser Phe Gly Cys Ser Trp Ser Met Tyr Phe Asn Gly Cys Lys Phe
1595                1600                1605

Gly Arg Ser Pro Ser Pro Arg Arg Phe Arg Ile Asp Pro Ser Ser
1610                1615                1620

Pro Leu His Glu Lys Asn Leu Glu Asp Asn Leu Gln Ser Leu Ala
1625                1630                1635

Thr Arg Leu Ala Pro Ile Tyr Lys Gln Tyr Ala Pro Val Ala Tyr
1640                1645                1650

Gln Asn Gln Val Glu Tyr Glu Asn Val Ala Arg Glu Cys Arg Leu
1655                1660                1665

Gly Ser Lys Glu Gly Arg Pro Phe Ser Gly Val Thr Ala Cys Leu
1670                1675                1680

Asp Phe Cys Ala His Pro His Arg Asp Ile His Asn Met Asn Asn
1685                1690                1695

Gly Ser Thr Val Val Cys Thr Leu Thr Arg Glu Asp Asn Arg Ser
1700                1705                1710

Leu Gly Val Ile Pro Gln Asp Glu Gln Leu His Val Leu Pro Leu
1715                1720                1725

Tyr Lys Leu Ser Asp Thr Asp Glu Phe Gly Ser Lys Glu Gly Met
1730                1735                1740

Glu Ala Lys Ile Lys Ser Gly Ala Ile Glu Val Leu Ala Pro Arg
1745                1750                1755
```

```
Arg Lys Lys Arg Thr Cys Phe Thr Gln Pro Val Pro Arg Ser Gly
    1760            1765               1770
Lys Lys Arg Ala Ala Met Met Thr Glu Val Leu Ala His Lys Ile
    1775            1780               1785
Arg Ala Val Glu Lys Lys Pro Ile Pro Arg Ile Lys Arg Lys Asn
    1790            1795               1800
Asn Ser Thr Thr Thr Asn Asn Ser Lys Pro Ser Ser Leu Pro Thr
    1805            1810               1815
Leu Gly Ser Asn Thr Glu Thr Val Gln Pro Glu Val Lys Ser Glu
    1820            1825               1830
Thr Glu Pro His Phe Ile Leu Lys Ser Ser Asp Asn Thr Lys Thr
    1835            1840               1845
Tyr Ser Leu Met Pro Ser Ala Pro His Pro Val Lys Glu Ala Ser
    1850            1855               1860
Pro Gly Phe Ser Trp Ser Pro Lys Thr Ala Ser Thr Pro Ala
    1865            1870               1875
Pro Leu Lys Asn Asp Ala Thr Ala Ser Cys Gly Phe Ser Glu Arg
    1880            1885               1890
Ser Ser Thr Pro His Cys Thr Met Pro Ser Gly Arg Leu Ser Gly
    1895            1900               1905
Ala Asn Ala Ala Ala Ala Asp Gly Pro Gly Ile Ser Gln Leu Gly
    1910            1915               1920
Glu Val Ala Pro Leu Pro Thr Leu Ser Ala Pro Val Met Glu Pro
    1925            1930               1935
Leu Ile Asn Ser Glu Pro Ser Thr Gly Val Thr Glu Pro Leu Thr
    1940            1945               1950
Pro His Gln Pro Asn His Gln Pro Ser Phe Leu Thr Ser Pro Gln
    1955            1960               1965
Asp Leu Ala Ser Ser Pro Met Glu Glu Asp Glu Gln His Ser Glu
    1970            1975               1980
Ala Asp Glu Pro Pro Ser Asp Glu Pro Leu Ser Asp Asp Pro Leu
    1985            1990               1995
Ser Pro Ala Glu Glu Lys Leu Pro His Ile Asp Glu Tyr Trp Ser
    2000            2005               2010
Asp Ser Glu His Ile Phe Leu Asp Ala Asn Ile Gly Gly Val Ala
    2015            2020               2025
Ile Ala Pro Ala His Gly Ser Val Leu Ile Glu Cys Ala Arg Arg
    2030            2035               2040
Glu Leu His Ala Thr Thr Pro Val Glu His Pro Asn Arg Asn His
    2045            2050               2055
Pro Thr Arg Leu Ser Leu Val Phe Tyr Gln His Lys Asn Leu Asn
    2060            2065               2070
Lys Pro Gln His Gly Phe Glu Leu Asn Lys Ile Lys Phe Glu Ala
    2075            2080               2085
Lys Glu Ala Lys Asn Lys Lys Met Lys Ala Ser Glu Gln Lys Asp
    2090            2095               2100
Gln Ala Ala Asn Glu Gly Pro Glu Gln Ser Ser Glu Val Asn Glu
    2105            2110               2115
Leu Asn Gln Ile Pro Ser His Lys Ala Leu Thr Leu Thr His Asp
    2120            2125               2130
Asn Val Val Thr Val Ser Pro Tyr Ala Leu Thr His Val Ala Gly
    2135            2140               2145
Pro Tyr Asn His Trp Val Ile Asp
```

-continued

```
            2150                2155
```

<210> SEQ ID NO 54
<211> LENGTH: 1179
<212> TYPE: PRT
<213> ORGANISM: Artificial Sequence
<220> FEATURE:
<223> OTHER INFORMATION: Synthetic Polypeptide

<400> SEQUENCE: 54

```
Met Gly Pro Ala Glu Leu Pro Thr Cys Ser Cys Leu Asp Arg Val Ile
1               5                   10                  15

Gln Lys Asp Lys Gly Pro Tyr Tyr Thr His Leu Gly Ala Gly Pro Ser
            20                  25                  30

Val Ala Val Arg Glu Ile Met Glu Asn Arg Tyr Gly Gln Lys Gly
        35                  40                  45

Asn Ala Ile Arg Ile Glu Ile Val Val Tyr Thr Gly Lys Glu Gly Lys
    50                  55                  60

Ser Ser His Gly Cys Pro Ile Ala Lys Trp Val Leu Arg Arg Ser Ser
65                  70                  75                  80

Asp Glu Glu Lys Val Leu Cys Leu Val Arg Gln Arg Thr Gly His His
                85                  90                  95

Cys Pro Thr Ala Val Met Val Val Leu Ile Met Val Trp Asp Gly Ile
            100                 105                 110

Pro Leu Pro Met Ala Asp Arg Leu Tyr Thr Glu Leu Thr Glu Asn Leu
        115                 120                 125

Lys Ser Tyr Asn Gly His Pro Thr Asp Arg Arg Cys Thr Leu Asn Glu
    130                 135                 140

Asn Arg Thr Cys Thr Cys Gln Gly Ile Asp Pro Glu Thr Cys Gly Ala
145                 150                 155                 160

Ser Phe Ser Phe Gly Cys Ser Trp Ser Met Tyr Phe Asn Gly Cys Lys
                165                 170                 175

Phe Gly Arg Ser Pro Ser Pro Arg Arg Phe Arg Ile Asp Pro Ser Ser
            180                 185                 190

Pro Leu His Glu Lys Asn Leu Glu Asp Asn Leu Gln Ser Leu Ala Thr
        195                 200                 205

Arg Leu Ala Pro Ile Tyr Lys Gln Tyr Ala Pro Val Ala Tyr Gln Asn
    210                 215                 220

Gln Val Glu Tyr Glu Asn Val Ala Arg Glu Cys Arg Leu Gly Ser Lys
225                 230                 235                 240

Glu Gly Arg Pro Phe Ser Gly Val Thr Ala Cys Leu Asp Phe Cys Ala
                245                 250                 255

His Pro His Arg Asp Ile His Asn Met Asn Asn Gly Ser Thr Val Val
            260                 265                 270

Cys Thr Leu Thr Arg Glu Asp Asn Arg Ser Leu Gly Val Ile Pro Gln
        275                 280                 285

Asp Glu Gln Leu His Val Leu Pro Leu Tyr Lys Leu Ser Asp Thr Asp
    290                 295                 300

Glu Phe Gly Ser Lys Glu Gly Met Glu Ala Lys Ile Lys Ser Gly Ala
305                 310                 315                 320

Ile Glu Val Leu Ala Pro Arg Arg Lys Lys Arg Thr Cys Phe Thr Gln
                325                 330                 335

Pro Val Pro Arg Ser Gly Lys Lys Arg Ala Ala Met Met Thr Glu Val
            340                 345                 350

Leu Ala His Lys Ile Arg Ala Val Glu Lys Lys Pro Ile Pro Arg Ile
```

```
               355                 360                 365
Lys Arg Lys Asn Asn Ser Thr Thr Asn Asn Ser Lys Pro Ser Ser
370                 375                 380

Leu Pro Thr Leu Gly Ser Asn Thr Glu Thr Val Gln Pro Glu Val Lys
385                 390                 395                 400

Ser Glu Thr Glu Pro His Phe Ile Leu Lys Ser Ser Asp Asn Thr Lys
                405                 410                 415

Thr Tyr Ser Leu Met Pro Ser Ala Pro His Pro Val Lys Glu Ala Ser
                420                 425                 430

Pro Gly Phe Ser Trp Ser Pro Lys Thr Ala Ser Ala Thr Pro Ala Pro
                435                 440                 445

Leu Lys Asn Asp Ala Thr Ala Ser Cys Gly Phe Ser Glu Arg Ser Ser
450                 455                 460

Thr Pro His Cys Thr Met Pro Ser Gly Arg Leu Ser Gly Ala Asn Ala
465                 470                 475                 480

Ala Ala Ala Asp Gly Pro Gly Ile Ser Gln Leu Gly Glu Val Ala Pro
                485                 490                 495

Leu Pro Thr Leu Ser Ala Pro Val Met Glu Pro Leu Ile Asn Ser Glu
                500                 505                 510

Pro Ser Thr Gly Val Thr Glu Pro Leu Thr Pro His Gln Pro Asn His
                515                 520                 525

Gln Pro Ser Phe Leu Thr Ser Pro Gln Asp Leu Ala Ser Ser Pro Met
530                 535                 540

Glu Glu Asp Glu Gln His Ser Glu Ala Asp Glu Pro Pro Ser Asp Glu
545                 550                 555                 560

Pro Leu Ser Asp Asp Pro Leu Ser Pro Ala Glu Glu Lys Leu Pro His
                565                 570                 575

Ile Asp Glu Tyr Trp Ser Asp Ser Glu His Ile Phe Leu Asp Ala Asn
                580                 585                 590

Ile Gly Gly Val Ala Ile Ala Pro Ala His Gly Ser Val Leu Ile Glu
                595                 600                 605

Cys Ala Arg Arg Glu Leu His Ala Thr Thr Pro Val Glu His Pro Asn
610                 615                 620

Arg Asn His Pro Thr Arg Leu Ser Leu Val Phe Tyr Gln His Lys Asn
625                 630                 635                 640

Leu Asn Lys Pro Gln His Gly Phe Glu Leu Asn Lys Ile Lys Phe Glu
                645                 650                 655

Ala Lys Glu Ala Lys Asn Lys Lys Met Lys Ala Ser Glu Gln Lys Asp
                660                 665                 670

Gln Ala Ala Asn Glu Gly Pro Glu Gln Ser Ser Glu Val Asn Glu Leu
                675                 680                 685

Asn Gln Ile Pro Ser His Lys Ala Leu Thr Leu Thr His Asp Asn Val
                690                 695                 700

Val Thr Val Ser Pro Tyr Ala Leu Thr His Val Ala Gly Pro Tyr Asn
705                 710                 715                 720

His Trp Val Ile Asp Gly Gly Gly Ser Asp Pro Lys Lys Lys Arg
                725                 730                 735

Lys Val Asp Pro Lys Lys Lys Arg Lys Val Asp Pro Lys Lys Lys Arg
                740                 745                 750

Lys Val Gly Ser Thr Gly Ser Arg Asn Asp Gly Gly Gly Ser Gly
                755                 760                 765

Gly Gly Gly Ser Gly Gly Gly Ser Gly Arg Ala Gly Ile Leu Pro
770                 775                 780
```

```
Pro Lys Lys Lys Arg Lys Val Ser Arg Gly Arg Ser Arg Leu Leu Glu
785                 790                 795                 800

Asp Phe Arg Asn Asn Arg Tyr Pro Asn Leu Gln Leu Arg Glu Ile Ala
            805                 810                 815

Gly His Ile Met Glu Phe Ser Gln Asp Gln His Gly Ser Arg Phe Ile
            820                 825                 830

Gln Leu Lys Leu Glu Arg Ala Thr Pro Ala Glu Arg Gln Leu Val Phe
        835                 840                 845

Asn Glu Ile Leu Gln Ala Ala Tyr Gln Leu Met Val Asp Val Phe Gly
850                 855                 860

Asn Tyr Val Ile Gln Lys Phe Phe Glu Phe Gly Ser Leu Glu Gln Lys
865                 870                 875                 880

Leu Ala Leu Ala Glu Arg Ile Arg Gly His Val Leu Ser Leu Ala Leu
                885                 890                 895

Gln Met Tyr Gly Ser Arg Val Ile Glu Lys Ala Leu Glu Phe Ile Pro
            900                 905                 910

Ser Asp Gln Gln Asn Glu Met Val Arg Glu Leu Asp Gly His Val Leu
        915                 920                 925

Lys Cys Val Lys Asp Gln Asn Gly Asn His Val Val Gln Lys Cys Ile
        930                 935                 940

Glu Cys Val Gln Pro Gln Ser Leu Gln Phe Ile Ile Asp Ala Phe Lys
945                 950                 955                 960

Gly Gln Val Phe Ala Leu Ser Thr His Pro Tyr Gly Cys Arg Val Ile
                965                 970                 975

Gln Arg Ile Leu Glu His Cys Leu Pro Asp Gln Thr Leu Pro Ile Leu
            980                 985                 990

Glu Glu Leu His Gln His Thr Glu Gln Leu Val Gln Asp Gln Tyr Gly
        995                 1000                1005

Asn Tyr Val Ile Gln His Val Leu Glu His Gly Arg Pro Glu Asp
    1010                1015                1020

Lys Ser Lys Ile Val Ala Glu Ile Arg Gly Asn Val Leu Val Leu
    1025                1030                1035

Ser Gln His Lys Phe Ala Ser Asn Val Val Glu Lys Cys Val Thr
    1040                1045                1050

His Ala Ser Arg Thr Glu Arg Ala Val Leu Ile Asp Glu Val Cys
    1055                1060                1065

Thr Met Asn Asp Gly Pro His Ser Ala Leu Tyr Thr Met Met Lys
    1070                1075                1080

Asp Gln Tyr Ala Asn Tyr Val Val Gln Lys Met Ile Asp Val Ala
    1085                1090                1095

Glu Pro Gly Gln Arg Lys Ile Val Met His Lys Ile Arg Pro His
    1100                1105                1110

Ile Ala Thr Leu Arg Lys Tyr Thr Tyr Gly Lys His Ile Leu Ala
    1115                1120                1125

Lys Leu Glu Lys Tyr Tyr Met Lys Asn Gly Val Asp Leu Gly Asp
    1130                1135                1140

Pro Lys Lys Arg Lys Val Asp Pro Lys Lys Arg Lys Val
    1145                1150                1155

Gly Gly Arg Gly Gly Gly Ser Gly Gly Gly Ser Gly Gly
    1160                1165                1170

Gly Gly Ser Gly Pro Ala
    1175
```

<210> SEQ ID NO 55
<211> LENGTH: 1178
<212> TYPE: PRT
<213> ORGANISM: Artificial Sequence
<220> FEATURE:
<223> OTHER INFORMATION: Synthetic Polypeptide

<400> SEQUENCE: 55

```
Met Ile Asp Gly Gly Gly Gly Ser Asp Pro Lys Lys Arg Lys Val
1               5                   10                  15

Asp Pro Lys Lys Arg Lys Val Asp Pro Lys Lys Arg Lys Val
            20                  25                  30

Gly Ser Thr Gly Ser Arg Asn Asp Gly Gly Gly Ser Gly Gly Gly
            35                  40                  45

Gly Ser Gly Gly Gly Ser Gly Arg Ala Gly Ile Leu Pro Pro Lys
    50                  55                  60

Lys Lys Arg Lys Val Ser Arg Gly Arg Ser Arg Leu Leu Glu Asp Phe
65                  70                  75                  80

Arg Asn Asn Arg Tyr Pro Asn Leu Gln Leu Arg Glu Ile Ala Gly His
                    85                  90                  95

Ile Met Glu Phe Ser Gln Asp Gln His Gly Ser Arg Phe Ile Gln Leu
                100                 105                 110

Lys Leu Glu Arg Ala Thr Pro Ala Glu Arg Gln Leu Val Phe Asn Glu
                115                 120                 125

Ile Leu Gln Ala Ala Tyr Gln Leu Met Val Asp Val Phe Gly Asn Tyr
    130                 135                 140

Val Ile Gln Lys Phe Phe Glu Phe Gly Ser Leu Glu Gln Lys Leu Ala
145                 150                 155                 160

Leu Ala Glu Arg Ile Arg Gly His Val Leu Ser Leu Ala Leu Gln Met
                165                 170                 175

Tyr Gly Ser Arg Val Ile Glu Lys Ala Leu Glu Phe Ile Pro Ser Asp
                180                 185                 190

Gln Gln Asn Glu Met Val Arg Glu Leu Asp Gly His Val Leu Lys Cys
        195                 200                 205

Val Lys Asp Gln Asn Gly Asn His Val Val Gln Lys Cys Ile Glu Cys
210                 215                 220

Val Gln Pro Gln Ser Leu Gln Phe Ile Ile Asp Ala Phe Lys Gly Gln
225                 230                 235                 240

Val Phe Ala Leu Ser Thr His Pro Tyr Gly Cys Arg Val Ile Gln Arg
                245                 250                 255

Ile Leu Glu His Cys Leu Pro Asp Gln Thr Leu Pro Ile Leu Glu Glu
                260                 265                 270

Leu His Gln His Thr Glu Gln Leu Val Gln Asp Gln Tyr Gly Asn Tyr
                275                 280                 285

Val Ile Gln His Val Leu Glu His Gly Arg Pro Glu Asp Lys Ser Lys
    290                 295                 300

Ile Val Ala Glu Ile Arg Gly Asn Val Leu Val Leu Ser Gln His Lys
305                 310                 315                 320

Phe Ala Ser Asn Val Val Glu Lys Cys Val Thr His Ala Ser Arg Thr
                325                 330                 335

Glu Arg Ala Val Leu Ile Asp Glu Val Cys Thr Met Asn Asp Gly Pro
                340                 345                 350

His Ser Ala Leu Tyr Thr Met Met Lys Asp Gln Tyr Ala Asn Tyr Val
            355                 360                 365
```

```
Val Gln Lys Met Ile Asp Val Ala Glu Pro Gly Gln Arg Lys Ile Val
    370                 375                 380

Met His Lys Ile Arg Pro His Ile Ala Thr Leu Arg Lys Tyr Thr Tyr
385                 390                 395                 400

Gly Lys His Ile Leu Ala Lys Leu Glu Lys Tyr Tyr Met Lys Asn Gly
                405                 410                 415

Val Asp Leu Gly Asp Pro Lys Lys Arg Lys Val Asp Pro Lys Lys
                420                 425                 430

Lys Arg Lys Val Gly Gly Arg Gly Gly Gly Ser Gly Gly Gly
                435                 440                 445

Ser Gly Gly Gly Ser Gly Pro Ala Glu Leu Pro Thr Cys Ser Cys
    450                 455                 460

Leu Asp Arg Val Ile Gln Lys Asp Lys Gly Pro Tyr Tyr Thr His Leu
465                 470                 475                 480

Gly Ala Gly Pro Ser Val Ala Ala Val Arg Glu Ile Met Glu Asn Arg
                485                 490                 495

Tyr Gly Gln Lys Gly Asn Ala Ile Arg Ile Glu Ile Val Val Tyr Thr
                500                 505                 510

Gly Lys Glu Gly Lys Ser Ser His Gly Cys Pro Ile Ala Lys Trp Val
    515                 520                 525

Leu Arg Arg Ser Ser Asp Glu Glu Lys Val Leu Cys Leu Val Arg Gln
    530                 535                 540

Arg Thr Gly His His Cys Pro Thr Ala Val Met Val Val Leu Ile Met
545                 550                 555                 560

Val Trp Asp Gly Ile Pro Leu Pro Met Ala Asp Arg Leu Tyr Thr Glu
                565                 570                 575

Leu Thr Glu Asn Leu Lys Ser Tyr Asn Gly His Pro Thr Asp Arg Arg
                580                 585                 590

Cys Thr Leu Asn Glu Asn Arg Thr Cys Thr Cys Gln Gly Ile Asp Pro
                595                 600                 605

Glu Thr Cys Gly Ala Ser Phe Ser Phe Gly Cys Ser Trp Ser Met Tyr
    610                 615                 620

Phe Asn Gly Cys Lys Phe Gly Arg Ser Pro Ser Pro Arg Arg Phe Arg
625                 630                 635                 640

Ile Asp Pro Ser Ser Pro Leu His Glu Lys Asn Leu Glu Asp Asn Leu
                645                 650                 655

Gln Ser Leu Ala Thr Arg Leu Ala Pro Ile Tyr Lys Gln Tyr Ala Pro
                660                 665                 670

Val Ala Tyr Gln Asn Gln Val Glu Tyr Glu Asn Val Ala Arg Glu Cys
                675                 680                 685

Arg Leu Gly Ser Lys Glu Gly Arg Pro Phe Ser Gly Val Thr Ala Cys
    690                 695                 700

Leu Asp Phe Cys Ala His Pro His Arg Asp Ile His Asn Met Asn Asn
705                 710                 715                 720

Gly Ser Thr Val Val Cys Thr Leu Thr Arg Glu Asp Asn Arg Ser Leu
                725                 730                 735

Gly Val Ile Pro Gln Asp Glu Gln Leu His Val Leu Pro Leu Tyr Lys
                740                 745                 750

Leu Ser Asp Thr Asp Glu Phe Gly Ser Lys Glu Gly Met Glu Ala Lys
                755                 760                 765

Ile Lys Ser Gly Ala Ile Glu Val Leu Ala Pro Arg Arg Lys Lys Arg
    770                 775                 780

Thr Cys Phe Thr Gln Pro Val Pro Arg Ser Gly Lys Lys Arg Ala Ala
```

```
            785                 790                 795                 800
Met Met Thr Glu Val Leu Ala His Lys Ile Arg Ala Val Glu Lys Lys
                805                 810                 815
Pro Ile Pro Arg Ile Lys Arg Lys Asn Asn Ser Thr Thr Asn Asn
            820                 825                 830
Ser Lys Pro Ser Ser Leu Pro Thr Leu Gly Ser Asn Thr Glu Thr Val
            835                 840                 845
Gln Pro Glu Val Lys Ser Glu Thr Glu Pro His Phe Ile Leu Lys Ser
        850                 855                 860
Ser Asp Asn Thr Lys Thr Tyr Ser Leu Met Pro Ser Ala Pro His Pro
865                 870                 875                 880
Val Lys Glu Ala Ser Pro Gly Phe Ser Trp Ser Pro Lys Thr Ala Ser
                885                 890                 895
Ala Thr Pro Ala Pro Leu Lys Asn Asp Ala Thr Ala Ser Cys Gly Phe
            900                 905                 910
Ser Glu Arg Ser Ser Thr Pro His Cys Thr Met Pro Ser Gly Arg Leu
            915                 920                 925
Ser Gly Ala Asn Ala Ala Ala Asp Gly Pro Gly Ile Ser Gln Leu
    930                 935                 940
Gly Glu Val Ala Pro Leu Pro Thr Leu Ser Ala Pro Val Met Glu Pro
945                 950                 955                 960
Leu Ile Asn Ser Glu Pro Ser Thr Gly Val Thr Glu Pro Leu Thr Pro
                965                 970                 975
His Gln Pro Asn His Gln Pro Ser Phe Leu Thr Ser Pro Gln Asp Leu
            980                 985                 990
Ala Ser Ser Pro Met Glu Glu Asp  Glu Gln His Ser Glu  Ala Asp Glu
        995                1000                 1005
Pro Pro  Ser Asp Glu Pro Leu  Ser Asp Asp Pro Leu  Ser Pro Ala
        1010                1015                1020
Glu Glu  Lys Leu Pro His Ile  Asp Glu Tyr Trp Ser  Asp Ser Glu
        1025                1030                 1035
His Ile  Phe Leu Asp Ala Asn  Ile Gly Gly Val Ala  Ile Ala Pro
        1040                1045                 1050
Ala His  Gly Ser Val Leu Ile  Glu Cys Ala Arg Arg  Glu Leu His
        1055                1060                 1065
Ala Thr  Thr Pro Val Glu His  Pro Asn Arg Asn His  Pro Thr Arg
        1070                1075                 1080
Leu Ser  Leu Val Phe Tyr Gln  His Lys Asn Leu Asn  Lys Pro Gln
        1085                1090                 1095
His Gly  Phe Glu Leu Asn Lys  Ile Lys Phe Glu Ala  Lys Glu Ala
        1100                1105                 1110
Lys Asn  Lys Lys Met Lys Ala  Ser Glu Gln Lys Asp  Gln Ala Ala
        1115                1120                 1125
Asn Glu  Gly Pro Glu Gln Ser  Ser Glu Val Asn Glu  Leu Asn Gln
        1130                1135                 1140
Ile Pro  Ser His Lys Ala Leu  Thr Leu Thr His Asp  Asn Val Val
        1145                1150                 1155
Thr Val  Ser Pro Tyr Ala Leu  Thr His Val Ala Gly  Pro Tyr Asn
        1160                1165                 1170

His Trp  Val Ile Asp
        1175

<210> SEQ ID NO 56
```

<211> LENGTH: 301
<212> TYPE: PRT
<213> ORGANISM: Artificial Sequence
<220> FEATURE:
<223> OTHER INFORMATION: Synthetic Polypeptide

<400> SEQUENCE: 56

Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val
    290                 295                 300

<210> SEQ ID NO 57
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 57

Gly Pro Met Glu Ile Tyr Lys Thr Val Ser Ala Trp Lys Arg Gln Pro
1               5                   10                  15

Val Arg Val Leu Ser Leu Phe Arg Asn Ile Asp Lys Val Leu Lys Ser

```
            20                  25                  30
Leu Gly Phe Leu Glu Ser Gly Ser Gly Gly Gly Thr Leu Lys
        35                  40                  45

Tyr Val Glu Asp Val Thr Asn Val Val Arg Arg Asp Val Glu Lys Trp
    50                  55                  60

Gly Pro Phe Asp Leu Val Tyr Gly Ser Thr Gln Pro Leu Gly Ser Ser
65                  70                  75                  80

Cys Asp Arg Cys Pro Gly Trp Tyr Met Phe Gln Phe His Arg Ile Leu
                85                  90                  95

Gln Tyr Ala Leu Pro Arg Gln Glu Ser Gln Arg Pro Phe Phe Trp Ile
            100                 105                 110

Phe Met Asp Asn Leu Leu Leu Thr Glu Asp Asp Gln Glu Thr Thr Thr
                115                 120                 125

Arg Phe Leu Gln Thr Glu Ala Val Thr Leu Gln Asp Val Arg Gly Arg
            130                 135                 140

Asp Tyr Gln Asn Ala Met Arg Val Trp Ser Asn Ile Pro Gly Leu Lys
145                 150                 155                 160

Ser Lys His Ala Pro Leu Thr Pro Lys Glu Glu Tyr Leu Gln Ala
                165                 170                 175

Gln Val Arg Ser Arg Ser Lys Leu Asp Ala Pro Lys Val Asp Leu Leu
            180                 185                 190

Val Lys Asn Cys Leu Leu Pro Leu Arg Glu Tyr Phe Lys Tyr Phe Ser
                195                 200                 205

Gln Asn Ser Leu Pro Leu
            210

<210> SEQ ID NO 58
<211> LENGTH: 543
<212> TYPE: PRT
<213> ORGANISM: Artificial Sequence
<220> FEATURE:
<223> OTHER INFORMATION: Synthetic Polypeptide

<400> SEQUENCE: 58

Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
```

165                 170                 175
Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
            245                 250                 255

Phe Gly Phe Pro Val His Tyr Thr Asp Val Ser Asn Met Ser Arg Leu
        260                 265                 270

Ala Arg Gln Arg Leu Leu Gly Arg Ser Trp Ser Val Pro Val Ile Arg
    275                 280                 285

His Leu Phe Ala Pro Leu Lys Glu Tyr Phe Ala Cys Val Ser Ser Gly
    290                 295                 300

Asn Ser Asn Ala Asn Ser Arg Gly Pro Ser Phe Ser Ser Gly Leu Val
305                 310                 315                 320

Pro Leu Ser Leu Arg Gly Ser His Met Gly Pro Met Glu Ile Tyr Lys
            325                 330                 335

Thr Val Ser Ala Trp Lys Arg Gln Pro Val Arg Val Leu Ser Leu Phe
        340                 345                 350

Arg Asn Ile Asp Lys Val Leu Lys Ser Leu Gly Phe Leu Glu Ser Gly
    355                 360                 365

Ser Gly Ser Gly Gly Gly Thr Leu Lys Tyr Val Glu Asp Val Thr Asn
    370                 375                 380

Val Val Arg Arg Asp Val Glu Lys Trp Gly Pro Phe Asp Leu Val Tyr
385                 390                 395                 400

Gly Ser Thr Gln Pro Leu Gly Ser Ser Cys Asp Arg Cys Pro Gly Trp
            405                 410                 415

Tyr Met Phe Gln Phe His Arg Ile Leu Gln Tyr Ala Leu Pro Arg Gln
        420                 425                 430

Glu Ser Gln Arg Pro Phe Phe Trp Ile Phe Met Asp Asn Leu Leu Leu
    435                 440                 445

Thr Glu Asp Asp Gln Glu Thr Thr Thr Arg Phe Leu Gln Thr Glu Ala
    450                 455                 460

Val Thr Leu Gln Asp Val Arg Gly Arg Asp Tyr Gln Asn Ala Met Arg
465                 470                 475                 480

Val Trp Ser Asn Ile Pro Gly Leu Lys Ser Lys His Ala Pro Leu Thr
            485                 490                 495

Pro Lys Glu Glu Glu Tyr Leu Gln Ala Gln Val Arg Ser Arg Ser Lys
        500                 505                 510

Leu Asp Ala Pro Lys Val Asp Leu Leu Val Lys Asn Cys Leu Leu Pro
    515                 520                 525

Leu Arg Glu Tyr Phe Lys Tyr Phe Ser Gln Asn Ser Leu Pro Leu
    530                 535                 540

<210> SEQ ID NO 59
<211> LENGTH: 1739
<212> TYPE: PRT
<213> ORGANISM: Artificial Sequence
<220> FEATURE:
<223> OTHER INFORMATION: Synthetic Polypeptide

<400> SEQUENCE: 59

```
Met Gly Pro Ala Asn His Asp Gln Glu Phe Asp Pro Pro Lys Val Tyr
1               5                   10                  15

Pro Pro Val Pro Ala Glu Lys Arg Lys Pro Ile Arg Val Leu Ser Leu
            20                  25                  30

Phe Asp Gly Ile Ala Thr Gly Leu Leu Val Leu Lys Asp Leu Gly Ile
        35                  40                  45

Gln Val Asp Arg Tyr Ile Ala Ser Glu Val Cys Glu Asp Ser Ile Thr
    50                  55                  60

Val Gly Met Val Arg His Gln Gly Lys Ile Met Tyr Val Gly Asp Val
65                  70                  75                  80

Arg Ser Val Thr Gln Lys His Ile Gln Glu Trp Gly Pro Phe Asp Leu
                85                  90                  95

Val Ile Gly Gly Ser Pro Cys Asn Asp Leu Ser Ile Val Asn Pro Ala
            100                 105                 110

Arg Lys Gly Leu Tyr Glu Gly Thr Gly Arg Leu Phe Phe Glu Phe Tyr
        115                 120                 125

Arg Leu Leu His Asp Ala Arg Pro Lys Glu Gly Asp Asp Arg Pro Phe
    130                 135                 140

Phe Trp Leu Phe Glu Asn Val Val Ala Met Gly Val Ser Asp Lys Arg
145                 150                 155                 160

Asp Ile Ser Arg Phe Leu Glu Ser Asn Pro Val Met Ile Asp Ala Lys
                165                 170                 175

Glu Val Ser Ala Ala His Arg Ala Arg Tyr Phe Trp Gly Asn Leu Pro
            180                 185                 190

Gly Met Asn Arg Pro Leu Ala Ser Thr Val Asn Asp Lys Leu Glu Leu
        195                 200                 205

Gln Glu Cys Leu Glu His Gly Arg Ile Ala Lys Phe Ser Lys Val Arg
    210                 215                 220

Thr Ile Thr Thr Arg Ser Asn Ser Ile Lys Gln Gly Lys Asp Gln His
225                 230                 235                 240

Phe Pro Val Phe Met Asn Glu Lys Glu Asp Ile Leu Trp Cys Thr Glu
                245                 250                 255

Met Glu Arg Val Phe Gly Phe Pro Val His Tyr Thr Asp Val Ser Asn
            260                 265                 270

Met Ser Arg Leu Ala Arg Gln Arg Leu Leu Gly Arg Ser Trp Ser Val
        275                 280                 285

Pro Val Ile Arg His Leu Phe Ala Pro Leu Lys Glu Tyr Phe Ala Cys
    290                 295                 300

Val Ile Asp Gly Gly Gly Ser Gly Gly Gly Ser Gly Gly Gly
305                 310                 315                 320

Gly Ser Met Tyr Pro Tyr Asp Val Pro Asp Tyr Ala Ser Pro Lys Lys
            325                 330                 335

Lys Arg Lys Val Glu Ala Ser Asp Lys Lys Tyr Ser Ile Gly Leu Ala
        340                 345                 350

Ile Gly Thr Asn Ser Val Gly Trp Ala Val Ile Thr Asp Glu Tyr Lys
    355                 360                 365

Val Pro Ser Lys Lys Phe Lys Val Leu Gly Asn Thr Asp Arg His Ser
370                 375                 380

Ile Lys Lys Asn Leu Ile Gly Ala Leu Leu Phe Asp Ser Gly Glu Thr
                385                 390                 395                 400

Ala Glu Ala Thr Arg Leu Lys Arg Thr Ala Arg Arg Arg Tyr Thr Arg
            405                 410                 415
```

```
Arg Lys Asn Arg Ile Cys Tyr Leu Gln Glu Ile Phe Ser Asn Glu Met
            420                 425                 430

Ala Lys Val Asp Asp Ser Phe Phe His Arg Leu Glu Glu Ser Phe Leu
        435                 440                 445

Val Glu Glu Asp Lys Lys His Glu Arg His Pro Ile Phe Gly Asn Ile
450                 455                 460

Val Asp Glu Val Ala Tyr His Glu Lys Tyr Pro Thr Ile Tyr His Leu
465                 470                 475                 480

Arg Lys Lys Leu Val Asp Ser Thr Asp Lys Ala Asp Leu Arg Leu Ile
                485                 490                 495

Tyr Leu Ala Leu Ala His Met Ile Lys Phe Arg Gly His Phe Leu Ile
            500                 505                 510

Glu Gly Asp Leu Asn Pro Asp Asn Ser Asp Val Asp Lys Leu Phe Ile
        515                 520                 525

Gln Leu Val Gln Thr Tyr Asn Gln Leu Phe Glu Glu Asn Pro Ile Asn
530                 535                 540

Ala Ser Gly Val Asp Ala Lys Ala Ile Leu Ser Ala Arg Leu Ser Lys
545                 550                 555                 560

Ser Arg Arg Leu Glu Asn Leu Ile Ala Gln Leu Pro Gly Glu Lys Lys
                565                 570                 575

Asn Gly Leu Phe Gly Asn Leu Ile Ala Leu Ser Leu Gly Leu Thr Pro
            580                 585                 590

Asn Phe Lys Ser Asn Phe Asp Leu Ala Glu Asp Ala Lys Leu Gln Leu
        595                 600                 605

Ser Lys Asp Thr Tyr Asp Asp Asp Leu Asp Asn Leu Leu Ala Gln Ile
610                 615                 620

Gly Asp Gln Tyr Ala Asp Leu Phe Leu Ala Ala Lys Asn Leu Ser Asp
625                 630                 635                 640

Ala Ile Leu Leu Ser Asp Ile Leu Arg Val Asn Thr Glu Ile Thr Lys
                645                 650                 655

Ala Pro Leu Ser Ala Ser Met Ile Lys Arg Tyr Asp Glu His His Gln
            660                 665                 670

Asp Leu Thr Leu Leu Lys Ala Leu Val Arg Gln Gln Leu Pro Glu Lys
        675                 680                 685

Tyr Lys Glu Ile Phe Phe Asp Gln Ser Lys Asn Gly Tyr Ala Gly Tyr
690                 695                 700

Ile Asp Gly Gly Ala Ser Gln Glu Glu Phe Tyr Lys Phe Ile Lys Pro
705                 710                 715                 720

Ile Leu Glu Lys Met Asp Gly Thr Glu Glu Leu Leu Val Lys Leu Asn
                725                 730                 735

Arg Glu Asp Leu Leu Arg Lys Gln Arg Thr Phe Asp Asn Gly Ser Ile
            740                 745                 750

Pro His Gln Ile His Leu Gly Glu Leu His Ala Ile Leu Arg Arg Gln
        755                 760                 765

Glu Asp Phe Tyr Pro Phe Leu Lys Asp Asn Arg Glu Lys Ile Glu Lys
770                 775                 780

Ile Leu Thr Phe Arg Ile Pro Tyr Tyr Val Gly Pro Leu Ala Arg Gly
785                 790                 795                 800

Asn Ser Arg Phe Ala Trp Met Thr Arg Lys Ser Glu Glu Thr Ile Thr
                805                 810                 815

Pro Trp Asn Phe Glu Glu Val Val Asp Lys Gly Ala Ser Ala Gln Ser
            820                 825                 830
```

-continued

Phe Ile Glu Arg Met Thr Asn Phe Asp Lys Asn Leu Pro Asn Glu Lys
            835                 840                 845

Val Leu Pro Lys His Ser Leu Leu Tyr Glu Tyr Phe Thr Val Tyr Asn
850                 855                 860

Glu Leu Thr Lys Val Lys Tyr Val Thr Glu Gly Met Arg Lys Pro Ala
865                 870                 875                 880

Phe Leu Ser Gly Glu Gln Lys Lys Ala Ile Val Asp Leu Leu Phe Lys
            885                 890                 895

Thr Asn Arg Lys Val Thr Val Lys Gln Leu Lys Glu Asp Tyr Phe Lys
            900                 905                 910

Lys Ile Glu Cys Phe Asp Ser Val Glu Ile Ser Gly Val Glu Asp Arg
            915                 920                 925

Phe Asn Ala Ser Leu Gly Thr Tyr His Asp Leu Leu Lys Ile Ile Lys
            930                 935                 940

Asp Lys Asp Phe Leu Asp Asn Glu Glu Asn Glu Asp Ile Leu Glu Asp
945                 950                 955                 960

Ile Val Leu Thr Leu Thr Leu Phe Glu Asp Arg Glu Met Ile Glu Glu
            965                 970                 975

Arg Leu Lys Thr Tyr Ala His Leu Phe Asp Asp Lys Val Met Lys Gln
            980                 985                 990

Leu Lys Arg Arg Arg Tyr Thr Gly Trp Gly Arg Leu Ser Arg Lys Leu
            995                 1000                1005

Ile Asn Gly Ile Arg Asp Lys Gln Ser Gly Lys Thr Ile Leu Asp
        1010                1015                1020

Phe Leu Lys Ser Asp Gly Phe Ala Asn Arg Asn Phe Met Gln Leu
        1025                1030                1035

Ile His Asp Asp Ser Leu Thr Phe Lys Glu Asp Ile Gln Lys Ala
        1040                1045                1050

Gln Val Ser Gly Gln Gly Asp Ser Leu His Glu His Ile Ala Asn
        1055                1060                1065

Leu Ala Gly Ser Pro Ala Ile Lys Lys Gly Ile Leu Gln Thr Val
        1070                1075                1080

Lys Val Val Asp Glu Leu Val Lys Val Met Gly Arg His Lys Pro
        1085                1090                1095

Glu Asn Ile Val Ile Glu Met Ala Arg Glu Asn Gln Thr Thr Gln
        1100                1105                1110

Lys Gly Gln Lys Asn Ser Arg Glu Arg Met Lys Arg Ile Glu Glu
        1115                1120                1125

Gly Ile Lys Glu Leu Gly Ser Gln Ile Leu Lys Glu His Pro Val
        1130                1135                1140

Glu Asn Thr Gln Leu Gln Asn Glu Lys Leu Tyr Leu Tyr Tyr Leu
        1145                1150                1155

Gln Asn Gly Arg Asp Met Tyr Val Asp Gln Glu Leu Asp Ile Asn
        1160                1165                1170

Arg Leu Ser Asp Tyr Asp Val Asp Ala Ile Val Pro Gln Ser Phe
        1175                1180                1185

Leu Lys Asp Asp Ser Ile Asp Asn Lys Val Leu Thr Arg Ser Asp
        1190                1195                1200

Lys Asn Arg Gly Lys Ser Asp Asn Val Pro Ser Glu Glu Val Val
        1205                1210                1215

Lys Lys Met Lys Asn Tyr Trp Arg Gln Leu Leu Asn Ala Lys Leu
        1220                1225                1230

Ile Thr Gln Arg Lys Phe Asp Asn Leu Thr Lys Ala Glu Arg Gly

```
            1235                1240                1245
Gly Leu Ser Glu Leu Asp Lys Ala Gly Phe Ile Lys Arg Gln Leu
            1250                1255                1260
Val Glu Thr Arg Gln Ile Thr Lys His Val Ala Gln Ile Leu Asp
            1265                1270                1275
Ser Arg Met Asn Thr Lys Tyr Asp Glu Asn Asp Lys Leu Ile Arg
            1280                1285                1290
Glu Val Lys Val Ile Thr Leu Lys Ser Lys Leu Val Ser Asp Phe
            1295                1300                1305
Arg Lys Asp Phe Gln Phe Tyr Lys Val Arg Glu Ile Asn Asn Tyr
            1310                1315                1320
His His Ala His Asp Ala Tyr Leu Asn Ala Val Val Gly Thr Ala
            1325                1330                1335
Leu Ile Lys Lys Tyr Pro Lys Leu Glu Ser Glu Phe Val Tyr Gly
            1340                1345                1350
Asp Tyr Lys Val Tyr Asp Val Arg Lys Met Ile Ala Lys Ser Glu
            1355                1360                1365
Gln Glu Ile Gly Lys Ala Thr Ala Lys Tyr Phe Phe Tyr Ser Asn
            1370                1375                1380
Ile Met Asn Phe Phe Lys Thr Glu Ile Thr Leu Ala Asn Gly Glu
            1385                1390                1395
Ile Arg Lys Arg Pro Leu Ile Glu Thr Asn Gly Glu Thr Gly Glu
            1400                1405                1410
Ile Val Trp Asp Lys Gly Arg Asp Phe Ala Thr Val Arg Lys Val
            1415                1420                1425
Leu Ser Met Pro Gln Val Asn Ile Val Lys Lys Thr Glu Val Gln
            1430                1435                1440
Thr Gly Gly Phe Ser Lys Glu Ser Ile Leu Pro Lys Arg Asn Ser
            1445                1450                1455
Asp Lys Leu Ile Ala Arg Lys Lys Asp Trp Asp Pro Lys Lys Tyr
            1460                1465                1470
Gly Gly Phe Asp Ser Pro Thr Val Ala Tyr Ser Val Leu Val Val
            1475                1480                1485
Ala Lys Val Glu Lys Gly Lys Ser Lys Lys Leu Lys Ser Val Lys
            1490                1495                1500
Glu Leu Leu Gly Ile Thr Ile Met Glu Arg Ser Ser Phe Glu Lys
            1505                1510                1515
Asn Pro Ile Asp Phe Leu Glu Ala Lys Gly Tyr Lys Glu Val Lys
            1520                1525                1530
Lys Asp Leu Ile Ile Lys Leu Pro Lys Tyr Ser Leu Phe Glu Leu
            1535                1540                1545
Glu Asn Gly Arg Lys Arg Met Leu Ala Ser Ala Gly Glu Leu Gln
            1550                1555                1560
Lys Gly Asn Glu Leu Ala Leu Pro Ser Lys Tyr Val Asn Phe Leu
            1565                1570                1575
Tyr Leu Ala Ser His Tyr Glu Lys Leu Lys Gly Ser Pro Glu Asp
            1580                1585                1590
Asn Glu Gln Lys Gln Leu Phe Val Glu Gln His Lys His Tyr Leu
            1595                1600                1605
Asp Glu Ile Ile Glu Gln Ile Ser Glu Phe Ser Lys Arg Val Ile
            1610                1615                1620
Leu Ala Asp Ala Asn Leu Asp Lys Val Leu Ser Ala Tyr Asn Lys
            1625                1630                1635
```

-continued

```
His Arg Asp Lys Pro Ile Arg Glu Gln Ala Glu Asn Ile Ile His
    1640            1645                1650

Leu Phe Thr Leu Thr Asn Leu Gly Ala Pro Ala Ala Phe Lys Tyr
    1655            1660                1665

Phe Asp Thr Thr Ile Asp Arg Lys Arg Tyr Thr Ser Thr Lys Glu
    1670            1675                1680

Val Leu Asp Ala Thr Leu Ile His Gln Ser Ile Thr Gly Leu Tyr
    1685            1690                1695

Glu Thr Arg Ile Asp Leu Ser Gln Leu Gly Gly Asp Ser Pro Lys
    1700            1705                1710

Lys Lys Arg Lys Val Glu Ala Ser Gly Gly Gly Ser Gly Gly
    1715            1720                1725

Gly Gly Ser Gly Gly Gly Gly Ser Gly Pro Ala
    1730            1735

<210> SEQ ID NO 60
<211> LENGTH: 1652
<212> TYPE: PRT
<213> ORGANISM: Artificial Sequence
<220> FEATURE:
<223> OTHER INFORMATION: Synthetic Polypeptide

<400> SEQUENCE: 60

Met Gly Pro Ala Gly Pro Met Glu Ile Tyr Lys Thr Val Ser Ala Trp
1               5                   10                  15

Lys Arg Gln Pro Val Arg Val Leu Ser Leu Phe Arg Asn Ile Asp Lys
                20                  25                  30

Val Leu Lys Ser Leu Gly Phe Leu Glu Ser Gly Ser Gly Ser Gly Gly
            35                  40                  45

Gly Thr Leu Lys Tyr Val Glu Asp Val Thr Asn Val Arg Arg Asp
        50                  55                  60

Val Glu Lys Trp Gly Pro Phe Asp Leu Val Tyr Gly Ser Thr Gln Pro
65                  70                  75                  80

Leu Gly Ser Ser Cys Asp Arg Cys Pro Gly Trp Tyr Met Phe Gln Phe
                85                  90                  95

His Arg Ile Leu Gln Tyr Ala Leu Pro Arg Gln Glu Ser Gln Arg Pro
            100                 105                 110

Phe Phe Trp Ile Phe Met Asp Asn Leu Leu Thr Glu Asp Asp Gln
        115                 120                 125

Glu Thr Thr Thr Arg Phe Leu Gln Thr Glu Ala Val Thr Leu Gln Asp
    130                 135                 140

Val Arg Gly Arg Asp Tyr Gln Asn Ala Met Arg Val Trp Ser Asn Ile
145                 150                 155                 160

Pro Gly Leu Lys Ser Lys His Ala Pro Leu Thr Pro Lys Glu Glu
                165                 170                 175

Tyr Leu Gln Ala Gln Val Arg Ser Arg Ser Lys Leu Asp Ala Pro Lys
            180                 185                 190

Val Asp Leu Leu Val Lys Asn Cys Leu Leu Pro Leu Arg Glu Tyr Phe
        195                 200                 205

Lys Tyr Phe Ser Gln Asn Ser Leu Pro Leu Ile Asp Gly Gly Gly
    210                 215                 220

Ser Gly Gly Gly Ser Gly Gly Gly Gly Ser Met Tyr Pro Tyr Asp
225                 230                 235                 240

Val Pro Asp Tyr Ala Ser Pro Lys Lys Lys Arg Lys Val Glu Ala Ser
                245                 250                 255
```

Asp Lys Lys Tyr Ser Ile Gly Leu Ala Ile Gly Thr Asn Ser Val Gly
            260                 265                 270

Trp Ala Val Ile Thr Asp Glu Tyr Lys Val Pro Ser Lys Lys Phe Lys
            275                 280                 285

Val Leu Gly Asn Thr Asp Arg His Ser Ile Lys Lys Asn Leu Ile Gly
            290                 295                 300

Ala Leu Leu Phe Asp Ser Gly Glu Thr Ala Glu Ala Thr Arg Leu Lys
305                 310                 315                 320

Arg Thr Ala Arg Arg Arg Tyr Thr Arg Arg Lys Asn Arg Ile Cys Tyr
                325                 330                 335

Leu Gln Glu Ile Phe Ser Asn Glu Met Ala Lys Val Asp Asp Ser Phe
            340                 345                 350

Phe His Arg Leu Glu Glu Ser Phe Leu Val Glu Glu Asp Lys Lys His
            355                 360                 365

Glu Arg His Pro Ile Phe Gly Asn Ile Val Asp Glu Val Ala Tyr His
            370                 375                 380

Glu Lys Tyr Pro Thr Ile Tyr His Leu Arg Lys Lys Leu Val Asp Ser
385                 390                 395                 400

Thr Asp Lys Ala Asp Leu Arg Leu Ile Tyr Leu Ala Leu Ala His Met
                405                 410                 415

Ile Lys Phe Arg Gly His Phe Leu Ile Glu Gly Asp Leu Asn Pro Asp
            420                 425                 430

Asn Ser Asp Val Asp Lys Leu Phe Ile Gln Leu Val Gln Thr Tyr Asn
            435                 440                 445

Gln Leu Phe Glu Glu Asn Pro Ile Asn Ala Ser Gly Val Asp Ala Lys
            450                 455                 460

Ala Ile Leu Ser Ala Arg Leu Ser Lys Ser Arg Arg Leu Glu Asn Leu
465                 470                 475                 480

Ile Ala Gln Leu Pro Gly Glu Lys Lys Asn Gly Leu Phe Gly Asn Leu
            485                 490                 495

Ile Ala Leu Ser Leu Gly Leu Thr Pro Asn Phe Lys Ser Asn Phe Asp
            500                 505                 510

Leu Ala Glu Asp Ala Lys Leu Gln Leu Ser Lys Asp Thr Tyr Asp Asp
            515                 520                 525

Asp Leu Asp Asn Leu Leu Ala Gln Ile Gly Asp Gln Tyr Ala Asp Leu
            530                 535                 540

Phe Leu Ala Ala Lys Asn Leu Ser Asp Ala Ile Leu Leu Ser Asp Ile
545                 550                 555                 560

Leu Arg Val Asn Thr Glu Ile Thr Lys Ala Pro Leu Ser Ala Ser Met
                565                 570                 575

Ile Lys Arg Tyr Asp Glu His His Gln Asp Leu Thr Leu Leu Lys Ala
            580                 585                 590

Leu Val Arg Gln Gln Leu Pro Glu Lys Tyr Lys Glu Ile Phe Phe Asp
            595                 600                 605

Gln Ser Lys Asn Gly Tyr Ala Gly Tyr Ile Asp Gly Gly Ala Ser Gln
            610                 615                 620

Glu Glu Phe Tyr Lys Phe Ile Lys Pro Ile Leu Glu Lys Met Asp Gly
625                 630                 635                 640

Thr Glu Glu Leu Leu Val Lys Leu Asn Arg Glu Asp Leu Leu Arg Lys
                645                 650                 655

Gln Arg Thr Phe Asp Asn Gly Ser Ile Pro His Gln Ile His Leu Gly
            660                 665                 670

```
Glu Leu His Ala Ile Leu Arg Arg Gln Glu Asp Phe Tyr Pro Phe Leu
            675                 680                 685

Lys Asp Asn Arg Glu Lys Ile Glu Lys Ile Leu Thr Phe Arg Ile Pro
690                 695                 700

Tyr Tyr Val Gly Pro Leu Ala Arg Gly Asn Ser Arg Phe Ala Trp Met
705                 710                 715                 720

Thr Arg Lys Ser Glu Glu Thr Ile Thr Pro Trp Asn Phe Glu Glu Val
            725                 730                 735

Val Asp Lys Gly Ala Ser Ala Gln Ser Phe Ile Glu Arg Met Thr Asn
            740                 745                 750

Phe Asp Lys Asn Leu Pro Asn Glu Lys Val Leu Pro Lys His Ser Leu
            755                 760                 765

Leu Tyr Glu Tyr Phe Thr Val Tyr Asn Glu Leu Thr Lys Val Lys Tyr
            770                 775                 780

Val Thr Glu Gly Met Arg Lys Pro Ala Phe Leu Ser Gly Glu Gln Lys
785                 790                 795                 800

Lys Ala Ile Val Asp Leu Leu Phe Lys Thr Asn Arg Lys Val Thr Val
            805                 810                 815

Lys Gln Leu Lys Glu Asp Tyr Phe Lys Lys Ile Glu Cys Phe Asp Ser
            820                 825                 830

Val Glu Ile Ser Gly Val Glu Asp Arg Phe Asn Ala Ser Leu Gly Thr
            835                 840                 845

Tyr His Asp Leu Leu Lys Ile Ile Lys Asp Lys Asp Phe Leu Asp Asn
            850                 855                 860

Glu Glu Asn Glu Asp Ile Leu Glu Asp Ile Val Leu Thr Leu Thr Leu
865                 870                 875                 880

Phe Glu Asp Arg Glu Met Ile Glu Glu Arg Leu Lys Thr Tyr Ala His
                885                 890                 895

Leu Phe Asp Asp Lys Val Met Lys Gln Leu Lys Arg Arg Arg Tyr Thr
            900                 905                 910

Gly Trp Gly Arg Leu Ser Arg Lys Leu Ile Asn Gly Ile Arg Asp Lys
            915                 920                 925

Gln Ser Gly Lys Thr Ile Leu Asp Phe Leu Lys Ser Asp Gly Phe Ala
            930                 935                 940

Asn Arg Asn Phe Met Gln Leu Ile His Asp Asp Ser Leu Thr Phe Lys
945                 950                 955                 960

Glu Asp Ile Gln Lys Ala Gln Val Ser Gly Gln Gly Asp Ser Leu His
            965                 970                 975

Glu His Ile Ala Asn Leu Ala Gly Ser Pro Ala Ile Lys Lys Gly Ile
            980                 985                 990

Leu Gln Thr Val Lys Val Val Asp  Glu Leu Val Lys  Val Met Gly Arg
            995                 1000                1005

His Lys  Pro Glu Asn Ile Val  Ile Glu Met Ala Arg  Glu Asn Gln
    1010                1015                1020

Thr Thr  Gln Lys Gly Gln Lys  Asn Ser Arg Glu Arg  Met Lys Arg
    1025                1030                1035

Ile Glu  Glu Gly Ile Lys Glu  Leu Gly Ser Gln Ile  Leu Lys Glu
    1040                1045                1050

His Pro  Val Glu Asn Thr Gln  Leu Gln Asn Glu Lys  Leu Tyr Leu
    1055                1060                1065

Tyr Tyr  Leu Gln Asn Gly Arg  Asp Met Tyr Val Asp  Gln Glu Leu
    1070                1075                1080

Asp Ile  Asn Arg Leu Ser Asp  Tyr Asp Val Asp Ala  Ile Val Pro
```

```
              1085                1090                1095

Gln  Ser  Phe  Leu  Lys  Asp  Asp  Ser  Ile  Asp  Asn  Lys  Val  Leu  Thr
              1100                1105                1110

Arg  Ser  Asp  Lys  Asn  Arg  Gly  Lys  Ser  Asp  Asn  Val  Pro  Ser  Glu
              1115                1120                1125

Glu  Val  Val  Lys  Lys  Met  Lys  Asn  Tyr  Trp  Arg  Gln  Leu  Leu  Asn
              1130                1135                1140

Ala  Lys  Leu  Ile  Thr  Gln  Arg  Lys  Phe  Asp  Asn  Leu  Thr  Lys  Ala
              1145                1150                1155

Glu  Arg  Gly  Gly  Leu  Ser  Glu  Leu  Asp  Lys  Ala  Gly  Phe  Ile  Lys
              1160                1165                1170

Arg  Gln  Leu  Val  Glu  Thr  Arg  Gln  Ile  Thr  Lys  His  Val  Ala  Gln
              1175                1180                1185

Ile  Leu  Asp  Ser  Arg  Met  Asn  Thr  Lys  Tyr  Asp  Glu  Asn  Asp  Lys
              1190                1195                1200

Leu  Ile  Arg  Glu  Val  Lys  Val  Ile  Thr  Leu  Lys  Ser  Lys  Leu  Val
              1205                1210                1215

Ser  Asp  Phe  Arg  Lys  Asp  Phe  Gln  Phe  Tyr  Lys  Val  Arg  Glu  Ile
              1220                1225                1230

Asn  Asn  Tyr  His  His  Ala  His  Asp  Ala  Tyr  Leu  Asn  Ala  Val  Val
              1235                1240                1245

Gly  Thr  Ala  Leu  Ile  Lys  Lys  Tyr  Pro  Lys  Leu  Glu  Ser  Glu  Phe
              1250                1255                1260

Val  Tyr  Gly  Asp  Tyr  Lys  Val  Tyr  Asp  Val  Arg  Lys  Met  Ile  Ala
              1265                1270                1275

Lys  Ser  Glu  Gln  Glu  Ile  Gly  Lys  Ala  Thr  Ala  Lys  Tyr  Phe  Phe
              1280                1285                1290

Tyr  Ser  Asn  Ile  Met  Asn  Phe  Phe  Lys  Thr  Glu  Ile  Thr  Leu  Ala
              1295                1300                1305

Asn  Gly  Glu  Ile  Arg  Lys  Arg  Pro  Leu  Ile  Glu  Thr  Asn  Gly  Glu
              1310                1315                1320

Thr  Gly  Glu  Ile  Val  Trp  Asp  Lys  Gly  Arg  Asp  Phe  Ala  Thr  Val
              1325                1330                1335

Arg  Lys  Val  Leu  Ser  Met  Pro  Gln  Val  Asn  Ile  Val  Lys  Lys  Thr
              1340                1345                1350

Glu  Val  Gln  Thr  Gly  Gly  Phe  Ser  Lys  Glu  Ser  Ile  Leu  Pro  Lys
              1355                1360                1365

Arg  Asn  Ser  Asp  Lys  Leu  Ile  Ala  Arg  Lys  Lys  Asp  Trp  Asp  Pro
              1370                1375                1380

Lys  Lys  Tyr  Gly  Gly  Phe  Asp  Ser  Pro  Thr  Val  Ala  Tyr  Ser  Val
              1385                1390                1395

Leu  Val  Val  Ala  Lys  Val  Glu  Lys  Gly  Lys  Ser  Lys  Lys  Leu  Lys
              1400                1405                1410

Ser  Val  Lys  Glu  Leu  Leu  Gly  Ile  Thr  Ile  Met  Glu  Arg  Ser  Ser
              1415                1420                1425

Phe  Glu  Lys  Asn  Pro  Ile  Asp  Phe  Leu  Glu  Ala  Lys  Gly  Tyr  Lys
              1430                1435                1440

Glu  Val  Lys  Lys  Asp  Leu  Ile  Ile  Lys  Leu  Pro  Lys  Tyr  Ser  Leu
              1445                1450                1455

Phe  Glu  Leu  Glu  Asn  Gly  Arg  Lys  Arg  Met  Leu  Ala  Ser  Ala  Gly
              1460                1465                1470

Glu  Leu  Gln  Lys  Gly  Asn  Glu  Leu  Ala  Leu  Pro  Ser  Lys  Tyr  Val
              1475                1480                1485
```

```
Asn Phe Leu Tyr Leu Ala Ser His Tyr Glu Lys Leu Lys Gly Ser
    1490                1495                1500

Pro Glu Asp Asn Glu Gln Lys Gln Leu Phe Val Glu Gln His Lys
    1505                1510                1515

His Tyr Leu Asp Glu Ile Ile Glu Gln Ile Ser Glu Phe Ser Lys
    1520                1525                1530

Arg Val Ile Leu Ala Asp Ala Asn Leu Asp Lys Val Leu Ser Ala
    1535                1540                1545

Tyr Asn Lys His Arg Asp Lys Pro Ile Arg Glu Gln Ala Glu Asn
    1550                1555                1560

Ile Ile His Leu Phe Thr Leu Thr Asn Leu Gly Ala Pro Ala Ala
    1565                1570                1575

Phe Lys Tyr Phe Asp Thr Thr Ile Asp Arg Lys Arg Tyr Thr Ser
    1580                1585                1590

Thr Lys Glu Val Leu Asp Ala Thr Leu Ile His Gln Ser Ile Thr
    1595                1600                1605

Gly Leu Tyr Glu Thr Arg Ile Asp Leu Ser Gln Leu Gly Gly Asp
    1610                1615                1620

Ser Pro Lys Lys Lys Arg Lys Val Glu Ala Ser Gly Gly Gly Gly
    1625                1630                1635

Ser Gly Gly Gly Gly Ser Gly Gly Gly Ser Gly Pro Ala
    1640                1645                1650

<210> SEQ ID NO 61
<211> LENGTH: 1981
<212> TYPE: PRT
<213> ORGANISM: Artificial Sequence
<220> FEATURE:
<223> OTHER INFORMATION: Synthetic Polypeptide

<400> SEQUENCE: 61

Met Gly Pro Ala Asn His Asp Gln Glu Phe Asp Pro Pro Lys Val Tyr
1               5                   10                  15

Pro Pro Val Pro Ala Glu Lys Arg Lys Pro Ile Arg Val Leu Ser Leu
                20                  25                  30

Phe Asp Gly Ile Ala Thr Gly Leu Leu Val Leu Lys Asp Leu Gly Ile
            35                  40                  45

Gln Val Asp Arg Tyr Ile Ala Ser Glu Val Cys Glu Asp Ser Ile Thr
        50                  55                  60

Val Gly Met Val Arg His Gln Gly Lys Ile Met Tyr Val Gly Asp Val
65                  70                  75                  80

Arg Ser Val Thr Gln Lys His Ile Gln Glu Trp Gly Pro Phe Asp Leu
                85                  90                  95

Val Ile Gly Gly Ser Pro Cys Asn Asp Leu Ser Ile Val Asn Pro Ala
            100                 105                 110

Arg Lys Gly Leu Tyr Glu Gly Thr Gly Arg Leu Phe Phe Glu Phe Tyr
        115                 120                 125

Arg Leu Leu His Asp Ala Arg Pro Lys Glu Gly Asp Asp Arg Pro Phe
    130                 135                 140

Phe Trp Leu Phe Glu Asn Val Val Ala Met Gly Val Ser Asp Lys Arg
145                 150                 155                 160

Asp Ile Ser Arg Phe Leu Glu Ser Asn Pro Val Met Ile Asp Ala Lys
                165                 170                 175

Glu Val Ser Ala Ala His Arg Ala Arg Tyr Phe Trp Gly Asn Leu Pro
            180                 185                 190
```

-continued

```
Gly Met Asn Arg Pro Leu Ala Ser Thr Val Asn Asp Lys Leu Glu Leu
        195                 200                 205

Gln Glu Cys Leu Glu His Gly Arg Ile Ala Lys Phe Ser Lys Val Arg
    210                 215                 220

Thr Ile Thr Thr Arg Ser Asn Ser Ile Lys Gln Gly Lys Asp Gln His
225                 230                 235                 240

Phe Pro Val Phe Met Asn Glu Lys Glu Asp Ile Leu Trp Cys Thr Glu
                245                 250                 255

Met Glu Arg Val Phe Gly Phe Pro Val His Tyr Thr Asp Val Ser Asn
                260                 265                 270

Met Ser Arg Leu Ala Arg Gln Arg Leu Leu Gly Arg Ser Trp Ser Val
                275                 280                 285

Pro Val Ile Arg His Leu Phe Ala Pro Leu Lys Glu Tyr Phe Ala Cys
                290                 295                 300

Val Ser Ser Gly Asn Ser Asn Ala Asn Ser Arg Gly Pro Ser Phe Ser
305                 310                 315                 320

Ser Gly Leu Val Pro Leu Ser Leu Arg Gly Ser His Met Gly Pro Met
                325                 330                 335

Glu Ile Tyr Lys Thr Val Ser Ala Trp Lys Arg Gln Pro Val Arg Val
                340                 345                 350

Leu Ser Leu Phe Arg Asn Ile Asp Lys Val Leu Lys Ser Leu Gly Phe
                355                 360                 365

Leu Glu Ser Gly Ser Gly Ser Gly Gly Thr Leu Lys Tyr Val Glu
370                 375                 380

Asp Val Thr Asn Val Val Arg Arg Asp Val Glu Lys Trp Gly Pro Phe
385                 390                 395                 400

Asp Leu Val Tyr Gly Ser Thr Gln Pro Leu Gly Ser Ser Cys Asp Arg
                405                 410                 415

Cys Pro Gly Trp Tyr Met Phe Gln Phe His Arg Ile Leu Gln Tyr Ala
                420                 425                 430

Leu Pro Arg Gln Glu Ser Gln Arg Pro Phe Phe Trp Ile Phe Met Asp
                435                 440                 445

Asn Leu Leu Leu Thr Glu Asp Asp Gln Glu Thr Thr Thr Arg Phe Leu
                450                 455                 460

Gln Thr Glu Ala Val Thr Leu Gln Asp Val Arg Gly Arg Asp Tyr Gln
465                 470                 475                 480

Asn Ala Met Arg Val Trp Ser Asn Ile Pro Gly Leu Lys Ser Lys His
                485                 490                 495

Ala Pro Leu Thr Pro Lys Glu Glu Tyr Leu Gln Ala Gln Val Arg
                500                 505                 510

Ser Arg Ser Lys Leu Asp Ala Pro Lys Val Asp Leu Leu Val Lys Asn
                515                 520                 525

Cys Leu Leu Pro Leu Arg Glu Tyr Phe Lys Tyr Phe Ser Gln Asn Ser
530                 535                 540

Leu Pro Leu Ile Asp Gly Gly Gly Ser Gly Gly Gly Ser Gly
545                 550                 555                 560

Gly Gly Gly Ser Met Tyr Pro Tyr Asp Val Pro Asp Tyr Ala Ser Pro
                565                 570                 575

Lys Lys Lys Arg Lys Val Glu Ala Ser Asp Lys Lys Tyr Ser Ile Gly
                580                 585                 590

Leu Ala Ile Gly Thr Asn Ser Val Gly Trp Ala Val Ile Thr Asp Glu
                595                 600                 605
```

```
Tyr Lys Val Pro Ser Lys Lys Phe Lys Val Leu Gly Asn Thr Asp Arg
    610             615                 620

His Ser Ile Lys Lys Asn Leu Ile Gly Ala Leu Leu Phe Asp Ser Gly
625             630                 635                 640

Glu Thr Ala Glu Ala Thr Arg Leu Lys Arg Thr Ala Arg Arg Arg Tyr
            645                 650                 655

Thr Arg Arg Lys Asn Arg Ile Cys Tyr Leu Gln Glu Ile Phe Ser Asn
            660                 665                 670

Glu Met Ala Lys Val Asp Asp Ser Phe Phe His Arg Leu Glu Glu Ser
            675                 680                 685

Phe Leu Val Glu Glu Asp Lys Lys His Glu Arg His Pro Ile Phe Gly
690                 695                 700

Asn Ile Val Asp Glu Val Ala Tyr His Glu Lys Tyr Pro Thr Ile Tyr
705                 710                 715                 720

His Leu Arg Lys Lys Leu Val Asp Ser Thr Asp Lys Ala Asp Leu Arg
                725                 730                 735

Leu Ile Tyr Leu Ala Leu Ala His Met Ile Lys Phe Arg Gly His Phe
            740                 745                 750

Leu Ile Glu Gly Asp Leu Asn Pro Asp Asn Ser Asp Val Asp Lys Leu
            755                 760                 765

Phe Ile Gln Leu Val Gln Thr Tyr Asn Gln Leu Phe Glu Glu Asn Pro
770                 775                 780

Ile Asn Ala Ser Gly Val Asp Ala Lys Ala Ile Leu Ser Ala Arg Leu
785                 790                 795                 800

Ser Lys Ser Arg Arg Leu Glu Asn Leu Ile Ala Gln Leu Pro Gly Glu
                805                 810                 815

Lys Lys Asn Gly Leu Phe Gly Asn Leu Ile Ala Leu Ser Leu Gly Leu
            820                 825                 830

Thr Pro Asn Phe Lys Ser Asn Phe Asp Leu Ala Glu Asp Ala Lys Leu
            835                 840                 845

Gln Leu Ser Lys Asp Thr Tyr Asp Asp Asp Leu Asp Asn Leu Leu Ala
850                 855                 860

Gln Ile Gly Asp Gln Tyr Ala Asp Leu Phe Leu Ala Ala Lys Asn Leu
865                 870                 875                 880

Ser Asp Ala Ile Leu Leu Ser Asp Ile Leu Arg Val Asn Thr Glu Ile
            885                 890                 895

Thr Lys Ala Pro Leu Ser Ala Ser Met Ile Lys Arg Tyr Asp Glu His
            900                 905                 910

His Gln Asp Leu Thr Leu Leu Lys Ala Leu Val Arg Gln Gln Leu Pro
    915                 920                 925

Glu Lys Tyr Lys Glu Ile Phe Phe Asp Gln Ser Lys Asn Gly Tyr Ala
    930                 935                 940

Gly Tyr Ile Asp Gly Gly Ala Ser Gln Glu Glu Phe Tyr Lys Phe Ile
945                 950                 955                 960

Lys Pro Ile Leu Glu Lys Met Asp Gly Thr Glu Glu Leu Leu Val Lys
                965                 970                 975

Leu Asn Arg Glu Asp Leu Leu Arg Lys Gln Arg Thr Phe Asp Asn Gly
            980                 985                 990

Ser Ile Pro His Gln Ile His Leu Gly Glu Leu His Ala Ile Leu Arg
            995                 1000                1005

Arg Gln Glu Asp Phe Tyr Pro Phe Leu Lys Asp Asn Arg Glu Lys
    1010                1015                1020

Ile Glu Lys Ile Leu Thr Phe Arg Ile Pro Tyr Tyr Val Gly Pro
```

-continued

```
            1025                1030                1035
Leu Ala Arg Gly Asn Ser Arg Phe Ala Trp Met Thr Arg Lys Ser
        1040                1045                1050
Glu Glu Thr Ile Thr Pro Trp Asn Phe Glu Glu Val Val Asp Lys
        1055                1060                1065
Gly Ala Ser Ala Gln Ser Phe Ile Glu Arg Met Thr Asn Phe Asp
        1070                1075                1080
Lys Asn Leu Pro Asn Glu Lys Val Leu Pro Lys His Ser Leu Leu
        1085                1090                1095
Tyr Glu Tyr Phe Thr Val Tyr Asn Glu Leu Thr Lys Val Lys Tyr
        1100                1105                1110
Val Thr Glu Gly Met Arg Lys Pro Ala Phe Leu Ser Gly Glu Gln
        1115                1120                1125
Lys Lys Ala Ile Val Asp Leu Leu Phe Lys Thr Asn Arg Lys Val
        1130                1135                1140
Thr Val Lys Gln Leu Lys Glu Asp Tyr Phe Lys Lys Ile Glu Cys
        1145                1150                1155
Phe Asp Ser Val Glu Ile Ser Gly Val Glu Asp Arg Phe Asn Ala
        1160                1165                1170
Ser Leu Gly Thr Tyr His Asp Leu Leu Lys Ile Ile Lys Asp Lys
        1175                1180                1185
Asp Phe Leu Asp Asn Glu Glu Asn Glu Asp Ile Leu Glu Asp Ile
        1190                1195                1200
Val Leu Thr Leu Thr Leu Phe Glu Asp Arg Glu Met Ile Glu Glu
        1205                1210                1215
Arg Leu Lys Thr Tyr Ala His Leu Phe Asp Asp Lys Val Met Lys
        1220                1225                1230
Gln Leu Lys Arg Arg Arg Tyr Thr Gly Trp Gly Arg Leu Ser Arg
        1235                1240                1245
Lys Leu Ile Asn Gly Ile Arg Asp Lys Gln Ser Gly Lys Thr Ile
        1250                1255                1260
Leu Asp Phe Leu Lys Ser Asp Gly Phe Ala Asn Arg Asn Phe Met
        1265                1270                1275
Gln Leu Ile His Asp Asp Ser Leu Thr Phe Lys Glu Asp Ile Gln
        1280                1285                1290
Lys Ala Gln Val Ser Gly Gln Gly Asp Ser Leu His Glu His Ile
        1295                1300                1305
Ala Asn Leu Ala Gly Ser Pro Ala Ile Lys Lys Gly Ile Leu Gln
        1310                1315                1320
Thr Val Lys Val Val Asp Glu Leu Val Lys Val Met Gly Arg His
        1325                1330                1335
Lys Pro Glu Asn Ile Val Ile Glu Met Ala Arg Glu Asn Gln Thr
        1340                1345                1350
Thr Gln Lys Gly Gln Lys Asn Ser Arg Glu Arg Met Lys Arg Ile
        1355                1360                1365
Glu Glu Gly Ile Lys Glu Leu Gly Ser Gln Ile Leu Lys Glu His
        1370                1375                1380
Pro Val Glu Asn Thr Gln Leu Gln Asn Glu Lys Leu Tyr Leu Tyr
        1385                1390                1395
Tyr Leu Gln Asn Gly Arg Asp Met Tyr Val Asp Gln Glu Leu Asp
        1400                1405                1410
Ile Asn Arg Leu Ser Asp Tyr Asp Val Asp Ala Ile Val Pro Gln
        1415                1420                1425
```

-continued

Ser Phe Leu Lys Asp Asp Ser Ile Asp Asn Lys Val Leu Thr Arg
1430                1435                1440

Ser Asp Lys Asn Arg Gly Lys Ser Asp Asn Val Pro Ser Glu Glu
1445                1450                1455

Val Val Lys Lys Met Lys Asn Tyr Trp Arg Gln Leu Leu Asn Ala
1460                1465                1470

Lys Leu Ile Thr Gln Arg Lys Phe Asp Asn Leu Thr Lys Ala Glu
1475                1480                1485

Arg Gly Gly Leu Ser Glu Leu Asp Lys Ala Gly Phe Ile Lys Arg
1490                1495                1500

Gln Leu Val Glu Thr Arg Gln Ile Thr Lys His Val Ala Gln Ile
1505                1510                1515

Leu Asp Ser Arg Met Asn Thr Lys Tyr Asp Glu Asn Asp Lys Leu
1520                1525                1530

Ile Arg Glu Val Lys Val Ile Thr Leu Lys Ser Lys Leu Val Ser
1535                1540                1545

Asp Phe Arg Lys Asp Phe Gln Phe Tyr Lys Val Arg Glu Ile Asn
1550                1555                1560

Asn Tyr His His Ala His Asp Ala Tyr Leu Asn Ala Val Val Gly
1565                1570                1575

Thr Ala Leu Ile Lys Lys Tyr Pro Lys Leu Glu Ser Glu Phe Val
1580                1585                1590

Tyr Gly Asp Tyr Lys Val Tyr Asp Val Arg Lys Met Ile Ala Lys
1595                1600                1605

Ser Glu Gln Glu Ile Gly Lys Ala Thr Ala Lys Tyr Phe Phe Tyr
1610                1615                1620

Ser Asn Ile Met Asn Phe Phe Lys Thr Glu Ile Thr Leu Ala Asn
1625                1630                1635

Gly Glu Ile Arg Lys Arg Pro Leu Ile Glu Thr Asn Gly Glu Thr
1640                1645                1650

Gly Glu Ile Val Trp Asp Lys Gly Arg Asp Phe Ala Thr Val Arg
1655                1660                1665

Lys Val Leu Ser Met Pro Gln Val Asn Ile Val Lys Lys Thr Glu
1670                1675                1680

Val Gln Thr Gly Gly Phe Ser Lys Glu Ser Ile Leu Pro Lys Arg
1685                1690                1695

Asn Ser Asp Lys Leu Ile Ala Arg Lys Lys Asp Trp Asp Pro Lys
1700                1705                1710

Lys Tyr Gly Gly Phe Asp Ser Pro Thr Val Ala Tyr Ser Val Leu
1715                1720                1725

Val Val Ala Lys Val Glu Lys Gly Lys Ser Lys Lys Leu Lys Ser
1730                1735                1740

Val Lys Glu Leu Leu Gly Ile Thr Ile Met Glu Arg Ser Ser Phe
1745                1750                1755

Glu Lys Asn Pro Ile Asp Phe Leu Glu Ala Lys Gly Tyr Lys Glu
1760                1765                1770

Val Lys Lys Asp Leu Ile Ile Lys Leu Pro Lys Tyr Ser Leu Phe
1775                1780                1785

Glu Leu Glu Asn Gly Arg Lys Arg Met Leu Ala Ser Ala Gly Glu
1790                1795                1800

Leu Gln Lys Gly Asn Glu Leu Ala Leu Pro Ser Lys Tyr Val Asn
1805                1810                1815

```
Phe Leu Tyr Leu Ala Ser His Tyr Glu Lys Leu Lys Gly Ser Pro
    1820                1825                1830

Glu Asp Asn Glu Gln Lys Gln Leu Phe Val Glu Gln His Lys His
    1835                1840                1845

Tyr Leu Asp Glu Ile Ile Glu Gln Ile Ser Glu Phe Ser Lys Arg
    1850                1855                1860

Val Ile Leu Ala Asp Ala Asn Leu Asp Lys Val Leu Ser Ala Tyr
    1865                1870                1875

Asn Lys His Arg Asp Lys Pro Ile Arg Glu Gln Ala Glu Asn Ile
    1880                1885                1890

Ile His Leu Phe Thr Leu Thr Asn Leu Gly Ala Pro Ala Ala Phe
    1895                1900                1905

Lys Tyr Phe Asp Thr Thr Ile Asp Arg Lys Arg Tyr Thr Ser Thr
    1910                1915                1920

Lys Glu Val Leu Asp Ala Thr Leu Ile His Gln Ser Ile Thr Gly
    1925                1930                1935

Leu Tyr Glu Thr Arg Ile Asp Leu Ser Gln Leu Gly Gly Asp Ser
    1940                1945                1950

Pro Lys Lys Lys Arg Lys Val Glu Ala Ser Gly Gly Gly Gly Ser
    1955                1960                1965

Gly Gly Gly Gly Ser Gly Gly Gly Gly Ser Gly Pro Ala
    1970                1975                1980

<210> SEQ ID NO 62
<211> LENGTH: 1738
<212> TYPE: PRT
<213> ORGANISM: Artificial Sequence
<220> FEATURE:
<223> OTHER INFORMATION: Synthetic Polypeptide

<400> SEQUENCE: 62

Met Ile Asp Gly Gly Gly Ser Gly Gly Gly Gly Ser Gly Gly Gly
1               5                   10                  15

Gly Ser Met Tyr Pro Tyr Asp Val Pro Asp Tyr Ala Ser Pro Lys Lys
            20                  25                  30

Lys Arg Lys Val Glu Ala Ser Asp Lys Lys Tyr Ser Ile Gly Leu Ala
        35                  40                  45

Ile Gly Thr Asn Ser Val Gly Trp Ala Val Ile Thr Asp Glu Tyr Lys
    50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
    130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190
```

```
Tyr Leu Ala Leu Ala His Met Ile Lys Phe Arg Gly His Phe Leu Ile
            195                 200                 205

Glu Gly Asp Leu Asn Pro Asp Asn Ser Asp Val Asp Lys Leu Phe Ile
210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
        275                 280                 285

Asn Phe Lys Ser Asn Phe Asp Leu Ala Glu Asp Ala Lys Leu Gln Leu
    290                 295                 300

Ser Lys Asp Thr Tyr Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
        355                 360                 365

Asp Leu Thr Leu Leu Lys Ala Leu Val Arg Gln Gln Leu Pro Glu Lys
    370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
            420                 425                 430

Arg Glu Asp Leu Leu Arg Lys Gln Arg Thr Phe Asp Asn Gly Ser Ile
        435                 440                 445

Pro His Gln Ile His Leu Gly Glu Leu His Ala Ile Leu Arg Arg Gln
    450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
            500                 505                 510

Pro Trp Asn Phe Glu Glu Val Val Asp Lys Gly Ala Ser Ala Gln Ser
        515                 520                 525

Phe Ile Glu Arg Met Thr Asn Phe Asp Lys Asn Leu Pro Asn Glu Lys
    530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
            580                 585                 590

Thr Asn Arg Lys Val Thr Val Lys Gln Leu Lys Glu Asp Tyr Phe Lys
        595                 600                 605

Lys Ile Glu Cys Phe Asp Ser Val Glu Ile Ser Gly Val Glu Asp Arg
```

```
                610                 615                 620
Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
                660                 665                 670

Arg Leu Lys Thr Tyr Ala His Leu Phe Asp Asp Lys Val Met Lys Gln
                675                 680                 685

Leu Lys Arg Arg Arg Tyr Thr Gly Trp Gly Arg Leu Ser Arg Lys Leu
            690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
                740                 745                 750

Gly Gln Gly Asp Ser Leu His Glu His Ile Ala Asn Leu Ala Gly Ser
            755                 760                 765

Pro Ala Ile Lys Lys Gly Ile Leu Gln Thr Val Lys Val Val Asp Glu
770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
                820                 825                 830

Ile Leu Lys Glu His Pro Val Glu Asn Thr Gln Leu Gln Asn Glu Lys
            835                 840                 845

Leu Tyr Leu Tyr Tyr Leu Gln Asn Gly Arg Asp Met Tyr Val Asp Gln
850                 855                 860

Glu Leu Asp Ile Asn Arg Leu Ser Asp Tyr Asp Val Asp Ala Ile Val
865                 870                 875                 880

Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
                900                 905                 910

Val Val Lys Lys Met Lys Asn Tyr Trp Arg Gln Leu Leu Asn Ala Lys
            915                 920                 925

Leu Ile Thr Gln Arg Lys Phe Asp Asn Leu Thr Lys Ala Glu Arg Gly
930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
                980                 985                 990

Val Ile Thr Leu Lys Ser Lys Leu Val Ser Asp Phe Arg Lys Asp Phe
            995                 1000                1005

Gln Phe Tyr Lys Val Arg Glu Ile Asn Asn Tyr His His Ala His
   1010                1015                1020

Asp Ala Tyr Leu Asn Ala Val Val Gly Thr Ala Leu Ile Lys Lys
   1025                1030                1035
```

```
Tyr Pro Lys Leu Glu Ser Glu Phe Val Tyr Gly Asp Tyr Lys Val
    1040            1045            1050

Tyr Asp Val Arg Lys Met Ile Ala Lys Ser Glu Gln Glu Ile Gly
    1055            1060            1065

Lys Ala Thr Ala Lys Tyr Phe Phe Tyr Ser Asn Ile Met Asn Phe
    1070            1075            1080

Phe Lys Thr Glu Ile Thr Leu Ala Asn Gly Glu Ile Arg Lys Arg
    1085            1090            1095

Pro Leu Ile Glu Thr Asn Gly Glu Thr Gly Glu Ile Val Trp Asp
    1100            1105            1110

Lys Gly Arg Asp Phe Ala Thr Val Arg Lys Val Leu Ser Met Pro
    1115            1120            1125

Gln Val Asn Ile Val Lys Lys Thr Glu Val Gln Thr Gly Gly Phe
    1130            1135            1140

Ser Lys Glu Ser Ile Leu Pro Lys Arg Asn Ser Asp Lys Leu Ile
    1145            1150            1155

Ala Arg Lys Lys Asp Trp Asp Pro Lys Lys Tyr Gly Gly Phe Asp
    1160            1165            1170

Ser Pro Thr Val Ala Tyr Ser Val Leu Val Val Ala Lys Val Glu
    1175            1180            1185

Lys Gly Lys Ser Lys Lys Leu Lys Ser Val Lys Glu Leu Leu Gly
    1190            1195            1200

Ile Thr Ile Met Glu Arg Ser Ser Phe Glu Lys Asn Pro Ile Asp
    1205            1210            1215

Phe Leu Glu Ala Lys Gly Tyr Lys Glu Val Lys Lys Asp Leu Ile
    1220            1225            1230

Ile Lys Leu Pro Lys Tyr Ser Leu Phe Glu Leu Glu Asn Gly Arg
    1235            1240            1245

Lys Arg Met Leu Ala Ser Ala Gly Glu Leu Gln Lys Gly Asn Glu
    1250            1255            1260

Leu Ala Leu Pro Ser Lys Tyr Val Asn Phe Leu Tyr Leu Ala Ser
    1265            1270            1275

His Tyr Glu Lys Leu Lys Gly Ser Pro Glu Asp Asn Glu Gln Lys
    1280            1285            1290

Gln Leu Phe Val Glu Gln His Lys His Tyr Leu Asp Glu Ile Ile
    1295            1300            1305

Glu Gln Ile Ser Glu Phe Ser Lys Arg Val Ile Leu Ala Asp Ala
    1310            1315            1320

Asn Leu Asp Lys Val Leu Ser Ala Tyr Asn Lys His Arg Asp Lys
    1325            1330            1335

Pro Ile Arg Glu Gln Ala Glu Asn Ile Ile His Leu Phe Thr Leu
    1340            1345            1350

Thr Asn Leu Gly Ala Pro Ala Ala Phe Lys Tyr Phe Asp Thr Thr
    1355            1360            1365

Ile Asp Arg Lys Arg Tyr Thr Ser Thr Lys Glu Val Leu Asp Ala
    1370            1375            1380

Thr Leu Ile His Gln Ser Ile Thr Gly Leu Tyr Glu Thr Arg Ile
    1385            1390            1395

Asp Leu Ser Gln Leu Gly Gly Asp Ser Pro Lys Lys Lys Arg Lys
    1400            1405            1410

Val Glu Ala Ser Gly Gly Gly Ser Gly Gly Gly Gly Ser Gly
    1415            1420            1425
```

Gly Gly Gly Ser Gly Pro Ala Asn His Asp Gln Glu Phe Asp Pro
    1430                1435                1440

Pro Lys Val Tyr Pro Pro Val Pro Ala Glu Lys Arg Lys Pro Ile
1445                1450                1455

Arg Val Leu Ser Leu Phe Asp Gly Ile Ala Thr Gly Leu Leu Val
1460                1465                1470

Leu Lys Asp Leu Gly Ile Gln Val Asp Arg Tyr Ile Ala Ser Glu
1475                1480                1485

Val Cys Glu Asp Ser Ile Thr Val Gly Met Val Arg His Gln Gly
1490                1495                1500

Lys Ile Met Tyr Val Gly Asp Val Arg Ser Val Thr Gln Lys His
1505                1510                1515

Ile Gln Glu Trp Gly Pro Phe Asp Leu Val Ile Gly Gly Ser Pro
1520                1525                1530

Cys Asn Asp Leu Ser Ile Val Asn Pro Ala Arg Lys Gly Leu Tyr
1535                1540                1545

Glu Gly Thr Gly Arg Leu Phe Phe Glu Phe Tyr Arg Leu Leu His
1550                1555                1560

Asp Ala Arg Pro Lys Glu Gly Asp Asp Arg Pro Phe Phe Trp Leu
1565                1570                1575

Phe Glu Asn Val Val Ala Met Gly Val Ser Asp Lys Arg Asp Ile
1580                1585                1590

Ser Arg Phe Leu Glu Ser Asn Pro Val Met Ile Asp Ala Lys Glu
1595                1600                1605

Val Ser Ala Ala His Arg Ala Arg Tyr Phe Trp Gly Asn Leu Pro
1610                1615                1620

Gly Met Asn Arg Pro Leu Ala Ser Thr Val Asn Asp Lys Leu Glu
1625                1630                1635

Leu Gln Glu Cys Leu Glu His Gly Arg Ile Ala Lys Phe Ser Lys
1640                1645                1650

Val Arg Thr Ile Thr Thr Arg Ser Asn Ser Ile Lys Gln Gly Lys
1655                1660                1665

Asp Gln His Phe Pro Val Phe Met Asn Glu Lys Glu Asp Ile Leu
1670                1675                1680

Trp Cys Thr Glu Met Glu Arg Val Phe Gly Phe Pro Val His Tyr
1685                1690                1695

Thr Asp Val Ser Asn Met Ser Arg Leu Ala Arg Gln Arg Leu Leu
1700                1705                1710

Gly Arg Ser Trp Ser Val Pro Val Ile Arg His Leu Phe Ala Pro
1715                1720                1725

Leu Lys Glu Tyr Phe Ala Cys Val Ile Asp
1730                1735

<210> SEQ ID NO 63
<211> LENGTH: 1651
<212> TYPE: PRT
<213> ORGANISM: Artificial Sequence
<220> FEATURE:
<223> OTHER INFORMATION: Synthetic Polypeptide

<400> SEQUENCE: 63

Met Ile Asp Gly Gly Gly Gly Ser Gly Gly Gly Ser Gly Gly Gly
1               5                   10                  15

Gly Ser Met Tyr Pro Tyr Asp Val Pro Asp Tyr Ala Ser Pro Lys Lys
            20                  25                  30

```
Lys Arg Lys Val Glu Ala Ser Asp Lys Lys Tyr Ser Ile Gly Leu Ala
             35                  40                  45

Ile Gly Thr Asn Ser Val Gly Trp Ala Val Ile Thr Asp Glu Tyr Lys
 50                  55                  60

Val Pro Ser Lys Lys Phe Lys Val Leu Gly Asn Thr Asp Arg His Ser
 65                  70                  75                  80

Ile Lys Lys Asn Leu Ile Gly Ala Leu Leu Phe Asp Ser Gly Glu Thr
                 85                  90                  95

Ala Glu Ala Thr Arg Leu Lys Arg Thr Ala Arg Arg Tyr Thr Arg
            100                 105                 110

Arg Lys Asn Arg Ile Cys Tyr Leu Gln Glu Ile Phe Ser Asn Glu Met
            115                 120                 125

Ala Lys Val Asp Asp Ser Phe Phe His Arg Leu Glu Glu Ser Phe Leu
130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
            195                 200                 205

Glu Gly Asp Leu Asn Pro Asp Asn Ser Asp Val Asp Lys Leu Phe Ile
            210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
            275                 280                 285

Asn Phe Lys Ser Asn Phe Asp Leu Ala Glu Asp Ala Lys Leu Gln Leu
290                 295                 300

Ser Lys Asp Thr Tyr Asp Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
            355                 360                 365

Asp Leu Thr Leu Leu Lys Ala Leu Val Arg Gln Gln Leu Pro Glu Lys
            370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
            420                 425                 430

Arg Glu Asp Leu Leu Arg Lys Gln Arg Thr Phe Asp Asn Gly Ser Ile
            435                 440                 445

Pro His Gln Ile His Leu Gly Glu Leu His Ala Ile Leu Arg Arg Gln
```

```
            450             455             460
Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
            500                 505                 510

Pro Trp Asn Phe Glu Glu Val Val Asp Lys Gly Ala Ser Ala Gln Ser
        515                 520                 525

Phe Ile Glu Arg Met Thr Asn Phe Asp Lys Asn Leu Pro Asn Glu Lys
    530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
            580                 585                 590

Thr Asn Arg Lys Val Thr Val Lys Gln Leu Lys Glu Asp Tyr Phe Lys
        595                 600                 605

Lys Ile Glu Cys Phe Asp Ser Val Glu Ile Ser Gly Val Glu Asp Arg
    610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
            660                 665                 670

Arg Leu Lys Thr Tyr Ala His Leu Phe Asp Asp Lys Val Met Lys Gln
        675                 680                 685

Leu Lys Arg Arg Arg Tyr Thr Gly Trp Gly Arg Leu Ser Arg Lys Leu
    690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
        755                 760                 765

Pro Ala Ile Lys Lys Gly Ile Leu Gln Thr Val Lys Val Val Asp Glu
    770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
            820                 825                 830

Ile Leu Lys Glu His Pro Val Glu Asn Thr Gln Leu Gln Asn Glu Lys
        835                 840                 845

Leu Tyr Leu Tyr Tyr Leu Gln Asn Gly Arg Asp Met Tyr Val Asp Gln
    850                 855                 860

Glu Leu Asp Ile Asn Arg Leu Ser Asp Tyr Asp Val Asp Ala Ile Val
865                 870                 875                 880
```

```
Pro Gln Ser Phe Leu Lys Asp Asp Ser Ile Asp Asn Lys Val Leu Thr
            885                 890                 895

Arg Ser Asp Lys Asn Arg Gly Lys Ser Asp Asn Val Pro Ser Glu Glu
            900                 905                 910

Val Val Lys Lys Met Lys Asn Tyr Trp Arg Gln Leu Leu Asn Ala Lys
            915                 920                 925

Leu Ile Thr Gln Arg Lys Phe Asp Asn Leu Thr Lys Ala Glu Arg Gly
        930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
            965                 970                 975

Met Asn Thr Lys Tyr Asp Glu Asn Asp Lys Leu Ile Arg Glu Val Lys
            980                 985                 990

Val Ile Thr Leu Lys Ser Lys Leu Val Ser Asp Phe Arg Lys Asp Phe
            995                 1000                1005

Gln Phe Tyr Lys Val Arg Glu Ile Asn Asn Tyr His His Ala His
        1010                1015                1020

Asp Ala Tyr Leu Asn Ala Val Val Gly Thr Ala Leu Ile Lys Lys
        1025                1030                1035

Tyr Pro Lys Leu Glu Ser Glu Phe Val Tyr Gly Asp Tyr Lys Val
        1040                1045                1050

Tyr Asp Val Arg Lys Met Ile Ala Lys Ser Glu Gln Glu Ile Gly
        1055                1060                1065

Lys Ala Thr Ala Lys Tyr Phe Phe Tyr Ser Asn Ile Met Asn Phe
        1070                1075                1080

Phe Lys Thr Glu Ile Thr Leu Ala Asn Gly Glu Ile Arg Lys Arg
        1085                1090                1095

Pro Leu Ile Glu Thr Asn Gly Glu Thr Gly Glu Ile Val Trp Asp
        1100                1105                1110

Lys Gly Arg Asp Phe Ala Thr Val Arg Lys Val Leu Ser Met Pro
        1115                1120                1125

Gln Val Asn Ile Val Lys Lys Thr Glu Val Gln Thr Gly Gly Phe
        1130                1135                1140

Ser Lys Glu Ser Ile Leu Pro Lys Arg Asn Ser Asp Lys Leu Ile
        1145                1150                1155

Ala Arg Lys Lys Asp Trp Asp Pro Lys Lys Tyr Gly Gly Phe Asp
        1160                1165                1170

Ser Pro Thr Val Ala Tyr Ser Val Leu Val Val Ala Lys Val Glu
        1175                1180                1185

Lys Gly Lys Ser Lys Lys Leu Lys Ser Val Lys Glu Leu Leu Gly
        1190                1195                1200

Ile Thr Ile Met Glu Arg Ser Ser Phe Glu Lys Asn Pro Ile Asp
        1205                1210                1215

Phe Leu Glu Ala Lys Gly Tyr Lys Glu Val Lys Lys Asp Leu Ile
        1220                1225                1230

Ile Lys Leu Pro Lys Tyr Ser Leu Phe Glu Leu Glu Asn Gly Arg
        1235                1240                1245

Lys Arg Met Leu Ala Ser Ala Gly Glu Leu Gln Lys Gly Asn Glu
        1250                1255                1260

Leu Ala Leu Pro Ser Lys Tyr Val Asn Phe Leu Tyr Leu Ala Ser
        1265                1270                1275
```

His Tyr Glu Lys Leu Lys Gly Ser Pro Glu Asp Asn Glu Gln Lys
    1280                1285                1290

Gln Leu Phe Val Glu Gln His Lys His Tyr Leu Asp Glu Ile Ile
    1295                1300                1305

Glu Gln Ile Ser Glu Phe Ser Lys Arg Val Ile Leu Ala Asp Ala
    1310                1315                1320

Asn Leu Asp Lys Val Leu Ser Ala Tyr Asn Lys His Arg Asp Lys
    1325                1330                1335

Pro Ile Arg Glu Gln Ala Glu Asn Ile Ile His Leu Phe Thr Leu
    1340                1345                1350

Thr Asn Leu Gly Ala Pro Ala Ala Phe Lys Tyr Phe Asp Thr Thr
    1355                1360                1365

Ile Asp Arg Lys Arg Tyr Thr Ser Thr Lys Glu Val Leu Asp Ala
    1370                1375                1380

Thr Leu Ile His Gln Ser Ile Thr Gly Leu Tyr Glu Thr Arg Ile
    1385                1390                1395

Asp Leu Ser Gln Leu Gly Gly Asp Ser Pro Lys Lys Lys Arg Lys
    1400                1405                1410

Val Glu Ala Ser Gly Gly Gly Gly Ser Gly Gly Gly Ser Gly
    1415                1420                1425

Gly Gly Gly Ser Gly Pro Ala Gly Pro Met Glu Ile Tyr Lys Thr
    1430                1435                1440

Val Ser Ala Trp Lys Arg Gln Pro Val Arg Val Leu Ser Leu Phe
    1445                1450                1455

Arg Asn Ile Asp Lys Val Leu Lys Ser Leu Gly Phe Leu Glu Ser
    1460                1465                1470

Gly Ser Gly Ser Gly Gly Gly Thr Leu Lys Tyr Val Glu Asp Val
    1475                1480                1485

Thr Asn Val Val Arg Arg Asp Val Glu Lys Trp Gly Pro Phe Asp
    1490                1495                1500

Leu Val Tyr Gly Ser Thr Gln Pro Leu Gly Ser Ser Cys Asp Arg
    1505                1510                1515

Cys Pro Gly Trp Tyr Met Phe Gln Phe His Arg Ile Leu Gln Tyr
    1520                1525                1530

Ala Leu Pro Arg Gln Glu Ser Gln Arg Pro Phe Phe Trp Ile Phe
    1535                1540                1545

Met Asp Asn Leu Leu Leu Thr Glu Asp Asp Gln Glu Thr Thr Thr
    1550                1555                1560

Arg Phe Leu Gln Thr Glu Ala Val Thr Leu Gln Asp Val Arg Gly
    1565                1570                1575

Arg Asp Tyr Gln Asn Ala Met Arg Val Trp Ser Asn Ile Pro Gly
    1580                1585                1590

Leu Lys Ser Lys His Ala Pro Leu Thr Pro Lys Glu Glu Glu Tyr
    1595                1600                1605

Leu Gln Ala Gln Val Arg Ser Arg Ser Lys Leu Asp Ala Pro Lys
    1610                1615                1620

Val Asp Leu Leu Val Lys Asn Cys Leu Leu Pro Leu Arg Glu Tyr
    1625                1630                1635

Phe Lys Tyr Phe Ser Gln Asn Ser Leu Pro Leu Ile Asp
    1640                1645                1650

<210> SEQ ID NO 64
<211> LENGTH: 1980
<212> TYPE: PRT

<213> ORGANISM: Artificial Sequence
<220> FEATURE:
<223> OTHER INFORMATION: Synthetic Polypeptide

<400> SEQUENCE: 64

```
Met Ile Asp Gly Gly Gly Ser Gly Gly Gly Gly Ser Gly Gly
1               5                   10                  15

Gly Ser Met Tyr Pro Tyr Asp Val Pro Asp Tyr Ala Ser Pro Lys Lys
            20                  25                  30

Lys Arg Lys Val Glu Ala Ser Asp Lys Lys Tyr Ser Ile Gly Leu Ala
        35                  40                  45

Ile Gly Thr Asn Ser Val Gly Trp Ala Val Ile Thr Asp Glu Tyr Lys
50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
        195                 200                 205

Glu Gly Asp Leu Asn Pro Asp Asn Ser Asp Val Asp Lys Leu Phe Ile
210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
        275                 280                 285

Asn Phe Lys Ser Asn Phe Asp Leu Ala Glu Asp Ala Lys Leu Gln Leu
290                 295                 300

Ser Lys Asp Thr Tyr Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
        355                 360                 365

Asp Leu Thr Leu Leu Lys Ala Leu Val Arg Gln Gln Leu Pro Glu Lys
370                 375                 380

Tyr Lys Glu Ile Phe Phe Asp Gln Ser Lys Asn Gly Tyr Ala Gly Tyr
```

```
385                 390                 395                 400
Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
                420                 425                 430

Arg Glu Asp Leu Leu Arg Lys Gln Arg Thr Phe Asp Asn Gly Ser Ile
                435                 440                 445

Pro His Gln Ile His Leu Gly Glu Leu His Ala Ile Leu Arg Arg Gln
                450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
                500                 505                 510

Pro Trp Asn Phe Glu Glu Val Val Asp Lys Gly Ala Ser Ala Gln Ser
                515                 520                 525

Phe Ile Glu Arg Met Thr Asn Phe Asp Lys Asn Leu Pro Asn Glu Lys
                530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
                580                 585                 590

Thr Asn Arg Lys Val Thr Val Lys Gln Leu Lys Glu Asp Tyr Phe Lys
                595                 600                 605

Lys Ile Glu Cys Phe Asp Ser Val Glu Ile Ser Gly Val Glu Asp Arg
                610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
                660                 665                 670

Arg Leu Lys Thr Tyr Ala His Leu Phe Asp Asp Lys Val Met Lys Gln
                675                 680                 685

Leu Lys Arg Arg Arg Tyr Thr Gly Trp Gly Arg Leu Ser Arg Lys Leu
                690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
                740                 745                 750

Gly Gln Gly Asp Ser Leu His Glu His Ile Ala Asn Leu Ala Gly Ser
                755                 760                 765

Pro Ala Ile Lys Lys Gly Ile Leu Gln Thr Val Lys Val Val Asp Glu
                770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815
```

-continued

Glu Arg Met Lys Arg Ile Glu Glu Gly Ile Lys Glu Leu Gly Ser Gln
              820                 825                 830

Ile Leu Lys Glu His Pro Val Glu Asn Thr Gln Leu Gln Asn Glu Lys
              835                 840                 845

Leu Tyr Leu Tyr Tyr Leu Gln Asn Gly Arg Asp Met Tyr Val Asp Gln
              850                 855                 860

Glu Leu Asp Ile Asn Arg Leu Ser Asp Tyr Asp Val Asp Ala Ile Val
865                 870                 875                 880

Pro Gln Ser Phe Leu Lys Asp Asp Ser Ile Asp Asn Lys Val Leu Thr
                    885                 890                 895

Arg Ser Asp Lys Asn Arg Gly Lys Ser Asp Asn Val Pro Ser Glu Glu
              900                 905                 910

Val Val Lys Lys Met Lys Asn Tyr Trp Arg Gln Leu Leu Asn Ala Lys
              915                 920                 925

Leu Ile Thr Gln Arg Lys Phe Asp Asn Leu Thr Lys Ala Glu Arg Gly
              930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
              965                 970                 975

Met Asn Thr Lys Tyr Asp Glu Asn Asp Lys Leu Ile Arg Glu Val Lys
              980                 985                 990

Val Ile Thr Leu Lys Ser Lys Leu Val Ser Asp Phe Arg Lys Asp Phe
              995                 1000                1005

Gln Phe Tyr Lys Val Arg Glu Ile Asn Asn Tyr His His Ala His
              1010                1015                1020

Asp Ala Tyr Leu Asn Ala Val Val Gly Thr Ala Leu Ile Lys Lys
              1025                1030                1035

Tyr Pro Lys Leu Glu Ser Glu Phe Val Tyr Gly Asp Tyr Lys Val
              1040                1045                1050

Tyr Asp Val Arg Lys Met Ile Ala Lys Ser Glu Gln Glu Ile Gly
              1055                1060                1065

Lys Ala Thr Ala Lys Tyr Phe Phe Tyr Ser Asn Ile Met Asn Phe
              1070                1075                1080

Phe Lys Thr Glu Ile Thr Leu Ala Asn Gly Glu Ile Arg Lys Arg
              1085                1090                1095

Pro Leu Ile Glu Thr Asn Gly Glu Thr Gly Glu Ile Val Trp Asp
              1100                1105                1110

Lys Gly Arg Asp Phe Ala Thr Val Arg Lys Val Leu Ser Met Pro
              1115                1120                1125

Gln Val Asn Ile Val Lys Lys Thr Glu Val Gln Thr Gly Gly Phe
              1130                1135                1140

Ser Lys Glu Ser Ile Leu Pro Lys Arg Asn Ser Asp Lys Leu Ile
              1145                1150                1155

Ala Arg Lys Lys Asp Trp Asp Pro Lys Lys Tyr Gly Gly Phe Asp
              1160                1165                1170

Ser Pro Thr Val Ala Tyr Ser Val Leu Val Val Ala Lys Val Glu
              1175                1180                1185

Lys Gly Lys Ser Lys Lys Leu Lys Ser Val Lys Glu Leu Leu Gly
              1190                1195                1200

Ile Thr Ile Met Glu Arg Ser Ser Phe Glu Lys Asn Pro Ile Asp
              1205                1210                1215

Phe Leu Glu Ala Lys Gly Tyr Lys Glu Val Lys Lys Asp Leu Ile
1220            1225                1230

Ile Lys Leu Pro Lys Tyr Ser Leu Phe Glu Leu Glu Asn Gly Arg
1235            1240                1245

Lys Arg Met Leu Ala Ser Ala Gly Glu Leu Gln Lys Gly Asn Glu
1250            1255                1260

Leu Ala Leu Pro Ser Lys Tyr Val Asn Phe Leu Tyr Leu Ala Ser
1265            1270                1275

His Tyr Glu Lys Leu Lys Gly Ser Pro Glu Asp Asn Glu Gln Lys
1280            1285                1290

Gln Leu Phe Val Glu Gln His Lys His Tyr Leu Asp Glu Ile Ile
1295            1300                1305

Glu Gln Ile Ser Glu Phe Ser Lys Arg Val Ile Leu Ala Asp Ala
1310            1315                1320

Asn Leu Asp Lys Val Leu Ser Ala Tyr Asn Lys His Arg Asp Lys
1325            1330                1335

Pro Ile Arg Glu Gln Ala Glu Asn Ile Ile His Leu Phe Thr Leu
1340            1345                1350

Thr Asn Leu Gly Ala Pro Ala Ala Phe Lys Tyr Phe Asp Thr Thr
1355            1360                1365

Ile Asp Arg Lys Arg Tyr Thr Ser Thr Lys Glu Val Leu Asp Ala
1370            1375                1380

Thr Leu Ile His Gln Ser Ile Thr Gly Leu Tyr Glu Thr Arg Ile
1385            1390                1395

Asp Leu Ser Gln Leu Gly Gly Asp Ser Pro Lys Lys Lys Arg Lys
1400            1405                1410

Val Glu Ala Ser Gly Gly Gly Gly Ser Gly Gly Gly Gly Ser Gly
1415            1420                1425

Gly Gly Gly Ser Gly Pro Ala Asn His Asp Gln Glu Phe Asp Pro
1430            1435                1440

Pro Lys Val Tyr Pro Pro Val Pro Ala Glu Lys Arg Lys Pro Ile
1445            1450                1455

Arg Val Leu Ser Leu Phe Asp Gly Ile Ala Thr Gly Leu Leu Val
1460            1465                1470

Leu Lys Asp Leu Gly Ile Gln Val Asp Arg Tyr Ile Ala Ser Glu
1475            1480                1485

Val Cys Glu Asp Ser Ile Thr Val Gly Met Val Arg His Gln Gly
1490            1495                1500

Lys Ile Met Tyr Val Gly Asp Val Arg Ser Val Thr Gln Lys His
1505            1510                1515

Ile Gln Glu Trp Gly Pro Phe Asp Leu Val Ile Gly Gly Ser Pro
1520            1525                1530

Cys Asn Asp Leu Ser Ile Val Asn Pro Ala Arg Lys Gly Leu Tyr
1535            1540                1545

Glu Gly Thr Gly Arg Leu Phe Phe Glu Phe Tyr Arg Leu Leu His
1550            1555                1560

Asp Ala Arg Pro Lys Glu Gly Asp Asp Arg Pro Phe Phe Trp Leu
1565            1570                1575

Phe Glu Asn Val Val Ala Met Gly Val Ser Asp Lys Arg Asp Ile
1580            1585                1590

Ser Arg Phe Leu Glu Ser Asn Pro Val Met Ile Asp Ala Lys Glu
1595            1600                1605

Val Ser Ala Ala His Arg Ala Arg Tyr Phe Trp Gly Asn Leu Pro

```
             1610                1615                1620

Gly Met Asn Arg Pro Leu Ala Ser Thr Val Asn Asp Lys Leu Glu
        1625                1630                1635

Leu Gln Glu Cys Leu Glu His Gly Arg Ile Ala Lys Phe Ser Lys
        1640                1645                1650

Val Arg Thr Ile Thr Thr Arg Ser Asn Ser Ile Lys Gln Gly Lys
        1655                1660                1665

Asp Gln His Phe Pro Val Phe Met Asn Glu Lys Glu Asp Ile Leu
        1670                1675                1680

Trp Cys Thr Glu Met Glu Arg Val Phe Gly Phe Pro Val His Tyr
        1685                1690                1695

Thr Asp Val Ser Asn Met Ser Arg Leu Ala Arg Gln Arg Leu Leu
        1700                1705                1710

Gly Arg Ser Trp Ser Val Pro Val Ile Arg His Leu Phe Ala Pro
        1715                1720                1725

Leu Lys Glu Tyr Phe Ala Cys Val Ser Ser Gly Asn Ser Asn Ala
        1730                1735                1740

Asn Ser Arg Gly Pro Ser Phe Ser Ser Gly Leu Val Pro Leu Ser
        1745                1750                1755

Leu Arg Gly Ser His Met Gly Pro Met Glu Ile Tyr Lys Thr Val
        1760                1765                1770

Ser Ala Trp Lys Arg Gln Pro Val Arg Val Leu Ser Leu Phe Arg
        1775                1780                1785

Asn Ile Asp Lys Val Leu Lys Ser Leu Gly Phe Leu Glu Ser Gly
        1790                1795                1800

Ser Gly Ser Gly Gly Gly Thr Leu Lys Tyr Val Glu Asp Val Thr
        1805                1810                1815

Asn Val Val Arg Arg Asp Val Glu Lys Trp Gly Pro Phe Asp Leu
        1820                1825                1830

Val Tyr Gly Ser Thr Gln Pro Leu Gly Ser Ser Cys Asp Arg Cys
        1835                1840                1845

Pro Gly Trp Tyr Met Phe Gln Phe His Arg Ile Leu Gln Tyr Ala
        1850                1855                1860

Leu Pro Arg Gln Glu Ser Gln Arg Pro Phe Phe Trp Ile Phe Met
        1865                1870                1875

Asp Asn Leu Leu Leu Thr Glu Asp Asp Gln Glu Thr Thr Thr Arg
        1880                1885                1890

Phe Leu Gln Thr Glu Ala Val Thr Leu Gln Asp Val Arg Gly Arg
        1895                1900                1905

Asp Tyr Gln Asn Ala Met Arg Val Trp Ser Asn Ile Pro Gly Leu
        1910                1915                1920

Lys Ser Lys His Ala Pro Leu Thr Pro Lys Glu Glu Glu Tyr Leu
        1925                1930                1935

Gln Ala Gln Val Arg Ser Arg Ser Lys Leu Asp Ala Pro Lys Val
        1940                1945                1950

Asp Leu Leu Val Lys Asn Cys Leu Leu Pro Leu Arg Glu Tyr Phe
        1955                1960                1965

Lys Tyr Phe Ser Gln Asn Ser Leu Pro Leu Ile Asp
        1970                1975                1980

<210> SEQ ID NO 65
<211> LENGTH: 761
<212> TYPE: PRT
<213> ORGANISM: Artificial Sequence
```

<220> FEATURE:
<223> OTHER INFORMATION: Synthetic Polypeptide

<400> SEQUENCE: 65

| Met | Gly | Pro | Ala | Asn | His | Asp | Gln | Glu | Phe | Asp | Pro | Pro | Lys | Val | Tyr |
|---|---|---|---|---|---|---|---|---|---|---|---|---|---|---|---|
| 1 | | | | 5 | | | | | 10 | | | | | 15 | |

Pro Pro Val Pro Ala Glu Lys Arg Lys Pro Ile Arg Val Leu Ser Leu
                20                  25                  30

Phe Asp Gly Ile Ala Thr Gly Leu Leu Val Leu Lys Asp Leu Gly Ile
            35                  40                  45

Gln Val Asp Arg Tyr Ile Ala Ser Glu Val Cys Glu Asp Ser Ile Thr
        50                  55                  60

Val Gly Met Val Arg His Gln Gly Lys Ile Met Tyr Val Gly Asp Val
65                  70                  75                  80

Arg Ser Val Thr Gln Lys His Ile Gln Glu Trp Gly Pro Phe Asp Leu
                85                  90                  95

Val Ile Gly Gly Ser Pro Cys Asn Asp Leu Ser Ile Val Asn Pro Ala
            100                 105                 110

Arg Lys Gly Leu Tyr Glu Gly Thr Gly Arg Leu Phe Phe Glu Phe Tyr
        115                 120                 125

Arg Leu Leu His Asp Ala Arg Pro Lys Glu Gly Asp Asp Arg Pro Phe
130                 135                 140

Phe Trp Leu Phe Glu Asn Val Val Ala Met Gly Val Ser Asp Lys Arg
145                 150                 155                 160

Asp Ile Ser Arg Phe Leu Glu Ser Asn Pro Val Met Ile Asp Ala Lys
                165                 170                 175

Glu Val Ser Ala Ala His Arg Ala Arg Tyr Phe Trp Gly Asn Leu Pro
            180                 185                 190

Gly Met Asn Arg Pro Leu Ala Ser Thr Val Asn Asp Lys Leu Glu Leu
        195                 200                 205

Gln Glu Cys Leu Glu His Gly Arg Ile Ala Lys Phe Ser Lys Val Arg
210                 215                 220

Thr Ile Thr Thr Arg Ser Asn Ser Ile Lys Gln Gly Lys Asp Gln His
225                 230                 235                 240

Phe Pro Val Phe Met Asn Glu Lys Glu Asp Ile Leu Trp Cys Thr Glu
                245                 250                 255

Met Glu Arg Val Phe Gly Phe Pro Val His Tyr Thr Asp Val Ser Asn
            260                 265                 270

Met Ser Arg Leu Ala Arg Gln Arg Leu Leu Gly Arg Ser Trp Ser Val
        275                 280                 285

Pro Val Ile Arg His Leu Phe Ala Pro Leu Lys Glu Tyr Phe Ala Cys
290                 295                 300

Val Ile Asp Gly Gly Gly Ser Asp Pro Lys Lys Lys Arg Lys Val
305                 310                 315                 320

Asp Pro Lys Lys Lys Arg Lys Val Asp Pro Lys Lys Lys Arg Lys Val
                325                 330                 335

Gly Ser Thr Gly Ser Arg Asn Asp Gly Gly Gly Ser Gly Gly
            340                 345                 350

Gly Ser Gly Gly Gly Ser Gly Arg Ala Gly Ile Leu Pro Lys
        355                 360                 365

Lys Lys Arg Lys Val Ser Arg Gly Arg Ser Leu Leu Glu Asp Phe
370                 375                 380

Arg Asn Asn Arg Tyr Pro Asn Leu Gln Leu Arg Glu Ile Ala Gly His
385                 390                 395                 400

Ile Met Glu Phe Ser Gln Asp Gln His Gly Ser Arg Phe Ile Gln Leu
            405                 410                 415

Lys Leu Glu Arg Ala Thr Pro Ala Glu Arg Gln Leu Val Phe Asn Glu
        420                 425                 430

Ile Leu Gln Ala Ala Tyr Gln Leu Met Val Asp Val Phe Gly Asn Tyr
    435                 440                 445

Val Ile Gln Lys Phe Phe Glu Phe Gly Ser Leu Glu Gln Lys Leu Ala
450                 455                 460

Leu Ala Glu Arg Ile Arg Gly His Val Leu Ser Leu Ala Leu Gln Met
465                 470                 475                 480

Tyr Gly Ser Arg Val Ile Glu Lys Ala Leu Glu Phe Ile Pro Ser Asp
                485                 490                 495

Gln Gln Asn Glu Met Val Arg Glu Leu Asp Gly His Val Leu Lys Cys
            500                 505                 510

Val Lys Asp Gln Asn Gly Asn His Val Val Lys Cys Ile Glu Cys
        515                 520                 525

Val Gln Pro Gln Ser Leu Gln Phe Ile Ile Asp Ala Phe Lys Gly Gln
    530                 535                 540

Val Phe Ala Leu Ser Thr His Pro Tyr Gly Cys Arg Val Ile Gln Arg
545                 550                 555                 560

Ile Leu Glu His Cys Leu Pro Asp Gln Thr Leu Pro Ile Leu Glu Glu
                565                 570                 575

Leu His Gln His Thr Glu Gln Leu Val Gln Asp Gln Tyr Gly Asn Tyr
            580                 585                 590

Val Ile Gln His Val Leu Glu His Gly Arg Pro Glu Asp Lys Ser Lys
        595                 600                 605

Ile Val Ala Glu Ile Arg Gly Asn Val Leu Val Leu Ser Gln His Lys
    610                 615                 620

Phe Ala Ser Asn Val Val Glu Lys Cys Val Thr His Ala Ser Arg Thr
625                 630                 635                 640

Glu Arg Ala Val Leu Ile Asp Glu Val Cys Thr Met Asn Asp Gly Pro
                645                 650                 655

His Ser Ala Leu Tyr Thr Met Met Lys Asp Gln Tyr Ala Asn Tyr Val
            660                 665                 670

Val Gln Lys Met Ile Asp Val Ala Glu Pro Gly Gln Arg Lys Ile Val
        675                 680                 685

Met His Lys Ile Arg Pro His Ile Ala Thr Leu Arg Lys Tyr Thr Tyr
    690                 695                 700

Gly Lys His Ile Leu Ala Lys Leu Glu Lys Tyr Tyr Met Lys Asn Gly
705                 710                 715                 720

Val Asp Leu Gly Asp Pro Lys Lys Arg Lys Val Asp Pro Lys Lys
                725                 730                 735

Lys Arg Lys Val Gly Gly Arg Gly Gly Gly Ser Gly Gly Gly
            740                 745                 750

Ser Gly Gly Gly Gly Ser Gly Pro Ala
            755                 760

<210> SEQ ID NO 66
<211> LENGTH: 674
<212> TYPE: PRT
<213> ORGANISM: Artificial Sequence
<220> FEATURE:
<223> OTHER INFORMATION: Synthetic Polypeptide

<400> SEQUENCE: 66

```
Met Gly Pro Ala Gly Pro Met Glu Ile Tyr Lys Thr Val Ser Ala Trp
1               5                   10                  15

Lys Arg Gln Pro Val Arg Val Leu Ser Leu Phe Arg Asn Ile Asp Lys
            20                  25                  30

Val Leu Lys Ser Leu Gly Phe Leu Glu Ser Gly Ser Gly Ser Gly Gly
        35                  40                  45

Gly Thr Leu Lys Tyr Val Glu Asp Val Thr Asn Val Val Arg Arg Asp
    50                  55                  60

Val Glu Lys Trp Gly Pro Phe Asp Leu Val Tyr Gly Ser Thr Gln Pro
65                  70                  75                  80

Leu Gly Ser Ser Cys Asp Arg Cys Pro Gly Trp Tyr Met Phe Gln Phe
                85                  90                  95

His Arg Ile Leu Gln Tyr Ala Leu Pro Arg Gln Glu Ser Gln Arg Pro
            100                 105                 110

Phe Phe Trp Ile Phe Met Asp Asn Leu Leu Leu Thr Glu Asp Asp Gln
        115                 120                 125

Glu Thr Thr Thr Arg Phe Leu Gln Thr Glu Ala Val Thr Leu Gln Asp
    130                 135                 140

Val Arg Gly Arg Asp Tyr Gln Asn Ala Met Arg Val Trp Ser Asn Ile
145                 150                 155                 160

Pro Gly Leu Lys Ser Lys His Ala Pro Leu Thr Pro Lys Glu Glu Glu
            165                 170                 175

Tyr Leu Gln Ala Gln Val Arg Ser Arg Ser Lys Leu Asp Ala Pro Lys
        180                 185                 190

Val Asp Leu Leu Val Lys Asn Cys Leu Leu Pro Leu Arg Glu Tyr Phe
            195                 200                 205

Lys Tyr Phe Ser Gln Asn Ser Leu Pro Leu Ile Asp Gly Gly Gly Gly
210                 215                 220

Ser Asp Pro Lys Lys Lys Arg Lys Val Asp Pro Lys Lys Lys Arg Lys
225                 230                 235                 240

Val Asp Pro Lys Lys Lys Arg Lys Val Gly Ser Thr Gly Ser Arg Asn
            245                 250                 255

Asp Gly Gly Gly Ser Gly Gly Gly Ser Gly Gly Gly Ser
            260                 265                 270

Gly Arg Ala Gly Ile Leu Pro Pro Lys Lys Arg Lys Val Ser Arg
        275                 280                 285

Gly Arg Ser Arg Leu Leu Glu Asp Phe Arg Asn Asn Arg Tyr Pro Asn
    290                 295                 300

Leu Gln Leu Arg Glu Ile Ala Gly His Ile Met Glu Phe Ser Gln Asp
305                 310                 315                 320

Gln His Gly Ser Arg Phe Ile Gln Leu Lys Leu Glu Arg Ala Thr Pro
            325                 330                 335

Ala Glu Arg Gln Leu Val Phe Asn Glu Ile Leu Gln Ala Ala Tyr Gln
        340                 345                 350

Leu Met Val Asp Val Phe Gly Asn Tyr Val Ile Gln Lys Phe Phe Glu
            355                 360                 365

Phe Gly Ser Leu Glu Gln Lys Leu Ala Leu Ala Glu Arg Ile Arg Gly
        370                 375                 380

His Val Leu Ser Leu Ala Leu Gln Met Tyr Gly Ser Arg Val Ile Glu
385                 390                 395                 400

Lys Ala Leu Glu Phe Ile Pro Ser Asp Gln Gln Asn Glu Met Val Arg
                405                 410                 415
```

```
Glu Leu Asp Gly His Val Leu Lys Cys Val Lys Asp Gln Asn Gly Asn
            420                 425                 430

His Val Val Gln Lys Cys Ile Glu Cys Val Gln Pro Gln Ser Leu Gln
            435                 440                 445

Phe Ile Ile Asp Ala Phe Lys Gly Gln Val Phe Ala Leu Ser Thr His
            450                 455                 460

Pro Tyr Gly Cys Arg Val Ile Gln Arg Ile Leu Glu His Cys Leu Pro
465                 470                 475                 480

Asp Gln Thr Leu Pro Ile Leu Glu Glu Leu His Gln His Thr Glu Gln
            485                 490                 495

Leu Val Gln Asp Gln Tyr Gly Asn Tyr Val Ile Gln His Val Leu Glu
            500                 505                 510

His Gly Arg Pro Glu Asp Lys Ser Lys Ile Val Ala Glu Ile Arg Gly
            515                 520                 525

Asn Val Leu Val Leu Ser Gln His Lys Phe Ala Ser Asn Val Val Glu
            530                 535                 540

Lys Cys Val Thr His Ala Ser Arg Thr Glu Arg Ala Val Leu Ile Asp
545                 550                 555                 560

Glu Val Cys Thr Met Asn Asp Gly Pro His Ser Ala Leu Tyr Thr Met
                    565                 570                 575

Met Lys Asp Gln Tyr Ala Asn Tyr Val Val Gln Lys Met Ile Asp Val
            580                 585                 590

Ala Glu Pro Gly Gln Arg Lys Ile Val Met His Lys Ile Arg Pro His
            595                 600                 605

Ile Ala Thr Leu Arg Lys Tyr Thr Tyr Gly Lys His Ile Leu Ala Lys
            610                 615                 620

Leu Glu Lys Tyr Tyr Met Lys Asn Gly Val Asp Leu Gly Asp Pro Lys
625                 630                 635                 640

Lys Lys Arg Lys Val Asp Pro Lys Lys Arg Lys Val Gly Gly Arg
                    645                 650                 655

Gly Gly Gly Gly Ser Gly Gly Gly Ser Gly Gly Gly Ser Gly
                    660                 665                 670

Pro Ala

<210> SEQ ID NO 67
<211> LENGTH: 760
<212> TYPE: PRT
<213> ORGANISM: Artificial Sequence
<220> FEATURE:
<223> OTHER INFORMATION: Synthetic Polypeptide

<400> SEQUENCE: 67

Met Ile Asp Gly Gly Gly Ser Asp Pro Lys Lys Lys Arg Lys Val
1               5                   10                  15

Asp Pro Lys Lys Lys Arg Lys Val Asp Pro Lys Lys Lys Arg Lys Val
                20                  25                  30

Gly Ser Thr Gly Ser Arg Asn Asp Gly Gly Gly Ser Gly Gly Gly
            35                  40                  45

Gly Ser Gly Gly Gly Ser Gly Arg Ala Gly Ile Leu Pro Pro Lys
        50                  55                  60

Lys Lys Arg Lys Val Ser Arg Gly Arg Ser Arg Leu Leu Glu Asp Phe
65                  70                  75                  80

Arg Asn Asn Arg Tyr Pro Asn Leu Gln Leu Arg Glu Ile Ala Gly His
                85                  90                  95

Ile Met Glu Phe Ser Gln Asp Gln His Gly Ser Arg Phe Ile Gln Leu
```

```
                100             105             110
Lys Leu Glu Arg Ala Thr Pro Ala Glu Arg Gln Leu Val Phe Asn Glu
            115                 120                 125

Ile Leu Gln Ala Ala Tyr Gln Leu Met Val Asp Val Phe Gly Asn Tyr
            130                 135                 140

Val Ile Gln Lys Phe Phe Glu Phe Gly Ser Leu Glu Gln Lys Leu Ala
145                 150                 155                 160

Leu Ala Glu Arg Ile Arg Gly His Val Leu Ser Leu Ala Leu Gln Met
                165                 170                 175

Tyr Gly Ser Arg Val Ile Glu Lys Ala Leu Glu Phe Ile Pro Ser Asp
                180                 185                 190

Gln Gln Asn Glu Met Val Arg Glu Leu Asp Gly His Val Leu Lys Cys
            195                 200                 205

Val Lys Asp Gln Asn Gly Asn His Val Val Gln Lys Cys Ile Glu Cys
            210                 215                 220

Val Gln Pro Gln Ser Leu Gln Phe Ile Ile Asp Ala Phe Lys Gly Gln
225                 230                 235                 240

Val Phe Ala Leu Ser Thr His Pro Tyr Gly Cys Arg Val Ile Gln Arg
                245                 250                 255

Ile Leu Glu His Cys Leu Pro Asp Gln Thr Leu Pro Ile Leu Glu Glu
                260                 265                 270

Leu His Gln His Thr Glu Gln Leu Val Gln Asp Gln Tyr Gly Asn Tyr
            275                 280                 285

Val Ile Gln His Val Leu Glu His Gly Arg Pro Glu Asp Lys Ser Lys
            290                 295                 300

Ile Val Ala Glu Ile Arg Gly Asn Val Leu Val Leu Ser Gln His Lys
305                 310                 315                 320

Phe Ala Ser Asn Val Val Glu Lys Cys Val Thr His Ala Ser Arg Thr
                325                 330                 335

Glu Arg Ala Val Leu Ile Asp Glu Val Cys Thr Met Asn Asp Gly Pro
                340                 345                 350

His Ser Ala Leu Tyr Thr Met Met Lys Asp Gln Tyr Ala Asn Tyr Val
            355                 360                 365

Val Gln Lys Met Ile Asp Val Ala Glu Pro Gly Gln Arg Lys Ile Val
            370                 375                 380

Met His Lys Ile Arg Pro His Ile Ala Thr Leu Arg Lys Tyr Thr Tyr
385                 390                 395                 400

Gly Lys His Ile Leu Ala Lys Leu Glu Lys Tyr Tyr Met Lys Asn Gly
                405                 410                 415

Val Asp Leu Gly Asp Pro Lys Lys Arg Lys Val Asp Pro Lys Lys
                420                 425                 430

Lys Arg Lys Val Gly Gly Arg Gly Gly Gly Ser Gly Gly Gly
            435                 440                 445

Ser Gly Gly Gly Ser Gly Pro Ala Asn His Asp Gln Glu Phe Asp
            450                 455                 460

Pro Pro Lys Val Tyr Pro Pro Val Pro Ala Glu Lys Arg Lys Pro Ile
465                 470                 475                 480

Arg Val Leu Ser Leu Phe Asp Gly Ile Ala Thr Gly Leu Leu Val Leu
                485                 490                 495

Lys Asp Leu Gly Ile Gln Val Asp Arg Tyr Ile Ala Ser Glu Val Cys
            500                 505                 510

Glu Asp Ser Ile Thr Val Gly Met Val Arg His Gln Gly Lys Ile Met
            515                 520                 525
```

Tyr Val Gly Asp Val Arg Ser Val Thr Gln Lys His Ile Gln Glu Trp
    530                 535                 540

Gly Pro Phe Asp Leu Val Ile Gly Gly Ser Pro Cys Asn Asp Leu Ser
545                 550                 555                 560

Ile Val Asn Pro Ala Arg Lys Gly Leu Tyr Glu Gly Thr Gly Arg Leu
                565                 570                 575

Phe Phe Glu Phe Tyr Arg Leu Leu His Asp Ala Arg Pro Lys Glu Gly
            580                 585                 590

Asp Asp Arg Pro Phe Phe Trp Leu Phe Glu Asn Val Val Ala Met Gly
        595                 600                 605

Val Ser Asp Lys Arg Asp Ile Ser Arg Phe Leu Glu Ser Asn Pro Val
    610                 615                 620

Met Ile Asp Ala Lys Glu Val Ser Ala Ala His Arg Ala Arg Tyr Phe
625                 630                 635                 640

Trp Gly Asn Leu Pro Gly Met Asn Arg Pro Leu Ala Ser Thr Val Asn
                645                 650                 655

Asp Lys Leu Glu Leu Gln Glu Cys Leu Glu His Gly Arg Ile Ala Lys
            660                 665                 670

Phe Ser Lys Val Arg Thr Ile Thr Thr Arg Ser Asn Ser Ile Lys Gln
        675                 680                 685

Gly Lys Asp Gln His Phe Pro Val Phe Met Asn Glu Lys Glu Asp Ile
    690                 695                 700

Leu Trp Cys Thr Glu Met Glu Arg Val Phe Gly Phe Pro Val His Tyr
705                 710                 715                 720

Thr Asp Val Ser Asn Met Ser Arg Leu Ala Arg Gln Arg Leu Leu Gly
                725                 730                 735

Arg Ser Trp Ser Val Pro Val Ile Arg His Leu Phe Ala Pro Leu Lys
            740                 745                 750

Glu Tyr Phe Ala Cys Val Ile Asp
        755                 760

<210> SEQ ID NO 68
<211> LENGTH: 673
<212> TYPE: PRT
<213> ORGANISM: Artificial Sequence
<220> FEATURE:
<223> OTHER INFORMATION: Synthetic Polypeptide

<400> SEQUENCE: 68

Met Ile Asp Gly Gly Gly Ser Asp Pro Lys Lys Lys Arg Lys Val
1               5                   10                  15

Asp Pro Lys Lys Lys Arg Lys Val Asp Pro Lys Lys Lys Arg Lys Val
                20                  25                  30

Gly Ser Thr Gly Ser Arg Asn Asp Gly Gly Gly Ser Gly Gly Gly
            35                  40                  45

Gly Ser Gly Gly Gly Gly Ser Gly Arg Ala Gly Ile Leu Pro Pro Lys
    50                  55                  60

Lys Lys Arg Lys Val Ser Arg Gly Arg Ser Arg Leu Leu Glu Asp Phe
65                  70                  75                  80

Arg Asn Asn Arg Tyr Pro Asn Leu Gln Leu Arg Glu Ile Ala Gly His
                85                  90                  95

Ile Met Glu Phe Ser Gln Asp Gln His Gly Ser Arg Phe Ile Gln Leu
            100                 105                 110

Lys Leu Glu Arg Ala Thr Pro Ala Glu Arg Gln Leu Val Phe Asn Glu
        115                 120                 125

```
Ile Leu Gln Ala Ala Tyr Gln Leu Met Val Asp Val Phe Gly Asn Tyr
130                 135                 140

Val Ile Gln Lys Phe Phe Glu Phe Gly Ser Leu Glu Gln Lys Leu Ala
145                 150                 155                 160

Leu Ala Glu Arg Ile Arg Gly His Val Leu Ser Leu Ala Leu Gln Met
            165                 170                 175

Tyr Gly Ser Arg Val Ile Glu Lys Ala Leu Glu Phe Ile Pro Ser Asp
            180                 185                 190

Gln Gln Asn Glu Met Val Arg Glu Leu Asp Gly His Val Leu Lys Cys
        195                 200                 205

Val Lys Asp Gln Asn Gly Asn His Val Val Gln Lys Cys Ile Glu Cys
210                 215                 220

Val Gln Pro Gln Ser Leu Gln Phe Ile Ile Asp Ala Phe Lys Gly Gln
225                 230                 235                 240

Val Phe Ala Leu Ser Thr His Pro Tyr Gly Cys Arg Val Ile Gln Arg
            245                 250                 255

Ile Leu Glu His Cys Leu Pro Asp Gln Thr Leu Pro Ile Leu Glu Glu
            260                 265                 270

Leu His Gln His Thr Glu Gln Leu Val Gln Asp Gln Tyr Gly Asn Tyr
        275                 280                 285

Val Ile Gln His Val Leu Glu His Gly Arg Pro Glu Asp Lys Ser Lys
290                 295                 300

Ile Val Ala Glu Ile Arg Gly Asn Val Leu Val Leu Ser Gln His Lys
305                 310                 315                 320

Phe Ala Ser Asn Val Val Glu Lys Cys Val Thr His Ala Ser Arg Thr
            325                 330                 335

Glu Arg Ala Val Leu Ile Asp Glu Val Cys Thr Met Asn Asp Gly Pro
            340                 345                 350

His Ser Ala Leu Tyr Thr Met Met Lys Asp Gln Tyr Ala Asn Tyr Val
        355                 360                 365

Val Gln Lys Met Ile Asp Val Ala Glu Pro Gly Gln Arg Lys Ile Val
370                 375                 380

Met His Lys Ile Arg Pro His Ile Ala Thr Leu Arg Lys Tyr Thr Tyr
385                 390                 395                 400

Gly Lys His Ile Leu Ala Lys Leu Glu Lys Tyr Tyr Met Lys Asn Gly
            405                 410                 415

Val Asp Leu Gly Asp Pro Lys Lys Arg Lys Val Asp Pro Lys Lys
            420                 425                 430

Lys Arg Lys Val Gly Gly Arg Gly Gly Gly Ser Gly Gly Gly
        435                 440                 445

Ser Gly Gly Gly Ser Gly Pro Ala Gly Pro Met Glu Ile Tyr Lys
    450                 455                 460

Thr Val Ser Ala Trp Lys Arg Gln Pro Val Arg Val Leu Ser Leu Phe
465                 470                 475                 480

Arg Asn Ile Asp Lys Val Leu Lys Ser Leu Gly Phe Leu Glu Ser Gly
            485                 490                 495

Ser Gly Ser Gly Gly Gly Thr Leu Lys Tyr Val Glu Asp Val Thr Asn
            500                 505                 510

Val Val Arg Arg Asp Val Glu Lys Trp Gly Pro Phe Asp Leu Val Tyr
        515                 520                 525

Gly Ser Thr Gln Pro Leu Gly Ser Ser Cys Asp Arg Cys Pro Gly Trp
530                 535                 540
```

```
Tyr Met Phe Gln Phe His Arg Ile Leu Gln Tyr Ala Leu Pro Arg Gln
545                 550                 555                 560

Glu Ser Gln Arg Pro Phe Phe Trp Ile Phe Met Asp Asn Leu Leu Leu
                565                 570                 575

Thr Glu Asp Asp Gln Glu Thr Thr Thr Arg Phe Leu Gln Thr Glu Ala
            580                 585                 590

Val Thr Leu Gln Asp Val Arg Gly Arg Asp Tyr Gln Asn Ala Met Arg
            595                 600                 605

Val Trp Ser Asn Ile Pro Gly Leu Lys Ser Lys His Ala Pro Leu Thr
610                 615                 620

Pro Lys Glu Glu Tyr Leu Gln Ala Gln Val Arg Ser Arg Ser Lys
625                 630                 635                 640

Leu Asp Ala Pro Lys Val Asp Leu Leu Val Lys Asn Cys Leu Leu Pro
                645                 650                 655

Leu Arg Glu Tyr Phe Lys Tyr Phe Ser Gln Asn Ser Leu Pro Leu Ile
            660                 665                 670

Asp

<210> SEQ ID NO 69
<211> LENGTH: 1002
<212> TYPE: PRT
<213> ORGANISM: Artificial Sequence
<220> FEATURE:
<223> OTHER INFORMATION: Synthetic Polypeptide

<400> SEQUENCE: 69

Met Ile Asp Gly Gly Gly Gly Ser Asp Pro Lys Lys Lys Arg Lys Val
1               5                   10                  15

Asp Pro Lys Lys Lys Arg Lys Val Asp Pro Lys Lys Lys Arg Lys Val
                20                  25                  30

Gly Ser Thr Gly Ser Arg Asn Asp Gly Gly Gly Ser Gly Gly Gly
            35                  40                  45

Gly Ser Gly Gly Gly Gly Ser Gly Arg Ala Gly Ile Leu Pro Lys
        50                  55                  60

Lys Lys Arg Lys Val Ser Arg Gly Arg Ser Arg Leu Leu Glu Asp Phe
65                  70                  75                  80

Arg Asn Asn Arg Tyr Pro Asn Leu Gln Leu Arg Glu Ile Ala Gly His
                85                  90                  95

Ile Met Glu Phe Ser Gln Asp Gln His Gly Ser Arg Phe Ile Gln Leu
            100                 105                 110

Lys Leu Glu Arg Ala Thr Pro Ala Glu Arg Gln Leu Val Phe Asn Glu
        115                 120                 125

Ile Leu Gln Ala Ala Tyr Gln Leu Met Val Asp Val Phe Gly Asn Tyr
    130                 135                 140

Val Ile Gln Lys Phe Phe Glu Phe Gly Ser Leu Glu Gln Lys Leu Ala
145                 150                 155                 160

Leu Ala Glu Arg Ile Arg Gly His Val Leu Ser Leu Ala Leu Gln Met
                165                 170                 175

Tyr Gly Ser Arg Val Ile Glu Lys Ala Leu Glu Phe Ile Pro Ser Asp
            180                 185                 190

Gln Gln Asn Glu Met Val Arg Glu Leu Asp Gly His Val Leu Lys Cys
        195                 200                 205

Val Lys Asp Gln Asn Gly Asn His Val Val Gln Lys Cys Ile Glu Cys
    210                 215                 220

Val Gln Pro Gln Ser Leu Gln Phe Ile Ile Asp Ala Phe Lys Gly Gln
```

```
            225                 230                 235                 240
    Val Phe Ala Leu Ser Thr His Pro Tyr Gly Cys Arg Val Ile Gln Arg
                        245                 250                 255

Ile Leu Glu His Cys Leu Pro Asp Gln Thr Leu Pro Ile Leu Glu Glu
                        260                 265                 270

Leu His Gln His Thr Glu Gln Leu Val Gln Asp Gln Tyr Gly Asn Tyr
                        275                 280                 285

Val Ile Gln His Val Leu Glu His Gly Arg Pro Glu Asp Lys Ser Lys
            290                 295                 300

Ile Val Ala Glu Ile Arg Gly Asn Val Leu Val Leu Ser Gln His Lys
305                 310                 315                 320

Phe Ala Ser Asn Val Val Glu Lys Cys Val Thr His Ala Ser Arg Thr
                        325                 330                 335

Glu Arg Ala Val Leu Ile Asp Glu Val Cys Thr Met Asn Asp Gly Pro
                        340                 345                 350

His Ser Ala Leu Tyr Thr Met Met Lys Asp Gln Tyr Ala Asn Tyr Val
                        355                 360                 365

Val Gln Lys Met Ile Asp Val Ala Glu Pro Gly Gln Arg Lys Ile Val
            370                 375                 380

Met His Lys Ile Arg Pro His Ile Ala Thr Leu Arg Lys Tyr Thr Tyr
385                 390                 395                 400

Gly Lys His Ile Leu Ala Lys Leu Glu Lys Tyr Tyr Met Lys Asn Gly
                        405                 410                 415

Val Asp Leu Gly Asp Pro Lys Lys Arg Lys Val Asp Pro Lys Lys
                        420                 425                 430

Lys Arg Lys Val Gly Gly Arg Gly Gly Gly Ser Gly Gly Gly Gly
            435                 440                 445

Ser Gly Gly Gly Gly Ser Gly Pro Ala Asn His Asp Gln Glu Phe Asp
            450                 455                 460

Pro Pro Lys Val Tyr Pro Pro Val Pro Ala Glu Lys Arg Lys Pro Ile
465                 470                 475                 480

Arg Val Leu Ser Leu Phe Asp Gly Ile Ala Thr Gly Leu Leu Val Leu
                        485                 490                 495

Lys Asp Leu Gly Ile Gln Val Asp Arg Tyr Ile Ala Ser Glu Val Cys
                        500                 505                 510

Glu Asp Ser Ile Thr Val Gly Met Val Arg His Gln Gly Lys Ile Met
                        515                 520                 525

Tyr Val Gly Asp Val Arg Ser Val Thr Gln Lys His Ile Gln Glu Trp
            530                 535                 540

Gly Pro Phe Asp Leu Val Ile Gly Gly Ser Pro Cys Asn Asp Leu Ser
545                 550                 555                 560

Ile Val Asn Pro Ala Arg Lys Gly Leu Tyr Glu Gly Thr Gly Arg Leu
                        565                 570                 575

Phe Phe Glu Phe Tyr Arg Leu Leu His Asp Ala Arg Pro Lys Glu Gly
                        580                 585                 590

Asp Asp Arg Pro Phe Phe Trp Leu Phe Glu Asn Val Val Ala Met Gly
                        595                 600                 605

Val Ser Asp Lys Arg Asp Ile Ser Arg Phe Leu Glu Ser Asn Pro Val
            610                 615                 620

Met Ile Asp Ala Lys Glu Val Ser Ala Ala His Arg Ala Arg Tyr Phe
625                 630                 635                 640

Trp Gly Asn Leu Pro Gly Met Asn Arg Pro Leu Ala Ser Thr Val Asn
                        645                 650                 655
```

Asp Lys Leu Glu Leu Gln Glu Cys Leu Glu His Gly Arg Ile Ala Lys
            660                 665                 670

Phe Ser Lys Val Arg Thr Ile Thr Thr Arg Ser Asn Ser Ile Lys Gln
        675                 680                 685

Gly Lys Asp Gln His Phe Pro Val Phe Met Asn Glu Lys Glu Asp Ile
    690                 695                 700

Leu Trp Cys Thr Glu Met Glu Arg Val Phe Gly Phe Pro Val His Tyr
705                 710                 715                 720

Thr Asp Val Ser Asn Met Ser Arg Leu Ala Arg Gln Arg Leu Leu Gly
                725                 730                 735

Arg Ser Trp Ser Val Pro Val Ile Arg His Leu Phe Ala Pro Leu Lys
            740                 745                 750

Glu Tyr Phe Ala Cys Val Ser Ser Gly Asn Ser Asn Ala Asn Ser Arg
        755                 760                 765

Gly Pro Ser Phe Ser Ser Gly Leu Val Pro Leu Ser Leu Arg Gly Ser
    770                 775                 780

His Met Gly Pro Met Glu Ile Tyr Lys Thr Val Ser Ala Trp Lys Arg
785                 790                 795                 800

Gln Pro Val Arg Val Leu Ser Leu Phe Arg Asn Ile Asp Lys Val Leu
                805                 810                 815

Lys Ser Leu Gly Phe Leu Glu Ser Gly Ser Gly Ser Gly Gly Gly Thr
            820                 825                 830

Leu Lys Tyr Val Glu Asp Val Thr Asn Val Val Arg Arg Asp Val Glu
        835                 840                 845

Lys Trp Gly Pro Phe Asp Leu Val Tyr Gly Ser Thr Gln Pro Leu Gly
    850                 855                 860

Ser Ser Cys Asp Arg Cys Pro Gly Trp Tyr Met Phe Gln Phe His Arg
865                 870                 875                 880

Ile Leu Gln Tyr Ala Leu Pro Arg Gln Glu Ser Gln Arg Pro Phe Phe
                885                 890                 895

Trp Ile Phe Met Asp Asn Leu Leu Thr Glu Asp Asp Gln Glu Thr
            900                 905                 910

Thr Thr Arg Phe Leu Gln Thr Glu Ala Val Thr Leu Gln Asp Val Arg
        915                 920                 925

Gly Arg Asp Tyr Gln Asn Ala Met Arg Val Trp Ser Asn Ile Pro Gly
    930                 935                 940

Leu Lys Ser Lys His Ala Pro Leu Thr Pro Lys Glu Glu Tyr Leu
945                 950                 955                 960

Gln Ala Gln Val Arg Ser Arg Ser Lys Leu Asp Ala Pro Lys Val Asp
                965                 970                 975

Leu Leu Val Lys Asn Cys Leu Pro Leu Arg Glu Tyr Phe Lys Tyr
            980                 985                 990

Phe Ser Gln Asn Ser Leu Pro Leu  Ile Asp
        995                 1000

<210> SEQ ID NO 70
<211> LENGTH: 129
<212> TYPE: RNA
<213> ORGANISM: Artificial Sequence
<220> FEATURE:
<223> OTHER INFORMATION: Synthetic Nucleotide

<400> SEQUENCE: 70
gcaggacggg ggcgcagaag agcagcggaa acagcaagca agaaaaaggc agccgacaac    60

```
gaaaaagggc accgagcggg ccaagggccc agagagagcc gagagccgag agccgagagc    120
cgagaagac                                                              129

<210> SEQ ID NO 71
<211> LENGTH: 127
<212> TYPE: RNA
<213> ORGANISM: Artificial Sequence
<220> FEATURE:
<223> OTHER INFORMATION: Synthetic Nucleotide

<400> SEQUENCE: 71 gcgccgggc agaagaagag cagcggaaac agcaagcaag aaaaaggcag ccgacaacga      60
aaaagggcac cgagcgggcc aagggcccag agagagccga gagccgagag ccgagagccg    120
agaagac                                                                127

<210> SEQ ID NO 72
<211> LENGTH: 133
<212> TYPE: RNA
<213> ORGANISM: Artificial Sequence
<220> FEATURE:
<223> OTHER INFORMATION: Synthetic Nucleotide

<400> SEQUENCE: 72
gccggccgcg cgggggaggc gaagagcagc ggaaacagca agcaagaaaa aggcagccga     60
caacgaaaaa gggcaccgag cgggccaagg gcccagagag agccgagagc cgagagccga    120
gagccgagaa gac                                                       133

<210> SEQ ID NO 73
<211> LENGTH: 133
<212> TYPE: RNA
<213> ORGANISM: Artificial Sequence
<220> FEATURE:
<223> OTHER INFORMATION: Synthetic Nucleotide

<400> SEQUENCE: 73
ggcaggcgag gaggggagg gaagagcagc ggaaacagca agcaagaaaa aggcagccga      60
caacgaaaaa gggcaccgag cgggccaagg gcccagagag agccgagagc cgagagccga    120
gagccgagaa gac                                                       133

<210> SEQ ID NO 74
<211> LENGTH: 187
<212> TYPE: DNA
<213> ORGANISM: Artificial Sequence
<220> FEATURE:
<223> OTHER INFORMATION: Synthetic Nucleotide

<400> SEQUENCE: 74
acagagttga gaaatttgac gtttaagagc tatgctggaa acagcatagc aagtttaaat     60
aaggctagtc cgttatcaac ttgaaaaagt ggcaccgagt cggtgccaat tgggtctcca    120
gattgtatgt agcctgtatg tagcctgtat gtagcctgta tgtagcctgt atgtaagatc    180
ttttttt                                                              187

<210> SEQ ID NO 75
<211> LENGTH: 187
<212> TYPE: DNA
<213> ORGANISM: Artificial Sequence
<220> FEATURE:
<223> OTHER INFORMATION: Synthetic Nucleotide

<400> SEQUENCE: 75
```

```
gtcaaatttc tcaactctgt gtttaagagc tatgctggaa acagcatagc aagtttaaat    60
aaggctagtc cgttatcaac ttgaaaaagt ggcaccgagt cggtgccaat tgggtctcca   120
gattgtatgt agcctgtatg tagcctgtat gtagcctgta tgtagcctgt atgtaagatc   180
ttttttt                                                             187

<210> SEQ ID NO 76
<211> LENGTH: 187
<212> TYPE: DNA
<213> ORGANISM: Artificial Sequence
<220> FEATURE:
<223> OTHER INFORMATION: Synthetic Nucleotide

<400> SEQUENCE: 76
gctcctaaaa acgaaccaat gtttaagagc tatgctggaa acagcatagc aagtttaaat    60
aaggctagtc cgttatcaac ttgaaaaagt ggcaccgagt cggtgccaat tgggtctcca   120
gattgtatgt agcctgtatg tagcctgtat gtagcctgta tgtagcctgt atgtaagatc   180
ttttttt                                                             187

<210> SEQ ID NO 77
<211> LENGTH: 187
<212> TYPE: DNA
<213> ORGANISM: Artificial Sequence
<220> FEATURE:
<223> OTHER INFORMATION: Synthetic Nucleotide

<400> SEQUENCE: 77
aaacgaacca ataggaagag gtttaagagc tatgctggaa acagcatagc aagtttaaat    60
aaggctagtc cgttatcaac ttgaaaaagt ggcaccgagt cggtgccaat tgggtctcca   120
gattgtatgt agcctgtatg tagcctgtat gtagcctgta tgtagcctgt atgtaagatc   180
ttttttt                                                             187

<210> SEQ ID NO 78
<211> LENGTH: 187
<212> TYPE: DNA
<213> ORGANISM: Artificial Sequence
<220> FEATURE:
<223> OTHER INFORMATION: Synthetic Nucleotide

<400> SEQUENCE: 78
cttcagcggc agctattgat gtttaagagc tatgctggaa acagcatagc aagtttaaat    60
aaggctagtc cgttatcaac ttgaaaaagt ggcaccgagt cggtgccaat tgggtctcca   120
gattgtatgt agcctgtatg tagcctgtat gtagcctgta tgtagcctgt atgtaagatc   180
ttttttt                                                             187

<210> SEQ ID NO 79
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 79
gcatctctgc tcctattggc gtttaagagc tatgctggaa acagcatagc aagtttaaat    60
aaggctagtc cgttatcaac ttgaaaaagt ggcaccgagt cggtgccaat tgggtctcca   120
gattgtatgt agcctgtatg tagcctgtat gtagcctgta tgtagcctgt atgtaagatc   180
```

```
tttttttt                                                            187

<210> SEQ ID NO 80
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 80
gcgccagatc acctcagcag gtttaagagc tatgctggaa acagcatagc aagtttaaat      60
aaggctagtc cgttatcaac ttgaaaaagt ggcaccgagt cggtgccaat tgggtctcca     120
gattgtatgt agcctgtatg tagcctgtat gtagcctgta tgtagcctgt atgtaagatc     180
ttttttt                                                             187

<210> SEQ ID NO 81
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 81
gcagagcgga ggaggtgctg tttaagagct atgctggaaa cagcatagca agtttaaata      60
aggctagtcc gttatcaact tgaaaaagtg gcaccgagtc ggtgccaatt gggtctccag     120
attgtatgta gcctgtatgt agcctgtatg tagcctgtat gtagcctgta tgtaagatct     180
tttttt                                                              186

<210> SEQ ID NO 82
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 82
gaaggaagaa cgtgagcacg gtttaagagc tatgctggaa acagcatagc aagtttaaat      60
aaggctagtc cgttatcaac ttgaaaaagt ggcaccgagt cggtgccaat tgggtctcca     120
gattgtatgt agcctgtatg tagcctgtat gtagcctgta tgtagcctgt atgtaagatc     180
ttttttt                                                             187

<210> SEQ ID NO 83
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 83
ggcagtagcc gcttcaggga gtttaagagc tatgctggaa acagcatagc aagtttaaat      60
aaggctagtc cgttatcaac ttgaaaaagt ggcaccgagt cggtgccaat tgggtctcca     120
gattgtatgt agcctgtatg tagcctgtat gtagcctgta tgtagcctgt atgtaagatc     180
ttttttt                                                             187

<210> SEQ ID NO 84
<211> LENGTH: 187
<212> TYPE: DNA
<213> ORGANISM: Artificial Sequence
```

```
<220> FEATURE:
<223> OTHER INFORMATION: Synthetic Polynucleotide

<400> SEQUENCE: 84
gcgcaagcgc atatccttct gtttaagagc tatgctggaa acagcatagc aagtttaaat      60
aaggctagtc cgttatcaac ttgaaaaagt ggcaccgagt cggtgccaat tgggtctcca    120
gattgtatgt agcctgtatg tagcctgtat gtagcctgta tgtagcctgt atgtaagatc    180
tttttt                                                               187
```